(12) United States Patent
Coffman et al.

(10) Patent No.: US 10,039,753 B2
(45) Date of Patent: Aug. 7, 2018

(54) IMIDAZO[4,5-C]QUINOLINE AND IMIDAZO[4,5-C][1,5]NAPHTHYRIDINE DERIVATIVES AS LRRK2 INHIBITORS

(71) Applicant: Pfizer Inc., New York, NY (US)

(72) Inventors: Karen Jean Coffman, Pawcatuck, CT (US); Paul Galatsis, Newton, MA (US); Michelle Renee Garnsey, Providence, RI (US); Jaclyn Louise Henderson, Cambridge, MA (US); Bethany Lyn Kormos, Somerville, MA (US); Ravi G. Kurumbail, East Lyme, CT (US); Martin Youngjin Pettersson, Littleton, MA (US); Matthew Richard Reese, Mystic, CT (US); Antonia Friederike Stepan, Biberach an der Riss (DE); Patrick Robert Verhoest, Newton, MA (US); Travis T. Wager, Brookline, MA (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 15/262,112

(22) Filed: Sep. 12, 2016

(65) Prior Publication Data
US 2017/0073343 A1 Mar. 16, 2017

Related U.S. Application Data

(60) Provisional application No. 62/375,646, filed on Aug. 16, 2016, provisional application No. 62/218,061, filed on Sep. 14, 2015.

(51) Int. Cl.
| | |
|---|---|
| *A61K 31/435* | (2006.01) |
| *C07D 215/38* | (2006.01) |
| *C07D 471/04* | (2006.01) |
| *C07D 519/00* | (2006.01) |
| *C07D 471/14* | (2006.01) |
| *C07D 215/42* | (2006.01) |
| *A61K 31/4745* | (2006.01) |

(52) U.S. Cl.
CPC ........ *A61K 31/435* (2013.01); *A61K 31/4745* (2013.01); *C07D 215/38* (2013.01); *C07D 215/42* (2013.01); *C07D 471/04* (2013.01); *C07D 471/14* (2013.01); *C07D 519/00* (2013.01)

(58) Field of Classification Search
CPC ... A61K 31/435; C07D 215/38; C07D 215/42
USPC ..................... 546/159; 544/127; 514/230.5
See application file for complete search history.

(56) References Cited

U.S. PATENT DOCUMENTS

| | | |
|---|---|---|
| 4,689,338 A | 10/1987 | Gerster et al. |
| 4,698,348 A * | 10/1987 | Gerster ............... C07D 215/42 |
| 4,929,624 A | 5/1990 | Gerster et al. |
| 5,389,640 A | 2/1995 | Gerster et al. |
| 5,502,187 A | 3/1996 | Ayer et al. |
| 5,506,347 A | 4/1996 | Erion et al. |
| 5,646,128 A | 7/1997 | Firestein et al. |
| 5,658,889 A | 8/1997 | Gruber et al. |
| 5,674,998 A | 10/1997 | Boyer et al. |
| 5,686,457 A | 11/1997 | Traxler et al. |
| 5,721,356 A | 2/1998 | Ugarkar et al. |
| 5,726,302 A | 5/1998 | Ugarkar et al. |
| 5,750,349 A | 5/1998 | Suzuki et al. |
| 5,763,596 A | 6/1998 | Boyer et al. |
| 5,763,597 A | 6/1998 | Ugarkar et al. |
| 5,795,977 A | 8/1998 | Ugarkar et al. |
| 5,864,033 A | 1/1999 | Browne et al. |
| 6,051,577 A | 4/2000 | Altmann |
| 6,096,749 A | 8/2000 | Traxler et al. |
| 6,610,847 B2 | 8/2003 | Blumenkopf et al. |

(Continued)

FOREIGN PATENT DOCUMENTS

| | | |
|---|---|---|
| CN | 1102644 | 5/1995 |
| DE | 4304455 | 8/1994 |

(Continued)

OTHER PUBLICATIONS

International Patent Application No. PCT/IB2014/066563, filed Dec. 3, 2014,International Preliminary Report on Patenetability, dated Jun. 21, 2016, 6 pages.

(Continued)

*Primary Examiner* — Craig D Ricci
*Assistant Examiner* — Janet L. Coppins
(74) *Attorney, Agent, or Firm* — Lisa A. Samuels

(57) ABSTRACT

The present invention provides novel imidazo[4,5-c]quinoline and imidazo[4,5-c][1,5]naphthyridine derivatives of Formula (I), and the pharmaceutically acceptable salts thereof

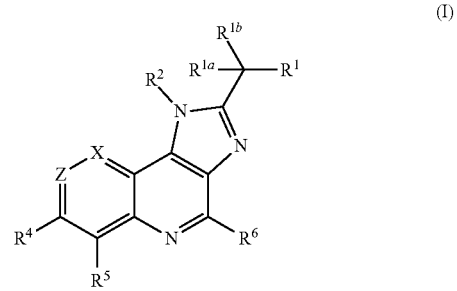

(I)

wherein $R^1$, $R^{1a}$, $R^{1b}$, $R^2$, $R^4$, $R^5$, $R^6$, X and Z are as defined in the specification. The invention is also directed to pharmaceutical compositions comprising the compounds of Formula (I) and to use of the compounds in the treatment of diseases associated with LRRK2, such as neurodegenerative diseases including Parkinson's disease or Alzheimer's disease, cancer, Crohn's disease or leprosy.

29 Claims, No Drawings

(56) References Cited

U.S. PATENT DOCUMENTS

| | | | |
|---|---|---|---|
| 6,635,762 B1 | 10/2003 | Blumenkopf et al. | |
| 6,790,961 B2 * | 9/2004 | Gerster | C07D 471/04 |
| 6,890,929 B2 | 5/2005 | Blumenkopf et al. | |
| 7,115,600 B2 | 10/2006 | Wager et al. | |
| 7,285,293 B2 | 10/2007 | Castillo et al. | |
| 7,569,569 B2 | 8/2009 | Blumenkopf et al. | |
| 7,687,507 B2 | 3/2010 | Blumenkopf et al. | |
| 7,964,607 B2 | 6/2011 | Verhoest et al. | |
| 7,998,966 B2 | 8/2011 | Bearss et al. | |
| 9,156,845 B2 | 10/2015 | Galatsis et al. | |
| 2002/0019526 A1 | 2/2002 | Blumenkopf et al. | |
| 2003/0019205 A1 | 1/2003 | DeNinno et al. | |
| 2003/0073655 A1 | 4/2003 | Chain | |
| 2003/0212273 A1 | 11/2003 | Blumenkopf et al. | |
| 2004/0058922 A1 | 3/2004 | Blumenkopf et al. | |
| 2004/0192889 A1 | 9/2004 | Bredesen | |
| 2004/0220186 A1 | 11/2004 | Bell et al. | |
| 2005/0019328 A1 | 1/2005 | Schenk | |
| 2005/0043354 A1 | 2/2005 | Wager et al. | |
| 2005/0048049 A1 | 3/2005 | Schenk | |
| 2005/0153989 A1 | 7/2005 | Grotzfeld et al. | |
| 2005/0171128 A1 | 8/2005 | Blumenkopf et al. | |
| 2005/0256135 A1 | 11/2005 | Lunn et al. | |
| 2005/0261331 A1 | 11/2005 | Nielsen et al. | |
| 2005/0267095 A1 | 12/2005 | Bernardelli et al. | |
| 2005/0267100 A1 | 12/2005 | Elliott et al. | |
| 2006/0106035 A1 | 5/2006 | Hendrix et al. | |
| 2006/0111372 A1 | 5/2006 | Hendrix et al. | |
| 2007/0031416 A1 | 2/2007 | Shoji et al. | |
| 2007/0049615 A1 | 3/2007 | Ibrahim et al. | |
| 2007/0149561 A1 | 6/2007 | Dhanak et al. | |
| 2007/0179175 A1 | 8/2007 | Lunn | |
| 2008/0096955 A1 | 4/2008 | Wager et al. | |
| 2008/0176925 A1 | 7/2008 | Butler et al. | |
| 2008/0293733 A1 | 11/2008 | Bearss et al. | |
| 2009/0005356 A1 | 1/2009 | Blaney et al. | |
| 2009/0018122 A1 | 1/2009 | Lindstrom et al. | |
| 2009/0118276 A1 | 5/2009 | Gopalsamy et al. | |
| 2009/0275533 A1 | 11/2009 | Hsieh et al. | |
| 2009/0298823 A1 | 12/2009 | Song et al. | |
| 2009/0325953 A1 | 12/2009 | Sahoo et al. | |
| 2010/0175140 A1 | 7/2010 | Smith | |
| 2010/0184790 A1 | 7/2010 | Meijer et al. | |
| 2011/0082140 A1 | 4/2011 | Dorsch et al. | |
| 2011/0166175 A1 | 7/2011 | Klein | |
| 2011/0190290 A1 | 8/2011 | Hood et al. | |
| 2011/0201599 A1 | 8/2011 | Bahceci et al. | |
| 2011/0218198 A1 | 9/2011 | Wucherer-Plietker et al. | |
| 2011/0269772 A1 | 11/2011 | Bearss et al. | |
| 2012/0245347 A1 | 9/2012 | Biehl et al. | |
| 2014/0256704 A1 | 9/2014 | Vankayalapati et al. | |
| 2015/0366874 A1 | 12/2015 | Galatsis et al. | |
| 2016/0324983 A1 | 11/2016 | Li | |
| 2016/0375148 A1 | 12/2016 | Li | |
| 2017/0002000 A1 | 1/2017 | Galatsis et al. | |
| 2017/0028079 A1 | 2/2017 | Li | |
| 2017/0056391 A1 | 3/2017 | Li | |
| 2017/0114137 A1 | 4/2017 | Li | |

FOREIGN PATENT DOCUMENTS

| | | | |
|---|---|---|---|
| DE | 102008025751 | 12/2009 | |
| EP | 339358 | 11/1989 | |
| EP | 535548 | 4/1993 | |
| EP | 631179 | 12/1994 | |
| EP | 676667 | 10/1995 | |
| EP | 0682027 | 11/1995 | |
| EP | 777150 | 6/1997 | |
| EP | 795556 | 9/1997 | |
| EP | 846981 | 6/1998 | |
| EP | 0994728 | 10/1998 | |
| EP | 1052264 | 11/2000 | |
| EP | 1070987 | 1/2001 | |
| EP | 1257584 | 10/2004 | |
| EP | 2210887 | 7/2010 | |
| EP | 2338486 | 6/2011 | |
| EP | 0386722 | 9/2012 | |
| JP | 3271289 | 12/1991 | |
| JP | 5310700 | 11/1993 | |
| JP | 6041114 | 2/1994 | |
| JP | 6116239 | 4/1994 | |
| JP | 6247966 | 9/1994 | |
| JP | 10177243 | 6/1998 | |
| JP | 10213887 | 8/1998 | |
| JP | 20011302515 | 10/2001 | |
| KR | 20100116765 | 11/2010 | |
| KR | 20120019785 | 3/2012 | |
| WO | 199215581 | 9/1992 | |
| WO | WO9215582 A1 * | 9/1992 | C07D 471/04 |
| WO | 199320847 | 10/1993 | |
| WO | 1993020078 | 10/1993 | |
| WO | 199408975 | 4/1994 | |
| WO | 199417043 | 8/1994 | |
| WO | 199511898 | 5/1995 | |
| WO | 1996040705 | 12/1996 | |
| WO | 1996040706 | 12/1996 | |
| WO | 1996040707 | 12/1996 | |
| WO | 1998023613 | 6/1998 | |
| WO | 1998044955 | 10/1998 | |
| WO | 199929693 | 6/1999 | |
| WO | 1999065908 | 12/1999 | |
| WO | 1999065909 | 12/1999 | |
| WO | 2000047719 | 8/2000 | |
| WO | 2001098301 | 12/2001 | |
| WO | 2002051837 | 7/2002 | |
| WO | 2002089811 | 11/2002 | |
| WO | 2003025003 | 3/2003 | |
| WO | 2003076658 | 9/2003 | |
| WO | 2004014368 | 2/2004 | |
| WO | 2004016609 | 2/2004 | |
| WO | 2004032829 | 4/2004 | |
| WO | 2004032868 | 7/2004 | |
| WO | 2004055024 | 7/2004 | |
| WO | 2005003065 | 1/2005 | |
| WO | 2005025616 | 3/2005 | |
| WO | 2005044181 | 5/2005 | |
| WO | 2005062795 | 7/2005 | |
| WO | 2005097740 | 10/2005 | |
| WO | 2005103050 | 11/2005 | |
| WO | 2005121175 | 12/2005 | |
| WO | 2005123079 | 12/2005 | |
| WO | 2006004703 | 1/2006 | |
| WO | 2006009832 | 1/2006 | |
| WO | 2006036291 | 4/2006 | |
| WO | 2006042102 | 4/2006 | |
| WO | 2006045392 | 5/2006 | |
| WO | 2006050976 | 5/2006 | |
| WO | 2006052568 | 5/2006 | |
| WO | 2006065280 | 6/2006 | |
| WO | 2006069081 | 6/2006 | |
| WO | 2006091568 | 8/2006 | |
| WO | 2006118959 | 11/2006 | |
| WO | 2006136924 | 12/2006 | |
| WO | 2007063385 | 6/2007 | |
| WO | 2007069053 | 6/2007 | |
| WO | 2007076423 | 7/2007 | |
| WO | 2007088450 | 8/2007 | |
| WO | 2007088462 | 8/2007 | |
| WO | 2007099423 | 9/2007 | |
| WO | 2007104763 | 9/2007 | |
| WO | 2007105053 | 9/2007 | |
| WO | 2007124096 | 11/2007 | |
| WO | 2007135380 | 11/2007 | |
| WO | 2007138431 | 12/2007 | |
| WO | 2007149798 | 12/2007 | |
| WO | 2008070908 | 6/2008 | |
| WO | 2008075007 | 6/2008 | |
| WO | 2008091799 | 7/2008 | |
| WO | 2008122789 | 10/2008 | |
| WO | 2008128072 | 10/2008 | |
| WO | 2008129152 | 10/2008 | |
| WO | 2008150914 | 12/2008 | |
| WO | 2008155000 | 12/2008 | |
| WO | 2009005730 | 1/2009 | |

(56) References Cited

FOREIGN PATENT DOCUMENTS

| WO | 2009030270 | 3/2009 |
|---|---|---|
| WO | 2009035159 | 3/2009 |
| WO | 2009071620 | 6/2009 |
| WO | 2009127642 | 10/2009 |
| WO | 2009131687 | 10/2009 |
| WO | 2009134658 | 11/2009 |
| WO | 2010000364 | 1/2010 |
| WO | 2010003133 | 1/2010 |
| WO | 2010020308 | 2/2010 |
| WO | 2010026335 | 3/2010 |
| WO | 2010031988 | 3/2010 |
| WO | 2010036380 | 4/2010 |
| WO | 2010080712 | 7/2010 |
| WO | 2010081835 | 7/2010 |
| WO | 2010085799 | 7/2010 |
| WO | 2010093191 | 8/2010 |
| WO | 2010106333 | 9/2010 |
| WO | 2010109005 | 9/2010 |
| WO | 2010127754 | 11/2010 |
| WO | 2010129053 | 11/2010 |
| WO | 2010141817 | 4/2011 |
| WO | 2011038572 | 4/2011 |
| WO | 2011045344 | 4/2011 |
| WO | 2014060113 | 4/2011 |
| WO | 2011053861 | 5/2011 |
| WO | 2011055911 | 5/2011 |
| WO | 2011057204 | 5/2011 |
| WO | 2011060295 | 5/2011 |
| WO | 2011106168 | 9/2011 |
| WO | 2011131980 | 10/2011 |
| WO | 2011137022 | 11/2011 |
| WO | 2011141756 | 11/2011 |
| WO | 201149827 | 12/2011 |
| WO | 201151360 | 12/2011 |
| WO | 2011144622 | 12/2011 |
| WO | 2011147756 | 12/2011 |
| WO | 2012028629 | 3/2012 |
| WO | 2012034526 | 3/2012 |
| WO | 2012038743 | 3/2012 |
| WO | 2012058193 | 5/2012 |
| WO | 2012062783 | 5/2012 |
| WO | 2012075046 | 6/2012 |
| WO | 2012118679 | 9/2012 |
| WO | 2012131365 | 10/2012 |
| WO | 2012135631 | 10/2012 |
| WO | 2012143143 | 10/2012 |
| WO | 2012143144 | 10/2012 |
| WO | 2012159079 | 11/2012 |
| WO | 2012162254 | 11/2012 |
| WO | 2012178015 | 12/2012 |
| WO | 2013007765 | 1/2013 |
| WO | 2013007768 | 1/2013 |
| WO | 2013046029 | 4/2013 |
| WO | 2013139882 | 9/2013 |
| WO | 2013164321 | 11/2013 |
| WO | 2013166276 | 11/2013 |
| WO | 2014001973 | 1/2014 |
| WO | 2014093383 | 6/2014 |
| WO | 2015022664 | 2/2015 |
| WO | 2015092592 | 6/2015 |
| WO | 2015103987 | 7/2015 |
| WO | 2015103989 | 7/2015 |
| WO | 2015103990 | 7/2015 |
| WO | 2016004876 | 1/2016 |
| WO | 2016034085 | 3/2016 |
| WO | 2016004875 | 4/2016 |

OTHER PUBLICATIONS

Korean Patent Application No. 2015-7002334 (PCT/IB2013/055039) Notice of Preliminary Rejection, dated Jul. 12, 2016, 12 pages.
U.S. Appl. No. 62/469,756, filed Mar. 10, 2017.
U.S. Appl. No. 62/469,468, filed Mar. 10, 2017.
Almansa, C., et al., "Versatile Three Component Coupling for the Synthesis of Pyrazolopyridines and Other Pyrido Fused Systems", Heterocycles, 2008, pp. 1695-1709, 75(7).
Banno, Tadashi, et al. "Some Applications of the Grignard Cross-Coupling Reaction in the Industrial Field", Journal of Organometallic Chemistry, Jul. 1, 2002, pp. 288-291, 653(1-2).
Boger, Dale, L., et al., "Thermal Cycloaddition of 1,3,5-Triazine with Enamines: Regiospecific Pyrimidine Annulation", Journal of Organic Chemistry, Jul. 1982, pp. 2673-2675, 47(13).
Bookser, B.C., et al., Adenosine Kinase Inhibitors. 6. Water Solubility and Antinociceptive Activity of 5-Phenyl-7-(5-deoxy-beta-D-ribofuranosyl)pyrrolo[2,3-d]pyrimidines Substituted at C4 with Glycinamides and Related Compounds, Journal of Medicinal Chemistry, Dec. 1, 2005, pp. 7808-7820, 48(24).
Boyer, S.H., et al., "Adenosine Kinase Inhibitors, 5. Synthesis, Enzyme Inhibition, and Analgesic Activity of Diaryl-erythrofuranosyltubercidin Analogues", Journal of Medicinal Chemistry, Oct. 6, 2005, pp. 6430-6441, 48(20).
Caravatti, G., et al., "Pyrrolo[2,3-d]pyrimidine and Pyrazolo[3,4-d]pyrimidine Derivatives as Selective Inhibitors of the EFG Receptor Tyrosine Kinase", ACS Symposium Series, Aug. 24, 2001, pp. 231-244, Chapter 14, vol. 796.
Chebanov, V., et al., "Cyclocondensation reactions of 5-aminopyrazoles, pyruvic acids and aldehydes. Multicomponent approaches to pyrazolopyridines and related products", Tetrahedron, 2007, pp. 1229-1242, 63(5).
Chen, Gang, et al., "Elucidating inhibitory models of the inhibitors of epidermal growth factor receptor by docking and 3D-QSAR", Bioorganic & Medicinal Chemistry, 2004, pp. 2409-2417, 12(9).
Chen, H., et al., "Discovery of Selective LRRK2 Inhibitors Guided by Computational Analysis and Molecular Modeling", Journal of Medicinal Chemistry, 2012, pp. 5536-5545, vol. 55.
Chen, Xiu-Mei, et al., "Structure-based and shape-complemented pharmacophore modeling for the discovery of novel checkpoint kinase 1 inhibitors", Journal of Molecular Modeling, 2010, pp. 1195-1204, 16(7).
Coumar, Mohane S., et al., "Identification, SAR Studies, and X-ray Co-crystallographic Analysis of a Novel Furanopyrimidine Aurora Kinase A Inhibitor", ChemMedChem, 2010, pp. 255-267, 5(2).
Erdik, Ender, "Transition Metal Catalyzed Reactions of Organozinc Reagents", Tetrahedron, 1992, pp. 9577-9648, 18(44).
Finnin, Barrie C., et al., "Transdermal Penetration Enhancers: Applications, Limitations, and Potential", The Journal of Pharmaceutical Sciences, Oct. 1999, pp. 955-958, 88(10).
Foloppe, N., et al., "Structure-Based Design of Novel Chk1 Inhibitors: Insights into Hydrogen Bonding and Protein-Ligand Affinity", Journal of Medicinal Chemistry, 2005, pp. 4332-4345, 48(13).
Gangloff, Anthony R., et al., "Synthesis of 3,5-disubstituted-1,2,4-oxadiazoles using tetrabutylammonium fluoride as mild and efficient catalyst", Tetrahedron Letters, Feb. 19, 2001, pp. 1441-1443, 42(8).
Gillardon, F., et al., "Parkinson's Disease-Linked Leucine-Rich Repeat Kinase 2(R1331G) Mutation Increases Proinflammatory Cytokine Release From Activated Primary Microglial Cells and Resultant Neurotoxicity", Neuroscience, Apr. 19, 2012, pp. 41-48, vol. 208.
Glenner, George G., et al., "Amyloidosis of the Nervous System", The Journal of Neurological Sciences, 1989, pp. 1-28, 94(1-3).
Haan, J., et al., "Amyloid in Central Nervous System Disease", Clinical Neurology and Neurosurgery, 1990, pp. 305-310, 92(4).
Haleblain, John, "Characterization of Habits and Crystalline Modification of Solids and Their Pharmaceutical Applications", The Journal of Pharmaceutical Sciences, Aug. 1975, pp. 1269-1288, 64(8).
International Patent Application PCT/IB2013/055039, filed Jun. 19, 2013, International Search Report, dated Oct. 14, 2013, 9 pages.
International Patent Application PCT/IB2013/055039, filed Jun. 19, 2013, Written Opinion of the International Searching Authority, dated Oct. 14, 2013, 10 pages.
International Patent Application PCT/IB2014/066563 Written Opinion & Search Report, dated Feb. 24, 2015, 10 pages.

(56) References Cited

OTHER PUBLICATIONS

Jorgensen, A., et al., "Synthesis of 7H-Pyrrolo[2,3-d]pyrimidin-4-amines", Liebigs Annalen Der Chemie, Jan. 1, 1985, pp. 142-148, vol. 1985.
Joshi, K., et al., "Synthesis of some new fluorine-containing 5-amino-1, 3-disubstituted pyrazoles and 1H-pyrazolo [3,4-b]pyridines", Journal of Heterocyclic Chemistry, Sep. 1979, pp. 1141-1145, 16(6).
KR20100116765, Korean Patent, published Nov. 2, 2010, Machine Translation.
KR20120019785, Korean Patent, published Mar. 3, 2007, Machine Translation.
Lewis, Patrick, et al., "LRRK2 and Human Disease: A Complicated Question or a Question of Complexes?", Science Signaling, Jan. 17, 2012, pp. pe2, 5(207).
Littke, Adam F., et al., "Versatile Catalysts for the Suzuki Cross-Coupling of Arylboronic Acids with Aryl and Vinyl Halides and Triflates under Mild Conditions", Journal of American Chemical Society, May 3, 2000, pp. 4020-4028, 122 (17).
Liu, Zhihua, et al., "The Kinase LRRK2 is a Regulator of the Transcription Factor NFAT That Modulates the Severity of Inflammatory Bowel Disease", Nature Immunology, 2011, pp. 1063-1070, 12(11).
Miyaura, Norio, et al., "Palladium-Catalyzed Cross-Coupling Reactions of Organoboron Compounds", Chemistry Review, 1995, pp. 2457-2483, 95(7).
Moehle, Mark S., et al., "LRRK2 Inhibition Attenuates Microglial Inflammatory Responses", The Journal of Neuroscience, Feb. 1, 2012, pp. 1602-1611, 32(5).
Peng, Tao, et al., 3D-QSAR and Receptor Modeling of Tyrosine Kinase Inhibitors with Flexible Atom Receptor Model (FLARM), Journal of Chemical Information and Computer Sciences, 2003, pp. 298-303, 43(1).
Peng, Tao, et al., "Flexible Atom Receptor Model Study on Tyrosine Kinase Inhibitors", Acta Chim. Sinica, 2003, pp. 29-33, 61(1), Abstract.
Peng, Tao, et al., "Pharmacophore Analysis of Epidermal Growth Factor Receptor Tyrosine Kinase Inhibitors", Institute of Process Engineering, Chinese Academy of Science, 2003, pp. 430-434, 61(3), Abstract.
Quiroga, J., et al., "A hydrogen-bonded dimer in 6-(4-bromophenyl)-3-methyl-1-phenyl-4,5-dihydro-1H-pyrazolo[3,4-b]pyridine and a chain of rings built from n-H . . . N and C—H . . . π(pyridine)hydrogen bonds in 3-(4-nitrophenyl)-4-phenyl-1H-pyrazolo[3,4-b]pyridine", Acta Crystallographica Sections C, Crystal Structure Communications, 2010, pp. o163-o167, 66(4).
Quiroga, J., et al., "Synthesis and Structural Analysis of 5-Cyanoldihydropyrazolo[3,4-b]pyridines", Journal of Heterocyclic Chemistry, Jan.-Feb. 2001, pp. 53-60, 38(1).
Quiroga J., et al., "Three 3-aryl-5-cyanopyrazolo[3,4-b]pyridines", Acta Crystallographica, Section C: Crystal Structure Communications, 1999, iii, IUC9900168/1-3, C55(12).
Reader, John C., et al., "Structure-Guided Evolution of Potent and Selective CHK1 Inhibitors through Scaffold Morphing", Journal of Medicinal Chemistry, 2011, pp. 8328-8242, 54(24).
Saleh, T., et al., "Ultrasound assisted one-pot, three-components synthesis of pyrimido[1,2-a]benzimidazoles and pyrazolol[3,4-b]pyridines: A new access via phenylsulfone synthon", Ultrasonics Sonochemistry, 2012, pp. 49-55, 19 (1).
Sanz, Roberto, et al., "Regioselective Synthesis of 4- and 7-Alkoxyindoles from 2,3-Dihalophenols" Application to the Preparation of Indole Inhibitors of Phospholipase A2, Journal of Organic Chemistry, Mar. 28, 2007, pp. 5113-5118, 72(14).
Saunder-Pullman, Rachel, et al., "LRRK2 G2019S Mutations are Associated with an Increased Cancer Risk in Parkinson Disease", Movement Disorders, 2010, pp. 2536-2541, 25(15).
Shie, Jiun-Jie, et al., "Microwave-Assisted One-Pot Tandem Reactions for Direct Conversion of Primary Alcohols and Aldehydes to Triazines and Tetrazoles in Aqueous Media", Journal of Organic Chemistry, Apr. 13, 2007, pp. 3141-3144, 72(8).
Singh, S.P., et al., "Synthesis of Some Novel Fluorinated Pyrazolo[3,4-b]Pyridines", Synthetic Communications, 2004, pp. 4359-4367, 34(23).
Suzuki, Akira, "Recent Advances in the Cross-Coupling Reactions of Organoboron Derivatives with Organic Electrophiles, 1995-1998", Journal of Organometallic Chemistry, Mar. 15, 1999, pp. 147-168, 576(1-2).
Taiwan Patent Application No. 102122705 Office Action including Search Report dated Jul. 3, 1014, 12 pages.
Taylor, E.C., et al., "Synthesis of 4-Amino-5-cyanopyrrolo[2,3-d]pyrimidines, the Agycone of Toyocamycin", Journal of the American Chemical Society, May 1, 1964, pp. 951-952, 86(5).
Taylor, Edward C., et al., "Synthesis of Pyrrolo[2,3-d]pyrimidines. The Aglycone of Toycamycin", Journal of the American Chemical Society, 1965, pp. 1995-2003, 87(9).
Ugarkar, B.G., et al., "Adenosine Kinase Inhibtors, 2. Synthesis, Enzymen Inhibition and Antiseizure Acitivity of Diaryltubercidin Analogues", Journal of Medicinal Chemistry, Jul. 27, 2000, pp. 2894-2905, 43(15).
Wempen, Iris, et al., "Pyrimidines. II. Synthesis of 6-Fluorouracil", Journal of Medicinal Chemistry, 1964, pp. 207-209, 7(2).
Wilder, L., et al., "7-Alkyl and 7-Cycloalkyl-5-aryl-pyrrolo[2,3-d]pyrimidines-Potent Inhibitors of the Tyrosine Kinase c-Src", Bioorganic and Medicinal Chemistry, Mar. 26, 2001, pp. 849-852, vol. 11.
Zak, Mark, "Discovery and Optimization of Selective JAK1 Inhibitors as Potential Treatments for Rheumatoid Arthritis", Molecular Medicine TriCon Mastering Medicinal Chemistry, San Francisco, CA, Feb. 15, 2013, 20 pages.
International Patent Application PCT/IB2016/0553258, filed Sep. 7, 2016, Search Report and Written Opinion, dated Oct. 24, 2016, 17 pages.
Wu, T., "One-Pot, Two-Step Microwave-Assisted Reaction in Constructing 4,5-Distributed Pyrazolopyrimidines", Organic Letters, Jun. 9, 2003, pp. 3587-3590, 5(20).
Zahran, M. A., et al., "Synthesis and Reactions of 2-Deoxy-β-D-ribofuranosyl Derivatives of 3-Aryl-4H-pyrrolo[2,3-d] pyrimidin-4-imines", Monatshefte fur Chemie, 1995, pp. 1271-1277, 126(11).
Zhao, Yi., et al., "LRRK2 Variant Associated with Alzheimer's Disease", Neurobiology of Aging, 2011, pp. 1990-1993, vol. 32.
Zimprich, Alexander, et al., "Mutations in LRRK2 Cause Autosomal-Dominant Parkinsonism with Pleomorphic Pathology", Neuron, Nov. 18, 2004, pp. 601-607, 44(4).
Singapore Patent Application No. 11201408044Q, Search Report and Written Opinion, dated Jan. 5, 2016, 10 pages.
Traxler, P.M., et al., "4-(Phenylamino)pyrrolopyrimidines: Potent and Selective ATP Site Directed Inhibitors of the EGF-Receptor Protein Tyrosine Kinase", Journal of Medicinal Chemistry, Jun. 1, 1996, pp. 2285-2292, 39(12).
Taweel, Abdel-Aziz, et al., "Heterocyclic Amidines: Synthesis of New Azaindene Derivatives", Alexandria Journal of Pharamaceutical Sciences, 1998, p. 11, 12(1).

\* cited by examiner

IMIDAZO[4,5-C]QUINOLINE AND IMIDAZO[4,5-C][1,5]NAPHTHYRIDINE DERIVATIVES AS LRRK2 INHIBITORS

This application is a Non-Provisional application under 35 U.S.C. 119(e) which claims the benefit of Provisional Patent Application No. 62/375,646 filed Aug. 16, 2016 and U.S. Provisional Patent Application No. 62/218,061 filed Sep. 14, 2015 the disclosures of which is hereby incorporated by reference in its entirety.

FIELD OF THE INVENTION

The present invention relates to small molecule inhibitors of leucine-rich repeat kinase 2 (LRRK2). This invention also relates to methods of inhibiting, in mammals, including humans, LRRK2 by administration of the small molecule LRRK2 inhibitors. The present invention also relates to the treatment of Parkinson's Disease (PD) and other neurodegenerative and/or neurological disorders in mammals, including humans with the LRRK2 inhibitors. More particularly, this invention relates to novel imidazo[4,5-c]quinoline and imidazo[4,5-c][1,5]naphthyridine compounds useful for the treatment of neurodegenerative and/or neurological disorders, such as PD, Alzheimer's Disease (AD) and other LRRK2 associated disorders.

BACKGROUND OF THE INVENTION

LRRK2 is a 286 kDa protein in the ROCO protein family with a complex multidomain structure. Protein motifs that have been established for LRRK2 include an armadillo-like (ARM) domain, an ankyrin-like (ANK) domain, a leucine-rich repeat (LRR) domain, a Ras (renin-angiotensin system) of complex (ROC) domain, a C-terminal of ROC (COR) domain, a kinase domain, and a C-terminal WD40 domain. The ROC domain binds guanosine triphosphate (GTP) and the COR domain may be a regulator of the ROC domain's GTPase activity. The kinase domain has structural homology to the MAP kinase kinase kinases (MAPKKK) and has been shown to phosphorylate a number of cellular proteins in vitro, but the endogenous substrate has yet to be determined. LRRK2 has been found in various regions of the brain as well as in a number of peripheral tissues including heart, lung, spleen, and kidney.

LRRK2 has the ability to potentially play a complex role in multiple cellular processes as a consequence of its multi-domain construct, each associated with putative protein-protein interactions, guanosine triphosphatase (GTPase) activity, and kinase activity. For example, LRRK2 has been associated with NFAT inhibition in the immune system and has been linked to vesicle trafficking, presynaptic homeostasis, mammalian target of rapamycin (mTOR) signaling, signaling through the receptor tyrosine kinase MET in papillary renal and thyroid carcinomas, cytoskeletal dynamics, the mitogen-activated protein kinase (MAPK) pathway, the tumor necrosis factor-α (TNF-α) pathway, the Wnt pathway and autophagy. Recent genome-wide association (GWA) genetic studies have implicated LRRK2 in the pathogenesis of various human diseases such as PD, inflammatory bowel disease (Crohn's disease), cancer and leprosy (Lewis, P. A. and Manzoni, C. Science Signaling 2012, 5(207), pe2).

Parkinson's disease (PD) is a relatively common age-related neurodegenerative disorder resulting from the progressive loss of dopamine-producing neurons and which affects up to 4% of the population over age 80. PD is characterized by both motor symptoms, such as tremor at rest, rigidity, akinesia and postural instability as well as non-motor symptoms such as impairment of cognition, sleep and sense of smell. GWA studies have linked LRRK2 to PD and many patients with point mutations in LRRK2 present symptoms that are indistinguishable from those with idiopathic PD. Over 20 LRRK2 mutations have been associated with autosomal-dominant Parkinsonism, and the R1441C, R1441G, R1441H, Y1699C, G2019S, I2020T and N1437H missense mutations are considered to be pathogenic. The LRRK2 R1441G mutation has been shown to increase the release of proinflammatory cytokines (higher levels of TNF-α, IL-1β, IL-12 and lower levels of IL-10) in microglial cells from transgenic mice and thus may result in direct toxicity to neurons (Gillardon, F. et al. Neuroscience 2012, 208, 41-48). In a murine model of neuroinflammation, induction of LRRK2 in microglia was observed and inhibition of LRRK2 kinase activity with small molecule LRRK2 inhibitors (LRRK2-IN-1 or sunitinib) or LRRK2 knockout resulted in attenuation of TNF-α secretion and nitric oxide synthase (iNOS) induction (Moehle, M. et al. J. Neurosci. 2012, 32(5), 1602-1611). The most common of the LRRK2 mutations, G2019S, is present in more than 85% of PD patients carrying LRRK2 mutations. This mutation, which is present in the LRRK2 kinase domain, leads to an enhancement of LRRK2 kinase activity. In the human brain LRRK2 expression is highest in the same regions of the brain that are impacted by PD, and LRRK2 is found in Lewy Bodies, a hallmark of PD. Recent studies indicate that a potent, selective, brain-penetrant kinase inhibitor for LRRK2 could be a therapeutic treatment for PD.

Dementia results from a wide variety of distinctive pathological processes. The most common pathological processes causing dementia are AD, cerebral amyloid angiopathy (CM) and prion-mediated diseases (see, e.g., Haan et al., Clin. Neurol. Neurosurg. 1990, 92(4):305-310; Glenner et al., J. Neurol. Sci. 1989, 94:1-28). AD is a progressive, neurodegenerative disorder characterized by memory impairment and cognitive dysfunction. AD affects nearly half of all people past the age of 85, the most rapidly growing portion of the United States population. As such, the number of AD patients in the United States is expected to increase from about 4 million to about 14 million by 2050. LRRK2 mutations have been associated with AD-like pathology, which suggests that there may be a partial overlap between the neurodegenerative pathways in both AD and PD (Zimprach, A. et al. Neuron 2004, 44, 601-607). In addition, the LRRK2 R1628P variant (COR domain) has been associated with an increased incidence of AD in a certain population, perhaps resulting from increased apoptosis and cell death (Zhao, Y. et al.; Neurobiology of Aging 2011, 32, 1990-1993).

An increased incidence of certain non-skin cancers such as renal, breast, lung and prostate cancers, as well as acute myelogenous leukemia (AML), has been reported in Parkinson's disease patients with the LRRK2 G2019S mutation (Saunders-Pullman, R. et al.; Movement Disorders, 2010, 25(15), 2536-2541). Since the G2019S mutation is associated with increased LRRK2 kinase activity, inhibition of this activity may be useful in the treatment of cancer, such as kidney, breast, lung, prostate and blood cancers.

Inflammatory bowel disease (IBD) or Crohn's disease (CD) is a complex disease and is believed to result from an inappropriate immune response to microbiota in the intestinal tract. GWA studies have recently identified LRRK2 as a major susceptibility gene for Crohn's disease, particularly the M2397T polymorphism in the WD40 domain (Liu, Z. et al. Nat. Immunol. 2011, 12, 1063-1070). In a recent study LRRK2 deficient mice were found to be more susceptible to dextran sodium sulfate induced colitis than their wild-type counterparts, indicating that LRRK2 may play a role in the pathogenesis of IBD (Liu, Z. and Lenardo, M.; Cell Research 2012, 1-3).

Both non-selective and selective small molecule compounds with LRRK2 inhibitory activity such as staurosporine, sunitinib, LRRK2-IN-1, CZC-25146, TAE684 and those in WO 2011/141756, WO 2012/028629 and WO 2012/058193 have been described. It is desirable to provide compounds which are potent and selective inhibitors of LRRK2 with a favorable pharmacokinetic profile and the ability to traverse the blood brain barrier. Accordingly, the present invention is directed to novel imidazo[4,5-c]quinoline and imidazo[4,5-c][1,5]naphthyridine compounds with LRRK2 inhibitory activity and the use of these compounds in the treatment of diseases associated with LRRK2, such as neurodegenerative diseases, including PD.

SUMMARY OF THE INVENTION

A first embodiment of a first aspect of the present invention is a compound of Formula (I)

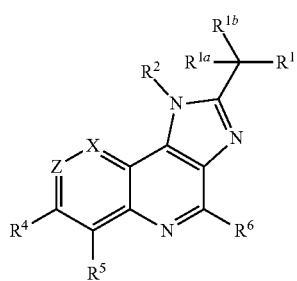

(I)

or a pharmaceutically acceptable salt thereof; wherein X is $CR^7$ or N; Z is $CR^3$ or N; $R^1$ is selected from the group consisting of hydrogen, cyano and a 5- to 10-membered heteroaryl which contains 1 to 5 heteroatoms independently selected from N, O and S; wherein the 5- to 10-membered heteroaryl is optionally substituted with 1 to 3 $R^8$; $R^{1a}$ and $R^{1b}$ are each independently hydrogen, halo, hydroxy or $C_1$-$C_3$alkyl; or $R^{1a}$ and $R^{1b}$ taken together with the carbon to which they are attached are a $C_3$-$C_6$cycloalkyl; $R^2$ is a $C_1$-$C_6$alkyl, $C_3$-$C_7$cycloalkyl or a 4- to 7-membered heterocycloalkyl which contains 1 to 3 heteroatoms independently selected from NR, O and S; wherein the $C_3$-$C_7$cycloalkyl and 4- to 7-membered heterocycloalkyl are each optionally substituted with 1 to 3 R9; and wherein the $C_1$-$C_6$alkyl is optionally substituted with 1 to 3 $R^{10}$; R is hydrogen, $C_1$-$C_6$alkyl or absent; $R^3$, $R^4$, $R^5$, $R^6$ and $R^7$ are each independently selected from the group consisting of hydrogen, deutero, amino, halo, hydroxy, cyano, $C_1$-$C_6$alkyl, $C_3$-$C_6$cycloalkyl and $C_1$-$C_6$alkoxy; wherein the $C_1$-$C_6$alkyl, $C_3$-$C_6$cycloalkyl and $C_1$-$C_6$alkoxy are each optionally substituted with 1 to 3 halo or $C_1$-$C_3$alkoxy; $R^8$ at each occurrence is independently selected from the group consisting of halo, —C(O)NH$_2$, —C(O)NH($C_1$-$C_3$alkyl), —C(O)N($C_1$-$C_3$alkyl)$_2$, $C_1$-$C_6$alkyl, $C_1$-$C_6$alkoxy and $C_3$-$C_6$cycloalkyl; wherein the $C_1$-$C_6$alkyl, $C_1$-$C_6$alkoxy and $C_3$-$C_6$cycloalkyl are each optionally substituted with 1 to 3 halo, cyano, hydroxy or $C_1$-$C_3$alkoxy; $R^9$ at each occurrence is independently selected from the group consisting of halo, hydroxy, $C_1$-$C_6$alkyl, $C_1$-$C_6$alkoxy, and $C_1$-$C_6$alkoxy$C_1$-$C_6$alkyl, wherein the $C_1$-$C_6$alkyl, $C_1$-$C_6$alkoxy, and $C_1$-$C_6$alkoxy$C_1$-$C_6$alkyl are optionally substituted with one to three halo or a cyano; and $R^{10}$ at each occurrence is independently selected from the group consisting of halo, $C_1$-$C_6$alkoxy, $C_1$-$C_6$thioalkoxy, amino, $C_1$-$C_6$alkylamino and di($C_1$-$C_6$alkyl)amino.

A second embodiment of a first aspect of the present invention is the compound of the first embodiment of the first aspect or a pharmaceutically acceptable salt thereof wherein X is $CR^7$; Z is $CR^3$; $R^3$ is hydrogen, bromo, chloro, fluoro, methoxy or cyano; and $R^4$, $R^5$, $R^6$ and $R^7$ are each hydrogen or deutero.

A third embodiment of a first aspect of the present invention is the compound of the second embodiment of the first aspect or a pharmaceutically acceptable salt thereof wherein $R^1$ is a 5- to 10-membered heteroaryl which contains 1 to 4 heteroatoms independently selected from N, O and S; wherein the 5- to 10-membered heteroaryl is optionally substituted with 1 to 2 $R^8$; $R^{1a}$ and $R^{1b}$ are each hydrogen; and $R^8$ at each occurrence is independently selected from the group consisting of halo, $C_1$-$C_3$alkyl, $C_1$-$C_3$alkoxy and $C_3$-$C_6$cycloalkyl; wherein the $C_1$-$C_3$alkyl is optionally substituted with 1 to 3 fluoro, hydroxy or $C_1$-$C_3$alkoxy.

A fourth embodiment of a first aspect of the present invention is the compound of the third embodiment of the first aspect or a pharmaceutically acceptable salt thereof wherein $R^1$ is a 5- to 10-membered heteroaryl selected from the group consisting of oxazolyl, isoxazolyl, oxadiazolyl, thiazolyl, pyrazolyl, triazolyl, tetrazolyl, pyridinyl, benzoxazolyl, benzoisoxazolyl, benzopyrazolyl, benzotriazolyl, imidazothiazolyl and imidazothiadiazolyl; each of which is optionally substituted with an $R^8$; and $R^8$ is selected from the group consisting of methyl, trifluoromethyl, isopropyl, 2-hydroxyisopropyl, methoxy, methoxymethyl, cyclopropyl and chloro.

A fifth embodiment of a first aspect of the present invention is the compound of the fourth embodiment of the first aspect or a pharmaceutically acceptable salt thereof wherein $R^1$ is selected from the group consisting of

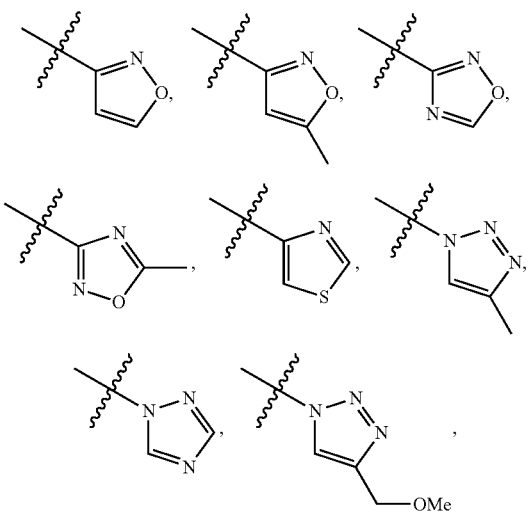

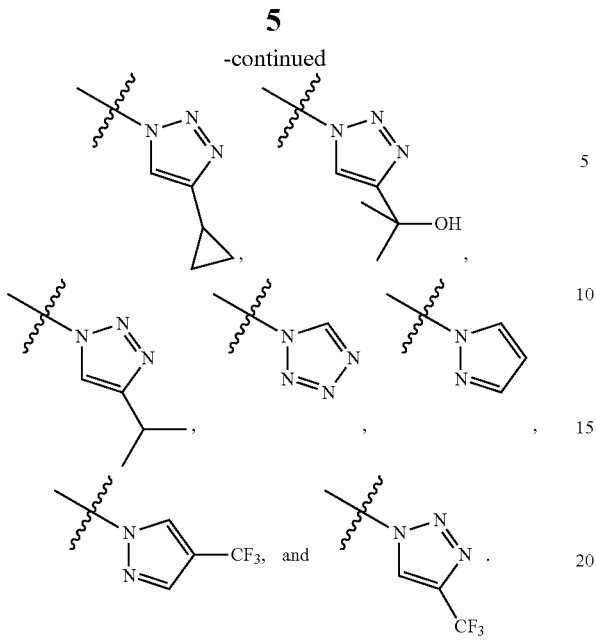

A sixth embodiment of a first aspect of the present invention is the compound of the fourth embodiment of the first aspect or a pharmaceutically acceptable salt thereof wherein $R^1$ is selected from the group consisting of

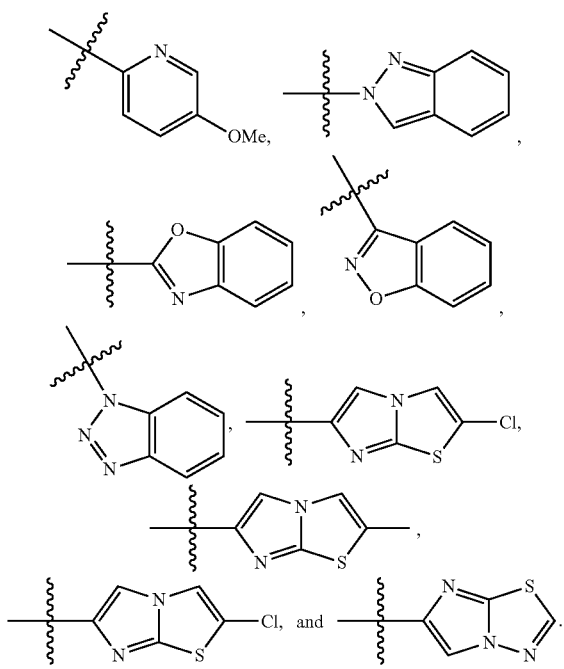

A seventh embodiment of a first aspect of the present invention is the compound of the fourth embodiment of the first aspect or a pharmaceutically acceptable salt thereof wherein $R^2$ is tetrahydropyranyl, cyclopentyl or cyclohexyl; each of which is optionally substituted with 1 to 2 $R^9$; and $R^9$ at each occurrence is independently methyl, ethyl, cyanomethyl, hydroxy or fluoro.

An eighth embodiment of a first aspect of the present invention is the compound of the seventh embodiment of the first aspect or a pharmaceutically acceptable salt thereof wherein $R^2$ is selected from the group consisting of

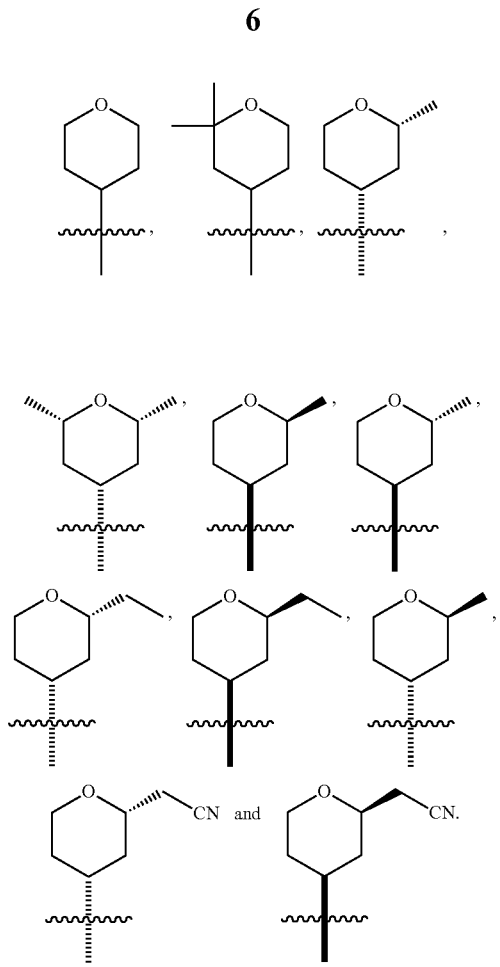

A ninth embodiment of a first aspect of the present invention is the compound of the eighth embodiment of the first aspect or a pharmaceutically acceptable salt thereof wherein $R^2$ is

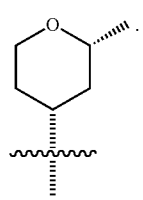

A tenth embodiment of a first aspect of the present invention is the compound of the seventh embodiment of the first aspect or a pharmaceutically acceptable salt thereof wherein $R^2$ is selected from the group consisting of

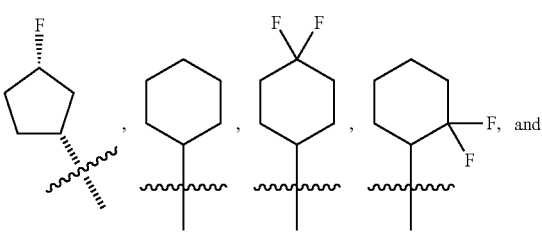

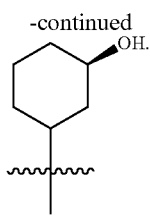

An eleventh embodiment of a first aspect of the present invention is the compound of claim 1 or a pharmaceutically acceptable salt thereof wherein X is N; Z is CR³; R¹ is a 5- to 10-membered heteroaryl selected from the group consisting of oxazolyl, isoxazolyl, oxadiazolyl, thiazolyl, pyrazolyl, triazolyl, tetrazolyl, pyridinyl, benzoxazolyl, benzoisoxazolyl, benzopyrazolyl, benzotriazolyl, imidazothiazolyl and imidazothiadiazolyl; each of which is optionally substituted with an R⁸; R¹ᵃ and R¹ᵇ are each hydrogen; and R⁸ is methyl, trifluoromethyl, isopropyl, 2-hydroxyisopropyl, methoxy, methoxymethyl, cyclopropyl or chloro.

A twelfth embodiment of a first aspect of the present invention is the compound of the eleventh embodiment of the first aspect or a pharmaceutically acceptable salt thereof wherein R² is

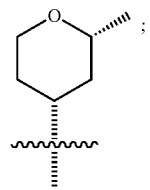

and R³, R⁴, R⁵ and R⁶ are each hydrogen or deutero.

A thirteenth embodiment of a first aspect of the present invention is the compound of the first embodiment of the first aspect or a pharmaceutically acceptable salt thereof wherein X is CR⁷; Z is CR³; R¹ is hydrogen or cyano; R¹ᵃ and R¹ᵇ are each hydrogen;
R² is tetrahydropyranyl or cyclopentyl; each of which is optionally substituted with 1 to 2 R⁹; and R⁹ at each occurrence is independently methyl, cyanomethyl or fluoro.

A fourteenth embodiment of a first aspect of the present invention is the compound of the thirteenth embodiment of the first aspect or a pharmaceutically acceptable salt thereof wherein R² is

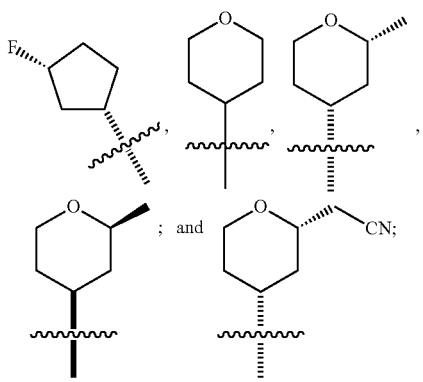

R³ is hydrogen, bromo, chloro, methoxy or cyano; and R⁴, R⁵, R⁶ and R⁷ are each hydrogen or deutero.

A fifteenth embodiment of a first aspect of the present invention is a compound or a pharmaceutically acceptable salt thereof as described in Examples 1-92 hereinbelow.

A sixteenth embodiment of a first aspect of the present invention is a compound of the first embodiment of the first aspect selected from the group consisting of
8-chloro-2-[(5-methoxypyridin-2-yl)methyl]-1-[(2R,4R)-2-methyltetrahydro-2H-pyran-4-yl]-1H-imidazo[4,5-c]quinoline;
2-[(5-methyl-1,2-oxazol-3-yl)methyl]-1-[(2R,4R)-2-methyltetrahydro-2H-pyran-4-yl]-1H-imidazo[4,5-c]quinoline-8-carbonitrile;
8-chloro-2-[(5-methyl-1,2-oxazol-3-yl)methyl]-1-[(2R,4R)-2-methyltetrahydro-2H-pyran-4-yl]-1H-imidazo[4,5-c]quinoline;
8-chloro-2-[(5-methyl-1,2,4-oxadiazol-3-yl)methyl]-1-[(2R,4R)-2-methyltetrahydro-2H-pyran-4-yl]-1H-imidazo[4,5-c]quinoline;
8-chloro-2-(imidazo[2,1-b][1,3,4]thiadiazol-6-ylmethyl)-1-[(2R,4R)-2-methyltetrahydro-2H-pyran-4-yl]-1H-imidazo[4,5-c]quinoline;
{8-chloro-1-[(2R,4R)-2-methyltetrahydro-2H-pyran-4-yl]-1H-imidazo[4,5-c]quinolin-2-yl}acetonitrile;
8-chloro-1-[(2R,4R)-2-methyltetrahydro-2H-pyran-4-yl]-2-(1,3-thiazol-4-ylmethyl)(4-²H)-1H-imidazo[4,5-c]quinoline; and
8-chloro-1-[(2R,4R)-2-methyltetrahydro-2H-pyran-4-yl]-2-[(4-methyl-1H-1,2,3-triazol-1-yl)methyl]-1H-imidazo[4,5-c]quinoline;
or a pharmaceutically acceptable salt thereof.

An seventeenth embodiment of a first aspect of the present invention is the compound of the first embodiment of the first aspect or a pharmaceutically acceptable salt thereof wherein X is CR⁷; Z is CR³; R¹ᵃ, Rib, R⁴, R⁵, R⁶ and R⁷ are each hydrogen; and R³ is chloro or cyano.

An eighteenth embodiment of a first aspect of the present invention is the compound of the seventeenth embodiment of the first aspect or a pharmaceutically acceptable salt thereof wherein R² is 1-methylpyrrolidinyl or 2-methyltetrahydropyranyl.

A nineteenth embodiment of a first aspect of the present invention is the compound of the eighteenth embodiment of the first aspect or a pharmaceutically acceptable salt thereof wherein R¹ is selected from the group consisting of isoxazolyl, pyrazolyl, triazolyl, oxadiazolyl, thiadiazolyl, pyrimidinyl and pyrazinyl; each of which is optionally substituted with an R⁸; and R⁸ is methyl or methoxy.

A twentieth embodiment of a first aspect of the present invention is the compound of the nineteenth embodiment of the first aspect or a pharmaceutically acceptable salt thereof wherein R¹ is selected from the group consisting of methylisoxazolyl, methoxypyrazolyl, methyltriazolyl, methyloxadiazolyl, methylthiadiazolyl, methylpyrimidinyl and methylpyrazinyl; R² is (2R,4R)-2-methyltetrahydro-2H-pyran-4-yl; and R³ is chloro.

A twentyfirst embodiment of a first aspect of the present invention is the compound of the nineteenth embodiment of the first aspect or a pharmaceutically acceptable salt thereof wherein R¹ is selected from the group consisting of methylisoxazolyl, methoxypyrazolyl, methyltriazolyl, methyloxadiazolyl, methylthiadiazolyl, methylpyrimidinyl and methylpyrazinyl; R² is 1-methylpyrrolidinyl; and R³ is cyano.

A twentysecond embodiment of a first aspect of the present invention is the compound of the nineteenth embodiment of the first aspect selected from the group consisting of 8-Chloro-2-[(5-methyl-1,2-oxazol-3-yl)methyl]-1-[(2R,4R)-2-methyltetrahydro-2H-pyran-4-yl]-1H-imidazo[4,5-c]quinoline;
8-Chloro-2-[(5-methyl-1,2,4-oxadiazol-3-yl)methyl]-1-[(2R,4R)-2-methyltetrahydro-2H-pyran-4-yl]-1H-imidazo[4,5-c]quinoline;
8-Chloro-1-[(2R,4R)-2-methyltetrahydro-2H-pyran-4-yl]-2-[(4-methyl-1H-1,2,3-triazol-1-yl)methyl]-1H-imidazo[4,5-c]quinoline;
8-Chloro-2-[(6-methylpyrimidin-4-yl)methyl]-1-[(2R,4R)-2-methyltetrahydro-2H-pyran-4-yl]-1H-imidazo[4,5-c]quinoline;
8-Chloro-2-[(5-methylpyrazin-2-yl)methyl]-1-[(2R,4R)-2-methyltetrahydro-2H-pyran-4-yl]-1H-imidazo[4,5-c]quinoline;
8-Chloro-2-[(4-m ethoxy-1H-pyrazol-1-yl)methyl]-1-[(2R,4R)-2-m ethyltetrahydro-2H-pyran-4-yl]-1H-imidazo[4,5-c]quinoline; and
8-Chloro-1-[(2R,4R)-2-methyltetrahydro-2H-pyran-4-yl]-2-[(5-methyl-1,3,4-thiadiazol-2-yl)methyl]-1H-imidazo[4,5-c]quinoline;
or a pharmaceutically acceptable salt thereof.

A twentythird embodiment of a first aspect of the present invention is the compound of the first embodiment of the first aspect or a pharmaceutically acceptable salt thereof wherein, in addition to the definitions of all variables as set forth therein, $R^{1a}$ and $R^{1b}$ taken together with the carbon to which they are attached can also be C(O).

A first embodiment of a second aspect of the present invention is a pharmaceutical composition comprising a therapeutically effective amount of a compound according to any one of the first through twentythird embodiments of the first aspect, or a pharmaceutically acceptable salt thereof together with a pharmaceutically acceptable carrier.

A first embodiment of a third aspect of the present invention is a method of treating Crohn's disease or Parkinson's disease in a patient, the method comprising administering to a patient in need thereof a therapeutically effective amount of a compound or pharmaceutically acceptable salt thereof according to any one of the first through twentythird embodiments of the first aspect of the invention.

Another embodiment of the present invention is the compound or pharmaceutically acceptable salt thereof according to any one of the first through twentythird embodiments of the first aspect of the present invention for use in the treatment of Crohn's disease or Parkinson's disease.

Another embodiment of the present invention is a method of inhibiting LRRK2 in a patient, the method comprising administering a LRRK2 inhibiting amount of a compound or a pharmaceutically acceptable salt thereof according to any one of the first through twentythird embodiments of the first aspect.

Another embodiment of the present invention is a method of treating a neurodegenerative disease in a patient, the method comprising administering to a patient in need thereof a therapeutically effective amount of a compound or pharmaceutically acceptable salt thereof according to any one of the first through twentythird embodiments of the first aspect.

Accordingly, the invention is also directed to methods of treating a patient (preferably a human) for diseases in which the LRRK2 kinase is involved, such as Parkinson's disease, by administering a therapeutically effective amount of a compound of any of the embodiments of Formula (I), or a pharmaceutically acceptable salt thereof, and a pharmaceutically acceptable carrier.

The invention is also directed to methods of inhibiting LRRK2 kinase activity, by administering a therapeutically effective amount of a compound of formula I or a pharmaceutically acceptable salt thereof, and a pharmaceutically acceptable carrier, to a mammal or a patient in need thereof. The invention is also directed to methods of treating disorders responsive to the inhibition of LRRK2 kinase activity, such as neurological disorders (particularly Parkinson's disease), certain cancers, and certain immunological disorders (such as Crohn's disease and leprosy) by administering a therapeutically effective amount of a compound of Formula (I) or a pharmaceutically acceptable salt thereof, and a pharmaceutically acceptable carrier, to a mammal or a patient in need thereof.

The invention is also directed to methods for treating conditions or diseases of the central nervous system and neurological disorders in which the LRRK2 kinase is involved, particularly Parkinson's disease (but also including other neurological diseases which may include migraine; epilepsy; Alzheimer's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's disease, Huntington's disease, Lewy body dementia, vascular dementia, drug-related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment); mental deficiency (including spasticity, Down syndrome and fragile X syndrome); sleep disorders (including hypersomnia, circadian rhythm sleep disorder, insomnia, parasomnia, and sleep deprivation) and psychiatric disorders such as anxiety (including acute stress disorder, generalized anxiety disorder, social anxiety disorder, panic disorder, post-traumatic stress disorder, agoraphobia, and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, seasonal depression, premenstrual syndrome (PMS) premenstrual dysphoric disorder (PDD), and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, obesity, compulsive eating disorders and pagophagia); sexual dysfunction disorders; urinary incontinence; neuronal damage disorders (including ocular damage, retinopathy or macular degeneration of the eye, tinnitus, hearing impairment and loss, and brain edema) and pediatric psychiatric disorders (including attention deficit disorder, attention deficit/hyperactive disorder, conduct disorder, and autism) in a mammal, preferably a human, comprising administering to said mammal a therapeutically effective amount of a compound of Formula (I) or a pharmaceutically acceptable salt thereof.

The present compounds of Formula (I) may be particularly suited to treatment of diseases or disorders such as Lewy body dementia, frontotemporal dementia, corticobasal dementia, progressive supranuclear palsy, leprosy, inflammatory bowel disease, inflammatory bowel syndrome, Alzheimer's disease, tauopathy diseases, Alpha-synucleinopathy, Parkinson's disease, Parkinson's disease with dementia, Parkinson's disease at risk syndrome, Lewy body variant of Alzheimer's disease, combined Parkinson's disease and Alzheimer's disease, multiple system atrophy, striatonigral degeneration, olivopontocerebellar atrophy, Shy-Drager syndrome, ulcerative colitis, juvenile parkinsonism, Steele-Richardson-Olszewski disease, Lytico-Bodig or parkinsonism-dementia-ALS complex of Guam, cortical basal ganglionic degeneration, progressive pallidal atrophy, Parkinsonism-dementia complex, pallidopyramidal disease, hereditary juvenile dystonia-parkinsonism, autosomal dominant Lewy body disease, Huntington disease, Wilson disease, hereditary ceruloplasmin deficiency, Hallervorden-Spatz disease, olivopontocerebellar and spinocerebellar degenerations, Machado-Joseph disease, familial amyotrophy-dementia-parkinsonism, disinhibition-dementia-parkinsonism-amyotrophycomplex, Gerstmann-Strausler-Scheinker disease, familial progressive subcortical gliosis, Lubag (x-linked dystonia parkinsonism), familial basal ganglia calcification, mitochondrial cytopathies with striatal necrosis, ceroid lipofuscinosis, familial Parkinsonism with peripheral neuropathy, Parkinsonism-pyramidal syndrome, neuroacanthocytosis and hereditary hemochromatosis.

The text revision of the fourth edition of the Diagnostic and Statistical Manual of Mental Disorders (DSM-IV-TR) (2000, American Psychiatric Association, Washington D.C.) provides a diagnostic tool for identifying many of the disorders described herein. The skilled artisan will recognize that there are alternative nomenclatures, nosologies, and classification systems for disorders described herein, including those as described in the DMS-IV-TR, and that terminology and classification systems evolve with medical scientific progress.

Preferred methods are for treating a neurological disorder, most preferably Parkinson's disease, (but also other neurological disorders such as migraine; epilepsy; Alzheimer's disease; Niemann-Pick type C; brain injury; stroke; cerebrovascular disease; cognitive disorder; sleep disorder) or a psychiatric disorder (such as anxiety; factitious disorder; impulse control disorder; mood disorder; psychomotor disorder; psychotic disorder; drug dependence; eating disorder; and pediatric psychiatric disorder) in a mammal, preferably a human, comprising administering to said mammal a therapeutically effective amount of a compound of Formula (I) or pharmaceutically acceptable salt thereof. In addition, the compounds of Formula (I) and pharmaceutically acceptable salts thereof may also be employed in methods of treating other disorders associated with LRRK2 such as Crohn's disease, leprosy and certain cancers, such as kidney, breast, lung, prostate, lung and blood cancer.

Also provided herein are compositions comprising a pharmaceutically effective amount of one or more of the compounds described herein and a pharmaceutically acceptable vehicle, carrier or excipient.

The present invention is also directed to the use of a combination of a LRRK2 inhibitor compound of Formula (I), and one or more additional pharmaceutically active agent(s).

Other features and advantages of this invention will be apparent from this specification and the appendent claims which describe the invention.

DEFINITIONS

The term "alkyl" refers to a linear or branched-chain saturated hydrocarbyl substituent (i.e., a substituent obtained from a hydrocarbon by removal of a hydrogen); in one embodiment from one to six carbon atoms (i.e., $C_1$-$C_6$alkyl); in another embodiment, from one to three carbon atoms (i.e., $C_1$-$C_3$alkyl). Examples of such substituents include methyl, ethyl, propyl (including n-propyl and isopropyl), butyl (including n-butyl, isobutyl, sec-butyl and tert-butyl), pentyl, isoamyl, hexyl and the like.

The term "alkoxy" refers to a linear or branched-chain saturated hydrocarbyl substituent (i.e., a substituent obtained from a hydrocarbon by removal of a hydrogen) which is in turn attached to an oxygen atom; in one embodiment from one to six carbon atoms (i.e., $C_1$-$C_6$alkoxy); in another embodiment, from one to three carbon atoms (i.e., $C_1$-$C_3$alkoxy). Examples of such substituents include methoxy, ethoxy, propoxy (including n-propoxy and isopropoxy), butoxy (including n-butoxy, isobutoxy, sec-butoxy and tert-butoxy), pentoxy and the like.

The term "cycloalkyl" refers to a carbocyclic substituent obtained by removing a hydrogen from a saturated carbocyclic molecule and having the specified number of carbon atoms. In one embodiment, a cycloalkyl substituent has three to seven carbon atoms (i.e., $C_3$-$C_7$cycloalkyl). Examples of cycloalkyl include cyclopropyl, cyclobutyl, cyclopentyl, cyclohexyl and cycloheptyl. In another embodiment, a cycloalkyl substituent has three to six carbon atoms (i.e., $C_3$-$C_6$cycloalkyl). The term "cycloalkyl" includes mono-, bi- and tricyclic saturated carbocycles, as well as bridged and fused ring carbocycles, as well as spiro-fused ring systems.

In some instances, the number of atoms in a cyclic substituent containing one or more heteroatoms (i.e., heteroaryl or heterocycloalkyl) is indicated by the prefix "x- to y-membered", wherein x is the minimum and y is the maximum number of atoms forming the cyclic moiety of the substituent. The term "heterocycloalkyl" refers to a substituent obtained by removing a hydrogen from a saturated or partially saturated ring structure containing the specified number of ring atoms, wherein at least one of the ring atoms is a heteroatom (i.e., oxygen, nitrogen, or sulfur), with the remaining ring atoms being independently selected from the group consisting of carbon, oxygen, nitrogen, and sulfur. If the heterocycloalkyl substituent is in turn substituted with a group or substituent, the group or substituent may be bound to a nitrogen heteroatom, or it may be bound to a ring carbon atom, as appropriate. As used herein, the term "heterocycloalkyl" as used herein refers to a monocyclic ring system containing the heteroatoms NR, O or S as specified. Thus, for example, "four- to seven-membered heterocycloalkyl" refers to a heterocycloalkyl containing from 4 to 7 atoms, including one or more heteroatoms, in the cyclic moiety of the heterocycloalkyl. The number of heteroatoms present in a given heterocycle may be as specified. If the heterocycloalkyl group contains a nitrogen moiety NR and is saturated then it is to be understood that R is hydrogen or $C_1$-$C_6$alkyl. If the heterocycloalkyl group contains a nitrogen moiety NR and that NR moiety is attached to an adjacent ring atom by a double bond then it is to be understood that R is absent.

Examples of single-ring heterocycloalkyls include tetrahydropyranyl, azetidinyl, oxetanyl, thietanyl, dihydrofuranyl, tetrahydrofuranyl, dihydrothiophenyl, tetrahydrothiophenyl, pyrrolinyl, pyrrolidinyl, imidazolinyl, imidazolidinyl, pyrazolinyl, pyrazolidinyl, thiazolinyl, isothiazolinyl, thiazolidinyl, isothiazolidinyl, dihydropyranyl, piperidinyl, morpholinyl, piperazinyl, azepinyl, oxepinyl, thiepinyl, and diazepinyl.

The term "hydrogen" refers to a hydrogen substituent, and may be depicted as —H. The term "deutero" refers to a deuterium substituent, and may be depicted as -D.

The term "hydroxy" or "hydroxyl" refers to —OH. Compounds bearing a carbon to which one or more hydroxy substituents are attached include, for example, alcohols, enols and phenol.

The term "halo" or "halogen" refers to fluoro (which may be depicted as —F), chloro (which may be depicted as —Cl), bromo (which may be depicted as —Br), or iodo (which may be depicted as —I).

The term "heteroaryl" refers to an aromatic ring structure containing the specified number of ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A five- to six-membered heteroaryl is an aromatic ring system which has five or six ring atoms with at least one of the ring atoms being N, O or S. Similarly, a five- to ten-membered heteroaryl is an aromatic ring system which has five to ten ring atoms with at least one of the ring atoms being N, O or S. A heteroaryl may be a single ring or 2 fused rings. Examples of heteroaryl substituents include 6-membered ring substituents such as pyridyl, pyrazyl, pyrimidinyl, and pyridazinyl; 5-membered ring substituents such as triazolyl, imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused rings such as quinolinyl, isoquinolinyl, cinnolinyl, quinazolinyl, and 1,4-benzoxazinyl. In a group that has a heteroaryl substituent, the ring atom of the heteroaryl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heteroaryl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom. The term "heteroaryl" also includes pyridyl N-oxides and groups containing a pyridine N-oxide ring.

Examples of 2-fused-ring heteroaryls include, indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, pyrrolopyridinyl, pyrazolopyridinyl and imidazothiazolyl.

Other examples of fused-ring heteroaryls include benzo-fused heteroaryls such as indolyl, isoindolyl, indoleninyl, isoindazolyl, benzazinyl (including quinolinyl or isoquinolinyl), phthalazinyl, quinoxalinyl, quinazolinyl, benzodiazinyl (including cinnolinyl or quinazolinyl).

The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-2-yl (C-attached).

If substituents are described as being "independently selected" from a group, each instance of a substituent is selected independent of the other. Each substituent therefore may be identical to or different from the other substituent(s).

As used herein the terms "formula I", "Formula I", "formula (I)" or "Formula (I)" may be referred to as a "compound(s) of the invention." Such terms are also defined to include all forms of the compound of formula I, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention may have asymmetric carbon atoms. The carbon-carbon bonds of the compounds of the invention may be depicted herein using a solid line (—), a solid wedge ( ▬ ), or a dotted wedge ( ⋯⋯⋯ ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula (I) may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula (I) can exist as enantiomers and diastereomers or as racemates and mixtures thereof. The use of a solid line to depict bonds to one or more asymmetric carbon atoms in a compound of Formula (I) and the use of a solid or dotted wedge to depict bonds to other asymmetric carbon atoms in the same compound is meant to indicate that a mixture of diastereomers is present.

Stereoisomers of Formula (I) include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The present invention comprises the tautomeric forms of compounds of the invention. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism. The various ratios of the tautomers in solid and liquid form are dependent on the various substituents on the molecule as well as the particular crystallization technique used to isolate a compound.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula (I) with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, p-hydroxybutyrate, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (i.e., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention which may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and V. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of any of Formula (I) with certain moieties known to those skilled in the art as "pro-moieties" as described, for example, in "Design of Prodrugs" by H. Bundgaard (Elsevier, 1985).

The present invention also includes isotopically labeled compounds, which are identical to those recited in Formula (I), but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorus, sulfur, fluorine and chlorine, such as $^2H$, $^3H$, $^{13}C$, $^{11}C$, $^{14}$, $^{15}N$, $^{18}O$, $^{17}O$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formula (I) of this invention and prodrugs thereof can generally be prepared by carrying out the procedures disclosed in the Schemes and/or in the Examples and Preparations below, by substituting a readily available isotopically labeled reagent for a non-isotopically labeled reagent.

DETAILED DESCRIPTION OF THE INVENTION

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, (hydroxypropyl)methyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a LRRK2 inhibitor compound as provided in Formula (I) and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula (I) or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of Formula (I), depending on the disease, disorder, or condition to be treated. For example, a pharmaceutical composition for use in treating Parkinson's disease may comprise a compound of Formula (I) or a pharmaceutically acceptable salt thereof together with another agent such as a dopamine (levodopa, either alone or with a DOPA decarboxylase inhibitor), a monoamine oxidase (MAO) inhibitor, a catechol O-methyltransferase (COMT) inhibitor or an anticholinergic agent, or any combination thereof. Particularly preferred agents to combine with the compounds of Formula (I) for use in treating Parkinson's disease include levodopa, carbidopa, tolcapone, entacapone, selegiline, benztropine and trihexyphenidyl, or any combination thereof. Pharmaceutically active agents that may be used in combination with the compounds of Formula (I) and compositions thereof include, without limitation:

(i) levodopa (or its methyl or ethyl ester), alone or in combination with a DOPA decarboxylase inhibitor (e.g., carbidopa (SINEMET, CARBILEV, PARCOPA), benserazide (MADOPAR), α-methyldopa, monofluoromethyldopa, difluoromethyldopa, brocresine, or m-hydroxybenzylhydrazine);

(ii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE), tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(iii) catechol O-methyltransferase (COMT) inhibitors, such as nitecapone, tolcapone (TASMAR), entacapone (COMTAN), and tropolone;

(iv) monoamine oxidase (MAO) inhibitors, such as selegiline (EMSAM), selegiline hydrochloride (1-deprenyl, ELDEPRYL, ZELAPAR), dimethylselegiline, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(v) acetylcholinesterase inhibitors, such as donepezil hydrochloride (ARICEPT®, MEMAC), physostigmine salicylate (ANTILIRIUM®), physostigmine sulfate (ESERINE), ganstigmine, rivastigmine (EXELON®), ladostigil, NP-0361, galantamine hydrobromide (RAZADYNE®, REMINYL®, NIVALIN®), tacrine (COGNEX®), tolserine, memoquin, huperzine A (HUP-A; Neuro-Hitech), phenserine, bisnorcymserine (also known as BNC), and INM-176;

(vi) amyloid-β (or fragments thereof), such as $A\beta_{1-15}$ conjugated to pan HLA DR-binding epitope (PADRE®), ACC-001 (Elan/Wyeth), and Affitope;

(vii) antibodies to amyloid-β (or fragments thereof), such as ponezumab, solanezumab, bapineuzumab (also known as AAB-001), AAB-002 (Wyeth/Elan), Gantenerumab, intravenous Ig (GAMMAGARD®), LY2062430 (humanized m266; Lilly), and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(viii) amyloid-lowering or -inhibiting agents (including those that reduce amyloid production, accumulation and fibrillization) such as eprodisate, celecoxib, lovastatin, anapsos, colostrinin, pioglitazone, clioquinol (also known as PBT1), PBT2 (Prana Biotechnology), flurbiprofen (ANSAID®, FROBEN®) and its R-enantiomer tarenflurbil (FLURIZAN®), nitroflurbiprofen, fenoprofen (FENOPRON, NALFON®), ibuprofen (ADVIL®, MOTRIN®, NUROFEN®), ibuprofen lysinate, meclofenamic acid, meclofenamate sodium (MECLOMEN®), indomethacin (INDOCIN®), diclofenac sodium (VOLTAREN®), diclofenac potassium, sulindac (CLINORIL®), sulindac sulfide, diflunisal (DOLOBID®), naproxen (NAPROSYN®), naproxen sodium (ANAPROX®, ALEVE®), insulin-degrading enzyme (also known as insulysin), the *gingko biloba* extract EGb-761 (ROKAN®, TEBONIN®), tramiprosate (CEREBRIL®, ALZHEMED®), KIACTA®), neprilysin (also known as neutral endopeptidase (NEP)), scyllo-inositol (also known as scyllitol), atorvastatin (LIPITOR®), simvastatin (ZOCOR®), ibutamoren mesylate, BACE inhibitors such as LY450139 (Lilly), BMS-782450, GSK-188909; gamma secretase modulators and inhibitors such as ELND-007, BMS-708163 (Avagacestat), and DSP8658 (Dainippon); and RAGE (receptor for advanced glycation end-products) inhibitors, such as TTP488 (Transtech) and TTP4000 (Transtech), and those disclosed in U.S. Pat. No. 7,285,293, including PTI-777;

(ix) alpha-adrenergic receptor agonists, and beta-adrenergic receptor blocking agents (beta blockers); anticholinergics; anticonvulsants; antipsychotics; calcium channel blockers; catechol O-methyltransferase (COMT) inhibitors; central nervous system stimulants; corticosteroids; dopamine receptor agonists and antagonists; dopamine reuptake inhibitors; gamma-aminobutyric acid (GABA) receptor agonists; immunosuppressants; interferons; muscarinic receptor agonists; neuroprotective drugs; nicotinic receptor agonists; norepinephrine (noradrenaline) reuptake inhibitors; quinolines; and trophic factors;

(x) histamine 3 (H3) antagonists, such as PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xi) N-methyl-D-aspartate (NMDA) receptor antagonists, such as memantine (NAMENDA, AXURA, EB IXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), methadone, (DOLOPHINE), neramexane, perzinfotel, phencyclidine, tianeptine (STABLON), dizocilpine (also known as MK-801), ibogaine, voacangine, tiletamine, riluzole (RILUTEK), aptiganel (CERESTAT), gavestinel, and remacimide;

(xii) phosphodiesterase (PDE) inhibitors, including (a) PDE1 inhibitors; (b) PDE2 inhibitors; (c) PDE3 inhibitors; (d) PDE4 inhibitors; (e) PDE5 inhibitors; (f) PDE9 inhibitors (e.g., PF-04447943, BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)); and (g) PDE10 inhibitors such as 2-({4-

[1-methyl-4-(pyridin-4-yl)-1H-pyrazol-3-yl] phenoxy}methyl)quinoline (PF-2545920);

(xiii) serotonin (5-hydroxytryptamine) 1A (5-HT$_{1A}$) receptor antagonists, such as spiperone, levo-pindolol, lecozotan;

(xiv) serotonin (5-hydroxytryptamine) 2C (5-HT$_{2c}$) receptor agonists, such as vabicaserin, and zicronapine; serotonin (5-hydroxytryptamine) 4 (5-HT$_4$) receptor agonists/antagonists, such as PRX-03140 (Epix) and PF-04995274;

(xv) serotonin (5-hydroxytryptamine) 3C (5-HT$_{3c}$) receptor antagonists, such as Ondansetron (Zofran);

(xvi) serotonin (5-hydroxytryptamine) 6 (5-HT$_6$) receptor antagonists, such as mianserin (TOLVON, BOLVIDON, NORVAL), methiothepin (also known as metitepine), ritanserin, SB-271046, SB-742457 (GlaxoSmithKline), Lu AE58054 (Lundbeck A/S), SAM-760, and PRX-07034 (Epix);

(xvii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine and tesofensine;

(xviii) Glycine transporter-1 inhibitors such as paliflutine, ORG-25935, and ORG-26041; and mGluR modulators such as AFQ-059 and amantidine;

(xix) AMPA-type glutamate receptor modulators such as perampanel, mibampator, selurampanel, GSK-729327, and N-{(3S,4S)-4-[4-(5-cyanothiophen-2-yl)phenoxy]tetrahydrofuran-3-yl}propane-2-sulfonamide;

(xx) P450 inhibitors, such as ritonavir;

(xxi) tau therapy targets, such as davunetide;

and the like.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

General Synthetic Schemes

The compounds of Formula (I) may be prepared by the methods described below, together with synthetic methods known in the art of organic chemistry, or modifications and transformations that are familiar to those of ordinary skill in the art.

The starting materials used herein are commercially available or may be prepared by routine methods known in the art [such as those methods disclosed in standard reference books such as the Compendium of Organic Synthetic Methods, Vol. I-XII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula (I), or their pharmaceutically acceptable salts, can be prepared according to the Reaction Schemes discussed herein below. Unless otherwise indicated, the substituents in the Schemes are defined as above. Isolation and purification of the products is accomplished by standard procedures, which are known to a chemist of ordinary skill.

One skilled in the art will recognize that in many cases, the compounds in Reaction Schemes 1 through 4 may be generated as a mixture of diastereomers and/or enantiomers; these may be separated at various stages of the synthetic schemes using conventional techniques or a combination of such techniques, such as, but not limited to, crystallization, normal-phase chromatography, reversed phase chromatography and chiral chromatography, to afford the single enantiomers of the invention.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

Compounds of Formula (I) and intermediates thereof may be prepared according to the following reaction schemes and accompanying discussion. Unless otherwise indicated, $R^1$, $R^{1a}$, $R^{1b}$, $R^2$, $R^3$, $R^4$, $R^5$, $R^6$, X and Z in the reaction schemes and discussions that follow are as defined as the same as hereinabove. In general the compounds of this invention may be made by processes which include processes analogous to those known in the chemical arts, particularly in light of the description contained herein. Certain processes for the manufacture of the compounds of this invention and intermediates thereof are provided as further features of the invention and are illustrated by the following reaction schemes. Other processes may be described in the experimental section. The schemes and examples provided herein (including the corresponding description) are for illustration only, and not intended to limit the scope of the present invention.

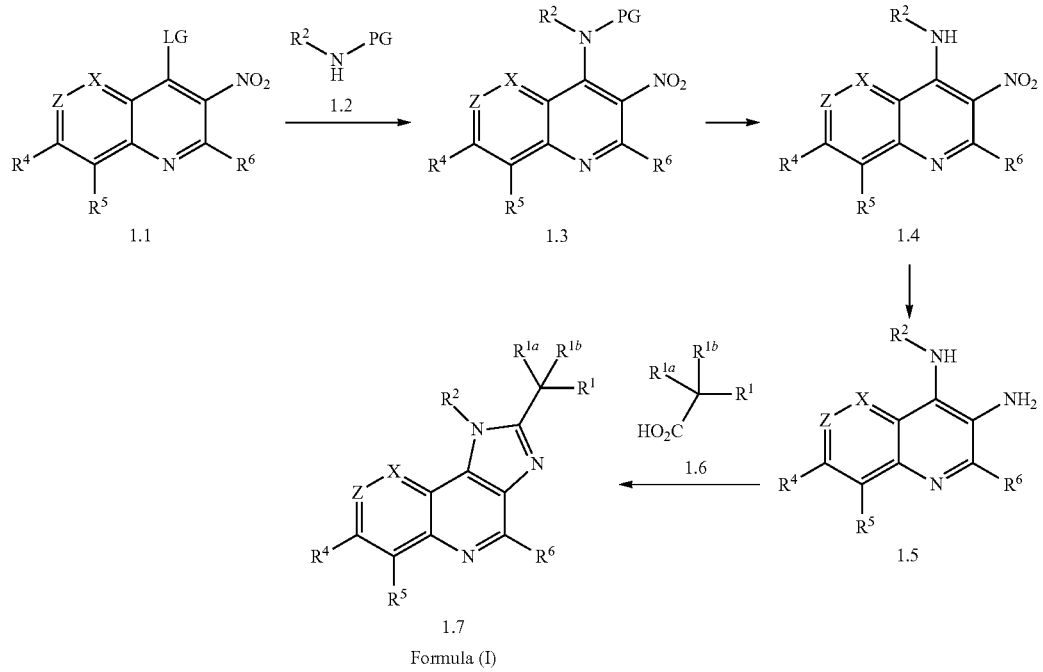

Reaction Scheme 1

Formula (I)

Reaction Scheme 1 depicts the preparation of compounds of Formula (I). Referring to Scheme 1, compounds 1.1 and 1.2 are either commercially available or can be made by methods described herein or other methods well known to those skilled in the art. In the compound of formula 1.1 the group designated LG represents an appropriate leaving group such as a halide (eg chloro or bromo) or triflate which is suitable to undergo nucleophilic displacement when reacted with the amine of formula 1.2. In the amine compound of formula 1.2 the group designated PG represents an appropriate amine protecting group such as an acid labile protecting group selected from 2,4-dimethoxybenzyl (DMB), 4-methoxybenzyl (PMB) and t-Butoxycarbonyl (Boc). The compounds of formulae 1.1 and 1.2 can be reacted, for example, in the presence of an appropriate base such as N,N-diisopropylethylamine (Hunig's base) or triethylamine in a suitable solvent such as acetonitrile or N,N-dimethylformamide (DMF) to afford the compound of formula 1.3. The reaction is typically carried out at an elevated temperature, such as 50 to 100° C. for a period of 1 to 48 hours. Removal of the protecting group, such as an acid labile protecting group (PG) from the compound of formula 1.3 can typically be accomplished by treatment of 1.3 with an appropriate acid such as acetic acid, trifluoroacetic acid or hydrochloric acid to provide the compound of formula 1.4. Also, it is to be understood that in certain instances the compound of formula 1.1 can be reacted with an unprotected amine of formula $R^2$—$NH_2$ to arrive directly to a compound of formula 1.4. Reduction of the nitro group in the compound of formula 1.4 using conditions congruent with the functionality present affords the compound of formula 1.5. For example, the nitro group in the compound of formula 1.4 can be reduced to the corresponding amine of formula 1.5 by treatment of 1.4 with zinc dust and ammonium hydroxide in methanol or alternatively by hydrogenation of 1.4 using an appropriate catalyst such as platinum (IV) oxide in an appropriate solvent such as methanol, acetonitrile or a mixture thereof. Coupling the diamine compound 1.5 with the carboxylic acid of formula 1.6 then provides the desired compound of Formula (I), also denoted as 1.7. The coupling reaction with the diamine of formula 1.5 and the carboxylic acid of formula 1.6 can be carried out in an appropriate solvent such as N,N-dimethylformamide in the presence of an appropriate base such as diisopropylethylamine and a coupling reagent such as 2,4,6-tripropyl-1,3,5,2,4,6-trioxatriphosphirane 2,4,6-trioxide.

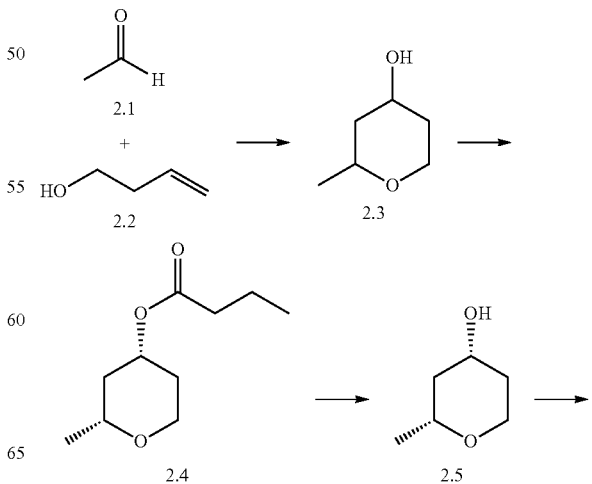

Reaction Scheme 2

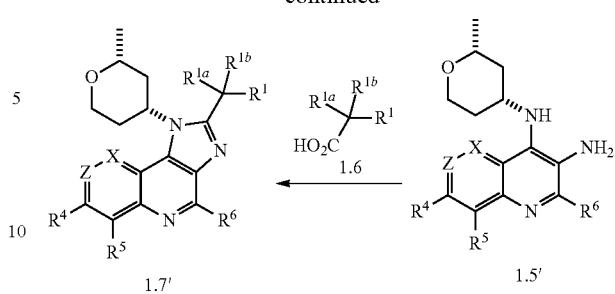

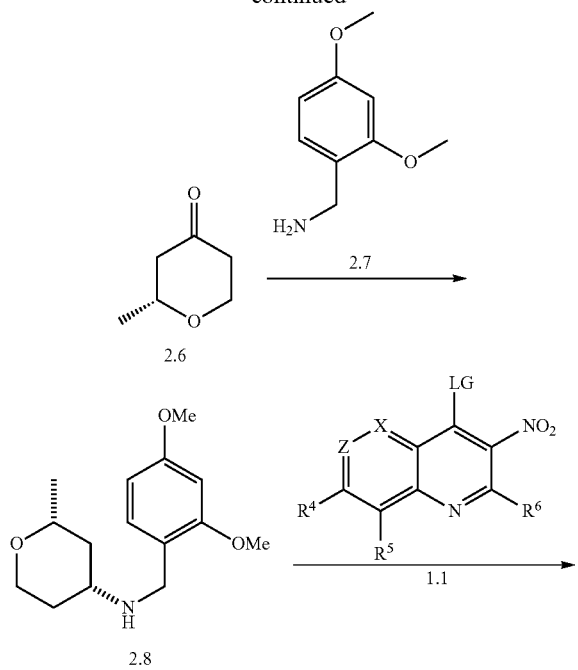

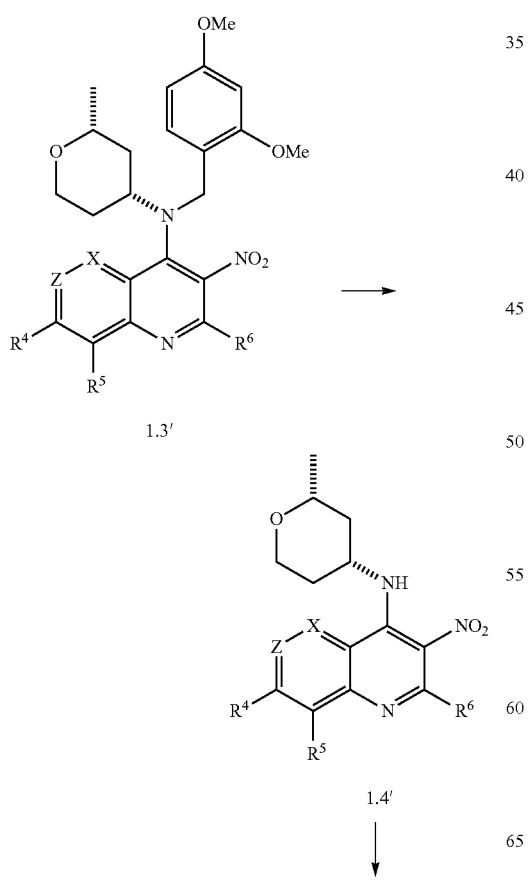

Reaction Scheme 2 depicts to the preparation of compounds of formula 1.7' which is a compound of Formula (I) in which $R^2$ is the chiral 2-methyltetrahydropyran-4-yl moiety as shown. Using a published procedure, Prins reaction of the compound 2.1 with the compound 2.2 generated the pyran 2.3. Chiral resolution to produce the separated enantiomers, using an enzyme-based method, afforded the compound of formula 2.5 after hydrolysis of the resolved ester 2.4. Oxidation of 2.5 gave ketone 2.6 which was reacted with the compound of formula 2.7 using reductive amination chemistry to provide the protected amine of formula 2.8. The protected amine of formula 2.8 can be reacted with the compound of formula 1.1 in a manner analogous to that previously described in Scheme 1 to provide the compound of formula 1.3'. The compounds of formulae 1.4', 1.5' and 1.7' can then be prepared in a manner analogous to the methods described in Scheme 1 for the compounds of formulae 1.4, 1.5 and 1.7, respectively.

Reaction Scheme 3

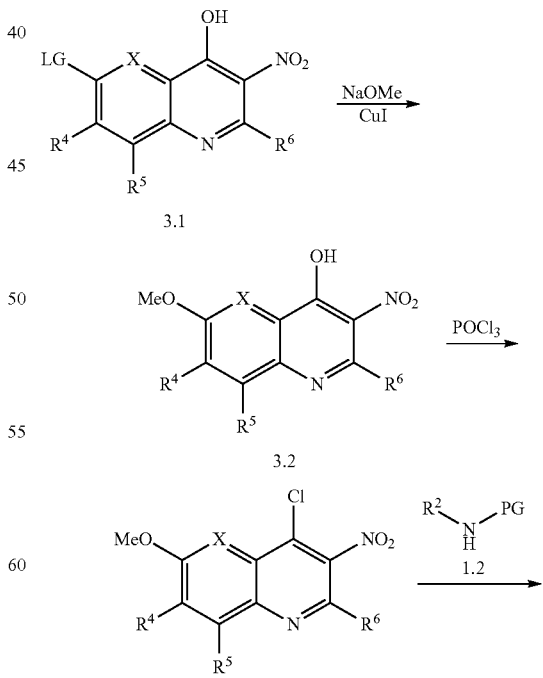

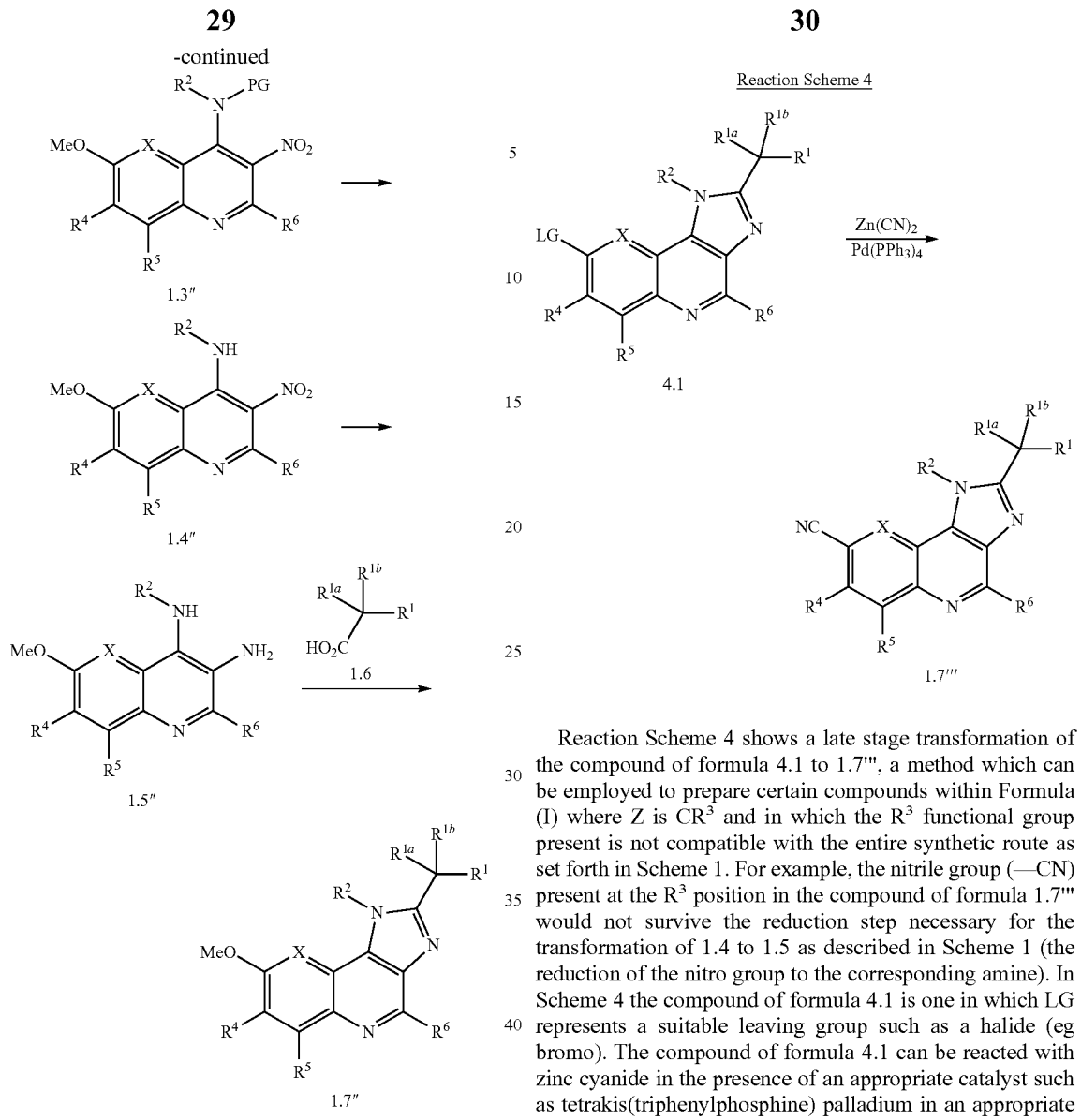

Reaction Scheme 3 depicts how the functional group at position $R^3$ of a compound of Formula (I) (i.e. when Z is $CR^3$) can be modified early in the synthesis. Modification, early in the synthesis of a compound such as commercially available 3.1 (wherein LG is bromo) allows one skilled in the art to introduce groups such as methoxy which are robust enough to be carried throughout the entire synthesis in a manner analogous to that described for Scheme 1. The compound of formula 3.1 can be reacted with sodium methoxide in the presence of copper iodide to provide the methoxy compound of formula 3.2. The compound of formula 3.2 can then be treated with phosphorous oxychloride in order to convert the hydroxy group present in the compound of formula 3.1 into the corresponding chloride of formula 1.1". The compound of formula 1.1" can then be reacted with the amine of formula 1.2 to provide the compound of 1.3" in a manner as previously described for Scheme 1. The compound of formula 1.3" can then be further elaborated to the compounds of formulae 1.4", 1.5" and 1.7" in a manner analogous to the corresponding steps described previously for Scheme 1.

Reaction Scheme 4 shows a late stage transformation of the compound of formula 4.1 to 1.7''', a method which can be employed to prepare certain compounds within Formula (I) where Z is $CR^3$ and in which the $R^3$ functional group present is not compatible with the entire synthetic route as set forth in Scheme 1. For example, the nitrile group (—CN) present at the $R^3$ position in the compound of formula 1.7''' would not survive the reduction step necessary for the transformation of 1.4 to 1.5 as described in Scheme 1 (the reduction of the nitro group to the corresponding amine). In Scheme 4 the compound of formula 4.1 is one in which LG represents a suitable leaving group such as a halide (eg bromo). The compound of formula 4.1 can be reacted with zinc cyanide in the presence of an appropriate catalyst such as tetrakis(triphenylphosphine) palladium in an appropriate solvent such as N,N-dimethylformamide. The reaction is typically carried out at a temperature range of approximately ambient temperature to 100° C. for a period of 1 to 48 hours to provide the compound of formula 1.7'''.

The methods generically described in Schemes 1-4 are not to be construed in a limiting manner. It is to be understood by one skilled in the art that variation in the order of certain reaction steps and conditions may be employed to provide compounds of Formula (I). The selection of which approach is best to utilize can be made by one skilled in the art of organic synthesis. More specific examples of the methods used to prepare compounds of Formula (I) are provided below in the Examples, and likewise these methods are also not to be construed by one skilled in the art in a limiting manner.

Experimental Procedures

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers of certain compounds of the invention (in some examples, the separated enantiomers are designated as ENT-1 and ENT-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated by the presence of (+/−) adjacent to the structure; in these cases, indicated stereochemistry represents the relative (rather than absolute) configuration of the compound's substituents.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times.

Preparation P1 cis-N-(2,4-Dimethoxybenzyl)-2-methyltetrahydro-2H-pyran-4-amine (P1)

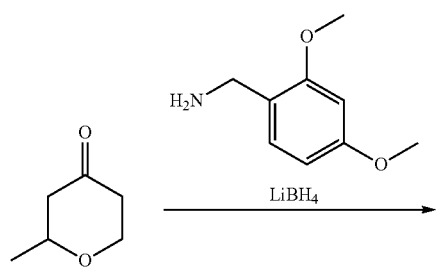

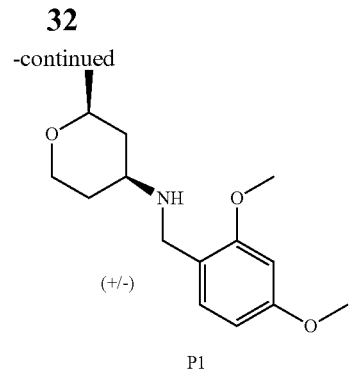

1-(2,4-Dimethoxyphenyl)methanamine (1.97 mL, 13.1 mmol) was added to a solution of 2-methyltetrahydro-4H-pyran-4-one (500 mg, 4.4 mmol) in methanol (10 mL). After stirring for 1 hour at room temperature, the reaction mixture was cooled to −78° C. and a solution of lithium borohydride (98%, 85 mg, 3.8 mmol) in tetrahydrofuran (1.5 mL) was added drop-wise. The reaction mixture was allowed to slowly warm to room temperature overnight, whereupon it was cooled to −20° C. and quenched via careful addition of saturated aqueous sodium bicarbonate solution. Ethyl acetate (25 mL) and sufficient water to solubilize the precipitate were added, and the aqueous layer was extracted with ethyl acetate. The combined organic layers were dried over magnesium sulfate, filtered, and concentrated in vacuo. Chromatography on silica gel [Gradient: 0% to 15% (10:1 methanol/concentrated ammonium hydroxide) in ethyl acetate] provided the product as a colorless oil. Yield: 936 mg, 3.53 mmol, 80%. $^1$H NMR (400 MHz, CDCl$_3$) δ 7.13 (d, J=8.0 Hz, 1H), 6.46 (d, half of AB quartet, J=2.2 Hz, 1H), 6.44 (dd, half of ABX pattern, J=8.1, 2.3 Hz, 1H), 4.00 (ddd, J=11.6, 4.6, 1.6 Hz, 1H), 3.82 (s, 3H), 3.81 (s, 3H), 3.76 (s, 2H), 3.37-3.46 (m, 2H), 2.63-2.72 (m, 1H), 1.85-1.92 (m, 1H), 1.78-1.85 (m, 1H), 1.37 (dddd, J=13, 12, 11, 4.6 Hz, 1H), 1.20 (d, J=6.2 Hz, 3H), 1.10 (ddd, J=12, 11, 11 Hz, 1H).

Alternate Preparation of P1 cis-N-(2,4-Dimethoxybenzyl)-2-methyltetrahydro-2H-pyran-4-amine (P1)

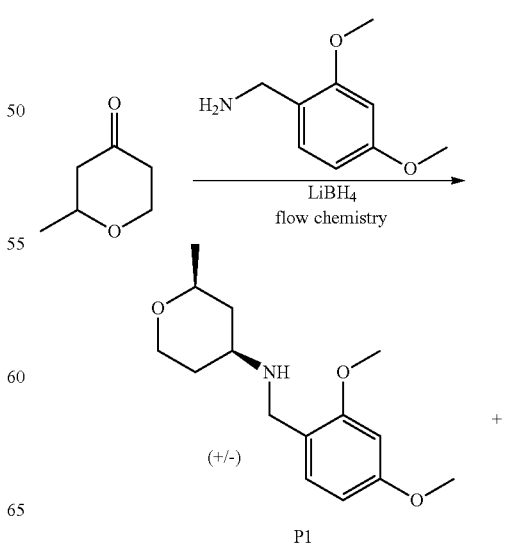

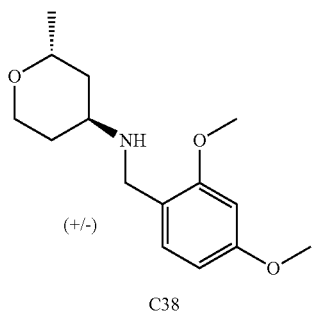

C38 (+/-)

Using a syringe pump, 2-methyltetrahydro-4H-pyran-4-one (7.00 g, 61.3 mmol) was added over 3.5 hours (2 mL/hour) to a solution of 1-(2,4-dimethoxyphenyl)methanamine (9.21 mL, 61.3 mmol) in methanol (137 mL). After completion of the addition, the reaction mixture was allowed to stir at room temperature for 1 hour. This solution was then reacted with lithium borohydride (0.48 M solution in tetrahydrofuran, 153.2 mL, 73.5 mmol) using a flow reactor [25 mL reactor made up of a 1 mL glass chip with two feeding channels and perfluoroalkoxy tubing (24 mL volume); Temperature: −78° C.; Reaction concentration: 0.2 M; Residence time: 10 minutes; Flow rate: 1.25 mL/minute on both streams]. The collected reaction mixture was diluted with saturated aqueous sodium bicarbonate solution and extracted with ethyl acetate. The combined organic layers were dried over sodium sulfate, filtered, and concentrated in vacuo. $^1$H NMR analysis at this point revealed a cis:trans ratio of 10.7:1. Silica gel chromatography (Gradient: 0% to 20% methanol in ethyl acetate) afforded cis product P1. Yield: 11.59 g, 43.68 mmol, 71%. $^1$H NMR (400 MHz, CDCl$_3$) δ 7.16 (d, J=8.0 Hz, 1H), 6.41-6.48 (m, 2H), 4.00 (ddd, J=11.7, 4.7, 1.8 Hz, 1H), 3.82 (s, 3H), 3.80 (s, 3H), 3.78 (s, 2H), 3.36-3.46 (m, 2H), 2.70 (tt, J=11.2, 4.1 Hz, 1H), 1.87-1.94 (m, 1H), 1.79-1.87 (m, 1H), 1.35-1.47 (m, 1H), 1.20 (d, J=6.2 Hz, 3H), 1.08-1.19 (m, 1H).

Also isolated was the trans isomer C38. Yield: 1.24 g, 4.67 mmol, 7.6%. $^1$H NMR (400 MHz, CDCl$_3$) δ 7.14 (d, J=8.2 Hz, 1H), 6.42-6.48 (m, 2H), 3.84-3.94 (m, 2H), 3.82 (s, 3H), 3.81 (s, 3H), 3.69-3.77 (m, 3H), 2.97-3.02 (m, 1H), 1.72-1.82 (m, 1H), 1.44-1.66 (m, 3H), 1.14 (d, J=6.2 Hz, 3H).

Preparation P2

(2R,4R)—N-(2,4-Dimethoxybenzyl)-2-methyltetrahydro-2H-pyran-4-amine (P2)

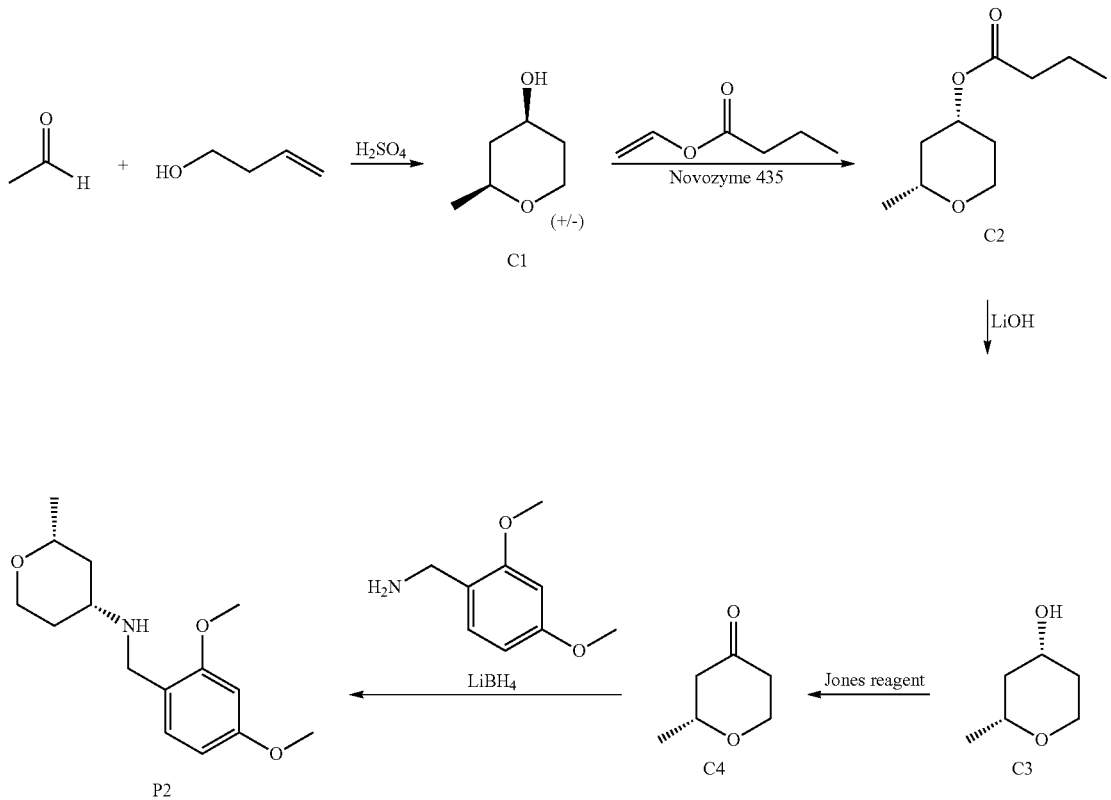

Step 1. Synthesis of cis-2-methyltetrahydro-2H-pyran-4-ol (C1)

But-3-en-1-ol (39.0 mL, 453 mmol) and acetaldehyde (25.5 mL, 454 mmol) were combined in aqueous sulfuric acid (20% w/w, 565 g) and stirred at 80° C. for 5 days. The reaction mixture was cooled to room temperature and extracted with diethyl ether, and then with dichloromethane; the combined organic layers were dried over magnesium sulfate, filtered, and concentrated in vacuo. Silica gel chromatography (Gradient: 0% to 25% ethyl acetate in heptane) afforded the product as a colorless oil. Yield: 11.2 g, 96.4 mmol, 21%. $^1$H NMR (400 MHz, $CDCl_3$) δ 3.99 (ddd, J=11.8, 4.9, 1.7 Hz, 1H), 3.71-3.80 (m, 1H), 3.35-3.46 (m, 2H), 1.82-1.98 (m, 3H), 1.48 (dddd, J=12.5, 12.4, 11.1, 4.9 Hz, 1H), 1.21 (d, J=6.2 Hz, 3H), 1.14-1.24 (m, 1H).

Step 2. Synthesis of (2R,4R)-2-methyltetrahydro-2H-pyran-4-yl butanoate (C2)

Ethenyl butanoate (78.6 mL, 620 mmol) and Novozyme 435 (immobilized *Candida antarctica* lipase B, 25 g) were added to a solution of C1 (150 g, 1.29 mol) in tetrahydrofuran (1.3 L). The reaction mixture was stirred at room temperature for 2 hours, whereupon it was filtered through a pad of diatomaceous earth, which was then rinsed twice with dichloromethane. The combined filtrates were concentrated in vacuo and purified via silica gel chromatography (Gradient: 0% to 10% ethyl acetate in heptane), providing the product as an oil. Yield: 51.5 g, 276 mmol, 45%. The absolute configurations of C2 and subsequent intermediates were confirmed via an X-ray structural determination carried out on C14 (see Example 2). $^1$H NMR (400 MHz, $CDCl_3$) δ 4.82-4.92 (m, 1H), 3.99 (ddd, J=11.9, 4.9, 1.7 Hz, 1H), 3.42-3.52 (m, 2H), 2.25 (t, J=7.4 Hz, 2H), 1.92-2.00 (m, 1H), 1.84-1.91 (m, 1H), 1.52-1.69 (m, 3H), 1.28 (ddd, J=12, 11, 11 Hz, 1H), 1.20 (d, J=6.2 Hz, 3H), 0.94 (t, J=7.4 Hz, 3H).

Step 3. Synthesis of (2R,4R)-2-methyltetrahydro-2H-pyran-4-ol (C3)

A solution of C2 (51.5 g, 276 mmol) in methanol and tetrahydrofuran (1:1, 700 mL) was treated with a solution of lithium hydroxide (19.9 g, 831 mmol) in water (120 mL), and the reaction mixture was stirred overnight at room temperature. After removal of the organic solvents via concentration under reduced pressure, the aqueous residue was extracted 4 times with dichloromethane; the combined organic layers were dried over magnesium sulfate, filtered, and concentrated in vacuo to afford the product as a colorless oil. Yield: 27.3 g, 235 mmol, 85%. $^1$H NMR (400 MHz, $CDCl_3$) δ 3.99 (ddd, J=11.8, 4.8, 1.7 Hz, 1H), 3.71-3.80 (m, 1H), 3.35-3.47 (m, 2H), 1.82-1.98 (m, 3H), 1.48 (dddd, J=12.5, 12.4, 11.1, 4.8 Hz, 1H), 1.21 (d, J=6.2 Hz, 3H), 1.14-1.24 (m, 1H).

Step 4. Synthesis of (2R)-2-methyltetrahydro-4H-pyran-4-one (C4)

A solution of C3 (27.3 g, 235 mmol) in acetone (980 mL) was cooled in an ice bath and treated drop-wise with Jones reagent (2.5 M, 103 mL, 258 mmol). The reaction mixture was stirred for 10 minutes at 0° C., then warmed to room temperature, stirred for a further 30 minutes, and cooled to 0° C. 2-Propanol (18 mL, 240 mmol) was added, and stirring was continued for 30 minutes. After the mixture had been concentrated in vacuo, the residue was partitioned between water and dichloromethane; the aqueous layer was extracted 3 times with dichloromethane, and the combined organic layers were dried over magnesium sulfate, filtered, and concentrated under reduced pressure to provide the product as a light yellow oil. Yield: 23 g, 200 mmol, 85%. $^1$H NMR (400 MHz, $CDCl_3$) δ 4.25 (ddd, J=11.5, 7.4, 1.3 Hz, 1H), 3.70 (dqd, J=12.2, 6.1, 2.7 Hz, 1H), 3.64 (ddd, J=12.2, 11.6, 2.8 Hz, 1H), 2.55 (dddd, J=14.6, 12.4, 7.4, 1.0 Hz, 1H), 2.37 (ddd, J=14.4, 2.3, 2.3 Hz, 1H), 2.21-2.31 (m, 2H), 1.29 (d, J=6.2 Hz, 3H).

Step 5. Synthesis of (2R,4R)-N-(2,4-dimethoxybenzyl)-2-methyltetrahydro-2H-pyran-4-amine (P2)

1-(2,4-Dimethoxyphenyl)methanamine (20.3 mL, 135 mmol) was added to a solution of C4 (10.3 g, 90.2 mmol) in methanol (200 mL), and the reaction mixture was stirred for 1 hour at room temperature. It was then cooled to −78° C.; lithium borohydride solution (2 M in tetrahydrofuran, 45.1 mL, 90.2 mmol) was added drop-wise, and stirring was continued at −78° C. for 2 hours. After slowly warming to room temperature overnight, the reaction mixture was quenched via careful addition of saturated aqueous sodium bicarbonate solution. Ethyl acetate (250 mL) and sufficient water to solubilize the precipitate were added, and the aqueous layer was extracted with ethyl acetate; the combined organic layers were dried over magnesium sulfate, filtered, and concentrated in vacuo. Silica gel chromatography (Gradient: 0% to 5% methanol in dichloromethane) provided the product as a colorless oil (10.4 g). Similar purification of mixed fractions afforded additional product (3.7 g). Combined yield: 14.1 g, 53.1 mmol, 59%. $^1$H NMR (400 MHz, $CDCl_3$) δ 7.13 (d, J=8.0 Hz, 1H), 6.42-6.47 (m, 2H), 3.99 (ddd, J=11.6, 4.6, 1.5 Hz, 1H), 3.82 (s, 3H), 3.80 (s, 3H), 3.76 (s, 2H), 3.36-3.45 (m, 2H), 2.63-2.73 (m, 1H), 1.85-1.92 (m, 1H), 1.78-1.85 (m, 1H), 1.38 (dddd, J=13, 12, 11, 4.7 Hz, 1H), 1.20 (d, J=6.2 Hz, 3H), 1.10 (ddd, J=11, 11, 11 Hz, 1H).

Alternate Preparation of P2

(2R,4R)-N-(2,4-Dimethoxybenzyl)-2-methyltetrahydro-2H-pyran-4-amine (P2)

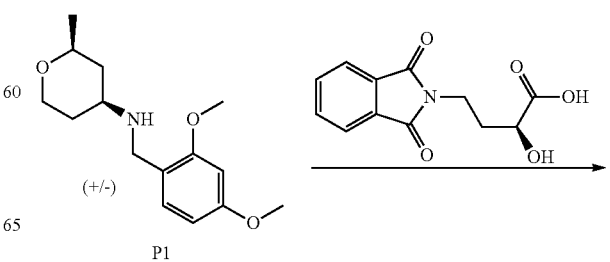

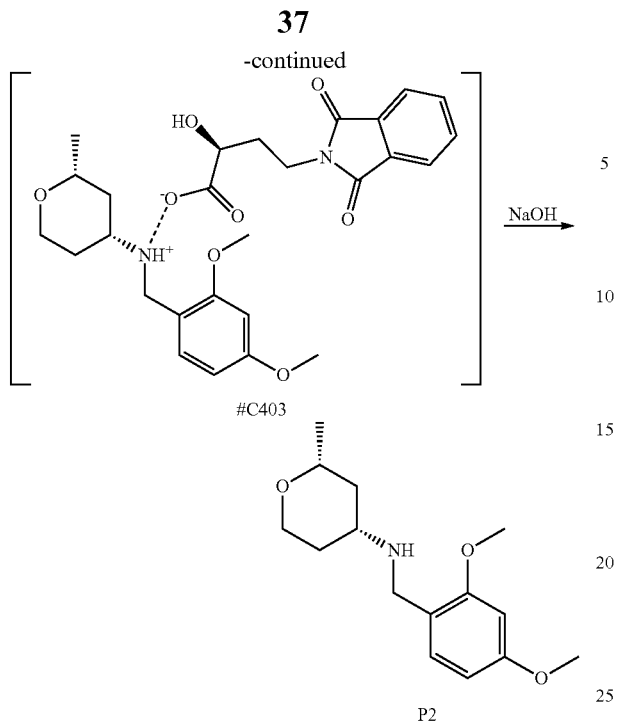

C403

P2

A solution of P1 (200 mg, 0.754 mmol) in acetonitrile (0.05 M) was added to a slurry of (+)-(2S)-4-(1,3-dioxo-1,3-dihydro-2H-isoindol-2-yl)-2-hydroxybutanoic acid (93.9 mg, 0.377 mmol) in acetonitrile (0.15 M). The reaction mixture was heated to 75° C. to effect complete dissolution, and was then allowed to cool to room temperature and stir for an additional 18 hours. The resulting solid (C39) was collected via filtration, washed with acetonitrile, and dissolved in dichloromethane. This solution was washed three times with 1 M aqueous sodium hydroxide solution and once with saturated aqueous sodium chloride solution, dried over sodium sulfate, filtered, and concentrated in vacuo to afford the product as a colorless oil. The indicated absolute configuration was established via chiral HPLC comparison with a known sample of P2. The enantiomeric excess of this batch of P2 was determined to be 77.5% by supercritical fluid chromatography (Column: Chiral Technologies Chiralpak AS, 5 μm; Mobile phase A: carbon dioxide; Mobile phase B: ethanol containing 0.2% ammonium hydroxide; Gradient: 5% to 60% B). In this system, P2 was the second-eluting enantiomer. Yield: 68 mg, 0.26 mmol, 69%. $^1$H NMR (400 MHz, CDCl$_3$) δ 7.13 (d, J=8.0 Hz, 1H), 6.46 (d, half of AB quartet, J=2.3 Hz, 1H), 6.44 (dd, half of ABX pattern, J=8.1, 2.4 Hz, 1H), 4.00 (ddd, J=11.7, 4.7, 1.8 Hz, 1H), 3.82 (s, 3H), 3.81 (s, 3H), 3.76 (s, 2H), 3.37-3.46 (m, 2H), 2.63-2.72 (m, 1H), 1.85-1.92 (m, 1H), 1.78-1.85 (m, 1H), 1.38 (dddd, J=12.7, 12.5, 11.3, 4.7 Hz, 1H), 1.20 (d, J=6.2 Hz, 3H), 1.10 (ddd, J=12.3, 11.3, 11.1 Hz, 1H).

Preparation P3 cis-3-Fluorocyclopentanamine, hydrochloride salt
(P3)

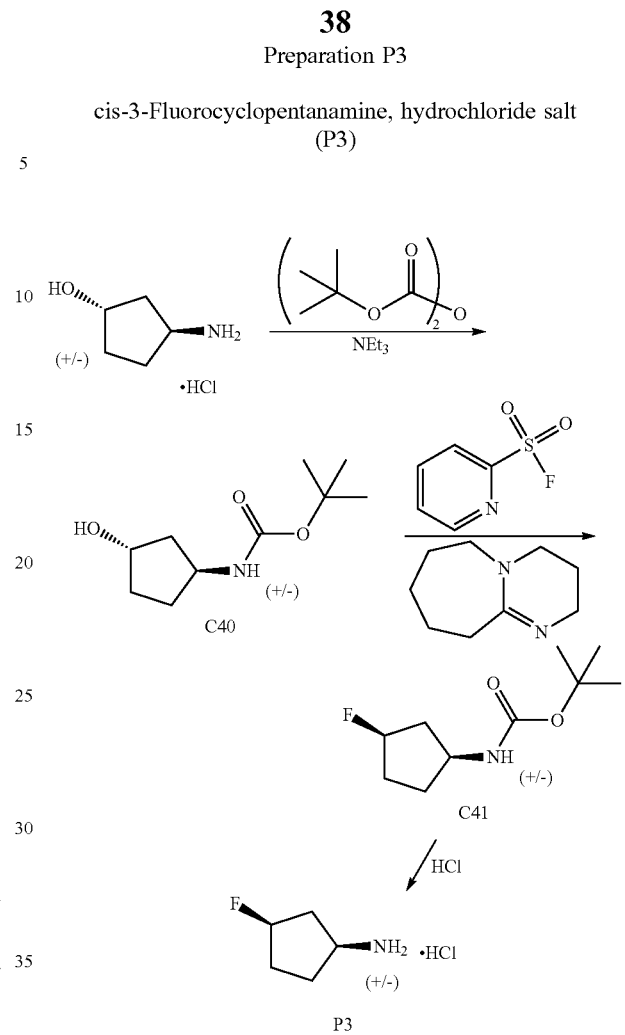

Step 1. Synthesis of tert-butyl (trans-3-hydroxycyclopentyl)carbamate (C40)

trans-3-Aminocyclopentanol, hydrochloride salt (9.7 g, 70 mmol) was mixed with dichloromethane (120 mL), whereupon triethylamine (21.6 mL, 155 mmol) was added, followed by di-tert-butyl dicarbonate (16.9 g, 77.4 mmol). After the reaction mixture had been stirred at room temperature overnight, water was added and the resulting mixture was extracted with dichloromethane. The organic layer was washed with water, dried over sodium sulfate, filtered, and concentrated in vacuo to afford a slightly yellow oil, which solidified upon addition of heptane. This material was collected via filtration, washed with heptane and crystallized from dichloromethane/heptane, providing the product as a white solid. Yield: 11.86 g, 58.93 mmol, 84%. $^1$H NMR (400 MHz, CDCl$_3$) δ 4.36-4.54 (m, 2H), 4.10-4.25 (br m, 1H), 2.16-2.28 (m, 1H), 1.97-2.09 (m, 2H), 1.55-1.71 (m, 2H), 1.45 (s, 9H), 1.36-1.48 (m, 2H).

Step 2. Synthesis of tert-butyl (cis-3-fluorocyclopentyl)carbamate (C41)

1,8-Diazabicyclo[5.4.0]undec-7-ene (7.43 mL, 49.7 mmol) was added to a mixture of C40 (5.00 g, 24.8 mmol), toluene (25 mL), and pyridine-2-sulfonyl fluoride (PyFluor; 4.40 g, 27.3 mmol). After 16 hours at room temperature, the reaction mixture was diluted with saturated aqueous sodium bicarbonate solution (50 mL) and extracted with heptane (3×100 mL). The combined organic layers were dried over sodium sulfate, filtered, and concentrated in vacuo. Silica gel chromatography (Gradient: 0% to 30% ethyl acetate in heptane) provided the product as a solid. Yield: 3.78 g, 18.6 mmol, 75%. $^1$H NMR (400 MHz, CDCl$_3$) δ [5.20-5.26 (m) and 5.07-5.13 (m), $J_{HF}$=54 Hz, total 1H], 4.75-4.89 (br m, 1H), 4.10-4.24 (br m, 1H), 1.99-2.21 (m, 3H), 1.66-1.95 (m, 3H), 1.45 (s, 9H).

Step 3. Synthesis of cis-3-fluorocyclopentanamine, hydrochloride salt (P3)

Hydrogen chloride (4 M solution in 1,4-dioxane, 46.2 mL, 185 mmol) was added to a 0° C. solution of C41 (3.76 g, 18.5 mmol) in tetrahydrofuran (54 mL), and the reaction mixture was allowed to slowly warm to room temperature overnight. Solvents were removed in vacuo, and the residue was recrystallized from 2-propanol/heptane, affording the product as a white solid. Yield: 2.45 g, 17.6 mmol, 95%. $^1$H NMR (400 MHz, D$_2$O) δ [5.31-5.35 (m) and 5.18-5.22 (m), $J_{HF}$=53 Hz, total 1H], 3.76-3.84 (m, 1H), 2.00-2.40 (m, 4H), 1.75-1.98 (m, 2H).

Preparation P4

Benzyl [(1R,3S)-3-fluorocyclopentyl]carbamate (P4)

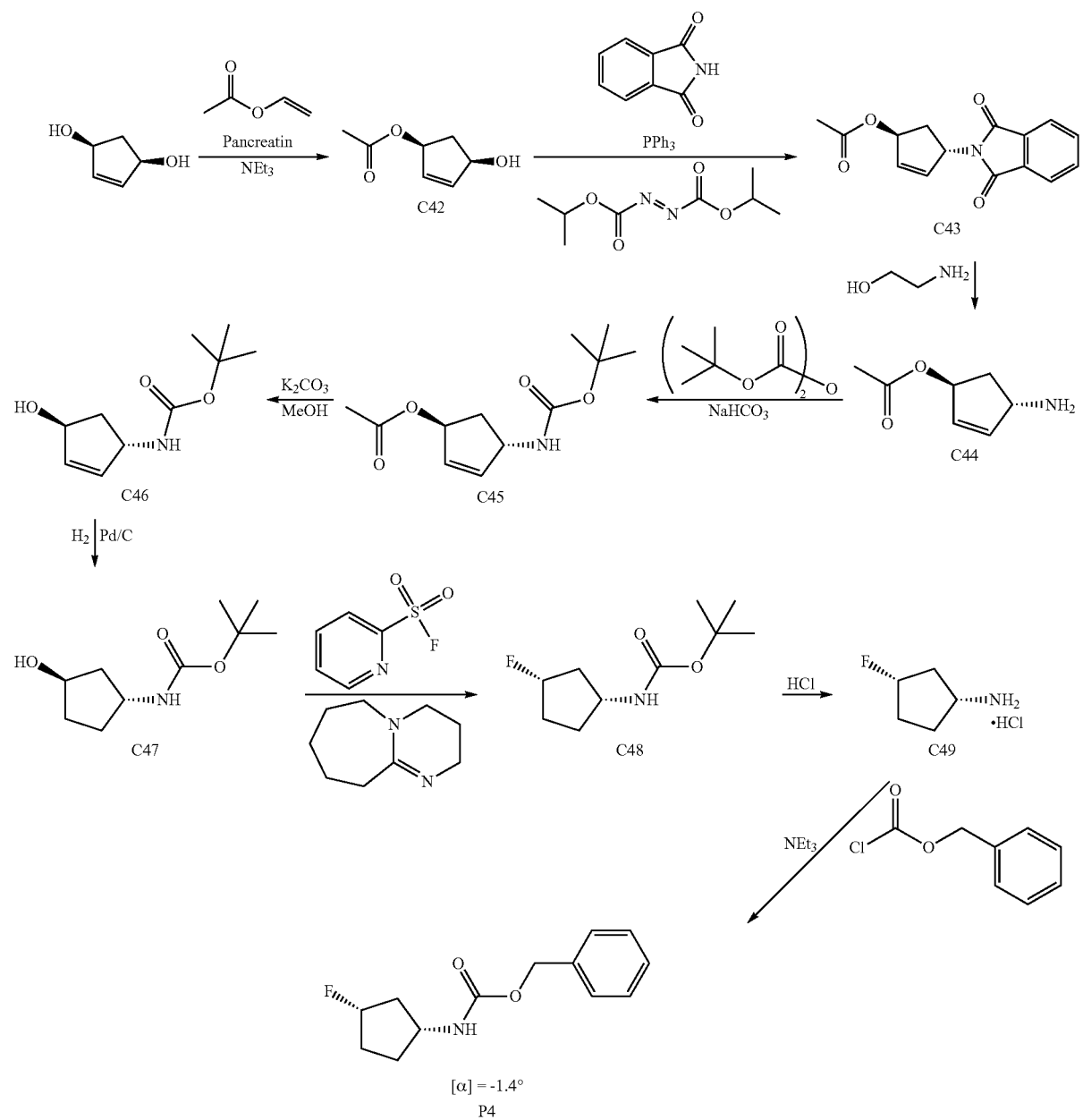

Step 1. Synthesis of (1S,4R)-4-hydroxycyclopent-2-en-1-yl acetate (C42)

Using the method of S. Specklin et al. (Tetrahedron Lett. 2014, 55, 6987-6991), pancreatin (Sigma, from porcine pancreas, 4×USP specifications; 15.2 g) was added to a stirring solution of cis-cyclopent-4-ene-1,3-diol (3.04 g, 30.4 mmol), vinyl acetate (19.6 mL, 213 mmol), and triethylamine (29.6 mL, 212 mmol) in tetrahydrofuran (76 mL). The resulting suspension was stirred for 22 hours at room temperature, whereupon it was filtered through a pad of diatomaceous earth. After the filter pad had been washed with ethyl acetate (50 mL), the combined filtrates were concentrated in vacuo and purified via silica gel chromatography (Gradient: 20% to 33% ethyl acetate in cyclohexane), affording the product as a yellow solid. Yield: 2.28 g, 16.0 mmol, 53%. $^1$H NMR (400 MHz, CDCl$_3$) δ 6.12 (ddd, J=5.5, 1.9, 1.3 Hz, 1H), 5.99 (ddd, J=5.5, 2.1, 1.2 Hz, 1H), 5.48-5.53 (m, 1H), 4.70-4.75 (m, 1H), 2.76-2.86 (m, 1H), 2.06 (s, 3H), 1.66 (ddd, J=14.6, 3.9, 3.7 Hz, 1H).

Step 2. Synthesis of (1S,4S)-4-(1,3-dioxo-1,3-dihydro-2H-isoindol-2-yl)cyclopent-2-en-1-yl acetate (C43)

Diisopropyl azodicarboxylate (94%, 2.73 mL, 13.0 mmol) was slowly added to a mixture of C42 (1.68 g, 11.8 mmol), tetrahydrofuran (50 mL), 1H-isoindole-1,3(2H)-dione (1.92 g, 13.0 mmol), and triphenylphosphine (98.5%, 3.47 g, 13.0 mmol). After the reaction mixture had been stirred at room temperature for 18 hours, it was eluted through a short pad of silica gel (100 g), which was then further eluted with ethyl acetate. Fractions containing the product were combined, concentrated in vacuo, and subjected to chromatography on silica gel (Gradient: 0% to 40% ethyl acetate in heptane), providing the product as a white solid (4.96 g). By $^1$H NMR, this material was contaminated with a substantial quantity of material derived from diisopropyl azodicarboxylate; a portion was taken to the following step without additional purification. GCMS m/z 211.0 [M-AcOH]$^+$. $^1$H NMR (400 MHz, CDCl$_3$), product peaks only: δ 7.81-7.84 (m, 2H), 7.70-7.73 (m, 2H), 6.16 (ddd, J=5.7, 2.3, 2.2 Hz, 1H), 6.01-6.06 (m, 1H), 5.98 (ddd, J=5.7, 2.2, 1.0 Hz, 1H), 5.52-5.58 (m, 1H), 2.57 (ddd, J=14.4, 7.2, 4.7 Hz, 1H), 2.27 (ddd, J=14.5, 8.5, 2.9 Hz, 1H), 2.07 (s, 3H).

Step 3. Synthesis of (1S,4S)-4-aminocyclopent-2-en-1-yl acetate (C44)

2-Aminoethanol (2.13 mL, 35.3 mmol) was added to a solution of C43 (from the previous step, 2.40 g, ≤6.29 mmol) in ethyl acetate (20 mL), and the reaction mixture was heated at reflux for 18 hours. More 2-aminoethanol (1.0 mL, 17 mmol) was added, and heating was continued for an additional 4 hours. After removal of solvent under reduced pressure, the residue was purified using silica gel chromatography [Gradient: 0% to 10% (2 M ammonia in methanol) in dichloromethane] to afford the product as a colorless oil (1.25 g). This material was taken directly into the following step.

Step 4. Synthesis of (1S,4S)-4-[(tert-butoxycarbonyl)amino]cyclopent-2-en-1-yl acetate (C45)

To a solution of C44 (from the previous step, ≤6.29 mmol) in dichloromethane (30 mL) was added sodium bicarbonate (3.72 g, 44.3 mmol) and di-tert-butyl dicarbonate (3.86 g, 17.7 mmol). The reaction mixture was stirred at room temperature overnight, whereupon it was concentrated in vacuo and used directly in the following step.

Step 5. Synthesis of tert-butyl [(1S,4S)-4-hydroxycyclopent-2-en-1-yl]carbamate (C46)

Potassium carbonate (2.44 g, 17.7 mmol) was added to a solution of C45 (from the previous step, ≤6.29 mmol) in methanol (20 mL). The reaction mixture was stirred at room temperature for 1 hour, whereupon it was diluted with water (50 mL) and extracted with diethyl ether (3×30 mL). The combined organic layers were dried over sodium sulfate, filtered, and concentrated in vacuo. Silica gel chromatography (Gradient: 0% to 60% ethyl acetate in heptane) provided the product as a white solid. Yield: 783 mg, 3.93 mmol, 62% over 4 steps. GCMS m/z 143.0 [M-2-methylprop-1-ene]$^+$. $^1$H NMR (400 MHz, CDCl$_3$) δ 5.96-6.00 (m, 1H), 5.92-5.96 (m, 1H), 4.85-5.01 (m, 2H), 2.19 (ddd, J=14.4, 7.4, 3.1 Hz, 1H), 1.95 (ddd, J=14.4, 7.0, 4.3 Hz, 1H), 1.45 (s, 9H).

Step 6. Synthesis of tert-butyl [(1R,3R)-3-hydroxycyclopentyl]carbamate (C47)

A mixture of C46 (315 mg, 1.58 mmol) and 10% palladium on carbon (150 mg) in methanol (20 mL) was hydrogenated at 60 psi for 4 hours. The catalyst was removed via filtration, and the filtrate was concentrated in vacuo and combined with the crude product from a similar reaction carried out using C46 (151 mg, 0.758 mmol). Chromatography on silica gel (Gradient: 0% to 60% ethyl acetate in heptane) afforded the product as a white solid. Combined yield: 286 mg, 1.42 mmol, 61%. GCMS m/z 145.0 [M-2-methylprop-1-ene]+. $^1$H NMR (400 MHz, CDCl$_3$) δ 4.49 (br s, 1H), 4.36-4.42 (m, 1H), 4.09-4.24 (br m, 1H), 2.15-2.26 (m, 1H), 1.95-2.08 (m, 2H), 1.8-2.0 (v br s, 1H), 1.55-1.69 (m, 2H), 1.44 (s, 9H), 1.33-1.45 (m, 1H).

Step 7. Synthesis of tert-butyl [(1R,3S)-3-fluorocyclopentyl]carbamate (C48)

Pyridine-2-sulfonyl fluoride (252 mg, 1.56 mmol) was added to a mixture of C47 (286 mg, 1.42 mmol) in toluene (1.4 mL). 1,8-Diazabicyclo[5.4.0]undec-7-ene (0.425 mL, 2.84 mmol) was then added, and the reaction mixture was stirred overnight at room temperature. Saturated aqueous sodium bicarbonate solution (10 mL) was added, and the resulting mixture was extracted with diethyl ether (3×10 mL). The combined organic layers were dried over sodium sulfate, filtered, concentrated in vacuo, and purified via silica gel chromatography (Gradient: 0% to 30% ethyl acetate in heptane), providing the product as a white solid. Yield: 181 mg, 0.890 mmol, 63%. $^1$H NMR (400 MHz, CDCl$_3$) δ [5.20-5.25 (m) and 5.07-5.12 (m), $J_{HF}$=54 Hz, total 1H], 4.76-4.88 (br m, 1H), 4.10-4.23 (br m, 1H), 1.99-2.20 (m, 3H), 1.66-1.94 (m, 3H), 1.45 (s, 9H).

Step 8. Synthesis of (1R,3S)-3-fluorocyclopentanamine, hydrochloride salt (C49)

A solution of hydrogen chloride in 1,4-dioxane (4 M, 2.2 mL, 8.8 mmol) was added to C48 (181 mg, 0.890 mmol), and the reaction mixture was stirred at room temperature for 3 hours. Concentration in vacuo afforded the product as a white solid. Yield: 121 mg, 0.867 mmol, 97%. $^1$H NMR (400

MHz, CD$_3$OD) δ [5.25-5.29 (m) and 5.11-5.16 (m), J$_{HF}$=53 Hz, total 1H], 3.67-3.76 (m, 1H), 2.35 (dddd, J=36.0, 15.6, 8.6, 4.7 Hz, 1H), 1.79-2.27 (m, 5H).

Step 9. Synthesis of benzyl [(1R,3S)-3-fluorocyclopentyl]carbamate (P4)

Triethylamine (2.6 mmol) and benzyl chloroformate (0.136 mL, 0.953 mmol) were added to a suspension of C49 (121 mg, 0.867 mmol) in dichloromethane (5 mL), and the reaction mixture was stirred at room temperature for 2 hours. It was then concentrated in vacuo and purified via chromatography on silica gel (Gradient: 0% to 40% ethyl acetate in heptane), affording the product as a white solid. Yield: 159 mg, 0.670 mmol, 77%. Specific rotation: [α]−1.4° (c 1.52, dichloromethane). GCMS m/z 237.0 [M$^+$]. $^1$H NMR (400 MHz, CDCl$_3$) δ 7.29-7.40 (m, 5H), 5.10 (s, 2H), 5.00-5.27 (m, 2H), 4.20-4.31 (br m, 1H), 2.00-2.20 (m, 3H), 1.69-1.98 (m, 3H).

Alternate Preparation of P4

Benzyl [(1R,3S)-3-fluorocyclopentyl]carbamate (P4)

ane (3×30 mL). The combined organic layers were dried over sodium sulfate, filtered, and concentrated in vacuo. The residue was recrystallized from dichloromethane/heptane to afford the product as a white solid (2.88 g). The mother liquors were concentrated and recrystallized from dichloromethane/heptane to provide additional product (286 mg). Combined yield: 3.17 g, 13.5 mmol, 81%. $^1$H NMR (400 MHz, CDCl$_3$) δ 7.29-7.40 (m, 5H), 5.10 (br s, 2H), 4.60-4.77 (br s, 1H), 4.38-4.46 (m, 1H), 4.19-4.33 (m, 1H), 2.18-2.32 (m, 1H), 1.98-2.13 (m, 2H), 1.57-1.74 (m, 2H), 1.38-1.49 (m, 1H), 1.38 (d, J=3.5 Hz, 1H).

Step 2. Synthesis of benzyl (cis-3-fluorocyclopentyl)carbamate (C51)

Pyridine-2-sulfonyl fluoride (2.17 g, 13.5 mmol), followed by 1,8-diazabicyclo[5.4.0]undec-7-ene (3.67 mL, 24.5 mmol), was added to a solution of C50 (2.88 g, 12.2 mmol) in toluene (20 mL). The reaction mixture was stirred for 64 hours, whereupon saturated aqueous sodium bicar-

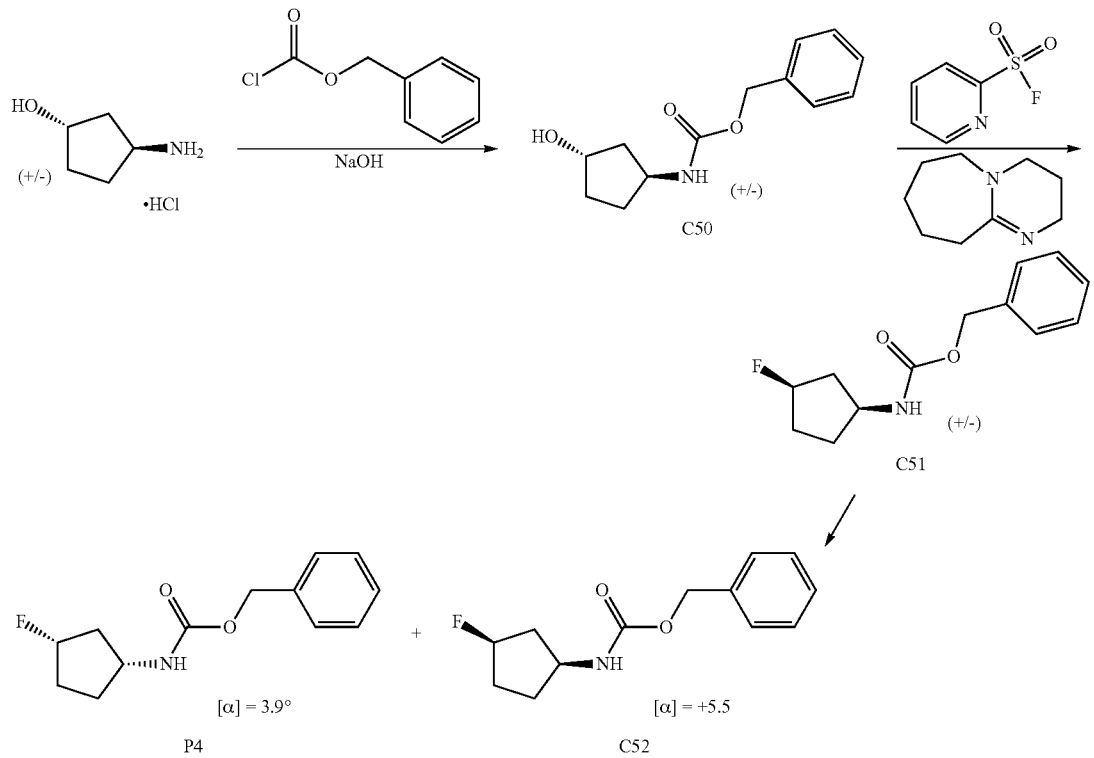

Step 1. Synthesis of benzyl (trans-3-hydroxycyclopentyl)carbamate (C50)

A mixture of trans-3-aminocyclopentanol, hydrochloride salt (2.30 g, 16.7 mmol) in water (15 mL) was cooled to 0° C. Aqueous sodium hydroxide solution (3 M, 12.3 mL, 36.9 mmol) and benzyl chloroformate (2.62 mL, 18.4 mmol) were added by turns. After completion of the additions, the reaction mixture was stirred at 0° C. for 3 hours, whereupon it was diluted with water and extracted with dichloromethbonate solution (20 mL) was added. The resulting mixture was extracted with ethyl acetate (3×20 mL); the combined organic layers were dried over sodium sulfate, filtered, and concentrated in vacuo. Silica gel chromatography (Gradient: 0% to 40% ethyl acetate in heptane) provided the product as a solid. Yield: 2.23 g, 9.40 mmol, 77%. $^1$H NMR (400 MHz, CDCl$_3$) δ 7.29-7.41 (m, 5H), 5.10 (br s, 2H), 5.00-5.27 (m, 2H), 4.20-4.31 (br m, 1H), 2.00-2.20 (m, 3H), 1.69-1.98 (m, 3H).

Step 3. Isolation of benzyl [(1R,3S)-3-fluorocyclopentyl]carbamate (P4) and benzyl [(1S,3R)-3-fluorocyclopentyl]carbamate (C52)

The component enantiomers of C51 (1.60 g) were separated using supercritical fluid chromatography [Column: Phenomenex Lux Amylose-2, 5 μm; Mobile phase: 9:1 carbon dioxide/(ethanol containing 0.2% ammonium hydroxide)]. The first-eluting enantiomer was P4, and the second-eluting enantiomer was C52. The absolute configurations shown were assigned to the enantiomers through comparison of their rotations with the sample of P4 synthesized in Preparation P4.

For P4, Yield: 612 mg, 38% for the separation. Specific rotation: [α]−3.9° (c 0.455, dichloromethane). LCMS m/z 238.5 [M+H]$^+$. $^1$H NMR (400 MHz, CDCl$_3$) δ 7.30-7.39 (m, 5H), 5.10 (s, 2H), 5.01-5.27 (m, 2H), 4.20-4.31 (br m, 1H), 2.00-2.21 (m, 3H), 1.69-1.98 (m, 3H).

For C52, Yield: 647 mg, 40% for the separation. Specific rotation: [α]+5.5° (c 0.445, dichloromethane). LCMS m/z 238.5 [M+H]$^+$. $^1$H NMR (400 MHz, CDCl$_3$) δ 7.29-7.39 (m, 5H), 5.10 (s, 2H), 5.01-5.27 (m, 2H), 4.20-4.31 (br m, 1H), 2.01-2.20 (m, 3H), 1.69-1.98 (m, 3H).

Example 1

8-Methoxy-2-[(5-methyl-1,2-oxazol-3-yl)methyl]-1-[(2R,4R)-2-methyltetrahydro-2H-pyran-4-yl]-1H-imidazo[4,5-c]quinoline (1)

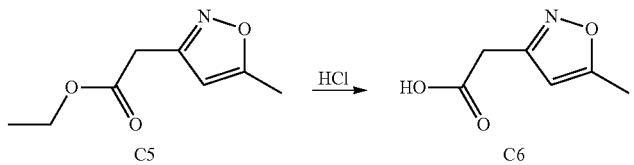

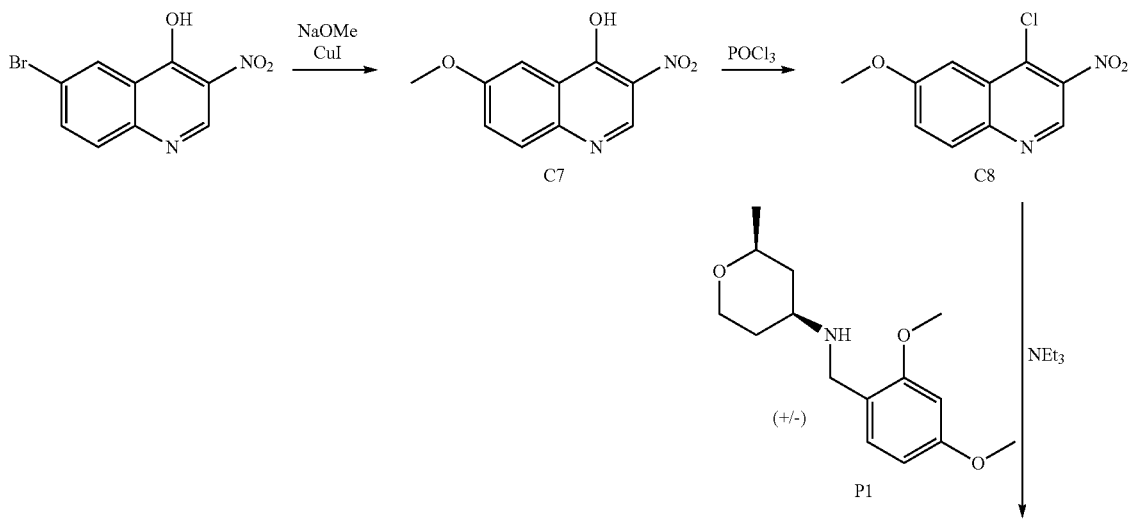

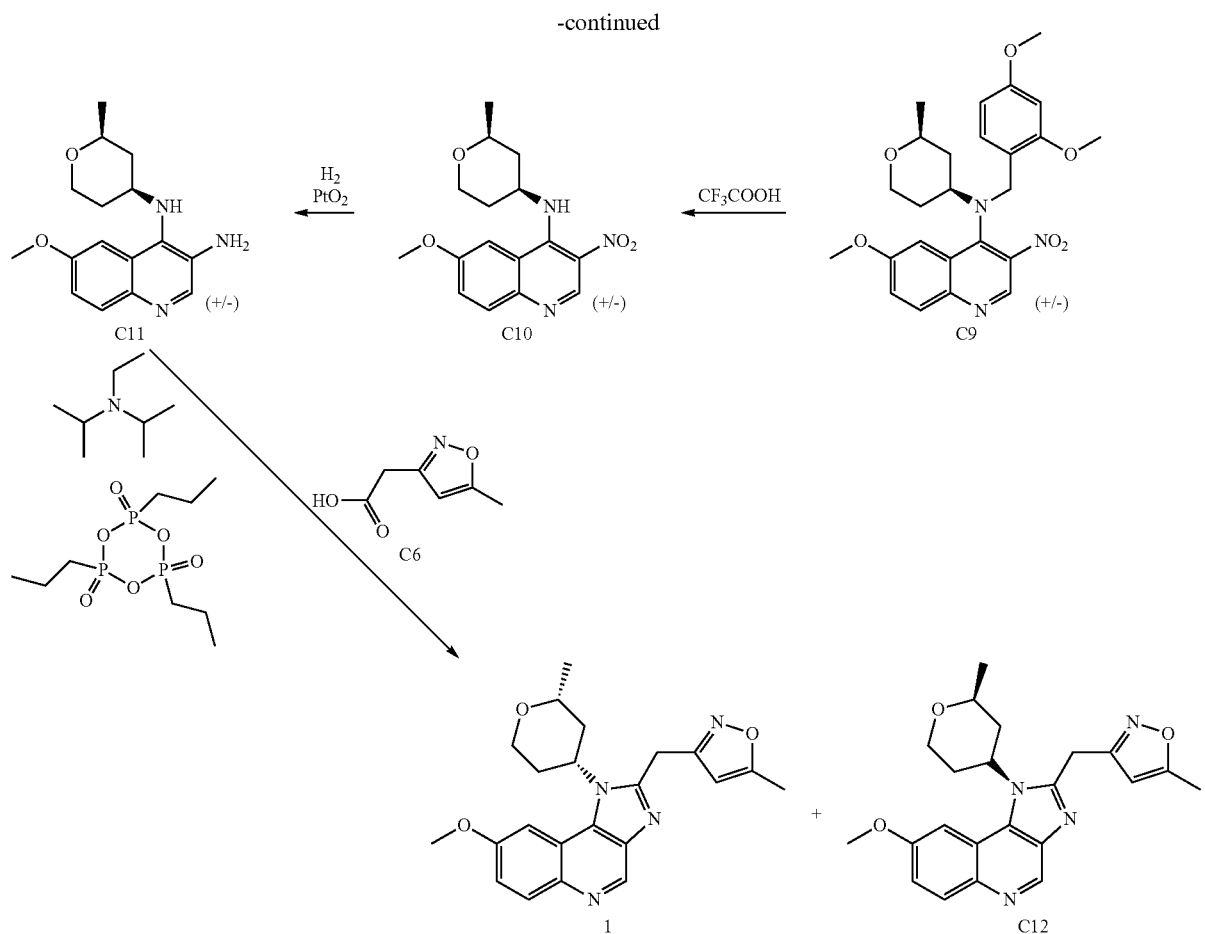

Step 1. Synthesis of (5-methyl-1,2-oxazol-3-yl)acetic acid (C6)

A mixture of C5 (which may be prepared according to J. Gainer et al., *J. Chem. Soc., Perkin Trans.* 1 (1972-1999) 1976, 9, 994-997; 400 mg, 2.36 mmol) and concentrated hydrochloric acid (5 ml) was heated at 50° C. overnight. The reaction mixture was concentrated to provide the product. Yield: 300 mg, 2.1 mmol, 89%. $^1$H NMR (400 MHz, DMSO-$d_6$) δ 6.18 (br s, 1H), 3.62 (s, 2H), 2.37 (d, J=0.6 Hz, 3H).

Step 2. Synthesis of 6-methoxy-3-nitroquinolin-4-ol (C7)

A mixture of sodium metal (1.3 g, 56 mmol) in methanol (50 ml) was stirred at room temperature for 30 minutes, whereupon N,N-dimethylformamide (50 mL) was introduced. Copper(I) iodide (4.25 g, 22.3 mmol) and 6-bromo-3-nitroquinolin-4-ol (5.00 g, 18.6 mmol) were added, and the reaction mixture was heated at 100° C. for 3 days. It was then cooled and filtered; the filtrate was concentrated in vacuo and the residue was diluted with water (200 mL). After adjustment of the pH to 5-6 via addition of concentrated hydrochloric acid, the mixture was filtered again, and the filter cake was washed with water (40 mL), affording the product as a brown solid. Yield: 2.8 g, 13 mmol, 70%. $^1$H NMR (400 MHz, DMSO-$d_6$) δ 9.12 (br s, 1H), 7.68 (br d, J=8.5 Hz, 1H), 7.65 (d, J=2.3 Hz, 1H), 7.42 (dd, J=8.8, 2.8 Hz, 1H), 3.87 (s, 3H).

Step 3. Synthesis of 4-chloro-6-methoxy-3-nitroquinoline (C8)

Phosphorus oxychloride (11.7 g, 76.3 mmol) was added drop-wise to a solution of C7 (5.8 g, 26 mmol) in N,N-dimethylformamide (50 mL), and the reaction mixture was stirred at room temperature for 2 hours, whereupon it was poured into ice water (100 mL). The resulting mixture was filtered and the filter cake was washed with water (300 mL) to provide the product as a brown solid. Yield: 4.5 g, 19 mmol, 73%.

Step 4. Synthesis of N-(2,4-dimethoxybenzyl)-6-methoxy-N-(cis-2-methyltetrahydro-2H-pyran-4-yl)-3-nitroquinolin-4-amine (C9)

This experiment was carried out in three batches. To a mixture of C8 (1.5 g, 6.3 mmol) and P1 (2.18 g, 8.22 mmol) in N,N-dimethylformamide (15 mL) was added triethylamine (1.3 g, 13 mmol), and the mixture was heated at 80° C. overnight. The three reaction mixtures were combined, diluted with water (300 mL), and extracted with dichloromethane (3×150 mL). The combined organic layers were washed with saturated aqueous sodium chloride solution (3×100 mL), dried over sodium sulfate, filtered, and concentrated in vacuo; purification via silica gel chromatography (Eluent: 5:1 petroleum ether/ethyl acetate) afforded the product as a yellow oil. Yield: 4.8 g, 10 mmol, 53%. $^1$H NMR (400 MHz, CDCl$_3$) δ 8.94 (s, 1H), 7.97 (d, J=9.2 Hz, 1H), 7.51 (d, J=2.9 Hz, 1H), 7.42 (dd, J=9.1, 2.8 Hz, 1H), 6.91 (d, J=8.3 Hz, 1H), 6.24 (dd, half of ABX pattern, J=8.3, 2.4 Hz, 1H), 6.21 (d, half of AB quartet, J=2.3 Hz, 1H), 4.32 (AB quartet, $J_{AB}$=14.8 Hz, $\Delta v_{AB}$=8.0 Hz, 2H), 3.98-4.05 (m, 1H), 3.88 (s, 3H), 3.73-3.84 (m, 1H), 3.70 (s, 3H), 3.48 (s, 3H), 3.38-3.47 (m, 2H), 1.82-2.00 (m, 3H), 1.51-1.62 (m, 1H), 1.18 (d, J=6.2 Hz, 3H).

Step 5. Synthesis of 6-methoxy-N-(cis-2-methyltetrahydro-2H-pyran-4-yl)-3-nitroquinolin-4-amine (C10)

A solution of C9 (4.8 g, 10 mmol) in trifluoroacetic acid (30 mL) was stirred at room temperature for 30 minutes, whereupon it was diluted with dichloromethane (200 mL). Saturated aqueous sodium bicarbonate solution (200 mL) was added, and the aqueous layer was extracted with dichloromethane (3×100 mL); the combined organic layers were washed with saturated aqueous sodium chloride solution (3×100 mL), dried over sodium sulfate, filtered, and concentrated under reduced pressure. The residue was washed with ethyl acetate (30 mL) to afford the product as a yellow solid. Yield: 2.5 g, 7.9 mmol, 79%. $^1$H NMR (400 MHz, CDCl$_3$) δ 9.26 (s, 1H), 8.87 (br d, J=8.9 Hz, 1H), 7.97 (d, J=10.0 Hz, 1H), 7.42-7.48 (m, 2H), 4.23-4.35 (m, 1H), 4.11 (br dd, J=12, 5 Hz, 1H), 3.93 (s, 3H), 3.45-3.55 (m, 2H), 2.09-2.19 (m, 2H), 1.7-1.84 (m, 1H), 1.48 (ddd, J=12, 12, 11 Hz, 1H), 1.26 (d, J=6.3 Hz, 3H).

Step 6. Synthesis of 6-methoxy-$N^4$-(cis-2-methyltetrahydro-2H-pyran-4-yl)quinoline-3,4-diamine (C11)

To a solution of C10 (2.5 g, 7.9 mmol) in a mixture of methanol (25 mL) and acetonitrile (100 mL) was added platinum(IV) oxide (500 mg, 2.2 mmol). The reaction mixture was degassed and purged with hydrogen three times, then stirred at room temperature for 3 hours under a balloon containing hydrogen. The reaction mixture was filtered and the filtrate was concentrated, providing the product as a black solid, which was used without further purification. Yield: 2.0 g, 7.0 mmol, 89%. LCMS m/z 287.9 [M+H]$^+$.

Step 7. Synthesis of 8-methoxy-2-[(5-methyl-1,2-oxazol-3-yl)methyl]-1-[(2R,4R)-2-methyltetrahydro-2H-pyran-4-yl]-1H-imidazo[4,5-c]quinoline (1) and 8-methoxy-2-[(5-methyl-1,2-oxazol-3-yl)methyl]-1-[(2S,4S)-2-methyltetrahydro-2H-pyran-4-yl]-1H-imidazo[4,5-c]quinoline (C12)

To a solution of C11 (350 mg, 1.22 mmol) and C6 (200 mg, 1.4 mmol) in N,N-dimethylformamide (15 mL) was added N,N-diisopropylethylamine (346 mg, 2.68 mmol) and 2,4,6-tripropyl-1,3,5,2,4,6-trioxatriphosphinane 2,4,6-trioxide (50% solution in ethyl acetate, 2.3 g, 3.6 mmol), and the reaction mixture was heated at 120° C. for 5 hours. It was then diluted with water (80 mL) and extracted with ethyl acetate (3×50 mL); the combined organic layers were washed with saturated aqueous sodium chloride solution (100 mL), dried over sodium sulfate, filtered, and concentrated in vacuo. Purification via reversed phase HPLC (Column: Agela Durashell C18, 5 μm; Mobile phase A: 0.225% formic acid in water; Mobile phase B: acetonitrile; Gradient 18% to 38% B) provided the racemic product as a white solid, which was then separated into its component enantiomers using supercritical fluid chromatography (Column: Chiralpak AD-3, 3 μm; Mobile phase A: carbon dioxide; Mobile phase B: methanol containing 0.05% diethylamine; Gradient: 5% to 40% B). The first-eluting compound was 1, isolated as a white solid. Yield: 9.2 mg, 23 μmol, 2%. LCMS m/z 393.0 [M+H]$^+$. Retention time: 5.51 minutes (Analytical column: Chiralpak AD-3, 4.6×150 mm, 3 μm; Mobile phase A: carbon dioxide; Mobile phase B: methanol containing 0.05% diethylamine; Gradient: 5% to 40% B; Flow rate: 1.5 mL/minute). $^1$H NMR (400 MHz, DMSO-d$_6$) δ 9.01 (s, 1H), 8.07 (d, J=9.2 Hz, 1H), 7.85-7.94 (br m, 1H), 7.35 (br d, J=9 Hz, 1H), 6.24 (s, 1H), 5.04-5.20 (br m, 1H), 4.60 (br s, 2H), 4.12-4.23 (br m, 1H), 3.97 (s, 3H), 3.54-3.72 (br m, 2H), 2.6-2.72 (br m, 1H, assumed; partially obscured by solvent peak), 2.39 (s, 3H), 2.24-2.35 (br m, 1H), 1.93-2.05 (br m, 1H), 1.78-1.90 (br m, 1H), 1.21 (d, J=5.9 Hz, 3H).

The second-eluting enantiomer was C12, also obtained as a white solid. Yield: 11.3 mg, 28.8 μmol, 2.4%. LCMS m/z 393.0 [M+H]$^+$. Retention time: 6.6 minutes (Analytical conditions identical to those used for 1) $^1$H NMR (400 MHz, DMSO-d$_6$) δ 9.01 (s, 1H), 8.07 (d, J=9.2 Hz, 1H), 7.85-7.94 (br m, 1H), 7.35 (dd, J=9.3, 2.5 Hz, 1H), 6.24 (s, 1H), 5.05-5.19 (br m, 1H), 4.59 (br s, 2H), 4.12-4.23 (br m, 1H), 3.97 (s, 3H), 3.55-3.72 (br m, 2H), 2.57-2.72 (br m, 1H), 2.39 (s, 3H), 2.22-2.36 (br m, 1H), 1.93-2.06 (br m, 1H), 1.78-1.91 (br m, 1H), 1.21 (d, J=6.0 Hz, 3H). The absolute configurations of 1 and C12 were assigned based on their relative biological activity (see Table 3, the X-ray crystal structure determination of C14 below, and the discussion in Example 5, Step 3).

Example 2
8-Chloro-2-[(5-methoxypyridin-2-yl)methyl]-1-[(2R,4R)-2-methyltetrahydro-2H-pyran-4-yl]-1H-imidazo[4,5-c]quinoline (2)
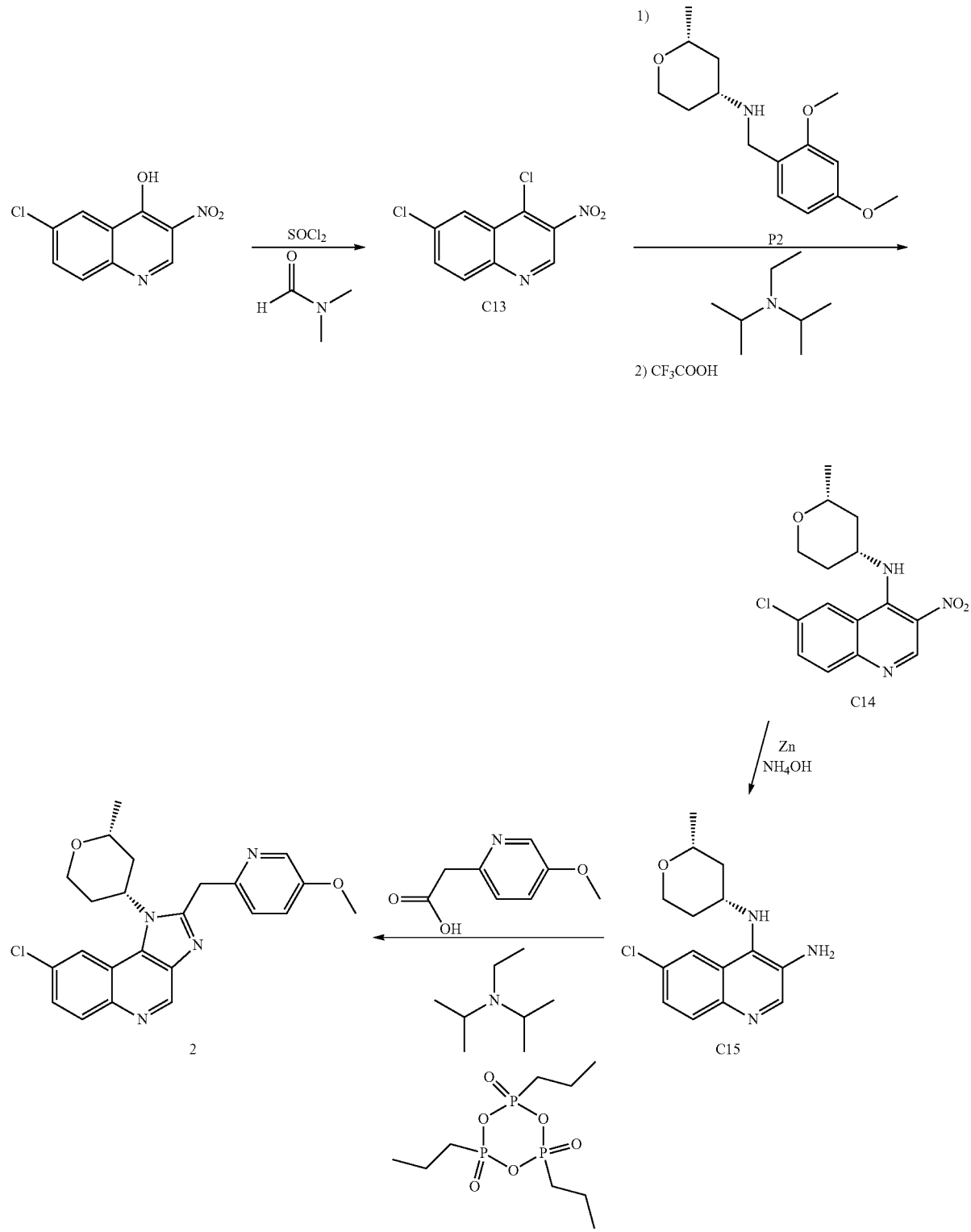

Step 1. Synthesis of 4,6-dichloro-3-nitroquinoline (C13)

N,N-Dimethylformamide (3.1 mL, 40 mmol) and thionyl chloride (97%, 6.9 mL, 93 mmol) were added to a suspension of 6-chloro-3-nitroquinolin-4-ol (15.38 g, 68.48 mmol) in dichloromethane (140 mL), and the reaction mixture was heated at reflux. After 5 hours, it was cooled to room temperature, diluted with additional dichloromethane (25 mL), and poured into saturated aqueous sodium bicarbonate solution (250 mL). The aqueous layer was extracted with dichloromethane (100 mL), then passed through a plug of diatomaceous earth, which was rinsed with dichloromethane (50 mL). The combined organic layers and organic filtrate were dried over magnesium sulfate, filtered, and concentrated in vacuo to afford the product as a pale tan solid. Yield: 16.8 g, quantitative. $^1$H NMR (400 MHz, CDCl$_3$) δ 9.25 (s, 1H), 8.42 (d, J=2.2 Hz, 1H), 8.17 (d, J=8.9 Hz, 1H), 7.89 (dd, J=9.0, 2.2 Hz, 1H).

Step 2. Synthesis of 6-chloro-N-[(2R,4R)-2-methyl-tetrahydro-2H-pyran-4-yl]-3-nitroquinolin-4-amine (C14)

Compound C13 (12.2 g, 50.2 mmol) was added to a solution of P2 (13.3 g, 50.1 mmol) and N,N-diisopropylethylamine (13.1 mL, 75.2 mmol) in acetonitrile (250 mL), and the reaction mixture was heated to 55° C. overnight. After concentration in vacuo, the residue was partitioned between aqueous sodium bicarbonate solution (100 mL) and dichloromethane (150 mL). The aqueous layer was extracted with dichloromethane (2×50 mL) and the combined organic layers were treated with trifluoroacetic acid (25 mL). {Caution: exotherm!}. After 20 minutes, saturated aqueous sodium carbonate solution (150 mL) was added portionwise, and the mixture was allowed to stir for 10 minutes. The aqueous layer was extracted twice with dichloromethane, and the combined organic layers were concentrated in vacuo, providing a reddish solid (17.3 g); this was triturated with diethyl ether (230 mL) to afford a yellow solid (14.0 g). A portion of this solid (10 g) was subjected to purification via supercritical fluid chromatography (Column: Lux Amylose-2, 5 µm; Mobile phase: 65:35 carbon dioxide/methanol), providing the product as a crystalline solid. The indicated absolute configuration was determined via single crystal X-ray structural determination on this material: see below. Yield: 7.1 g, 22 mmol, 62% (yield corrected for material omitted from purification). $^1$H NMR (400 MHz, CDCl$_3$) δ 9.36 (s, 1H), 9.11 (br d, J=9 Hz, 1H), 8.12 (d, J=2.0 Hz, 1H), 7.98 (d, J=8.9 Hz, 1H), 7.73 (dd, J=8.9, 2.2 Hz, 1H), 4.21-4.33 (m, 1H), 4.08-4.15 (m, 1H), 3.50-3.60 (m, 2H), 2.11-2.22 (m, 2H), 1.77 (dddd, J=12, 12, 12, 5 Hz, 1H), 1.49 (ddd, J=12, 12, 11 Hz, 1H), 1.28 (d, J=6.2 Hz, 3H).

Single-Crystal X-Ray Structural Determination of C14

Single Crystal X-Ray Analysis

Data collection was performed on a Bruker APEX diffractometer at room temperature. Data collection consisted of omega and phi scans.

The structure was solved by direct methods using SHELX software suite in the space group P2$_1$2$_1$2$_1$. The structure was subsequently refined by the full-matrix least squares method. All non-hydrogen atoms were found and refined using anisotropic displacement parameters.

The hydrogen atom located on nitrogen was found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek, 2003). The results indicate that the absolute structure has been correctly assigned. The method calculates that the probability that the structure is correct is 100.0. The Hooft parameter is reported as 0.017 with an esd of 0.09.

The final R-index was 4.8%. A final difference Fourier revealed no missing or misplaced electron density.

Pertinent crystal, data collection and refinement information is summarized in Table A. Atomic coordinates, bond lengths, bond angles, torsion angles and displacement parameters are listed in Tables B-E.

SOFTWARE AND REFERENCES

SHELXTL, Version 5.1, Bruker AXS, 1997.

PLATON, A. L. Spek, *J. Appl. Cryst.* 2003, 36, 7-13.

MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.

OLEX2, O. V. Dolomanov, L. J. Bourhis, R. J. Gildea, J. A. K. Howard, and H. Puschmann, *J. Appl. Cryst.* 2009, 42, 339-341.

R. W. W. Hooft, L. H. Straver, and A. L. Spek, *J. Appl. Cryst.* 2008, 41, 96-103.

H. D. Flack, *Acta Cryst.* 1983, A39, 867-881.

TABLE A

| Crystal data and structure refinement for C14. | | |
|---|---|---|
| Empirical formula | C$_{15}$H$_{16}$ClN$_3$O$_3$ | |
| Formula weight | 321.76 | |
| Temperature | 273(2) K | |
| Wavelength | 1.54178 Å | |
| Crystal system | Orthorhombic | |
| Space group | P2(1)2(1)2(1) | |
| Unit cell dimensions | a = 6.7882(13) Å | α = 90° |
|  | b = 10.0703(19) Å | β = 90° |
|  | c = 21.883(4) Å | γ = 90° |
| Volume | 1495.9(5) Å$^3$ | |
| Z | 4 | |
| Density (calculated) | 1.429 Mg/m$^3$ | |
| Absorption coefficient | 2.415 mm$^{-1}$ | |
| F(000) | 672 | |
| Crystal size | 0.22 × 0.16 × 0.10 mm$^3$ | |
| Theta range for data collection | 4.04 to 70.57° | |
| Index ranges | −8 <= h <= 7, −12 <= k <= 12, −26 <= l <= 24 | |
| Reflections collected | 12473 | |
| Independent reflections | 2784 [R(int) = 0.1613] | |
| Completeness to theta = 70.57° | 97.3% | |
| Absorption correction | Empirical | |
| Max. and min. transmission | 0.7943 and 0.6187 | |
| Refinement method | Full-matrix least-squares on F$^2$ | |
| Data/restraints/parameters | 2784/1/204 | |
| Goodness-of-fit on F$^2$ | 1.130 | |
| Final R indices [I > 2sigma(I)] | R1 = 0.0481, wR2 = 0.1164 | |
| R indices (all data) | R1 = 0.0514, wR2 = 0.1254 | |
| Absolute structure parameter | −0.02(2) | |
| Extinction coefficient | 0.0061(8) | |
| Largest diff. peak and hole | 0.236 and −0.393 e.Å$^{-3}$ | |

TABLE B

Atomic coordinates (×10$^4$) and equivalent isotropic displacement parameters (Å$^2$ × 10$^3$) for C14. U(eq) is defined as one-third of the trace of the orthogonalized U$^{ij}$ tensor.

|       | x       | y        | z        | U(eq)  |
|-------|---------|----------|----------|--------|
| C(1)  | 1294(3) | −465(2)  | 8392(1)  | 41(1)  |
| C(2)  | 2045(4) | −1731(2) | 8096(1)  | 47(1)  |
| C(3)  | 5002(4) | −692(3)  | 7811(1)  | 59(1)  |
| C(4)  | 4408(4) | 620(3)   | 8086(1)  | 50(1)  |
| C(5)  | 2992(3) | 394(2)   | 8615(1)  | 37(1)  |
| C(6)  | 2190(3) | 2218(2)  | 9392(1)  | 33(1)  |
| C(7)  | 2088(3) | 3612(2)  | 9478(1)  | 36(1)  |
| C(8)  | 2116(3) | 4182(2)  | 10060(1) | 41(1)  |
| C(9)  | 2196(3) | 2165(2)  | 10525(1) | 36(1)  |
| C(10) | 2142(3) | 1467(2)  | 9960(1)  | 33(1)  |
| C(11) | 1948(3) | 75(2)    | 9985(1)  | 39(1)  |
| C(12) | 1914(4) | −574(2)  | 10537(1) | 47(1)  |
| C(13) | 2053(4) | 111(2)   | 11090(1) | 49(1)  |
| C(14) | 2179(3) | 1449(2)  | 11077(1) | 46(1)  |
| C(15) | 394(5)  | −2575(3) | 7835(1)  | 72(1)  |
| Cl(1) | 1654(2) | −2285(1) | 10550(1) | 79(1)  |
| N(1)  | 2317(3) | 1690(2)  | 8834(1)  | 44(1)  |
| N(2)  | 2029(3) | 4530(2)  | 8976(1)  | 46(1)  |
| N(3)  | 2205(3) | 3529(2)  | 10573(1) | 44(1)  |
| O(1)  | 3340(3) | −1422(2) | 7603(1)  | 56(1)  |
| O(2)  | 1960(3) | 4131(2)  | 8443(1)  | 59(1)  |
| O(3)  | 2016(4) | 5719(2)  | 9091(1)  | 78(1)  |

TABLE C

Bond lengths [Å] and angles [°] for C14.

| | |
|---|---|
| C(1)—C(2) | 1.518(3) |
| C(1)—C(5) | 1.521(3) |
| C(2)—O(1) | 1.425(3) |
| C(2)—C(15) | 1.517(3) |
| C(3)—O(1) | 1.421(3) |
| C(3)—C(4) | 1.507(4) |
| C(4)—C(5) | 1.522(3) |
| C(5)—N(1) | 1.464(3) |
| C(6)—N(1) | 1.336(2) |
| C(6)—C(7) | 1.418(3) |
| C(6)—C(10) | 1.456(3) |
| C(7)—C(8) | 1.396(3) |
| C(7)—N(2) | 1.436(3) |
| C(8)—N(3) | 1.304(3) |
| C(9)—N(3) | 1.378(3) |
| C(9)—C(14) | 1.406(3) |
| C(9)—C(10) | 1.422(3) |
| C(10)—C(11) | 1.409(3) |
| C(11)—C(12) | 1.374(3) |
| C(12)—C(13) | 1.395(3) |
| C(12)—Cl(1) | 1.733(2) |
| C(13)—C(14) | 1.351(3) |
| N(2)—O(3) | 1.223(2) |
| N(2)—O(2) | 1.236(3) |
| C(2)—C(1)—C(5) | 111.09(18) |
| O(1)—C(2)—C(15) | 107.09(19) |
| O(1)—C(2)—C(1) | 110.31(17) |
| C(15)—C(2)—C(1) | 112.5(2) |
| O(1)—C(3)—C(4) | 111.7(2) |
| C(3)—C(4)—C(5) | 109.98(19) |
| N(1)—C(5)—C(1) | 112.00(18) |
| N(1)—C(5)—C(4) | 108.27(17) |
| C(1)—C(5)—C(4) | 108.68(15) |
| N(1)—C(6)—C(7) | 121.25(17) |
| N(1)—C(6)—C(10) | 125.16(17) |
| C(7)—C(6)—C(10) | 113.60(16) |
| C(8)—C(7)—C(6) | 121.78(18) |
| C(8)—C(7)—N(2) | 115.67(17) |
| C(6)—C(7)—N(2) | 122.51(18) |
| N(3)—C(8)—C(7) | 125.41(18) |
| N(3)—C(9)—C(14) | 116.46(18) |
| N(3)—C(9)—C(10) | 123.97(19) |
| C(14)—C(9)—C(10) | 119.54(17) |
| C(11)—C(10)—C(9) | 117.44(18) |
| C(11)—C(10)—C(6) | 123.46(17) |
| C(9)—C(10)—C(6) | 119.03(16) |
| C(12)—C(11)—C(10) | 120.51(18) |
| C(11)—C(12)—C(13) | 121.77(19) |
| C(11)—C(12)—Cl(1) | 119.23(16) |
| C(13)—C(12)—Cl(1) | 119.00(17) |
| C(14)—C(13)—C(12) | 118.66(19) |
| C(13)—C(14)—C(9) | 121.96(19) |
| C(6)—N(1)—C(5) | 132.47(17) |
| O(3)—N(2)—O(2) | 120.82(18) |
| O(3)—N(2)—C(7) | 118.24(18) |
| O(2)—N(2)—C(7) | 120.93(17) |
| C(8)—N(3)—C(9) | 115.92(17) |
| C(3)—O(1)—C(2) | 111.14(16) |

Symmetry transformations used to generate equivalent atoms.

TABLE D

Anisotropic displacement parameters (Å$^2$ × 10$^3$) for C14. The anisotropic displacement factor exponent takes the form: $-2\pi^2[h^2 a^{*2}U^{11} + \ldots + 2 h k a^* b^* U^{12}]$.

|       | U11    | U22   | U33   | U23    | U13    | U12    |
|-------|--------|-------|-------|--------|--------|--------|
| C(1)  | 48(1)  | 44(1) | 31(1) | 0(1)   | −2(1)  | −4(1)  |
| C(2)  | 70(2)  | 38(1) | 33(1) | 0(1)   | −9(1)  | −3(1)  |
| C(3)  | 62(2)  | 71(2) | 45(1) | −12(1) | 15(1)  | 1(1)   |
| C(4)  | 61(1)  | 54(1) | 36(1) | −7(1)  | 12(1)  | −13(1) |
| C(5)  | 50(1)  | 38(1) | 24(1) | −5(1)  | 1(1)   | −2(1)  |
| C(6)  | 33(1)  | 38(1) | 30(1) | −4(1)  | 2(1)   | 0(1)   |
| C(7)  | 36(1)  | 36(1) | 38(1) | 0(1)   | 4(1)   | −1(1)  |
| C(8)  | 43(1)  | 35(1) | 44(1) | −9(1)  | 3(1)   | −1(1)  |
| C(9)  | 34(1)  | 44(1) | 31(1) | −8(1)  | 2(1)   | 6(1)   |
| C(10) | 30(1)  | 41(1) | 28(1) | −4(1)  | 4(1)   | 2(1)   |
| C(11) | 49(1)  | 40(1) | 28(1) | −4(1)  | 3(1)   | 2(1)   |
| C(12) | 60(1)  | 43(1) | 39(1) | 2(1)   | 6(1)   | 8(1)   |
| C(13) | 60(1)  | 57(1) | 29(1) | 6(1)   | 3(1)   | 15(1)  |
| C(14) | 53(1)  | 58(1) | 26(1) | −7(1)  | 2(1)   | 11(1)  |
| C(15) | 97(2)  | 53(2) | 65(2) | −7(1)  | −25(2) | −21(1) |
| Cl(1) | 138(1) | 40(1) | 60(1) | 9(1)   | 18(1)  | 5(1)   |
| N(1)  | 67(1)  | 36(1) | 29(1) | −3(1)  | 0(1)   | 3(1)   |
| N(2)  | 49(1)  | 40(1) | 47(1) | 5(1)   | 2(1)   | −1(1)  |
| N(3)  | 50(1)  | 44(1) | 37(1) | −12(1) | 0(1)   | 2(1)   |
| O(1)  | 82(1)  | 56(1) | 32(1) | −14(1) | 6(1)   | −2(1)  |
| O(2)  | 87(1)  | 53(1) | 38(1) | 8(1)   | 8(1)   | 3(1)   |
| O(3)  | 127(2) | 35(1) | 73(1) | 5(1)   | −4(1)  | −4(1)  |

TABLE E

Hydrogen coordinates (×10$^4$) and isotropic displacement parameters (Å$^2$ × 10$^3$) for C14.

|        | x        | y        | z         | U(eq) |
|--------|----------|----------|-----------|-------|
| H(1A)  | 451      | −690     | 8735      | 49    |
| H(1B)  | 515      | 31       | 8099      | 49    |
| H(2A)  | 2765     | −2251    | 8401      | 57    |
| H(3A)  | 5887     | −535     | 7470      | 71    |
| H(3B)  | 5704     | −1210    | 8114      | 71    |
| H(4A)  | 3779     | 1166     | 7777      | 60    |
| H(4B)  | 5569     | 1085     | 8231      | 60    |
| H(5)   | 3684     | −67      | 8945      | 45    |
| H(8)   | 2068     | 5104     | 10083     | 49    |
| H(11)  | 1842     | −409     | 9624      | 47    |
| H(13)  | 2060     | −345     | 11459     | 59    |
| H(14)  | 2257     | 1911     | 11444     | 55    |
| H(15A) | −305     | −2077    | 7531      | 108   |
| H(15B) | −495     | −2820    | 8157      | 108   |
| H(15C) | 938      | −3361    | 7654      | 108   |
| H(111) | 2170(50) | 2330(30) | 8481(13)  | 95    |

Step 3. Synthesis of 6-chloro-N⁴-[(2R,4R)-2-methyltetrahydro-2H-pyran-4-yl]quinoline-3,4-diamine (C15)

Zinc dust (97.5%, 12.3 g, 183 mmol) was added in one portion to a suspension of C14 (7.40 g, 23.0 mmol) in methanol (100 mL) and concentrated ammonium hydroxide (100 mL). After 1 hour, the reaction mixture was filtered through diatomaceous earth; the filter pad was rinsed with dichloromethane (70 mL). The filtrate was diluted with water, and the aqueous layer was extracted with dichloromethane (2×60 mL). The combined organic layers were dried over sodium sulfate, filtered, concentrated in vacuo, and purified via silica gel chromatography (Gradient: 40% to 100% ethyl acetate in heptane) to provide the product. Yield: 3.68 g, 12.6 mmol, 55%. $^1$H NMR (400 MHz, CDCl$_3$) δ 8.48 (s, 1H), 7.91 (d, J=8.9 Hz, 1H), 7.74 (d, J=2.2 Hz, 1H), 7.40 (dd, J=8.9, 2.2 Hz, 1H), 4.02 (br dd, J=12, 5 Hz, 1H), 3.88 (br s, 2H), 3.29-3.56 (m, 4H), 1.82-1.96 (m, 2H), 1.56 (dddd, J=12, 12, 12, 5 Hz, 1H), 1.21-1.31 (m, 1H), 1.21 (d, J=6.2 Hz, 3H).

Step 4. Synthesis of 8-chloro-2-[(5-methoxypyridin-2-yl)methyl]-1-[(2R,4R)-2-methyltetrahydro-2H-pyran-4-yl]-1H-imidazo[4,5-c]quinoline (2)

To a mixture of C15 (400 mg, 1.37 mmol) and (5-methoxypyridin-2-yl)acetic acid (229 mg, 1.37 mmol) in N,N-dimethylformamide (3 mL) was added N,N-diisopropylethylamine (532 mg, 4.12 mmol) and 2,4,6-tripropyl-1,3,5,2,4,6-trioxatriphosphinane 2,4,6-trioxide (1.31 g, 4.12 mmol, as a 50% solution in ethyl acetate). The reaction mixture was heated at 100° C. overnight, whereupon it was cooled to room temperature, combined with two similar, small-scale, reactions carried out on C15 (total of 40 mg, 0.14 mmol) and diluted with water (100 mL). The resulting mixture was extracted with dichloromethane (2×200 mL), and the combined organic layers were concentrated in vacuo. Silica gel chromatography (Eluent: 2% methanol in ethyl acetate), followed by reversed phase HPLC (Column: DIKMA Diamonsil (2) C18, 5 μm; Mobile phase A: 0.225% formic acid in water; Mobile phase B: acetonitrile; Gradient: 22% to 42% B), afforded the product as a yellow solid. Yield: 147 mg, 0.348 mmol, 23%. LCMS m/z 423.0 [M+H]⁺. $^1$H NMR (400 MHz, CD$_3$OD) δ 9.16 (s, 1H), 8.70-8.82 (br m, 1H), 8.17-8.22 (m, 2H), 7.75 (dd, J=8.8, 2.1 Hz, 1H), 7.35-7.43 (m, 2H), 5.23-5.42 (br m, 1H), 4.69 (s, 2H), 4.18-4.26 (m, 1H), 3.86 (s, 3H), 3.61-3.76 (br m, 2H), 2.56-2.69 (br m, 1H), 2.24-2.41 (br m, 1H), 1.75-1.91 (br m, 1H), 1.61-1.75 (br m, 1H), 1.28 (d, J=6.2 Hz, 3H).

Example 3

2-[(5-Methyl-1,2-oxazol-3-yl)methyl]-1-[(2R,4R)-2-methyltetrahydro-2H-pyran-4-yl]-1H-imidazo[4,5-c]quinoline-8-carbonitrile (3)

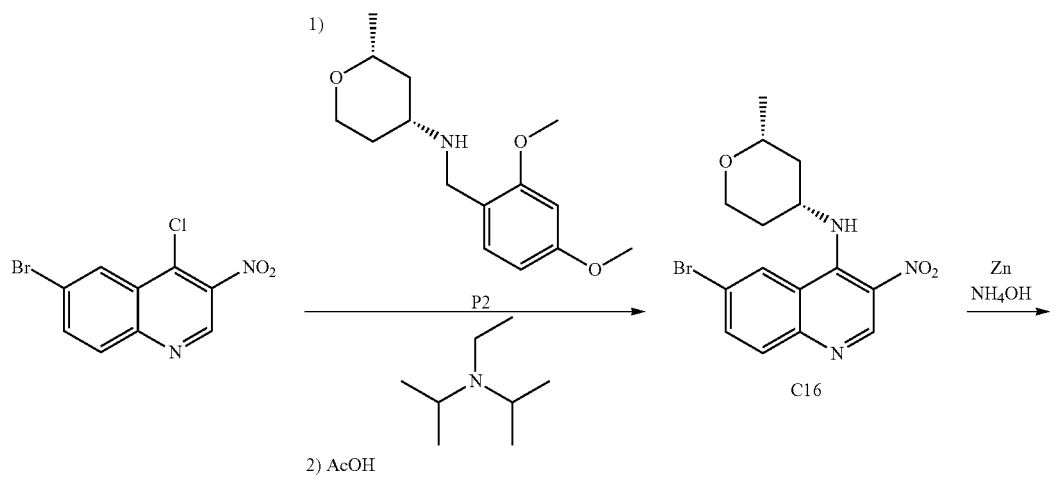

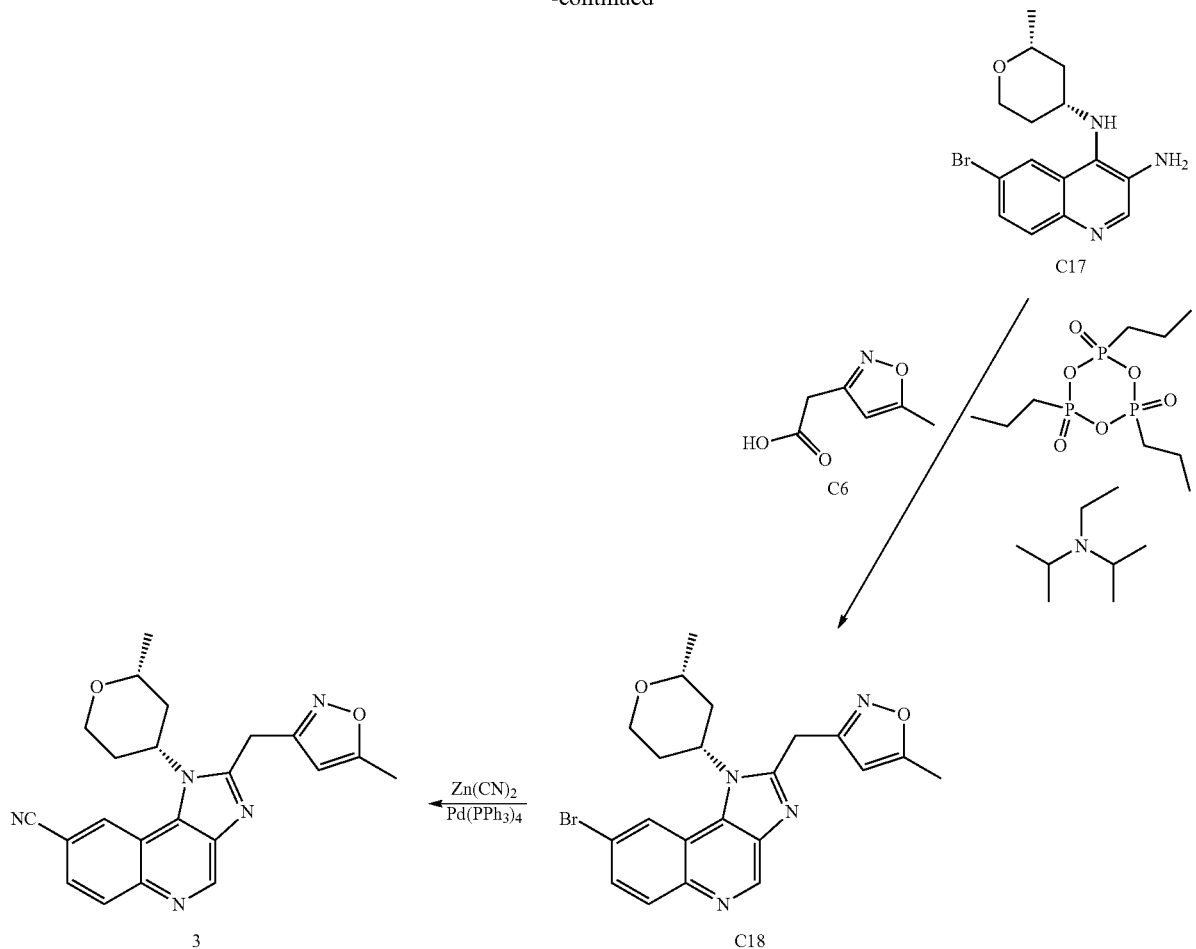

Step 1. Synthesis of 6-bromo-N-[(2R,4R)-2-methyl-tetrahydro-2H-pyran-4-yl]-3-nitroquinolin-4-amine (C16)

6-Bromo-4-chloro-3-nitroquinoline (1.93 g, 6.71 mmol) was added to a solution of P2 (2.35 g, 8.86 mmol) and N,N-diisopropylethylamine (3.4 mL, 20 mmol) in acetonitrile (39 mL), and the reaction mixture was heated to 45° C. for 18 hours. Acetic acid (1.8 mL, 24 mmol) was then added, and stirring was continued for 5 hours at 100° C., whereupon the reaction mixture was allowed to cool to room temperature and stir for 18 hours. After solvent had been removed in vacuo, the residue was taken up in dichloromethane and washed with saturated aqueous sodium bicarbonate solution. The organic layer was loaded onto a silica gel column and eluted (Gradient: 0% to 5% methanol in dichloromethane), affording the product as a brown oil. Yield: 1.40 g, 3.82 mmol, 57%. LCMS m/z 366.0, 368.2 [M+H]$^+$. $^1$H NMR (400 MHz, CDCl$_3$) δ 9.37 (s, 1H), 9.13 (br d, J=9 Hz, 1H), 8.30 (br d, J=2.0 Hz, 1H), 7.91 (br d, half of AB quartet, J=8.8 Hz, 1H), 7.86 (dd, half of ABX pattern, J=8.9, 2.0 Hz, 1H), 4.21-4.32 (m, 1H), 4.12 (ddd, J=12.1, 4.7, 1.7 Hz, 1H), 3.52-3.60 (m, 2H), 2.11-2.21 (m, 2H), 1.78 (dddd, J=12, 12, 11, 5 Hz, 1H), 1.49 (ddd, J=13, 11, 11 Hz, 1H), 1.28 (d, J=6.2 Hz, 3H).

Step 2. Synthesis of 6-bromo-N$^4$-[(2R,4R)-2-methyltetrahydro-2H-pyran-4-yl]quinoline-3,4-diamine (C17)

Zinc (97.5%, 2.33 g, 34.7 mmol) was added in one portion to a 0° C. suspension of C16 (1.40 g, 3.82 mmol) in methanol (6 mL) and concentrated ammonium hydroxide (6 mL), and the reaction mixture was stirred at 0° C. for 30 minutes. It was then allowed to warm to room temperature and stir for 45 minutes, whereupon it was filtered through diatomaceous earth. The filter cake was rinsed with dichloromethane, and the combined filtrates were diluted with water. The aqueous layer was extracted with dichloromethane, and the combined organic layers were dried over magnesium sulfate, filtered, and concentrated in vacuo. Silica gel chromatography (Gradient: 0% to 3% methanol in dichloromethane) provided the product as a tan foam. Yield: 836 mg, 2.49 mmol, 65%. LCMS m/z 336.1, 338.2 [M+H]$^+$. $^1$H NMR (400 MHz, CDCl$_3$) δ 8.49 (s, 1H), 7.92 (d, J=2.1 Hz, 1H), 7.84 (d, J=8.8 Hz, 1H), 7.53 (dd, J=8.9, 2.1 Hz, 1H), 4.03 (ddd, J=11.8, 4.7, 1.7 Hz, 1H), 3.88 (br s, 2H), 3.33-3.56 (m, 4H), 1.82-1.96 (m, 2H), 1.50-1.62 (m, 1H), 1.26 (ddd, J=12, 11, 11 Hz, 1H), 1.21 (d, J=6.2 Hz, 3H).

Step 3. Synthesis of 8-bromo-2-[(5-methyl-1,2-oxazol-3-yl)methyl]-1-[(2R,4R)-2-methyltetrahydro-2H-pyran-4-yl]-1H-imidazo[4,5-c]quinoline (C18)

A mixture of C17 (836 mg, 2.49 mmol), C6 (281 mg, 1.99 mmol), 2,4,6-tripropyl-1,3,5,2,4,6-trioxatriphosphinane 2,4,6-trioxide (50% solution in ethyl acetate, 1.9 mL, 3.2 mmol), and N,N-diisopropylethylamine (0.87 mL, 5.0 mmol) in ethyl acetate (10 mL) was stirred at 50° C. overnight. Acetic acid (1 equivalent) was added, and heating was continued at 115° C. for 5 hours, whereupon the reaction mixture was allowed to cool to room temperature and stir for 18 hours. After removal of volatiles in vacuo, the residue was taken up in dichloromethane and washed with saturated aqueous sodium bicarbonate solution. The organic layer was loaded onto a silica gel column and eluted (Gradient: 0% to 5% methanol in dichloromethane) to provide the product as a tan solid. Yield: 507 mg, 1.15 mmol, 58%. LCMS m/z 441.2, 443.3 [M+H]$^+$.

Step 4. Synthesis of 2-[(5-methyl-1,2-oxazol-3-yl)methyl]-1-[(2R,4R)-2-methyltetrahydro-2H-pyran-4-yl]-1H-imidazo[4,5-c]quinoline-8-carbonitrile (3)

Tetrakis(triphenylphosphine)palladium(0) (262 mg, 0.227 mmol) was added to a mixture of C18 (500 mg, 1.13 mmol) and zinc cyanide (99%, 644 mg, 5.43 mmol) in N,N-dimethylformamide (5 mL), and the reaction flask was subjected to three cycles of evacuation followed by nitrogen fill. The reaction mixture was then heated at 100° C. for 20 hours, whereupon it was partitioned between water and ethyl acetate, and filtered through diatomaceous earth. The filter cake was rinsed with ethyl acetate, and the aqueous layer from the combined filtrates was extracted twice with ethyl acetate. The combined organic layers were washed 5 times with water, dried over magnesium sulfate, filtered, and concentrated in vacuo. Silica gel chromatography (Gradient, 0% to 3% methanol in methylene chloride) provided a mixture of product and C18 (324 mg, ~1:1), so this material was resubjected to the reaction conditions. Tetrakis(triphenylphosphine)palladium(0) (172 mg, 0.149 mmol) was added to a mixture of zinc cyanide (99%, 422 mg, 3.56 mmol) and the material containing C18 and 3 (324 mg) in N,N-dimethylformamide (2 mL), and the reaction flask was subjected to three cycles of evacuation followed by nitrogen fill. The reaction mixture was then heated at 100° C. for 2 hours, partitioned between water and ethyl acetate, and filtered through diatomaceous earth. The filter cake was rinsed with ethyl acetate and with water, and the aqueous layer from the combined filtrates was extracted twice with ethyl acetate. The combined organic layers were washed 5 times with water, dried over magnesium sulfate, filtered, and concentrated in vacuo. Silica gel chromatography (Gradient: 0% to 5% methanol in dichloromethane) yielded an oil, which was triturated with diethyl ether to afford a tan solid. This was recrystallized from ethyl acetate/heptane to provide the product as an off-white solid. Yield: 97 mg, 0.25 mmol, 22%. LCMS m/z 388.2 [M+H]$^+$. $^1$H NMR (400 MHz, CDCl$_3$) δ 9.41 (s, 1H), 8.9-9.1 (br m, 1H), 8.38 (d, J=8.7 Hz, 1H), 7.86 (dd, J=8.6, 1.5 Hz, 1H), 6.02 (br s, 1H), 5.15-5.28 (br m, 1H), 4.53 (s, 2H), 4.32 (br dd, J=12, 5 Hz, 1H), 3.66-3.79 (br m, 2H), 2.53-2.69 (br m, 1H), 2.41 (s, 3H), 2.23-2.4 (br m, 1H), 1.66-1.96 (br m, 2H), 1.36 (d, J=6.2 Hz, 3H).

Example 4

8-Chloro-2-[(5-methyl-1,2-oxazol-3-yl)methyl]-1-[(2R,4R)-2-methyltetrahydro-2H-pyran-4-yl]-1H-imidazo[4,5-c]quinoline (4)

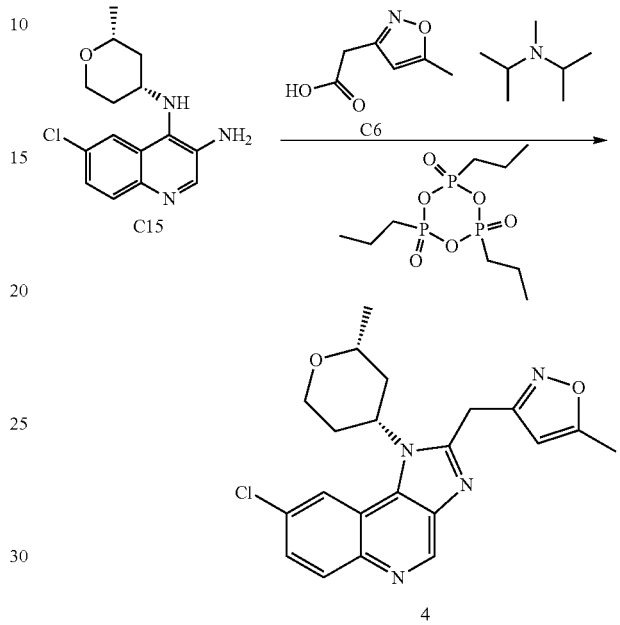

A mixture of C15 (400 mg, 1.4 mmol), (5-methyl-1,2-oxazol-3-yl)acetic acid (155 mg, 1.10 mmol), 2,4,6-tripropyl-1,3,5,2,4,6-trioxatriphosphinane 2,4,6-trioxide (50% solution in ethyl acetate, 1.0 mL, 1.7 mmol), and N,N-diisopropylethylamine (0.48 mL, 2.8 mmol) in ethyl acetate (10 mL) was stirred at 50° C. overnight. The reaction mixture was concentrated in vacuo to remove most of the ethyl acetate, then diluted with acetic acid and heated to 115° C. When the reaction was judged to be complete by LCMS analysis, the reaction mixture was concentrated under reduced pressure, taken up in dichloromethane, and washed with saturated aqueous sodium bicarbonate solution. The aqueous layer was extracted once with dichloromethane, and the combined organic layers were adsorbed onto silica gel and chromatographed (Eluent: ethyl acetate). The product (405 mg) was mixed with diethyl ether and allowed to stir for 2 days, whereupon the solid was collected by filtration and washed with a mixture of 3:1 heptane/diethyl ether, to afford the product (239 mg) as a solid. This material was shown to be crystalline via powder X-ray diffraction. The combined filtrates were concentrated in vacuo, mixed with diethyl ether (4 mL), and stirred for 2 hours, whereupon heptane (1 mL) was added. After 2 hours, heptane (2 mL) was again added, and stirring was continued overnight. Additional heptane (1 mL) was added, and after stirring overnight once more, the solid present was isolated via filtration and rinsed with heptane, to provide additional product (99 mg). Total yield: 338 mg, 0.852 mmol, 77%. LCMS m/z 397.3, 399.3 [M+H]$^+$. $^1$H NMR (400 MHz, CDCl$_3$), characteristic peaks: δ 9.29 (s, 1H), 8.58-8.73 (br m, 1H), 8.23 (d, J=9.0 Hz, 1H), 7.64 (dd, J=8.8, 2.0 Hz, 1H), 6.00 (br s, 1H), 5.09-5.25 (br m, 1H), 4.51 (s, 2H), 4.30 (br dd, J=12, 5 Hz, 1H), 3.65-3.79 (br m, 2H), 2.59-2.77 (br m, 1H), 2.40 (s, 3H), 2.32-2.47 (m, 1H), 1.73-1.88 (br m, 1H), 1.35 (d, J=6.2 Hz, 3H).

Example 5

8-Chloro-2-[(5-methyl-1,2,4-oxadiazol-3-yl)methyl]-1-[(2R,4R)-2-methyltetrahydro-2H-pyran-4-yl]-1H-imidazo[4,5-c]quinoline (5)

acid (1 M, 500 mL), and the aqueous layer was extracted with ethyl acetate (2×100 mL); the combined organic layers were washed with saturated aqueous sodium bicarbonate solution (1 L) until the pH reached 7, then dried over sodium sulfate, filtered, and concentrated under reduced pressure. Silica gel chromatography (Gradient: 0% to 20% ethyl acetate in petroleum ether) afforded the product as a colorless oil. Yield: 20.0 g, 118 mmol, 21%. $^1$H NMR (400 MHz, CDCl$_3$) δ 4.20 (q, J=7.1 Hz, 2H), 3.76 (s, 2H), 2.58 (s, 3H), 1.26 (t, J=7.2 Hz, 3H).

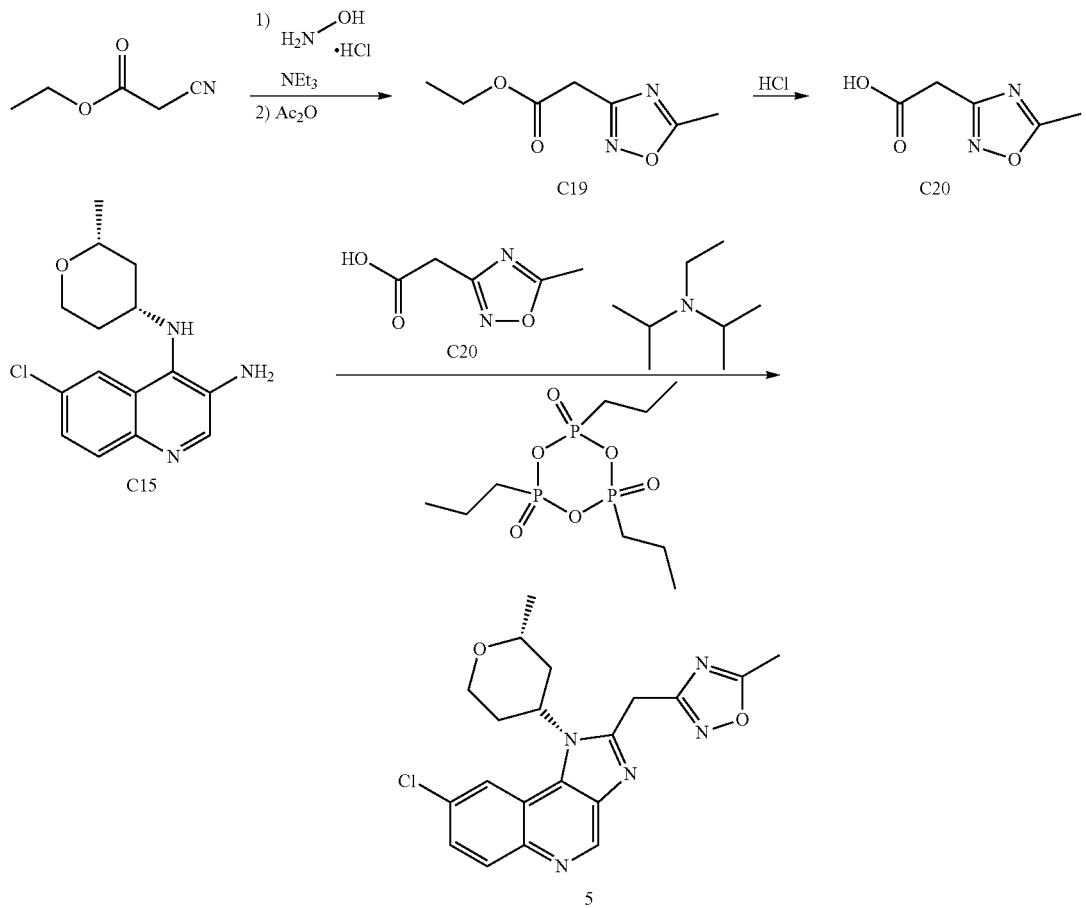

Step 1. Synthesis of ethyl (5-methyl-1,2,4-oxadiazol-3-yl)acetate (C19)

This experiment was carried out in two identical batches. To a 0° C. mixture of hydroxylamine hydrochloride (39.3 g, 566 mmol) in ethanol (1.2 L) was added triethylamine (86 g, 850 mmol). After this mixture had stirred for 10 minutes, ethyl cyanoacetate (32 g, 280 mmol) was added drop-wise, and the reaction mixture was allowed to warm to room temperature and stir overnight. Additional triethylamine (86 g, 850 mmol) was introduced, followed by acetic anhydride (89.5 g, 877 mmol), and stirring was continued for 2 hours at room temperature. The reaction mixture was then stirred overnight at 90° C. At this point, the two batches were combined and concentrated in vacuo. The residue was partitioned between ethyl acetate (1 L) and hydrochloric Step 2. Synthesis of (5-methyl-1,2,4-oxadiazol-3-yl)acetic acid (C20)

A mixture of C19 (4.30 g, 25.3 mmol) and hydrochloric acid (2 M, 50 mL, 100 mmol) was stirred for 2 days at room temperature, then warmed to 50° C. for 2 days. Concentrated hydrochloric acid (2 mL) was added, and heating was continued at 50° C. for 66 hours, whereupon the reaction mixture was cooled to room temperature and concentrated in vacuo, to a volume of approximately 10 mL. This was extracted eight times with dichloromethane, and the combined organic layers were dried over magnesium sulfate, filtered, and concentrated under reduced pressure to afford the product as a white solid. Yield: 2.85 g, 20.1 mmol, 79%. $^1$H NMR (400 MHz, CDCl$_3$) δ 9.43 (br s, 1H), 3.86 (s, 2H), 2.62 (s, 3H).

Step 3. Synthesis of 8-chloro-2-[(5-methyl-1,2,4-oxadiazol-3-yl)methyl]-1-[(2R,4R)-2-methyltetrahydro-2H-pyran-4-yl]-1H-imidazo[4,5-c]quinoline (5)

A mixture of C15 (770 mg, 2.64 mmol), C20 (300 mg, 2.11 mmol), 2,4,6-tripropyl-1,3,5,2,4,6-trioxatriphosphinane 2,4,6-trioxide (50% solution in ethyl acetate, 2.0 mL, 3.4 mmol), and N,N-diisopropylethylamine (0.92 mL, 5.3 mmol) in ethyl acetate (10 mL) was heated at 60° C. for 2 hours, then at reflux for 2 hours. Additional 2,4,6-tripropyl-1,3,5,2,4,6-trioxatriphosphinane 2,4,6-trioxide (50% solution in ethyl acetate, 2.0 mL, 3.4 mmol) was introduced, and heating at reflux was continued overnight. The reaction mixture was concentrated in vacuo to remove the majority of the ethyl acetate, then diluted with acetic acid and heated to 100° C. overnight. After removal of solvents under reduced pressure, the residue was taken up in dichloromethane and washed with saturated aqueous sodium bicarbonate solution; the aqueous layer was extracted with dichloromethane, and the combined organic layers were adsorbed onto diatomaceous earth and chromatographed using silica gel (Gradient: 0% to 5% methanol in dichloromethane). The product (739 mg) was mixed with diethyl ether (7 mL) and stirred for 2 days. The resulting solid was collected via filtration and rinsed with 3:1 heptane/diethyl ether, affording the product as an off-white solid (329 mg). The combined filtrates were concentrated in vacuo, dissolved in diethyl ether (3 mL) and stirred for 2 days. Filtration and washing of the filter cake with 3:1 heptane/diethyl ether provided additional product as an off-white solid. Combined yield: 390 mg, 0.98 mmol, 46%. LCMS m/z 398.2, 400.2 [M+H]$^+$. $^1$H NMR (400 MHz, CDCl$_3$) δ 9.29 (s, 1H), 8.56-8.78 (br m, 1H), 8.24 (d, J=8.8 Hz, 1H), 7.65 (dd, J=8.9, 1.9 Hz, 1H), 4.94-5.17 (br m, 1H), 4.60 (s, 2H), 4.28-4.39 (m, 1H), 3.63-3.81 (br m, 2H), 2.67-2.88 (br m, 1H), 2.60 (s, 3H), 2.38-2.6 (br m, 1H), 1.80-2.08 (br m, 2H), 1.38 (d, J=6.2 Hz, 3H).

Compared to Example 5, the enantiomer of Example 5 (Example 51) proved to be significantly less potent (See Table 3 for biological activity data). The absolute configurations of separated enantiomers described herein were assigned on the basis of their relative biological activity in accordance with these two compounds.

Example 6

8-Bromo-1-[(1S,3R)-3-fluorocyclopentyl]-2-methyl-1H-imidazo[4,5-c]quinoline (6)

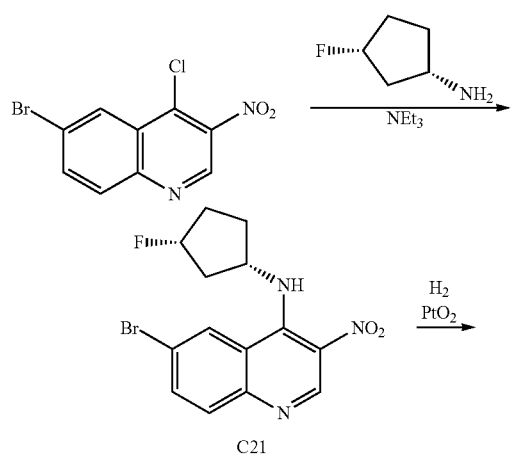

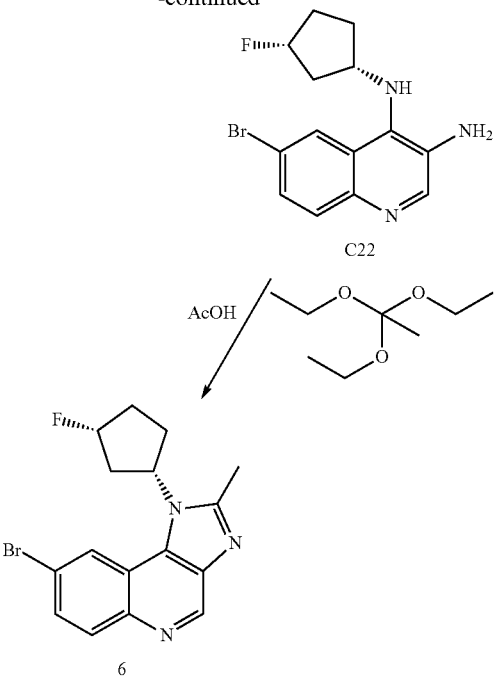

Step 1. Synthesis of 6-bromo-N-[(1S,3R)-3-fluorocyclopentyl]-3-nitroquinolin-4-amine (C21)

Triethylamine (364 mg, 3.60 mmol) was added to a mixture of 6-bromo-4-chloro-3-nitroquinoline (515 mg, 1.79 mmol) and (1S,3R)-3-fluorocyclopentanamine (250 mg, 2.4 mmol) in tetrahydrofuran (10 mL), and the reaction mixture was heated at 45° C. for 2 hours. It was then diluted with water (50 mL) and extracted with ethyl acetate (3×20 mL); the combined organic layers were washed with saturated aqueous sodium chloride solution (100 mL), dried over sodium sulfate, filtered, and concentrated in vacuo, providing the product as a yellow solid. Yield: 439 mg, 1.24 mmol, 69%. LCMS m/z 355.6 [M+H]$^+$.

Step 2. Synthesis of 6-bromo-N$^4$-[(1S,3R)-3-fluorocyclopentyl]quinoline-3,4-diamine (C22)

To a mixture of C21 (500 mg, 1.4 mmol) in methanol (50 mL) and acetonitrile (10 mL) was added platinum(IV) oxide (50 mg, 0.22 mmol). The suspension was degassed and purged with hydrogen three times, whereupon the reaction mixture was stirred at room temperature for 1.5 hours under a balloon of hydrogen. After filtration of the reaction mixture, the filter cake was washed with acetonitrile (3×10 mL), and the combined filtrates were concentrated in vacuo to provide the product as a yellow oil. Yield: 400 mg, 1.2 mmol, 86%. LCMS m/z 323.8 [M+H]$^+$.

Step 3. Synthesis of 8-bromo-1-[(1S,3R)-3-fluorocyclopentyl]-2-methyl-1H-imidazo[4,5-c]quinoline (6)

A solution of C22 (90 mg, 0.28 mmol) and acetic acid (catalytic quantity) in 1,1,1-triethoxyethane (5 mL) was stirred at 110° C. overnight, whereupon the reaction mixture was concentrated in vacuo. Purification via reversed phase HPLC (Column: YMC-Actus Triart C18, 5 μm; Mobile phase A: 0.225% formic acid in water; Mobile phase B: acetonitrile; Gradient: 25% to 45% B) provided the product as a yellow solid. Yield: 30.2 mg, 86.7 μmol, 31%. LCMS m/z 350.0 [M+H]$^+$. $^1$H NMR (400 MHz, DMSO-d$_6$) δ 9.22 (s, 1H), 8.69-8.73 (m, 1H), 8.11 (d, J=9.0 Hz, 1H), 7.86 (dd, J=8.9, 1.9 Hz, 1H), 5.40-5.53 (m, 1.5H), 5.31-5.38 (m, 0.5H), 2.8-2.96 (m, 1H), 2.78 (s, 3H), 2.01-2.5 (m, 5H).

Example 7
1-[(2R,4R)-2-Methyltetrahydro-2H-pyran-4-yl]-2-(1,3-thiazol-4-ylmethyl)-1H-imidazo[4,5-c][1,5]naphthyridine (7)
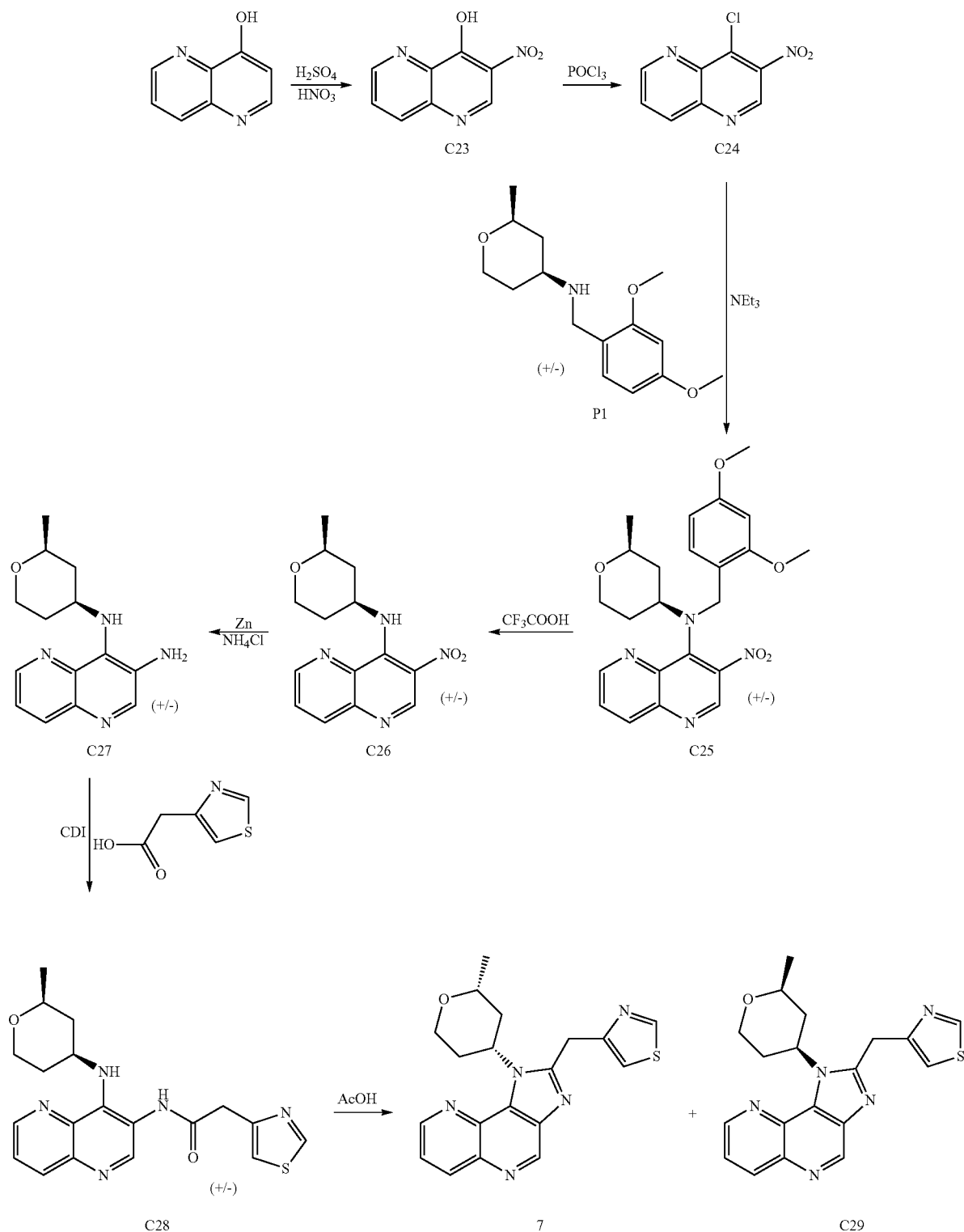

Step 1. Synthesis of 3-nitro-1,5-naphthyridin-4-ol (C23)

Concentrated nitric acid (1.5 mL) was added to a solution of 1,5-naphthyridin-4-ol (600 mg, 4.1 mmol) in concentrated sulfuric acid (4.5 mL), and the reaction mixture was stirred at 90° C. overnight. It was then poured into water, cooled in an ice bath, and adjusted to a pH of 6-7 by addition of aqueous ammonium hydroxide. The resulting mixture was stirred in the ice bath for 10 minutes, then filtered; the collected solid was washed with water to afford the product as a yellow solid. Yield: 0.60 g, 3.1 mmol, 76%. $^1$H NMR (400 MHz, DMSO-$d_6$) δ 8.96 (s, 1H), 8.55-8.60 (m, 1H), 7.98 (br d, J=8.2 Hz, 1H), 7.54 (dd, J=8.3, 4.3 Hz, 1H).

Step 2. Synthesis of 4-chloro-3-nitro-1,5-naphthyridine (C24)

Phosphorus oxychloride (624 mg, 4.08 mmol) was added drop-wise to a solution of C23 (0.60 g, 3.1 mmol) in N,N-dimethylformamide (10 mL). The reaction mixture was stirred at room temperature for 2 hours, whereupon it was poured into ice water (80 mL). The resulting mixture was filtered and the filter cake was washed with water (30 mL), affording the product as a yellow solid. Yield: 0.36 g, 1.7 mmol, 55%. $^1$H NMR (400 MHz, DMSO-$d_6$) δ 9.50 (s, 1H), 9.28 (dd, J=4.1, 1.5 Hz, 1H), 8.65 (dd, J=8.5, 1.5 Hz, 1H), 8.09 (dd, J=8.5, 4.1 Hz, 1H).

Step 3. Synthesis of N-(2,4-dimethoxybenzyl)-N-(cis-2-methyltetrahydro-2H-pyran-4-yl)-3-nitro-1,5-naphthyridin-4-amine (C25)

Triethylamine (580 mg, 5.7 mmol) was added to a mixture of C24 (600 mg, 2.9 mmol) and P1 (761 mg, 2.87 mmol) in N,N-dimethylformamide (10 mL). The reaction mixture was heated at 50° C. for 1 hour, whereupon it was diluted with water (50 mL) and extracted with ethyl acetate (3×30 mL). After the combined organic layers had been washed with saturated aqueous sodium chloride solution (100 mL), they were dried over sodium sulfate, filtered, and concentrated in vacuo. Chromatography on silica gel (Gradient: 0% to 40% ethyl acetate in petroleum ether) provided the product as a yellow solid. Yield: 1.0 g, 2.3 mmol, 80%. $^1$H NMR (400 MHz, CDCl$_3$) δ 8.96 (s, 1H), 8.90 (dd, J=4.1, 1.7 Hz, 1H), 8.29 (dd, J=8.5, 1.7 Hz, 1H), 7.65 (dd, J=8.5, 4.1 Hz, 1H), 6.89 (d, J=9.0 Hz, 1H), 6.16-6.20 (m, 2H), 4.76-4.86 (m, 1H), 4.56 (AB quartet, $J_{AB}$=16.1 Hz, $\Delta v_{AB}$=18.6 Hz, 2H), 4.07-4.14 (m, 1H), 3.69 (s, 3H), 3.47-3.55 (m, 2H), 3.46 (s, 3H), 2.25-2.34 (m, 2H), 2.04-2.16 (m, 1H), 1.76-1.88 (m, 1H), 1.27 (d, J=6.3 Hz, 3H).

Step 4. Synthesis of N-(cis-2-methyltetrahydro-2H-pyran-4-yl)-3-nitro-1,5-naphthyridin-4-amine (C26)

A mixture of C25 (1.0 g, 2.3 mmol) and trifluoroacetic acid (20 mL) was stirred at room temperature for 30 minutes, whereupon it was concentrated in vacuo. After the residue had been adjusted to a pH of 7-8 via addition of saturated aqueous sodium bicarbonate solution (100 mL), it was extracted with ethyl acetate (3×30 mL). The combined organic layers were washed with saturated aqueous sodium chloride solution (100 mL), dried over sodium sulfate, filtered, and concentrated under reduced pressure to afford the product as a yellow solid. Yield: 0.60 g, 2.1 mmol, 91%. $^1$H NMR (400 MHz, CDCl$_3$), characteristic peaks: δ 9.41 (br s, 1H), 8.83 (dd, J=4.1, 1.6 Hz, 1H), 8.29 (br dd, J=8.4, 1.6 Hz, 1H), 7.69 (dd, J=8.5, 4.1 Hz, 1H), 4.11 (br dd, J=12, 4 Hz, 1H), 3.59-3.69 (m, 2H), 2.15-2.30 (m, 2H), 1.61-1.74 (m, 1H), 1.35-1.45 (m, 1H), 1.28 (d, J=6.3 Hz, 3H).

Step 5. Synthesis of N$^4$-(cis-2-methyltetrahydro-2H-pyran-4-yl)-1,5-naphthyridine-3,4-diamine (C27)

To a suspension of C26 (600 mg, 2.1 mmol) in tetrahydrofuran (10 mL) and water (5 mL) was added zinc dust (677 mg, 10.4 mmol) and ammonium chloride (551 mg, 10.3 mmol). The reaction mixture was then stirred at 60° C. for 40 minutes, whereupon it was diluted with water (50 mL) and extracted with ethyl acetate (3×50 mL). The combined organic layers were washed with saturated aqueous sodium chloride solution (100 mL), dried over sodium sulfate, filtered, and concentrated in vacuo to afford the product as a yellow solid. Yield: 0.40 g, 1.5 mmol, 71%. LCMS m/z 259.0 [M+H]$^+$.

Step 6. Synthesis of N-{4-[(cis-2-methyltetrahydro-2H-pyran-4-yl)amino]-1,5-naphthyridin-3-yl}-2-(1,3-thiazol-4-yl)acetamide (C28)

1,1'-Carbonyldiimidazole (CDI, 250 mg, 1.54 mmol) was added to a mixture of C27 (200 mg, 0.77 mmol) and 1,3-thiazol-4-ylacetic acid (138 mg, 0.964 mmol) in N,N-dimethylformamide (3 mL). The reaction mixture was heated at 50° C. overnight, whereupon it was diluted with water (30 mL) and extracted with ethyl acetate (3×30 mL). The combined organic layers were washed with saturated aqueous sodium chloride solution (100 mL), dried over sodium sulfate, filtered, and concentrated under reduced pressure to afford the product, which was carried directly into the following step. LCMS m/z 384.2 [M+H]$^+$.

Step 7. Synthesis of 1-[(2R,4R)-2-methyltetrahydro-2H-pyran-4-yl]-2-(1,3-thiazol-4-ylmethyl)-1H-imidazo[4,5-c][1,5]naphthyridine (7) and 1-[(2S,4S)-2-methyltetrahydro-2H-pyran-4-yl]-2-(1,3-thiazol-4-ylmethyl)-1H-imidazo[4,5-c][1,5]naphthyridine (C29)

Compound C28 (from the previous step, 295 mg, <0.77 mmol) and acetic acid (2 mL) were combined in a sealed tube and heated in a microwave reactor at 155° C. for 20 minutes. The reaction mixture was concentrated in vacuo and purified by reversed phase HPLC (Column: YMC-Actus Triart C18, 5 μm; Mobile phase A: 0.225% formic acid in water; Mobile phase B: acetonitrile; Gradient: 23% to 43% B) to afford a racemic mixture of the products as a yellow solid. Yield: 25 mg, 68 μmol, 9% over 2 steps. The component enantiomers were separated via supercritical fluid chromatography (Column: Chiralcel OD-3, 3 μm; Mobile phase A: carbon dioxide; Mobile phase B: methanol containing 0.05% diethylamine; Gradient: 5% to 40% B).

Example 7, the second-eluting enantiomer, was isolated as a yellow solid. Yield: 9.0 mg, 25 μmol, 3% over two steps. Retention time: 6.37 minutes (Analytical column: Chiralcel OD-3, 4.6×150 mm, 3 μm; same gradient as above; Flow rate: 1.5 mL/minute). LCMS m/z 366.0 [M+H]$^+$. $^1$H NMR (400 MHz, DMSO-$d_6$) δ 9.26 (s, 1H), 9.05 (d, J=1.9 Hz, 1H), 9.02 (dd, J=4.3, 1.6 Hz, 1H), 8.53 (dd, J=8.5, 1.7 Hz, 1H), 7.74 (dd, J=8.5, 4.3 Hz, 1H), 7.65 (br s, 1H), 4.86-5.05 (br m, 1H), 4.76 (s, 2H), 3.96-4.05 (m, 1H), 3.44-3.60 (m, 2H), 3.13-3.3 (br m, 1H), 2.85-3.07 (br m, 1H), 1.31-1.55 (br m, 2H), 1.13 (d, J=6.2 Hz, 3H).

Enantiomer C29 eluted first, and was also isolated as a yellow solid. Yield: 6.5 mg, 18 μmol, 2% over two steps. Retention time: 6.16 minutes using an identical analytical HPLC system. LCMS m/z 366.0 [M+H]$^+$. $^1$H NMR (400 MHz, DMSO-d$_6$) δ 9.26 (s, 1H), 9.05 (d, J=2.0 Hz, 1H), 9.02 (dd, J=4.1, 1.6 Hz, 1H), 8.53 (dd, J=8.4, 1.6 Hz, 1H), 7.74 (dd, J=8.4, 4.3 Hz, 1H), 7.65 (br s, 1H), 4.86-5.05 (br m, 1H), 4.76 (s, 2H), 3.97-4.04 (m, 1H), 3.44-3.60 (m, 2H), 3.14-3.28 (br m, 1H), 2.86-3.08 (br m, 1H), 1.31-1.56 (br m, 2H), 1.13 (d, J=6.2 Hz, 3H).

Example 8

8-Chloro-2-(imidazo[2,1-b][1,3,4]thiadiazol-6-ylmethyl)-1-[(2R,4R)-2-methyltetrahydro-2H-pyran-4-yl]-1H-imidazo[4,5-c]quinoline (8)

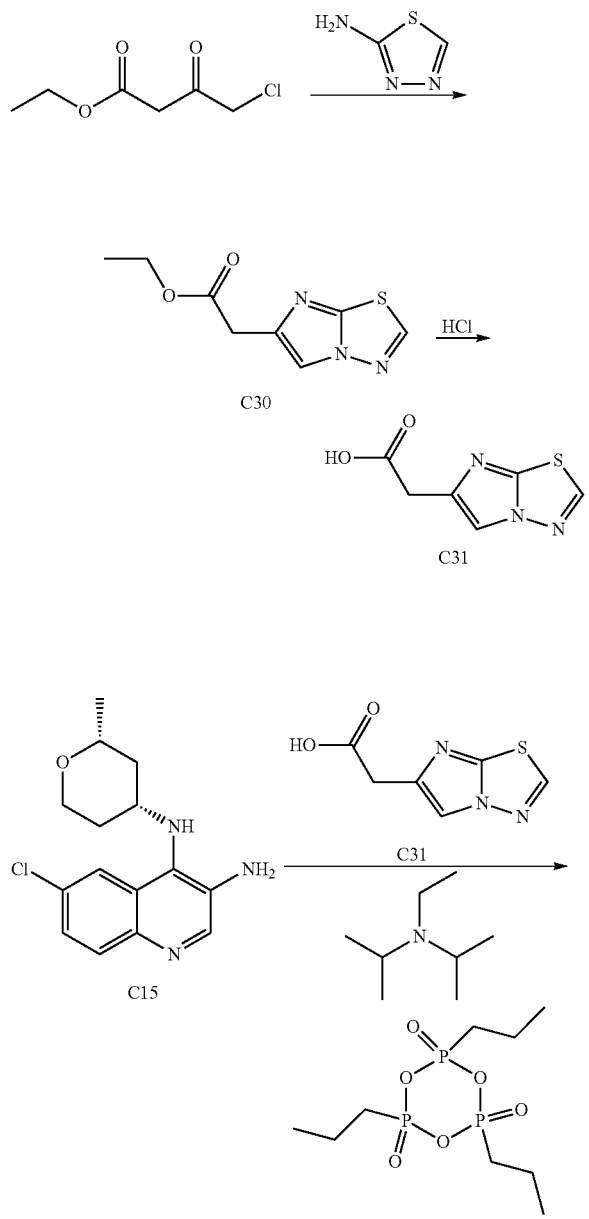

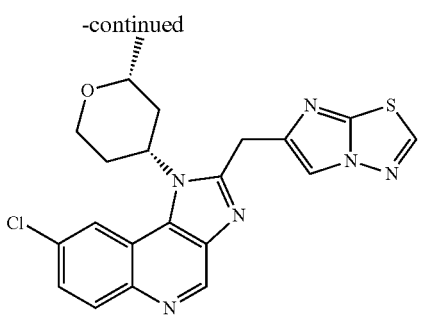

Step 1. Synthesis of ethyl imidazo[2,1-b][1,3,4]thiadiazol-6-ylacetate (C30)

A solution of 1,3,4-thiadiazol-2-amine (3.0 g, 30 mmol) and ethyl 4-chloro-3-oxobutanoate (7.4 g, 45 mmol) in anhydrous ethanol (50 mL) was heated at reflux for 24 hours, whereupon the reaction mixture was concentrated in vacuo. The residue was dissolved in 10% hydrochloric acid, and washed with chloroform (3×50 mL); the aqueous layer was then neutralized with sodium bicarbonate and extracted with chloroform (3×50 mL). The combined organic extracts were washed with saturated aqueous sodium chloride solution (100 mL), dried over sodium sulfate, filtered, and concentrated in vacuo to provide the product as a yellow oil. Yield: 1.0 g, 4.7 mmol, 16%. $^1$H NMR (400 MHz, CDCl$_3$) δ 8.51 (s, 1H), 7.80 (t, J=0.7 Hz, 1H), 4.21 (q, J=7.2 Hz, 2H), 3.77 (d, J=0.6 Hz, 2H), 1.29 (t, J=7.2 Hz, 3H).

Step 2. Synthesis of imidazo[2,1-b][1,3,4]thiadiazol-6-ylacetic acid (C31)

A solution of C30 (1.0 g, 4.7 mmol) in hydrochloric acid (5 mL) was heated at reflux overnight. The reaction mixture was then concentrated in vacuo, and the residue was washed with dichloromethane (10 mL) to afford the product as a brown solid. Yield: 1 g, quantitative. LCMS m/z 184.0 [M+H]$^+$. $^1$H NMR (400 MHz, DMSO-d$_6$) δ 9.40 (s, 1H), 8.28 (br s, 1H), 3.79 (br s, 2H).

Step 3. Synthesis of 8-chloro-2-(imidazo[2,1-b][1,3,4]thiadiazol-6-ylmethyl)-1-[(2R,4R)-2-methyltetrahydro-2H-pyran-4-yl]-1H-imidazo[4,5-c]quinoline (8)

To a mixture of C15 (850 mg, 2.91 mmol) and C31 (640 mg, 3.5 mmol) in N,N-dimethylformamide (20 mL) was added N,N-diisopropylethylamine (828 mg, 6.41 mmol) and 2,4,6-tripropyl-1,3,5,2,4,6-trioxatriphosphinane 2,4,6-trioxide (50% solution in ethyl acetate, 5.5 g, 8.6 mmol). The reaction mixture was heated at 100° C. overnight, whereupon it was diluted with water (50 mL) and extracted with dichloromethane (3×50 mL). The combined organic layers were washed with saturated aqueous sodium chloride solution (150 mL), dried over sodium sulfate, filtered, and concentrated in vacuo. Silica gel chromatography (Eluent: 10:1 dichloromethane/methanol) provided the product as a yellow solid. Yield: 372 mg, 0.848 mmol, 29%. LCMS m/z 438.9 [M+H]$^+$. $^1$H NMR (400 MHz, CDCl$_3$) δ 9.29 (s, 1H), 8.60-8.75 (br m, 1H), 8.53 (s, 1H), 8.22 (d, J=8.8 Hz, 1H), 7.79 (s, 1H), 7.63 (dd, J=8.7, 1.9 Hz, 1H), 5.29-5.42 (m, 1H), 4.58 (br s, 2H), 4.30 (br dd, J=12, 5 Hz, 1H), 3.65-3.80 (br m, 2H), 2.61-2.82 (br m, 1H), 2.34-2.54 (br m, 1H), 1.71-1.97 (br m, 2H), 1.35 (d, J=6.2 Hz, 3H).

Example 9

{8-Chloro-1-[(2R,4R)-2-methyltetrahydro-2H-pyran-4-yl]-1H-imidazo[4,5-c]quinolin-2-yl}acetonitrile (9)

A mixture of C15 (280 mg, 0.96 mmol), cyanoacetic acid (65.3 mg, 0.768 mmol), 2,4,6-tripropyl-1,3,5,2,4,6-trioxatriphosphinane 2,4,6-trioxide (635 mg, 2.00 mmol, as a 50% solution in ethyl acetate), and N,N-diisopropylethylamine (0.34 mL, 2.0 mmol) in ethyl acetate (8 mL) was stirred for 1 hour, then treated with additional 2,4,6-tripropyl-1,3,5,2,4,6-trioxatriphosphinane 2,4,6-trioxide (50% solution in ethyl acetate, 1.0 mL, 1.7 mmol) and heated at reflux overnight. The reaction mixture was cooled to room temperature, diluted with additional ethyl acetate and washed with saturated aqueous sodium bicarbonate solution. The aqueous layer was extracted with ethyl acetate, and the combined organic layers were dried over magnesium sulfate, filtered, and concentrated in vacuo. Chromatography on silica gel (Gradient: 50% to 100% ethyl acetate in heptane) afforded the product as a white solid. Yield: 159 mg, 0.466 mmol, 61%. LCMS m/z 341.2, 343.2 [M+H]$^+$. $^1$H NMR (400 MHz, CDCl$_3$) δ 9.30 (s, 1H), 8.5-8.8 (v br m, 1H), 8.26 (d, J=9.0 Hz, 1H), 7.69 (dd, J=8.8, 2.0 Hz, 1H), 4.8-5.1 (v br m, 1H), 4.35-4.43 (m, 1H), 4.29 (s, 2H), 3.73-3.86 (m, 2H), 2.35-2.95 (v br m, 2H), 2.05-2.29 (br m, 2H), 1.41 (d, J=6.0 Hz, 3H).

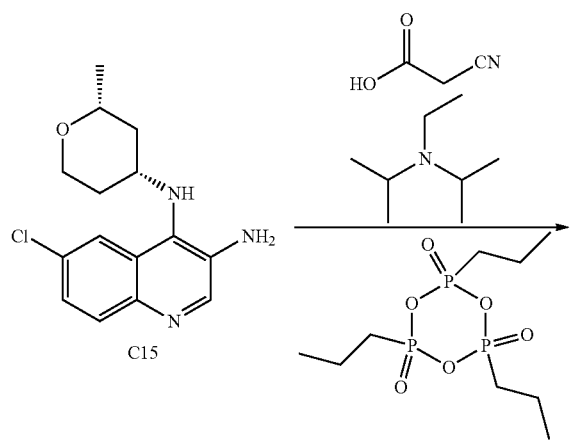

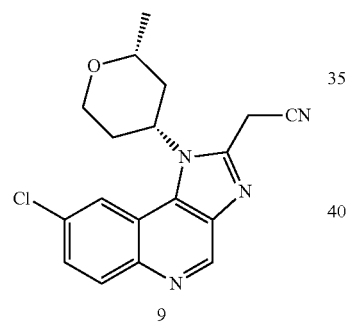

Example 10

8-Chloro-1-[(2R,4R)-2-methyltetrahydro-2H-pyran-4-yl]-2-(1,3-thiazol-4-ylmethyl)(4-$^2$H)-1H-imidazo[4,5-c]quinoline (10)

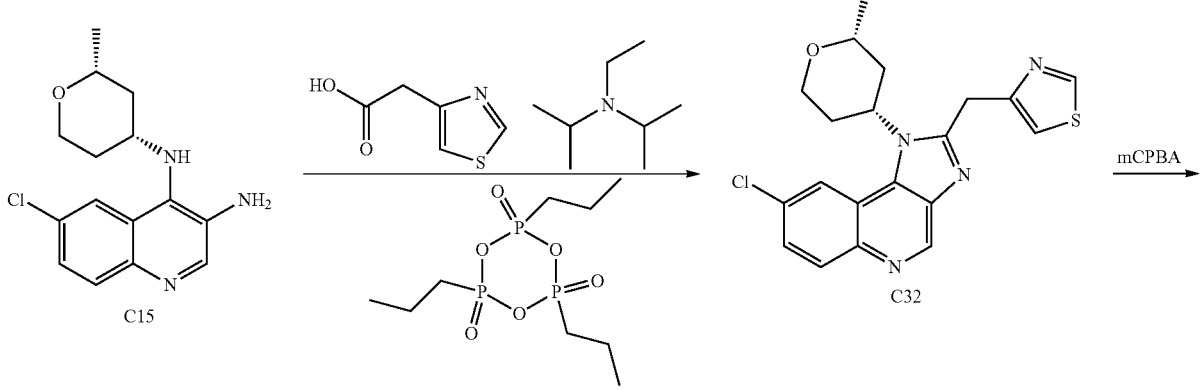

-continued

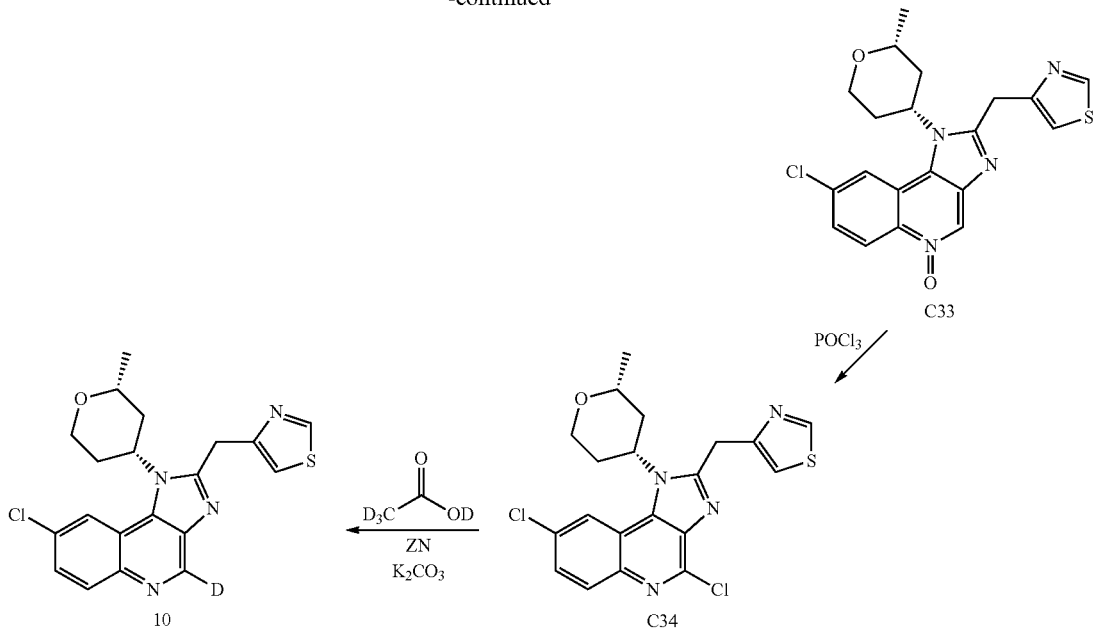

Step 1. Synthesis of 8-chloro-1-[(2R,4R)-2-methyl-tetrahydro-2H-pyran-4-yl]-2-(1,3-thiazol-4-ylmethyl)-H-imidazo[4,5-c]quinoline (C32)

A mixture of C15 (889 mg, 3.05 mmol), 1,3-thiazol-4-ylacetic acid (438 mg, 2.44 mmol), 2,4,6-tripropyl-1,3,5,2,4,6-trioxatriphosphinane 2,4,6-trioxide (50% solution in ethyl acetate, 2.3 mL, 3.9 mmol), and N,N-diisopropylethylamine (1.1 mL, 6.3 mmol) in ethyl acetate (14 mL) was stirred for 1 hour and 45 minutes at room temperature, then heated at 50° C. for 1 hour. Acetic acid (30 mL) was added, and the reaction mixture was stirred at 115° C. for 66 hours. Solvents were removed in vacuo; the residue was diluted with saturated aqueous sodium bicarbonate solution and extracted three times with ethyl acetate. The combined organic layers were dried over magnesium sulfate, filtered, and concentrated under reduced pressure. After silica gel chromatography (Gradient: 0% to 5% methanol in dichloromethane), the material obtained from the clean fractions was dissolved in ethyl acetate, treated with activated charcoal, and filtered. The filtrate was concentrated in vacuo and purified via silica gel chromatography (Eluent: diethyl ether) to afford the product as a white foam. Yield: 584 mg, 1.46 mmol, 60%. LCMS m/z 399.2, 401.0 [M+H]$^+$. $^1$H NMR (400 MHz, CDCl$_3$), characteristic peaks: δ 9.29 (s, 1H), 8.80-8.83 (m, 1H), 8.58-8.71 (br m, 1H), 8.22 (d, J=8.9 Hz, 1H), 7.63 (dd, J=9.0, 2.0 Hz, 1H), 7.24 (br s, 1H), 5.20-5.34 (m, 1H), 4.72 (s, 2H), 4.29 (br dd, J=12, 5 Hz, 1H), 3.60-3.76 (br m, 2H), 2.60-2.80 (br m, 1H), 2.33-2.51 (br m, 1H), 1.7-1.87 (br m, 1H), 1.34 (d, J=6.0 Hz, 3H).

Step 2. Synthesis of 8-chloro-1-[(2R,4R)-2-methyl-tetrahydro-2H-pyran-4-yl]-2-(1,3-thiazol-4-ylmethyl)-1H-imidazo[4,5-c]quinoline 5-oxide (C33)

3-Chloroperoxybenzoic acid (mCPBA, 547 mg, 3.17 mmol) was added to a solution of C32 (972 mg, 2.44 mmol) in dichloromethane (12 mL). After stirring at room temperature overnight, the reaction mixture was treated with saturated aqueous sodium bicarbonate solution (30 mL) and stirred for an additional 20 minutes. The aqueous layer was extracted three times with dichloromethane, and the combined organic layers were dried over magnesium sulfate, filtered, and concentrated in vacuo. Silica gel chromatography (Gradient: 0% to 5% methanol in dichloromethane) provided the product as a yellow solid. Yield: 1.0 g, 2.4 mmol, 98%. LCMS m/z 415.3, 417.2 [M+H]$^+$. $^1$H NMR (400 MHz, CDCl$_3$), characteristic peaks: δ 9.05 (d, J=9.4 Hz, 1H), 9.03 (s, 1H), 8.81 (d, J=1.8 Hz, 1H), 8.63-8.76 (br m, 1H), 7.70 (dd, J=9.4, 1.8 Hz, 1H), 5.23-5.36 (m, 1H), 4.68 (s, 2H), 4.30 (dd, J=12.1, 5.1 Hz, 1H), 3.61-3.80 (m, 2H), 2.53-2.71 (br m, 1H), 2.25-2.42 (br m, 1H), 1.78-1.93 (br m, 1H), 1.65-1.78 (br m, 1H), 1.34 (d, J=6.2 Hz, 3H).

Step 3. Synthesis of 4,8-dichloro-1-[(2R,4R)-2-methyltetrahydro-2H-pyran-4-yl]-2-(1,3-thiazol-4-ylmethyl)-H-imidazo[4,5-c]quinoline (C34)

Phosphorus oxychloride (98%, 0.17 mL, 1.8 mmol) was added to a solution of C33 (300 mg, 0.72 mmol) in chloroform (4 mL), and the reaction mixture was heated to 70° C. for 1.5 hours. After cooling to room temperature, it was poured into a stirring mixture of water and dichloromethane and allowed to stir for 20 minutes. The mixture was basified via addition of saturated aqueous sodium bicarbonate solution; the aqueous layer was extracted once with dichloromethane, and the combined organic layers were dried over magnesium sulfate, filtered, and concentrated in vacuo. Silica gel chromatography (Gradient: 50% to 100% ethyl acetate in heptane) provided the product as a white foam. Yield: 290 mg, 0.669 mmol, 93%. LCMS m/z 433.2, 435.2, 437.1 [M+H]$^+$. $^1$H NMR (400 MHz, CDCl$_3$) δ 8.78 (d, J=1.8 Hz, 1H), 8.56-8.67 (br m, 1H), 8.07 (d, J=8.9 Hz, 1H), 7.59 (dd, J=9.0, 2.0 Hz, 1H), 7.23-7.29 (br m, 1H), 5.23-5.35 (m, 1H), 4.75 (s, 2H), 4.26 (dd, J=11.9, 4.9 Hz, 1H), 3.57-3.72 (m, 2H), 2.53-2.74 (br m, 1H), 2.26-2.46 (br m, 1H), 1.69-1.83 (br m, 1H), 1.55-1.69 (br m, 1H), 1.31 (d, J=6.2 Hz, 3H).

Step 4. Synthesis of 8-chloro-1-[(2R,4R)-2-methyl-tetrahydro-2H-pyran-4-yl]-2-(1,3-thiazol-4-ylmethyl) (4-²H)-1H-imidazo[4,5-c]quinoline (10)

Compound C34 (45 mg, 0.10 mmol) was combined with zinc dust (98%, 55.5 mg, 0.832 mmol) in (²H₄)acetic acid (0.5 mL) and heated at 100° C. for 15 minutes. The reaction mixture was cooled to room temperature, treated with 1 M aqueous sodium hydroxide solution, and extracted with dichloromethane. The combined organic layers were dried over magnesium sulfate, filtered, and concentrated in vacuo. The residue was mixed with acetic acid (2 mL) and heated to 100° C. for 10 minutes; after removal of solvent under reduced pressure, the residue was dissolved in dichloromethane and washed with saturated aqueous sodium bicarbonate solution. The aqueous layer was extracted once with dichloromethane, and the combined organic layers were dried over magnesium sulfate, filtered, and concentrated in vacuo. Silica gel chromatography (Eluent: ethyl acetate, followed by a gradient of 0% to 5% methanol in dichloromethane) afforded the product as a white solid. Yield: 10.1 mg, 25.3 μmol, 25%. This material exhibited ~85% deuterium incorporation by ¹H NMR analysis. LCMS m/z 400.3, 402.2 [M+H]⁺. ¹H NMR (400 MHz, CDCl₃), characteristic peaks: δ 9.29 (residual protio peak), 8.81 (d, J=1.8 Hz, 1H), 8.59-8.70 (br m, 1H), 8.22 (d, J=9.0 Hz, 1H), 7.63 (dd, J=9.0, 2.1 Hz, 1H), 7.22-7.25 (m, 1H), 5.20-5.33 (m, 1H), 4.73 (s, 2H), 4.29 (br dd, J=12, 5 Hz, 1H), 3.61-3.75 (br m, 2H), 2.61-2.79 (br m, 1H), 2.33-2.52 (br m, 1H), 1.70-1.85 (br m, 1H), 1.34 (d, J=6.2 Hz, 3H).

Example 11

8-Chloro-1-[(2R,4R)-2-methyltetrahydro-2H-pyran-4-yl]-2-[(4-methyl-1H-1,2,3-triazol-1-yl)methyl]-1H-imidazo[4,5-c]quinoline (11)

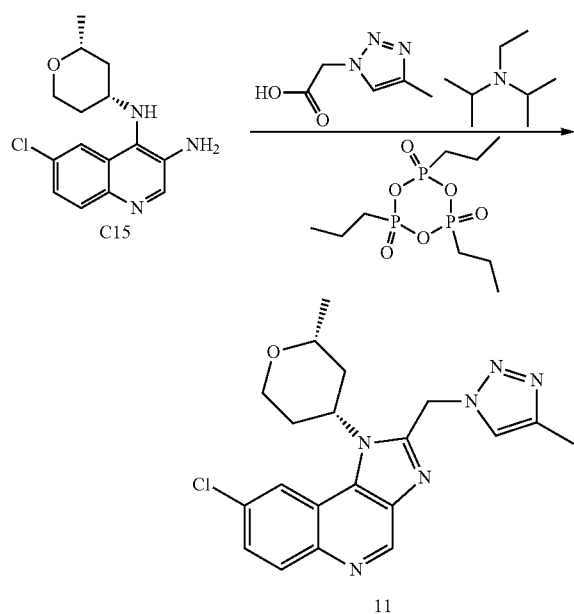

N,N-Diisopropylethylamine (828 mg, 6.41 mmol) and 2,4,6-tripropyl-1,3,5,2,4,6-trioxatriphosphinane 2,4,6-trioxide (50% solution in ethyl acetate, 5.5 g, 8.7 mmol) were added to a mixture of C15 (850 mg, 2.91 mmol) and (4-methyl-1H-1,2,3-triazol-1-yl)acetic acid (493 mg, 3.49 mmol) in N,N-dimethylformamide (20 mL). The reaction mixture was heated at 100° C. overnight, whereupon it was diluted with water (50 mL) and extracted with dichloromethane (3×50 mL). The combined organic layers were washed with saturated aqueous sodium chloride solution (150 mL), dried over sodium sulfate, filtered, and concentrated in vacuo. Purification via reversed phase HPLC (Column: YMC-Actus Triart C18, 5 μm; Mobile phase A: water containing 0.225% formic acid; Mobile phase B: acetonitrile; Eluent: 42% B) afforded the product as a yellow solid. Yield: 340 mg, 0.86 mmol, 30%. LCMS m/z 396.9 [M+H]⁺. ¹H NMR (400 MHz, CDCl₃) δ 9.31 (s, 1H), 8.58-8.72 (br m, 1H), 8.23 (d, J=8.9 Hz, 1H), 7.67 (dd, J=8.9, 2.0 Hz, 1H), 7.47 (br s, 1H), 5.99 (s, 2H), 5.30-5.42 (m, 1H), 4.29 (br dd, J=12, 5 Hz, 1H), 3.68-3.81 (m, 2H), 2.56-2.74 (br m, 1H), 2.32 (s, 3H), 2.3-2.46 (br m, 1H), 1.43-1.90 (2 br m, 2H, assumed; partially obscured by water peak), 1.34 (d, J=6.0 Hz, 3H).

Alternate Synthesis of Example 11

8-Chloro-1-[(2R,4R)-2-methyltetrahydro-2H-pyran-4-yl]-2-[(4-methyl-1H-1,2,3-triazol-1-yl)methyl]-1H-imidazo[4,5-c]quinoline (11)

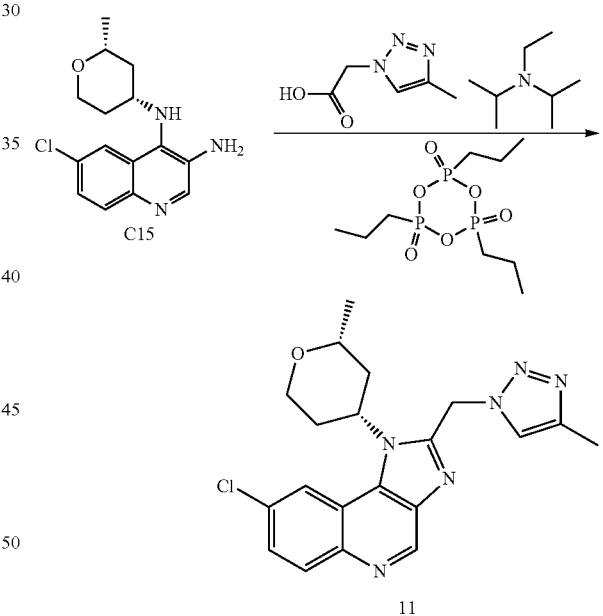

A mixture of C15 (500 mg, 1.71 mmol) and (4-methyl-1H-1,2,3-triazol-1-yl)acetic acid (247 mg, 1.75 mmol) was purged three times with nitrogen and then mixed with toluene (5.7 mL). N,N-Diisopropylethylamine (0.30 mL, 1.72 mmol) was added, followed by 2,4,6-tripropyl-1,3,5,2,4,6-trioxatriphosphinane 2,4,6-trioxide (50% solution in ethyl acetate, 1.48 mL, 2.49 mmol). The reaction mixture was heated to 70° C. for 70 minutes, at which time LCMS analysis indicated consumption of starting material and an approximately 2:1 ratio of intermediate amide: 11. The reaction mixture was then heated at 110° C. for 3 hours, whereupon it was cooled, diluted with ethyl acetate, and washed with saturated aqueous sodium bicarbonate solution.

The organic layer was dried over magnesium sulfate, filtered, and concentrated in vacuo. Silica gel chromatography (Gradient: 0% to 10% methanol in dichloromethane) afforded the product as a solid. Yield: 585 mg, 1.47 mmol, 86%. LCMS m/z 397.4 (chlorine isotope pattern observed) [M+H]+. $^1$H NMR (400 MHz, CDCl$_3$) δ 9.30 (s, 1H), 8.55-8.73 (br m, 1H), 8.23 (d, J=9.0 Hz, 1H), 7.66 (dd, J=8.8, 2.2 Hz, 1H), 7.43-7.50 (br m, 1H), 5.99 (s, 2H), 5.29-5.42 (m, 1H), 4.29 (br dd, J=12.1, 4.7 Hz, 1H), 3.65-3.81 (m, 2H), 2.54-2.75 (br m, 1H), 2.31 (s, 3H), 2.24-2.47 (br m, 1H), 1.43-1.75 (br m, 2H), 1.34 (d, J=6.1 Hz, 3H).

Example 93

8-Chloro-1-(cis-3-fluorocyclopentyl)-2-[(4-methyl-1H-1,2,3-triazol-1-yl)methyl]-1H-imidazo[4,5-c]quinoline, ENT-1 (93)

bicarbonate solution, the mixture was extracted with dichloromethane, and the combined organic layers were dried over sodium sulfate, filtered, and concentrated in vacuo. Silica gel chromatography (Gradient: 0% to 40% ethyl acetate in heptane) provided the product as a solid. Yield: 3.78 g, 12.2 mmol, 89%. LCMS m/z 310.3 (chlorine isotope pattern observed) [M+H]+. $^1$H NMR (400 MHz, CDCl$_3$) δ 9.79 (br d, 1H), 9.35 (s, 1H), 8.23 (d, J=2.3 Hz, 1H), 7.95 (d, J=9.0 Hz, 1H), 7.71 (dd, J=9.0, 2.2 Hz, 1H), [5.38-5.43 (m) and 5.25-5.30 (m), total 1H], 4.71-4.80 (m, 1H), 2.43-2.54 (m, 1H), 2.27-2.43 (m, 3H), 2.15-2.27 (m, 1H), 1.87-2.08 (m, 1H).

Step 2. Synthesis of 6-chloro-N$^4$-(cis-3-fluorocyclopentyl)quinoline-3,4-diamine (C54)

Zinc (8.66 g, 132 mmol) was added in one portion to a mixture of C53 (4.00 g, 12.9 mmol) in methanol (64 mL)

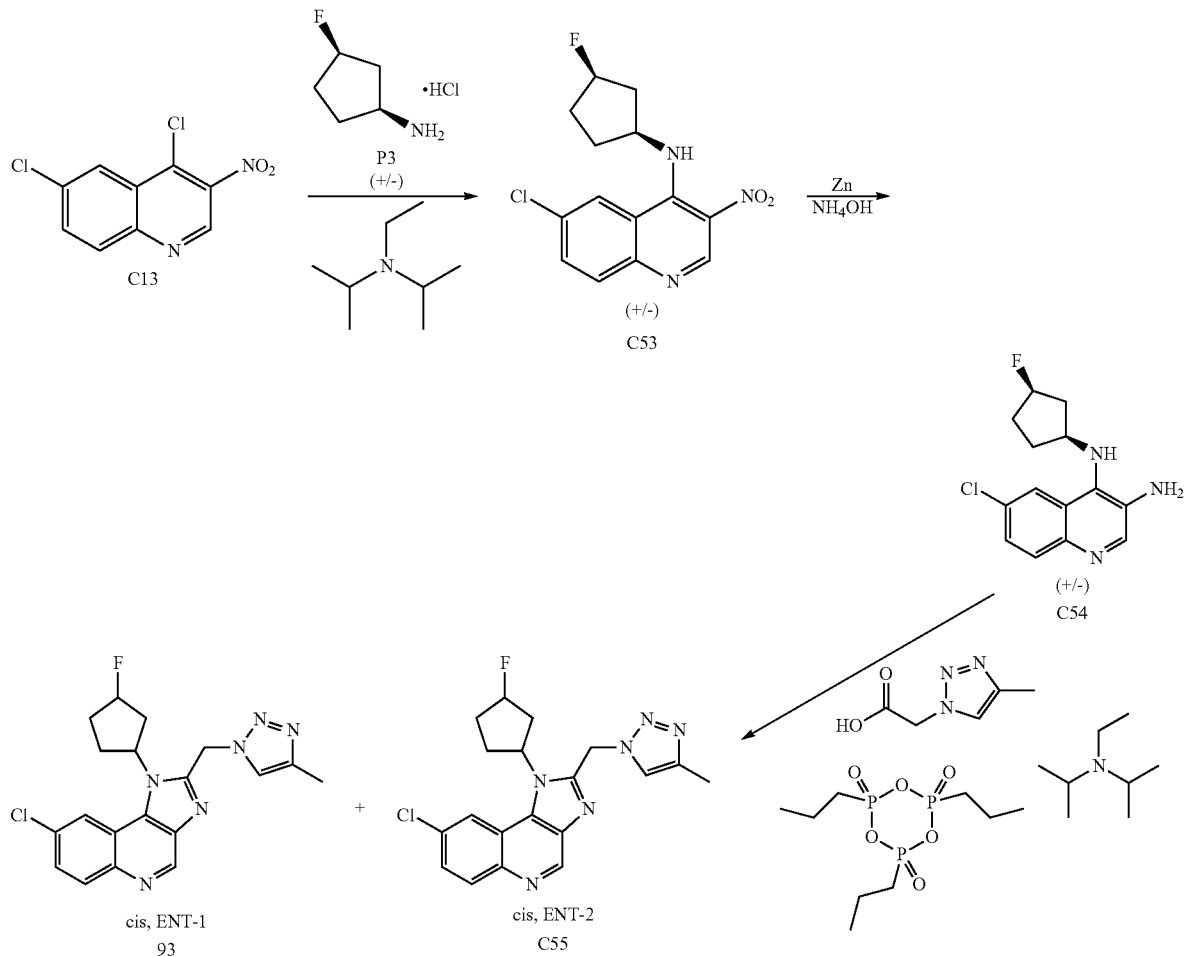

Step 1. Synthesis of 6-chloro-N-(cis-3-fluorocyclopentyl)-3-nitroquinolin-4-amine (C53)

N,N-Diisopropylethylamine (8.33 mL, 47.8 mmol) was added to a suspension of C13 (3.32 g, 13.7 mmol) and P3 (2.00 g, 14.3 mmol) in acetonitrile (80 mL). The reaction mixture was stirred at room temperature for 5 minutes and then heated to 55° C. for 6 hours, whereupon it was cooled to room temperature. After addition of aqueous sodium and concentrated ammonium hydroxide (64 mL). After 2 hours at room temperature, the reaction mixture was filtered through diatomaceous earth, and the filter pad was washed with dichloromethane and methanol. The combined filtrates were concentrated in vacuo; the residue was diluted with water and extracted with dichloromethane (3×100 mL). The combined organic layers were washed with saturated aqueous sodium chloride solution, dried over sodium sulfate, filtered, and concentrated under reduced pressure. Silica gel chromatography (Gradient: 0% to 60% ethyl acetate in heptane, followed by 100% ethyl acetate) and subsequent trituration with diethyl ether afforded the product as a solid. Yield: 1.68 g, 6.01 mmol, 47%. LCMS m/z 280.4 (chlorine isotope pattern observed) [M+H]$^+$. $^1$H NMR (400 MHz, CDCl$_3$) δ 8.47 (s, 1H), 7.89 (d, J=9.0 Hz, 1H), 7.85 (d, J=2.2 Hz, 1H), 7.39 (dd, J=8.9, 2.2 Hz, 1H), [5.36-5.41 (m) and 5.23-5.28 (m), J$_{HF}$=54 Hz, total 1H], 4.16-4.26 (m, 1H), 3.81-3.92 (m, 3H), 1.78-2.34 (m, 6H).

Step 3. Synthesis of 8-chloro-1-(cis-3-fluorocyclopentyl)-2-[(4-methyl-1H-1,2,3-triazol-1-yl)methyl]-1H-imidazo[4,5-c]quinoline, ENT-1 (93) and 8-chloro-1-(cis-3-fluorocyclopentyl)-2-[(4-methyl-1H-1,2,3-triazol-1-yl)methyl]-1H-imidazo[4,5-c]quinoline, ENT-2 (C55)

N,N-Diisopropylethylamine (0.280 mL, 1.61 mmol) and 2,4,6-tripropyl-1,3,5,2,4,6-trioxatriphosphinane 2,4,6-trioxide (50% solution in ethyl acetate, 0.958 mL, 1.61 mmol) were added to a mixture of C54 (150 mg, 0.536 mmol) and (4-methyl-1H-1,2,3-triazol-1-yl)acetic acid (75.7 mg, 0.536 mmol) in ethyl acetate (3.2 mL). The reaction mixture was heated at 80° C. overnight, whereupon it was diluted with ethyl acetate and washed with water. The aqueous layer was extracted once with ethyl acetate, and the combined organic layers were washed with saturated aqueous sodium chloride solution, dried over sodium sulfate, filtered, and concentrated in vacuo. Chromatography on silica gel (Gradient: 0% to 5% methanol in dichloromethane), followed by trituration with heptane containing a small amount of ethyl acetate, provided a mixture of 93 and C55 as an off-white solid. Yield of racemic product: 148 mg, 0.384 mmol, 72%. The component enantiomers were separated using supercritical fluid chromatography [Column: Phenomenex Lux Amylose-1, 5 µm; Mobile phase: 7:3 carbon dioxide/(1:1 acetonitrile/methanol)]. The first-eluting enantiomer was triturated with diethyl ether to afford 93, obtained as a white solid. Yield: 52 mg. 0.135 mmol, 35% for the separation. LCMS m/z 385.4 (chlorine isotope pattern observed) [M+H]$^+$. $^1$H NMR (400 MHz, CDCl$_3$) δ 9.31 (s, 1H), 8.49-8.53 (m, 1H), 8.22 (d, J=9.0 Hz, 1H), 7.67 (dd, J=9.0, 2.2 Hz, 1H), 7.47 (br s, 1H), 5.99 (AB quartet, J$_{AB}$=15.6 Hz, Δν$_{AB}$=11.0 Hz, 2H), [5.43-5.56 (m) and 5.32-5.38 (m), total 2H], 2.42-2.78 (m, 4H), 2.33 (d, J=0.6 Hz, 3H), 1.98-2.18 (m, 1H), 1.88-1.98 (m, 1H).

The second-eluting enantiomer was C55, also isolated as a white solid after trituration with diethyl ether. Yield: 58 mg, 0.151 mmol, 39% for the separation. LCMS m/z 385.4 (chlorine isotope pattern observed) [M+H]$^+$. $^1$H NMR (400 MHz, CDCl$_3$) δ 9.31 (s, 1H), 8.49-8.53 (m, 1H), 8.22 (d, J=9.0 Hz, 1H), 7.67 (dd, J=9.0, 2.2 Hz, 1H), 7.47 (br s, 1H), 5.99 (AB quartet, J$_{AB}$=15.6 Hz, Δν$_{AB}$=11.0 Hz, 2H), [5.43-5.56 (m) and 5.32-5.38 (m), total 2H], 2.42-2.77 (m, 4H), 2.33 (d, J=0.6 Hz, 3H), 1.98-2.18 (m, 1H), 1.88-1.98 (m, 1H).

Example 94

1-[cis-3-Fluorocyclopentyl]-2-[(4-methyl-1H-pyrazol-1-yl)methyl]-1H-imidazo[4,5-c]quinoline-8-carbonitrile, ENT-1 (94)

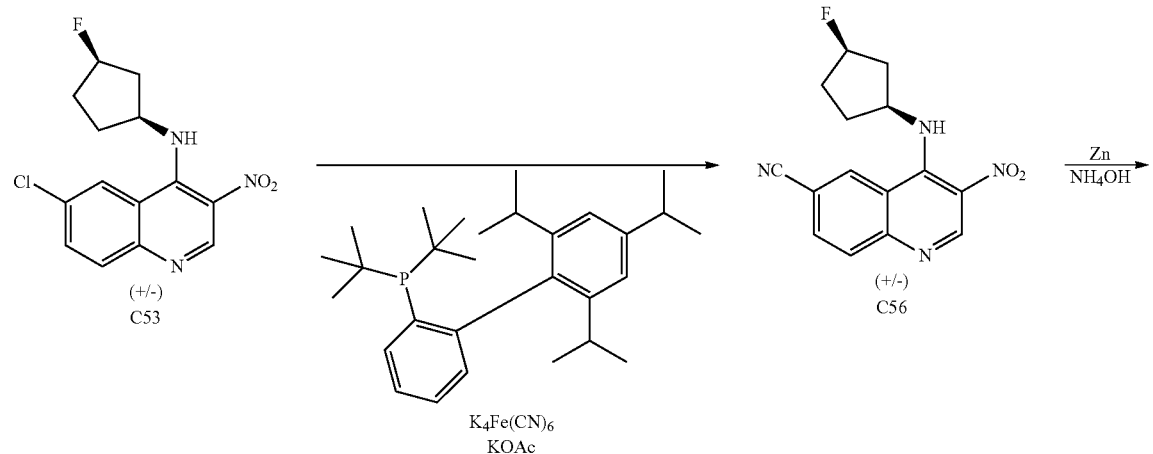

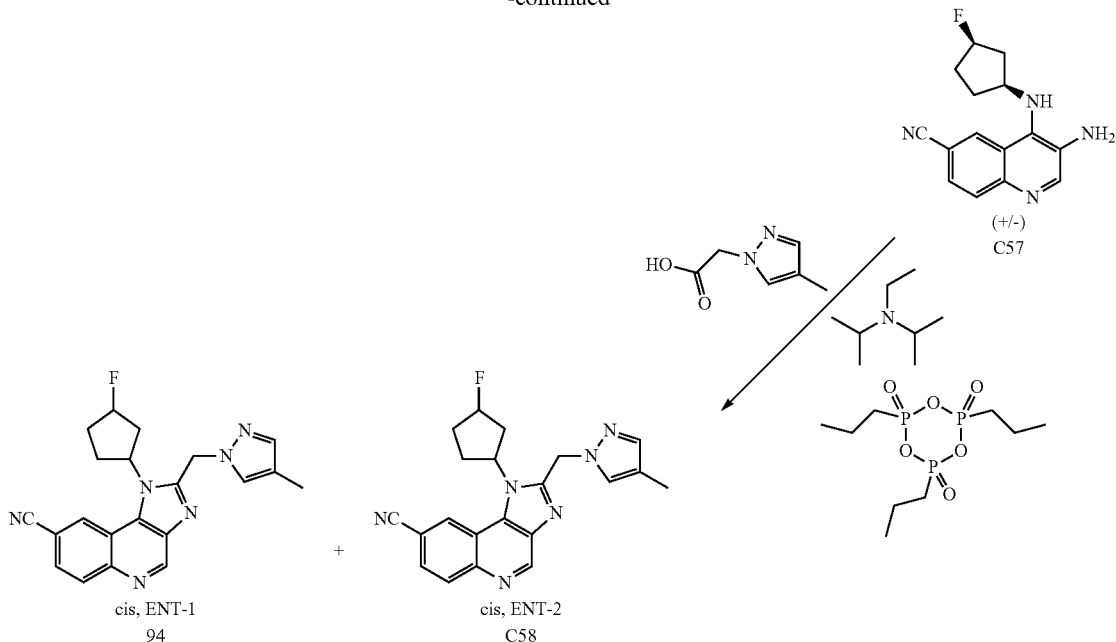

Step 1. Synthesis of 4-[(cis-3-fluorocyclopentyl)amino]-3-nitroquinoline-6-carbonitrile (C56)

A reaction vessel containing a mixture of C53 (6.00 g, 19.4 mmol), potassium ferrocyanide(II) trihydrate (4.09 g, 9.68 mmol), [(2-di-tert-butylphosphino-2',4',6'-triisopropyl-1,1'-biphenyl)-2-(2'-amino-1,1'-biphenyl)] palladium(II) methanesulfonate (tBuXPhos Pd G3 precatalyst; 769 mg, 0.968 mmol), and di-tert-butyl[2',4',6'-tri(propan-2-yl)biphenyl-2-yl]phosphane (411 mg, 0.968 mmol) was evacuated and charged with nitrogen. This evacuation cycle was repeated twice, and then 1,4-dioxane (previously degassed by bubbling nitrogen through it for 2 hours with vigorous stirring; 39 mL) and aqueous potassium acetate solution (0.0625 M, prepared using degassed deionized water; 38.7 mL, 2.42 mmol) were added. The reaction mixture was placed into a preheated 100° C. oil bath and stirred at 100° C. for 2 hours, whereupon it was removed from the oil bath, cooled to room temperature, and partitioned between ethyl acetate and saturated aqueous sodium bicarbonate solution. The aqueous layer was extracted with ethyl acetate (3×100 mL) and dichloromethane (100 mL), and the combined organic layers were dried over sodium sulfate, filtered, and concentrated in vacuo. The residue was triturated with dichloromethane and heptane, and the resulting solid was recrystallized from dichloromethane/heptane to provide the product as a solid. Yield: 4.70 g, 15.6 mmol, 80%. $^1$H NMR (400 MHz, CDCl$_3$) δ 9.98-10.09 (br m, 1H), 9.46 (s, 1H), 8.61 (d, J=1.8 Hz, 1H), 8.09 (d, half of AB quartet, J=8.6 Hz, 1H), 7.92 (dd, half of ABX pattern, J=8.8, 1.8 Hz, 1H), [5.42-5.46 (m) and 5.29-5.33 (m), total 1H], 4.71-4.80 (m, 1H), 2.48-2.59 (m, 1H), 2.29-2.46 (m, 3H), 2.19-2.29 (m, 1H), 1.92-2.13 (m, 1H).

Step 2. Synthesis of 3-amino-4-[(cis-3-fluorocyclopentyl)amino]quinoline-6-carbonitrile (C57)

Zinc (4.46 g, 66.4 mmol) was added in one portion to a mixture of C56 (2.00 g, 6.63 mmol) in methanol (33 mL) and concentrated ammonium hydroxide (33 mL). After 1 hour, the reaction mixture was filtered through a pad of diatomaceous earth; the filter pad was rinsed with dichloromethane and a small amount of methanol, and the combined filtrates were diluted with a 1:1 mixture of water and saturated aqueous sodium chloride solution. The aqueous layer was extracted with dichloromethane, and the combined organic layers were washed with saturated aqueous sodium chloride solution, dried over sodium sulfate, filtered, and concentrated in vacuo. Trituration of the residue with diethyl ether for 30 minutes provided the product as a yellow solid. Yield: 1.49 g, 5.51 mmol, 83%. LCMS m/z 271.4 [M+H]$^+$. $^1$H NMR (400 MHz, CDCl$_3$) δ 8.58 (s, 1H), 8.28 (d, J=1.6 Hz, 1H), 8.02 (d, J=8.6 Hz, 1H), 7.60 (dd, J=8.7, 1.7 Hz, 1H), [5.39-5.44 (m) and 5.26-5.30 (m), $J_{HF}$=53 Hz, total 1H], 4.23-4.33 (m, 1H), 3.98-4.07 (m, 1H), 3.91 (br s, 2H), 2.20-2.36 (m, 1H), 2.04-2.18 (m, 2H), 1.81-2.03 (m, 3H).

Step 3. Synthesis of 1-[cis-3-fluorocyclopentyl]-2-[(4-methyl-1H-pyrazol-1-yl)methyl]-1H-imidazo[4,5-c]quinoline-8-carbonitrile, ENT-1 (94) and 1-[cis-3-fluorocyclopentyl]-2-[(4-methyl-1H-pyrazol-1-yl)methyl]-1H-imidazo[4,5-c]quinoline-8-carbonitrile, ENT-2 (C58)

N,N-Diisopropylethylamine (0.374 mL, 2.15 mmol) and 2,4,6-tripropyl-1,3,5,2,4,6-trioxatriphosphinane 2,4,6-trioxide (50% solution in ethyl acetate, 1.28 mL, 2.15 mmol) were added to a mixture of C57 (200 mg, 0.740 mmol) and (4-methyl-1H-pyrazol-1-yl)acetic acid (100 mg, 0.714 mmol) in ethyl acetate (4.4 mL), and the reaction mixture was heated at 80° C. overnight. It was then partitioned between ethyl acetate and water. The aqueous layer was extracted with ethyl acetate, and the combined organic layers were washed with saturated aqueous sodium chloride solution, dried over sodium sulfate, filtered, and concentrated in vacuo. Silica gel chromatography (Gradient: 0% to 5% methanol in dichloromethane), followed by trituration with diethyl ether, provided a mixture of 94 and C58 as an off-white solid. Yield of racemic material: 203 mg, 0.542 mmol, 76%. This was separated into its component enantiomers using supercritical fluid chromatography [Column: Chiral Technologies Chiralpak AD-H, 5 µm; Mobile phase: 4:1 carbon dioxide/(ethanol containing 0.2% ammonium hydroxide)]. The first-eluting enantiomer was 94, isolated as a white solid. Yield: 78 mg, 0.21 mmol, 39% for the separation. LCMS m/z 375.5 [M+H]$^+$. $^1$H NMR (400 MHz, CDCl$_3$) δ 9.43 (s, 1H), 8.94-9.00 (m, 1H), 8.36 (d, J=8.6 Hz, 1H), 7.86 (dd, J=8.6, 1.6 Hz, 1H), 7.37 (s, 1H), 7.28 (s, 1H), 5.75 (s, 2H), 5.53-5.65 (m, 1H), [5.47-5.53 (m) and 5.34-5.40 (m), J$_{HF}$=54 Hz, total 1H], 2.43-2.70 (m, 4H), 2.04 (s, 3H), 1.92-2.14 (m, 1H), 1.82-1.92 (m, 1H).

The second-eluting compound, also obtained as a white solid, was C58. Yield: 91 mg, 0.24 mmol, 44% for the separation. LCMS m/z 375.5 [M+H]$^+$. $^1$H NMR (400 MHz, CDCl$_3$) δ 9.43 (s, 1H), 8.95-9.00 (m, 1H), 8.36 (d, J=8.6 Hz, 1H), 7.86 (dd, J=8.7, 1.7 Hz, 1H), 7.37 (s, 1H), 7.28 (s, 1H), 5.75 (s, 2H), 5.52-5.65 (m, 1H), [5.48-5.53 (m) and 5.34-5.40 (m), J$_{HF}$=54 Hz, total 1H], 2.43-2.70 (m, 4H), 2.04 (s, 3H), 1.92-2.14 (m, 1H), 1.82-1.92 (m, 1H).

Example 95

2-[(3-Methyl-1,2-oxazol-5-yl)methyl]-1-[(2R,4R)-2-methyltetrahydro-2H-pyran-4-yl]-1H-imidazo[4,5-c]quinoline-8-carbonitrile (95)

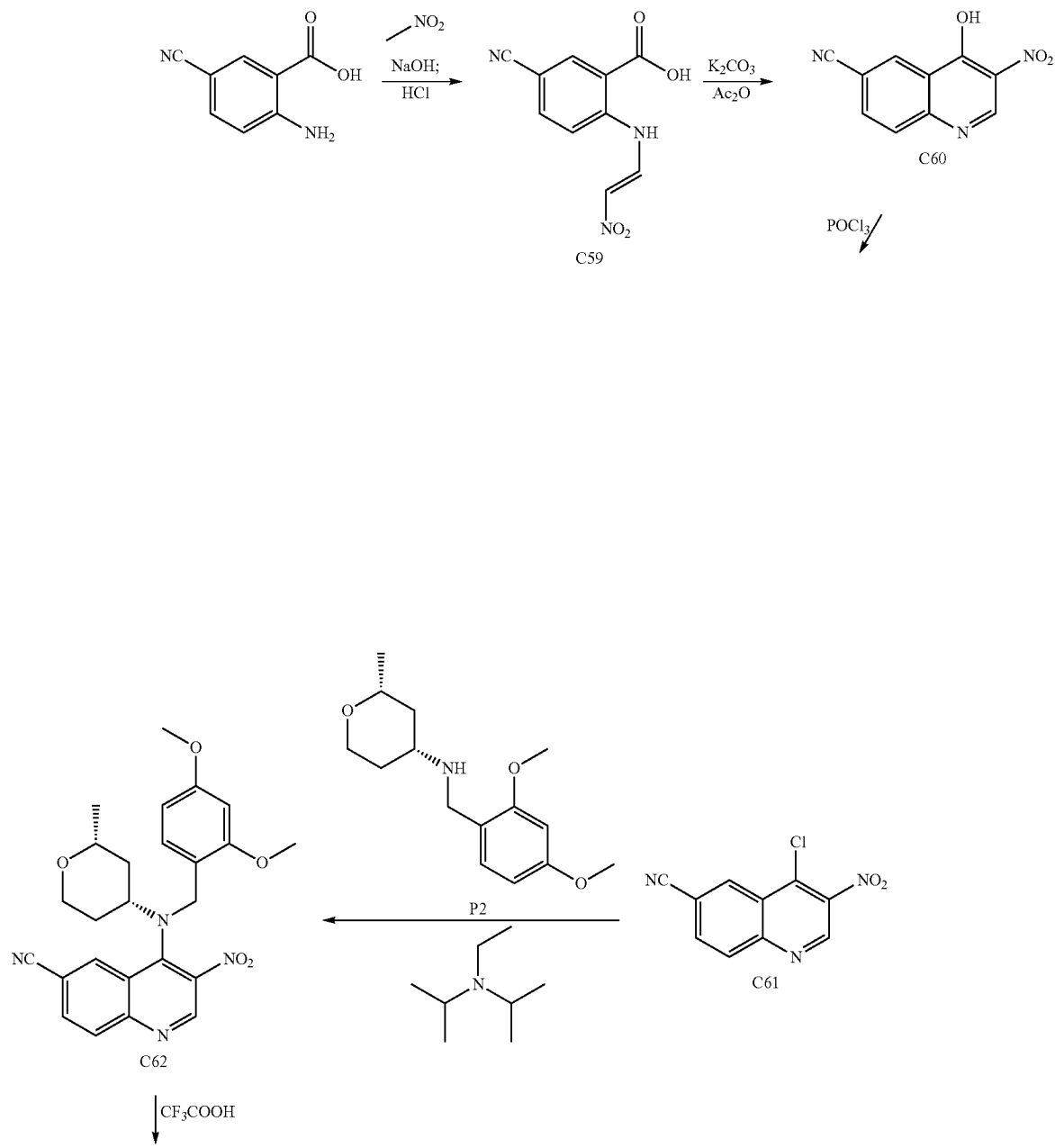

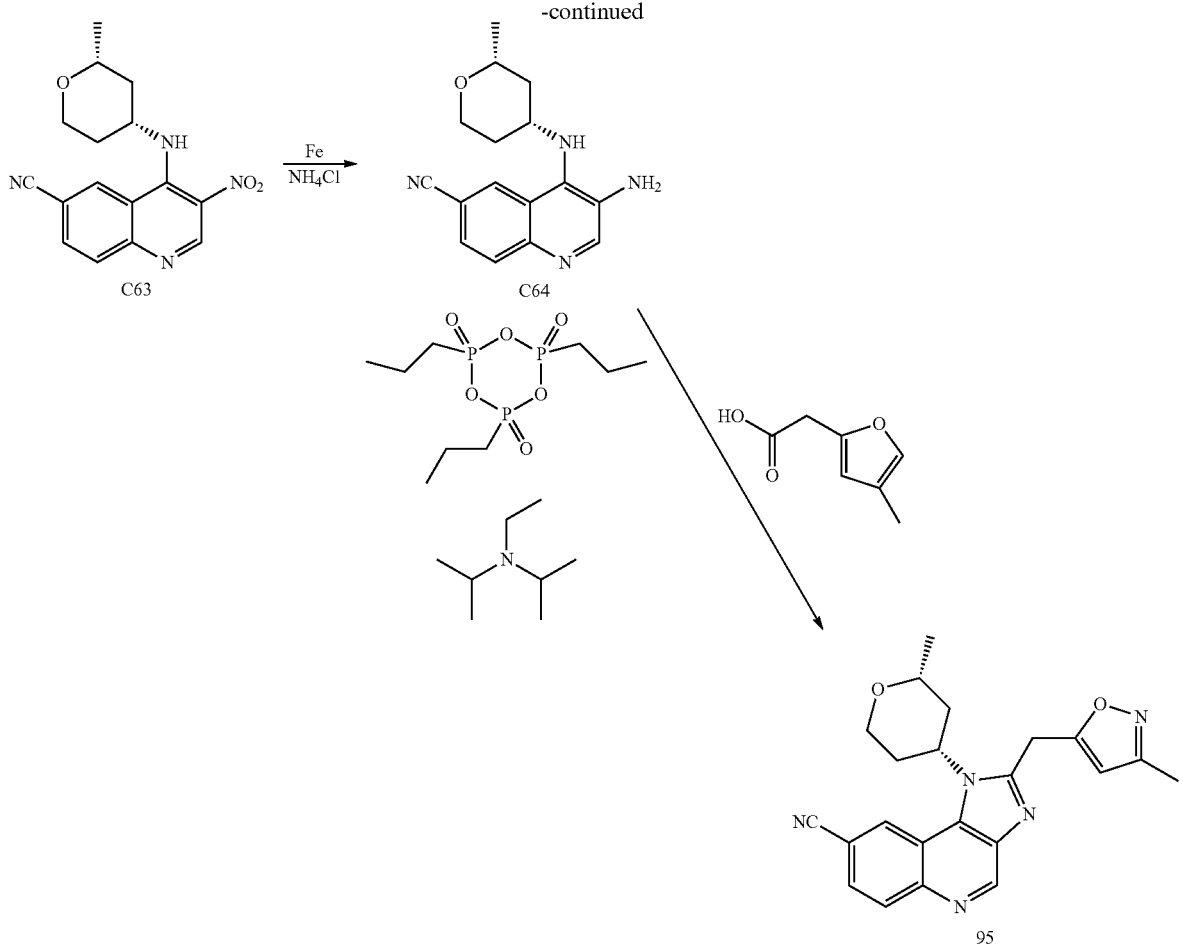

Step 1. Synthesis of 5-cyano-2-{[(E)-2-nitroethenyl]amino}benzoic acid (C59)

This experiment was run in two identical batches. {Caution: this reaction should not be carried out on greater than a 1 gram scale, due to highly energetic reactants and intermediates. Use of proper safety precautions and a blast shield is essential.} Nitromethane (4.71 g, 77.2 mmol) was added in a drop-wise manner to a solution of sodium hydroxide (3.95 g, 98.8 mmol) in water (25 mL), and the resulting solution was allowed to heat to 45° C. over 5 minutes, whereupon it was cooled in a water bath and treated with concentrated hydrochloric acid (12 M, 10 mL) until the pH of the solution became acidic. This was then added to a suspension of 2-amino-5-cyanobenzoic acid (5.0 g, 31 mmol) in water (50 mL), acetone (10 mL) and concentrated hydrochloric acid (12 M, 50 mL) at 25° C., and the reaction mixture was allowed to stir at 25° C. for 15 hours. The two batches were combined at this point, and the resulting suspension was filtered; the collected solid was washed with water to provide the product as a yellow solid. From analysis of the $^1$H NMR, the product was presumed to exist as a mixture of rotamers. Yield: 13.8 g, 59.2 mmol, 95%. $^1$H NMR (400 MHz, DMSO-$d_6$) δ [13.15 (s) and 13.12 (s), total 1H], 8.37 (d, J=2.0 Hz, 1H), 8.07-8.15 (m, 2H), 7.92 (d, half of AB quartet, J=9.0 Hz, 1H), 6.86 (d, J=6.0 Hz, 1H).

Step 2. Synthesis of 4-hydroxy-3-nitroquinoline-6-carbonitrile (C60)

Potassium carbonate (39.1 g, 283 mmol) was added to a suspension of C59 (22.0 g, 94.4 mmol) in acetic anhydride (200 mL). After the reaction mixture had been heated to 90° C. for 2 hours, it was filtered, and the collected material was washed with tert-butyl methyl ether (100 mL) and with water (400 mL), affording the product as a brown solid. Yield: 17.0 g, 79.0 mmol, 84%. LCMS m/z 215.9 [M+H]$^+$. $^1$H NMR (400 MHz, DMSO-$d_6$) δ 9.14 (s, 1H), 8.55 (dd, J=2.0, 0.5 Hz, 1H), 7.98 (dd, J=8.5, 2.0 Hz, 1H), 7.77 (dd, J=8.5, 0.5 Hz, 1H).

Step 3. Synthesis of 4-chloro-3-nitroquinoline-6-carbonitrile (C61)

Conversion of C60 to the product was carried out using the method described for synthesis of C8 from C7 in Example 1. The product was isolated as a brown solid. Yield: 9.1 g, 39 mmol, 86%. $^1$H NMR (400 MHz, DMSO-$d_6$) δ 9.26 (s, 1H), 8.59 (d, J=1.8 Hz, 1H), 8.16 (dd, J=8.7, 1.9 Hz, 1H), 7.93 (d, J=8.8 Hz, 1H).

Step 4. Synthesis of 4-{(2,4-dimethoxybenzyl)[(2R,4R)-2-methyltetrahydro-2H-pyran-4-yl]amino}-3-nitroquinoline-6-carbonitrile (C62)

To a solution of C61 (8.81 g, 37.7 mmol) in acetonitrile (80 mL) was added P2 (11.0 g, 41.5 mmol), followed by N,N-diisopropylethylamine (5.85 g, 45.3 mmol). The reaction mixture was stirred for 2 hours at room temperature, whereupon it was concentrated in vacuo and purified via silica gel chromatography (Eluent: 4:1 petroleum ether/ethyl acetate), affording the product as a viscous orange oil that slowly solidified. Yield: 15.0 g, 32.4 mmol, 86%. LCMS m/z 313.0 [M-(2,4-dimethoxybenzyl)+H]$^+$. $^1$H NMR (400 MHz, DMSO-d$_6$) δ 9.18 (s, 1H), 8.55 (br dd, J=1.3, 1 Hz, 1H), 8.15 (d, J=1.0 Hz, 2H), 6.88 (d, J=8.0 Hz, 1H), 6.24-6.30 (m, 2H), 4.33 (br AB quartet, J$_{AB}$=14.5 Hz, Δν$_{AB}$=12 Hz, 2H), 3.76-3.92 (m, 2H), 3.62 (s, 3H), 3.42 (s, 3H), 3.3-3.4 (m, 2H, assumed; largely obscured by water peak), 1.83-2.00 (m, 2H), 1.70-1.83 (m, 1H), 1.42-1.54 (m, 1H), 1.09 (d, J=6.0 Hz, 3H).

Step 5. Synthesis of 4-{[(2R,4R)-2-methyltetrahydro-2H-pyran-4-yl]amino}-3-nitroquinoline-6-carbonitrile (C63)

A mixture of C62 (15.0 g, 32.4 mmol) and trifluoroacetic acid (18.5 g, 162 mmol) in dichloromethane (150 mL) was stirred at room temperature for 30 minutes, whereupon it was concentrated to a volume of 20 mL and treated with saturated aqueous sodium bicarbonate solution (200 mL). The aqueous layer was extracted with dichloromethane (3×150 mL), and the combined organic layers were dried over sodium sulfate, filtered, and concentrated in vacuo to provide the product as a yellow solid. Yield: 5.68 g, 18.2 mmol, 56%. LCMS m/z 313.0 [M+H]$^+$. $^1$H NMR (400 MHz, DMSO-d$_6$) δ 9.06-9.09 (m, 2H), 8.30 (br d, J=9.0 Hz, 1H), 8.14 (dd, half of ABX pattern, J=8.7, 1.6 Hz, 1H), 8.01 (d, half of AB quartet, J=8.8 Hz, 1H), 3.87-3.93 (m, 1H), 3.69-3.82 (m, 1H), 3.3-3.5 (m, 2H, assumed; largely obscured by water peak), 1.87-2.03 (m, 2H), 1.60-1.72 (m, 1H), 1.36-1.47 (m, 1H), 1.11 (d, J=6.0 Hz, 3H).

Step 6. Synthesis of 3-amino-4-{[(2R,4R)-2-methyltetrahydro-2H-pyran-4-yl]amino}quinoline-6-carbonitrile (C64)

Ethanol (60 mL) and water (15 mL) were added to a mixture of C63 (5.68 g, 18.2 mmol), iron (10.2 g, 183 mmol), and ammonium chloride (9.73 g, 182 mmol). The reaction mixture was heated to 80° C. for 1 hour, whereupon it was diluted with ethanol (100 mL) and filtered. The filtrate was concentrated in vacuo, and the resulting solid was partitioned between saturated aqueous sodium bicarbonate solution (100 mL) and dichloromethane (300 mL). The organic layer was dried over sodium sulfate, filtered, and concentrated under reduced pressure to afford the product as a brown solid. Yield: 4.73 g, 16.8 mmol, 92%. LCMS m/z 282.9 [M+H]$^+$. $^1$H NMR (400 MHz, CD$_3$OD) δ 8.55 (d, J=1.2 Hz, 1H), 8.51 (s, 1H), 7.90 (d, J=8.8 Hz, 1H), 7.60 (dd, J=8.5, 1.8 Hz, 1H), 3.92-4.00 (m, 1H), 3.58-3.69 (m, 1H), 3.39-3.50 (m, 2H), 1.78-1.94 (m, 2H), 1.56-1.69 (m, 1H), 1.29-1.40 (m, 1H), 1.17 (d, J=6.0 Hz, 3H).

Step 7. Synthesis of 2-[(3-methyl-1,2-oxazol-5-yl)methyl]-1-[(2R,4R)-2-methyltetrahydro-2H-pyran-4-yl]-1H-imidazo[4,5-c]quinoline-8-carbonitrile (95)

2,4,6-Tripropyl-1,3,5,2,4,6-trioxatriphosphinane 2,4,6-trioxide (50% solution in ethyl acetate, 1.8 g, 2.8 mmol) and N,N-diisopropylethylamine (439 mg, 3.40 mmol) were added to a mixture of C64 (320 mg, 1.13 mmol) and (3-methyl-1,2-oxazol-5-yl)acetic acid (192 mg, 1.36 mmol) in ethyl acetate (5 mL) at room temperature (18° C.). After the reaction mixture had been heated at 80° C. for 2.5 days, it was cooled to room temperature (18° C.), and partitioned between saturated aqueous sodium chloride solution (40 mL) and ethyl acetate (6×40 mL). The combined organic layers were concentrated in vacuo and purified via silica gel chromatography (Gradient: 0% to 8% methanol in dichloromethane) to give a brown gum, which was triturated with a mixture of petroleum ether and ethyl acetate (2:1, 30 mL). The resulting solid was washed with a mixture of petroleum ether and ethyl acetate (1:1, 10 mL) and then with petroleum ether (10 mL), providing the product as a brownish solid. Yield: 160 mg, 0.413 mmol, 37%. LCMS m/z 388.0 [M+H]$^+$. $^1$H NMR (400 MHz, CDCl$_3$) δ 9.40 (s, 1H), 8.80-9.15 (br m, 1H), 8.39 (d, J=8.5 Hz, 1H), 7.88 (br d, J=8.5 Hz, 1H), 6.10 (s, 1H), 4.99-5.25 (br m, 1H), 4.63 (s, 2H), 4.35 (br dd, J=12, 5 Hz, 1H), 3.65-3.83 (m, 2H), 2.51-2.78 (br m, 1H), 2.22-2.48 (br m, 1H), 2.29 (s, 3H), 1.75-2.19 (br m, 2H), 1.38 (d, J=6.0 Hz, 3H).

Example 96

2-[(5-Methoxypyridin-2-yl)methyl]-1-[(2R,4R)-2-methyltetrahydro-2H-pyran-4-yl]-1H-imidazo[4,5-c]quinoline-8-carbonitrile, formate salt (96)

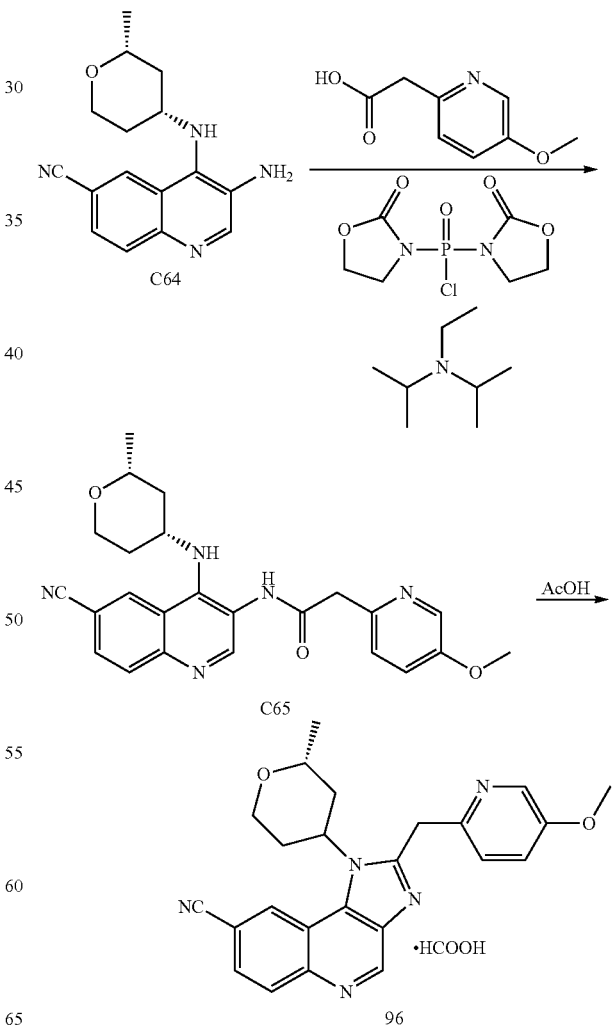

Step 1. Synthesis of N-(6-cyano-4-{[(2R,4R)-2-methyltetrahydro-2H-pyran-4-yl]amino}quinolin-3-yl)-2-(5-methoxypyridin-2-yl)acetamide (C65)

A solution of C64 in N,N-dimethylacetamide (0.1 M, 1.0 mL, 100 μmol) was added to (5-methoxypyridin-2-yl)acetic acid (25 mg, 150 μmol). N,N-Diisopropylethylamine (50 μL, 300 μmol) was added, followed by bis(2-oxo-1,3-oxazolidin-3-yl)phosphinic chloride (BOP—Cl, 38.1 mg, 150 μmol), and the reaction vial was capped and shaken at 30° C. for 16 hours. After solvent had been removed using a Speedvac® concentrator, the residue was washed and extracted with ethyl acetate (3×1.5 mL). The combined organic layers were dried over magnesium sulfate, filtered, and concentrated in vacuo, affording the product, which was taken directly to the next step

Step 2. Synthesis of 2-[(5-methoxypyridin-2-yl)methyl]-1-[(2R,4R)-2-methyltetrahydro-2H-pyran-4-yl]-1H-imidazo[4,5-c]quinoline-8-carbonitrile, formate salt (96)

Acetic acid (1 mL) was added to C65 (from the previous step, 5100 μmol), and the reaction vial was capped and shaken at 80° C. for 16 hours. Purification via reversed phase HPLC (Column: Agela Durashell C18, 5 μm; Mobile phase A: 0.225% formic acid in water; Mobile phase B: acetonitrile; Gradient: 20% to 50% B) provided the product. Yield: 4.0 mg, 8.7 μmol, 9% over 2 steps. LCMS m/z 414 [M+H]$^+$. Retention time: 2.44 minutes via analytical HPLC (Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL/minute).

Example 97

1-[(1R,3S)-3-Fluorocyclopentyl]-2-[(5-methyl-1,2-oxazol-3-yl)methyl]-1H-imidazo[4,5-c]quinoline-8-carbonitrile (97)

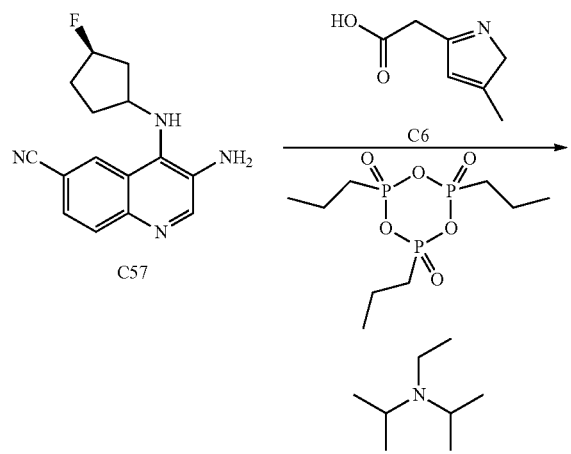

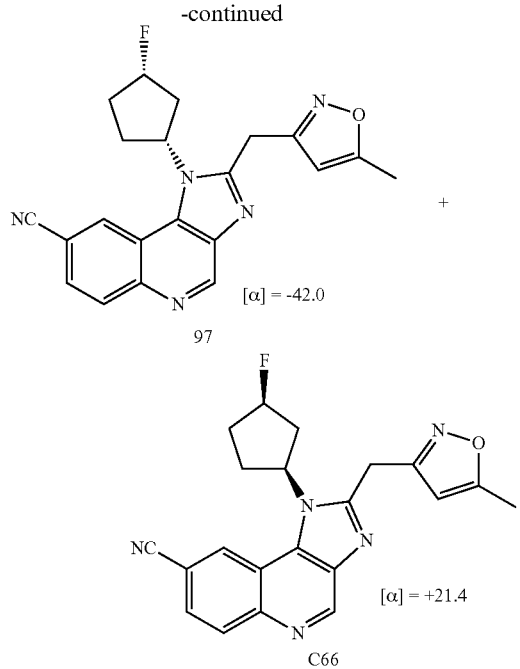

N,N-Diisopropylethylamine (0.387 mL, 2.22 mmol) and 2,4,6-tripropyl-1,3,5,2,4,6-trioxatriphosphinane 2,4,6-trioxide (50% solution in ethyl acetate, 1.32 mL, 2.22 mmol) were added to a mixture of C57 (200 mg, 0.740 mmol) and C6 (104 mg, 0.737 mmol) in ethyl acetate (4.4 mL), and the reaction mixture was heated at 80° C. overnight. It was then diluted with additional ethyl acetate and washed with water. The aqueous layer was extracted once with ethyl acetate, and the combined organic layers were washed with saturated aqueous sodium chloride solution, dried over sodium sulfate, filtered, and concentrated in vacuo. Silica gel chromatography (Eluent: ethyl acetate), followed by trituration with diethyl ether, provided a mixture of 97 and C66 as an off-white solid. Yield of racemic product: 141 mg, 0.376 mmol, 51%. This material was separated into its component enantiomers via supercritical fluid chromatography (Column: Phenomenex Lux Amylose-1, 5 μm; Mobile phase: 4:1 carbon dioxide/ethanol). The first-eluting enantiomer was 97, obtained as a white solid. Yield: 63.4 mg, 0.169 mmol, 45% for the separation. LCMS m/z 376.2 [M+H]$^+$. $^1$H NMR (400 MHz, CDCl$_3$) δ 9.40 (s, 1H), 8.92-8.97 (m, 1H), 8.35 (d, J=8.6 Hz, 1H), 7.85 (dd, J=8.6, 1.6 Hz, 1H), 6.00 (s, 1H), [5.48-5.54 (m) and 5.32-5.44 (m), total 2H], 4.53 (s, 2H), 2.46-2.76 (m, 4H), 2.40 (s, 3H), 1.92-2.15 (m, 2H). A sample of 97 synthesized and isolated in the same way gave specific rotation [α]–42.0° (c 0.105, dichloromethane).

An X-ray structural determination (see below) was carried out on a sample of 97 that had been crystallized from heptane/ethyl acetate; this provided confirmation of the cis-configuration of the nitrogen and fluorine atoms on the cyclopentane ring. The indicated absolute stereochemistry of 97 is strongly inferred from the Alternate Synthesis of Example 97 described below; the absolute configuration of reagent C49 would be identical to that of its precursor P4, which is predicted based on its enzymatic synthesis in Preparation P4.

The second-eluting enantiomer, also isolated as a white solid, was C66, 1-[(1 S,3R)-3-fluorocyclopentyl]-2-[(5-methyl-1,2-oxazol-3-yl)methyl]-1H-imidazo[4,5-c]quinoline-8-carbonitrile. Yield: 65.3 mg, 0.174 mmol, 46% for the separation. LCMS m/z 376.2 [M+H]+. $^1$H NMR (400 MHz, CDCl$_3$) δ 9.40 (s, 1H), 8.92-8.97 (m, 1H), 8.35 (d, J=8.8 Hz, 1H), 7.85 (dd, J=8.6, 1.6 Hz, 1H), 6.00 (s, 1H), [5.48-5.54 (m) and 5.32-5.44 (m), total 2H], 4.53 (s, 2H), 2.45-2.76 (m, 4H), 2.40 (s, 3H), 1.92-2.15 (m, 2H). A sample of C66 synthesized and isolated in the same way gave specific rotation [α]+21.4° (c 0.180, dichloromethane).

Single-Crystal X-Ray Structural Determination of 97

Single Crystal X-Ray Analysis

Data collection was performed on a Bruker APEX diffractometer at −150° C. Data collection consisted of omega and phi scans.

The structure was solved by direct methods using SHELX software suite in the triclinic class space group P1 as two molecules per asymmetric unit. The structure was subsequently refined by the full-matrix least squares method. All non-hydrogen atoms were found and refined using anisotropic displacement parameters.

The remaining hydrogen atoms were placed in calculated positions and were allowed to ride on their carrier atoms. The final refinement included isotropic displacement parameters for all hydrogen atoms.

Analysis of the absolute structure using likelihood methods (Hooft 2008) was performed using PLATON (Spek 2010). The analysis could not determine the absolute configuration in this case because of the weak intensity of the Friedel pairs.

The final R-index was 7.5%. A final difference Fourier revealed no missing or misplaced electron density.

Pertinent crystal, data collection, and refinement information is summarized in Table F. Atomic coordinates, bond lengths, bond angles, and displacement parameters are listed in Tables G, H, and J.

SOFTWARE AND REFERENCES

SHELXTL, Version 5.1, Bruker AXS, 1997.
PLATON, A. L. Spek, *J. Appl. Cryst.* 2003, 36, 7-13.
MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.
OLEX2, O. V. Dolomanov, L. J. Bourhis, R. J. Gildea, J. A. K. Howard, and H. Puschmann, *J. Appl. Cryst.* 2009, 42, 339-341.
R. W. W. Hooft, L. H. Straver, and A. L. Spek, *J. Appl. Cryst.* 2008, 41, 96-103.
H. D. Flack, *Acta Cryst.* 1983, A39, 867-881.

TABLE F

Crystal data and structure refinement for 97.

| | |
|---|---|
| Empirical formula | C$_{21}$H$_{18}$FN$_5$O |
| Formula weight | 375.40 |
| Temperature | 123(2) K |
| Wavelength | 1.54178 Å |
| Crystal system | Triclinic |
| Space group | P1 |
| Unit cell dimensions | a = 6.6809(5) Å, α = 97.338(4) |
| | b = 10.5609(6) Å, β = 92.773(4) |
| | c = 12.5604(8) Å, γ = 92.341(4) |
| Volume | 876.94(10) Å$^3$ |
| Z | 2 |
| Density (calculated) | 1.422 Mg/m$^3$ |
| Absorption coefficient | 0.813 mm$^{-1}$ |
| F(000) | 392 |
| Crystal size | 0.180 × 0.120 × 0.020 mm$^3$ |
| Theta range for data collection | 3.553 to 58.645° |
| Index ranges | −6 <= h <= 7, −11 <= k <= 11, −13 <= l <= 13 |
| Reflections collected | 8340 |
| Independent reflections | 3796 [R(int) = 0.0438] |
| Completeness to theta = 70.57° | 97.0% |
| Absorption correction | Empirical |
| Refinement method | Full-matrix least-squares on F$^2$ |
| Data/restraints/parameters | 3796/3/507 |
| Goodness-of-fit on F$^2$ | 0.993 |
| Final R indices [I > 2sigma(I)] | R1 = 0.0746, wR2 = 0.1843 |
| R indices (all data) | R1 = 0.0883, wR2 = 0.1955 |
| Absolute structure parameter | 1.5(4) |
| Extinction coefficient | n/a |
| Largest diff. peak and hole | 0.604 and −0.245 e.Å$^{-3}$ |

TABLE G

Atomic coordinates (×10$^4$) and equivalent isotropic displacement parameters (Å$^2$ × 10$^3$) for 97. U(eq) is defined as one-third of the trace of the orthogonalized U$^{ij}$ tensor.

| | x | y | z | U(eq) |
|---|---|---|---|---|
| F(1) | 7859(9) | 12178(5) | 6737(4) | 37(2) |
| F(2) | 2943(9) | 2661(5) | 6627(4) | 36(2) |
| N(1) | 7364(12) | 8661(8) | 4631(7) | 27(2) |
| N(2) | 10870(13) | 8715(9) | 2754(7) | 37(2) |
| N(3) | 7267(12) | 6622(8) | 3861(7) | 29(2) |
| N(4) | 7159(15) | 11575(10) | 9548(7) | 47(3) |
| N(5) | 7575(13) | 5781(9) | 6617(8) | 34(2) |
| N(6) | 2796(12) | 6149(8) | 8712(6) | 26(2) |
| N(7) | −732(13) | 6150(8) | 10595(7) | 35(2) |
| N(8) | 2796(12) | 8221(8) | 9481(7) | 30(2) |
| N(9) | 2035(15) | 3181(9) | 3800(7) | 45(2) |
| N(10) | 2461(12) | 9018(8) | 6724(7) | 28(2) |
| O(1) | 12265(10) | 9555(7) | 2371(5) | 35(2) |
| O(2) | −2130(11) | 5284(8) | 10978(6) | 36(2) |
| C(1) | 5526(15) | 10746(10) | 4916(8) | 32(2) |
| C(2) | 6340(15) | 12139(9) | 5006(8) | 32(2) |
| C(3) | 8312(15) | 12114(8) | 5638(7) | 31(2) |
| C(4) | 9197(15) | 10826(9) | 5263(8) | 32(2) |
| C(5) | 7411(14) | 10062(11) | 4620(8) | 27(2) |
| C(6) | 7303(15) | 7810(10) | 3693(8) | 28(2) |
| C(7) | 7239(16) | 8230(11) | 2603(8) | 30(2) |
| C(8) | 9121(16) | 8993(11) | 2370(8) | 30(2) |
| C(9) | 9279(17) | 9965(10) | 1695(8) | 36(3) |
| C(10) | 11224(18) | 10286(11) | 1720(8) | 36(3) |
| C(11) | 12450(19) | 11244(12) | 1223(10) | 47(3) |
| C(12) | 7385(15) | 7922(10) | 5473(8) | 27(2) |
| C(13) | 7332(14) | 6641(10) | 4949(8) | 27(2) |
| C(14) | 7434(15) | 5645(10) | 5578(9) | 30(3) |
| C(15) | 7611(14) | 7000(11) | 7129(8) | 28(3) |
| C(16) | 7449(15) | 8129(10) | 6612(8) | 27(2) |
| C(17) | 7376(14) | 9326(10) | 7276(8) | 27(2) |
| C(18) | 7498(15) | 9383(9) | 8371(8) | 26(2) |
| C(19) | 7345(16) | 10601(10) | 9030(8) | 33(3) |
| C(20) | 7737(18) | 8274(12) | 8885(9) | 32(2) |
| C(21) | 7751(15) | 7141(11) | 8272(8) | 31(3) |
| C(22) | 4511(15) | 4067(9) | 8136(8) | 30(2) |
| C(23) | 3541(15) | 2723(9) | 7729(8) | 33(2) |
| C(24) | 1654(14) | 2632(8) | 8328(8) | 32(2) |

TABLE G-continued

Atomic coordinates (×10⁴) and equivalent isotropic displacement parameters ($Å^2 \times 10^3$) for 97. U(eq) is defined as one-third of the trace of the orthogonalized $U^{ij}$ tensor.

|       | x        | y        | z         | U(eq) |
|-------|----------|----------|-----------|-------|
| C(25) | 886(15)  | 3984(9)  | 8399(8)   | 28(2) |
| C(26) | 2850(16) | 4768(10) | 8751(8)   | 29(2) |
| C(27) | 2833(15) | 7014(11) | 9650(9)   | 30(2) |
| C(28) | 2892(16) | 6600(12) | 10745(8)  | 37(3) |
| C(29) | 1018(16) | 5881(11) | 10978(8)  | 31(2) |
| C(30) | 874(16)  | 4847(10) | 11605(8)  | 31(2) |
| C(31) | −1119(17)| 4540(10) | 11584(8)  | 32(2) |
| C(32) | −2364(19)| 3594(11) | 12067(10) | 47(3) |
| C(33) | 2666(15) | 6903(11) | 7875(8)   | 28(2) |
| C(34) | 2670(14) | 8137(10) | 8372(8)   | 28(2) |
| C(35) | 2579(15) | 9177(10) | 7778(9)   | 31(2) |
| C(36) | 2448(15) | 7797(10) | 6195(8)   | 29(3) |
| C(37) | 2508(14) | 6644(10) | 6722(8)   | 25(2) |
| C(38) | 2410(15) | 5491(10) | 6084(8)   | 28(2) |
| C(39) | 2280(14) | 5384(11) | 4961(8)   | 31(3) |
| C(40) | 2144(16) | 4159(11) | 4335(8)   | 34(3) |
| C(41) | 2238(15) | 6518(11) | 4451(8)   | 32(3) |
| C(42) | 2298(14) | 7671(11) | 5059(9)   | 32(3) |

TABLE H

Bond lengths [Å] and angles [°] for 97.

| F(1)—C(3)     | 1.421(11) |
| F(2)—C(23)    | 1.415(11) |
| N(1)—C(6)     | 1.385(14) |
| N(1)—C(12)    | 1.393(13) |
| N(1)—C(5)     | 1.480(14) |
| N(2)—C(8)     | 1.302(14) |
| N(2)—O(1)     | 1.405(11) |
| N(3)—C(6)     | 1.299(13) |
| N(3)—C(13)    | 1.362(14) |
| N(4)—C(19)    | 1.160(15) |
| N(5)—C(14)    | 1.292(15) |
| N(5)—C(15)    | 1.362(16) |
| N(6)—C(27)    | 1.394(14) |
| N(6)—C(33)    | 1.399(13) |
| N(6)—C(26)    | 1.467(14) |
| N(7)—C(29)    | 1.299(14) |
| N(7)—O(2)     | 1.423(11) |
| N(8)—C(27)    | 1.320(15) |
| N(8)—C(34)    | 1.382(14) |
| N(9)—C(40)    | 1.155(14) |
| N(10)—C(35)   | 1.312(14) |
| N(10)—C(36)   | 1.373(15) |
| O(1)—C(10)    | 1.378(13) |
| O(2)—C(31)    | 1.341(13) |
| C(1)—C(5)     | 1.516(15) |
| C(1)—C(2)     | 1.536(13) |
| C(2)—C(3)     | 1.508(14) |
| C(3)—C(4)     | 1.533(13) |
| C(4)—C(5)     | 1.545(14) |
| C(6)—C(7)     | 1.491(14) |
| C(7)—C(8)     | 1.526(15) |
| C(8)—C(9)     | 1.416(15) |
| C(9)—C(10)    | 1.327(16) |
| C(10)—C(11)   | 1.493(14) |
| C(12)—C(16)   | 1.418(15) |
| C(12)—C(13)   | 1.425(15) |
| C(13)—C(14)   | 1.397(14) |
| C(15)—C(16)   | 1.434(14) |
| C(15)—C(21)   | 1.423(15) |
| C(16)—C(17)   | 1.426(16) |
| C(17)—C(18)   | 1.367(14) |

TABLE H-continued

Bond lengths [Å] and angles [°] for 97.

| C(18)—C(20)        | 1.418(15) |
| C(18)—C(19)        | 1.448(15) |
| C(20)—C(21)        | 1.338(17) |
| C(22)—C(26)        | 1.542(15) |
| C(22)—C(23)        | 1.550(13) |
| C(23)—C(24)        | 1.505(13) |
| C(24)—C(25)        | 1.530(13) |
| C(25)—C(26)        | 1.538(14) |
| C(27)—C(28)        | 1.495(15) |
| C(28)—C(29)        | 1.498(16) |
| C(29)—C(30)        | 1.428(15) |
| C(30)—C(31)        | 1.356(15) |
| C(31)—C(32)        | 1.481(15) |
| C(33)—C(34)        | 1.371(16) |
| C(33)—C(37)        | 1.438(15) |
| C(34)—C(35)        | 1.406(15) |
| C(36)—C(42)        | 1.415(15) |
| C(36)—C(37)        | 1.459(14) |
| C(37)—C(38)        | 1.367(16) |
| C(38)—C(39)        | 1.398(15) |
| C(39)—C(40)        | 1.423(17) |
| C(39)—C(41)        | 1.429(15) |
| C(41)—C(42)        | 1.350(17) |
| C(6)—N(1)—C(12)    | 106.3(9)  |
| C(6)—N(1)—C(5)     | 122.1(8)  |
| C(12)—N(1)—C(5)    | 131.7(9)  |
| C(8)—N(2)—O(1)     | 105.8(9)  |
| C(6)—N(3)—C(13)    | 105.9(9)  |
| C(14)—N(5)—C(15)   | 116.7(10) |
| C(27)—N(6)—C(33)   | 104.9(9)  |
| C(27)—N(6)—C(26)   | 121.3(8)  |
| C(33)—N(6)—C(26)   | 133.9(9)  |
| C(29)—N(7)—O(2)    | 105.7(9)  |
| C(27)—N(8)—C(34)   | 103.0(9)  |
| C(35)—N(10)—C(36)  | 118.4(9)  |
| N(2)—O(1)—C(10)    | 107.7(8)  |
| C(31)—O(2)—N(7)    | 108.5(8)  |
| C(5)—C(1)—C(2)     | 99.8(8)   |
| C(3)—C(2)—C(1)     | 102.8(7)  |
| F(1)—C(3)—C(2)     | 106.6(8)  |
| F(1)—C(3)—C(4)     | 110.0(7)  |
| C(2)—C(3)—C(4)     | 106.5(7)  |
| C(5)—C(4)—C(3)     | 103.0(8)  |
| N(1)—C(5)—C(1)     | 117.3(8)  |
| N(1)—C(5)—C(4)     | 115.8(8)  |
| C(1)—C(5)—C(4)     | 107.3(9)  |
| N(3)—C(6)—N(1)     | 113.3(9)  |
| N(3)—C(6)—C(7)     | 123.9(10) |
| N(1)—C(6)—C(7)     | 122.8(9)  |
| C(6)—C(7)—C(8)     | 114.0(8)  |
| N(2)—C(8)—C(9)     | 111.8(9)  |
| N(2)—C(8)—C(7)     | 120.0(10) |
| C(9)—C(8)—C(7)     | 128.0(10) |
| C(10)—C(9)—C(8)    | 105.1(10) |
| C(9)—C(10)—O(1)    | 109.6(9)  |
| C(9)—C(10)—C(11)   | 134.3(11) |
| O(1)—C(10)—C(11)   | 116.0(11) |
| N(1)—C(12)—C(16)   | 137.5(10) |
| N(1)—C(12)—C(13)   | 103.9(9)  |
| C(16)—C(12)—C(13)  | 118.6(9)  |
| N(3)—C(13)—C(14)   | 130.6(10) |
| N(3)—C(13)—C(12)   | 110.7(9)  |
| C(14)—C(13)—C(12)  | 118.6(10) |
| N(5)—C(14)—C(13)   | 125.3(11) |
| N(5)—C(15)—C(16)   | 125.4(10) |
| N(5)—C(15)—C(21)   | 116.4(10) |
| C(16)—C(15)—C(21)  | 118.2(10) |
| C(17)—C(16)—C(12)  | 126.8(10) |

TABLE H-continued

Bond lengths [Å] and angles [°] for 97.

| | |
|---|---|
| C(17)—C(16)—C(15) | 118.0(9) |
| C(12)—C(16)—C(15) | 115.1(10) |
| C(18)—C(17)—C(16) | 120.3(9) |
| C(17)—C(18)—C(20) | 121.8(10) |
| C(17)—C(18)—C(19) | 119.5(9) |
| C(20)—C(18)—C(19) | 118.7(9) |
| N(4)—C(19)—C(18) | 177.9(12) |
| C(21)—C(20)—C(18) | 118.4(10) |
| C(20)—C(21)—C(15) | 123.2(10) |
| C(26)—C(22)—C(23) | 104.2(8) |
| F(2)—C(23)—C(24) | 106.9(8) |
| F(2)—C(23)—C(22) | 109.3(7) |
| C(24)—C(23)—C(22) | 105.3(8) |
| C(23)—C(24)—C(25) | 103.5(7) |
| C(24)—C(25)—C(26) | 99.9(8) |
| N(6)—C(26)—C(22) | 116.5(8) |
| N(6)—C(26)—C(25) | 116.0(9) |
| C(22)—C(26)—C(25) | 105.9(9) |
| N(8)—C(27)—N(6) | 114.0(9) |
| N(8)—C(27)—C(28) | 123.4(11) |
| N(6)—C(27)—C(28) | 122.6(10) |
| C(29)—C(28)—C(27) | 113.6(9) |
| N(7)—C(29)—C(30) | 111.5(9) |
| N(7)—C(29)—C(28) | 121.5(11) |
| C(30)—C(29)—C(28) | 127.0(10) |
| C(31)—C(30)—C(29) | 104.3(9) |
| O(2)—C(31)—C(30) | 109.9(9) |
| O(2)—C(31)—C(32) | 115.5(10) |
| C(30)—C(31)—C(32) | 134.6(10) |
| C(34)—C(33)—N(6) | 105.1(9) |
| C(34)—C(33)—C(37) | 120.1(10) |
| N(6)—C(33)—C(37) | 134.7(11) |
| C(33)—C(34)—N(8) | 113.0(9) |
| C(33)—C(34)—C(35) | 121.5(10) |
| N(8)—C(34)—C(35) | 125.6(10) |
| N(10)—C(35)—C(34) | 121.9(10) |
| N(10)—C(36)—C(42) | 116.4(9) |
| N(10)—C(36)—C(37) | 124.7(9) |
| C(42)—C(36)—C(37) | 118.8(10) |
| C(38)—C(37)—C(33) | 128.9(10) |
| C(38)—C(37)—C(36) | 117.8(9) |
| C(33)—C(37)—C(36) | 113.3(10) |
| C(37)—C(38)—C(39) | 122.6(10) |
| C(38)—C(39)—C(40) | 120.3(10) |
| C(38)—C(39)—C(41) | 119.3(10) |
| C(40)—C(39)—C(41) | 120.4(9) |
| N(9)—C(40)—C(39) | 178.1(11) |
| C(42)—C(41)—C(39) | 119.5(10) |
| C(41)—C(42)—C(36) | 121.9(10) |

Symmetry transformations used to generate equivalent atoms.

TABLE J

Anisotropic displacement parameters (Å$^2$ × 10$^3$) for 97. The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| F(1) | 58(4) | 32(3) | 21(3) | 1(2) | 3(2) | 3(3) |
| F(2) | 55(4) | 32(3) | 20(3) | 0(2) | 3(2) | −1(3) |
| N(1) | 30(5) | 24(5) | 27(5) | 9(4) | 1(3) | 0(3) |
| N(2) | 37(6) | 43(6) | 31(5) | 6(4) | 1(4) | −3(4) |
| N(3) | 29(5) | 20(5) | 36(5) | 0(4) | 4(4) | 4(3) |
| N(4) | 61(7) | 45(6) | 35(5) | 5(5) | 1(4) | 10(5) |
| N(5) | 28(5) | 30(6) | 45(6) | 11(4) | 4(4) | 2(4) |
| N(6) | 39(5) | 21(5) | 19(4) | 2(3) | 4(3) | 0(4) |
| N(7) | 42(6) | 29(5) | 35(5) | 10(4) | 7(4) | 3(4) |
| N(8) | 29(5) | 24(5) | 37(6) | 4(4) | −2(4) | 0(4) |

TABLE J-continued

Anisotropic displacement parameters (Å$^2$ × 10$^3$) for 97. The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| N(9) | 71(7) | 37(6) | 27(5) | 8(4) | −2(4) | 10(5) |
| N(10) | 32(5) | 21(5) | 33(5) | 14(4) | −1(4) | −2(4) |
| O(1) | 45(5) | 36(5) | 23(4) | 3(3) | 4(3) | −1(3) |
| O(2) | 39(4) | 35(4) | 37(4) | 11(3) | 6(3) | 1(3) |
| C(1) | 34(6) | 28(5) | 36(6) | 17(4) | −1(4) | 0(4) |
| C(2) | 38(6) | 24(5) | 36(6) | 2(4) | 7(4) | 8(4) |
| C(3) | 43(6) | 16(4) | 34(5) | 3(4) | 5(4) | −5(4) |
| C(4) | 32(6) | 25(5) | 39(6) | 4(4) | 4(4) | 2(4) |
| C(5) | 30(6) | 29(6) | 21(5) | 6(4) | 5(4) | 1(4) |
| C(6) | 34(6) | 21(6) | 30(6) | 4(5) | 4(4) | −4(4) |
| C(7) | 40(7) | 28(6) | 21(5) | 2(4) | 2(4) | 2(5) |
| C(8) | 41(7) | 35(7) | 14(5) | 0(4) | 3(4) | −3(5) |
| C(9) | 49(8) | 34(7) | 28(6) | 5(5) | 2(5) | 11(5) |
| C(10) | 56(8) | 31(7) | 22(6) | 6(5) | 8(5) | 3(5) |
| C(11) | 64(9) | 41(8) | 40(7) | 17(6) | 15(5) | −2(6) |
| C(12) | 37(6) | 15(5) | 30(6) | 5(5) | 2(4) | 2(4) |
| C(13) | 24(6) | 24(6) | 32(6) | 6(5) | 3(4) | −2(4) |
| C(14) | 26(6) | 22(6) | 45(7) | 8(5) | 4(4) | 2(4) |
| C(15) | 18(5) | 30(7) | 36(6) | 12(5) | −2(4) | −1(4) |
| C(16) | 24(6) | 25(6) | 33(6) | 7(5) | 9(4) | 0(4) |
| C(17) | 21(5) | 23(5) | 41(6) | 13(4) | 1(4) | 6(4) |
| C(18) | 33(6) | 22(5) | 25(6) | 9(4) | 4(4) | 0(4) |
| C(19) | 48(7) | 32(6) | 21(5) | 10(5) | −1(4) | 0(5) |
| C(20) | 21(6) | 45(7) | 33(6) | 18(5) | 2(4) | 3(5) |
| C(21) | 36(7) | 30(7) | 28(6) | 15(5) | −3(4) | −3(5) |
| C(22) | 37(6) | 18(5) | 33(5) | −1(4) | −1(4) | 4(4) |
| C(23) | 37(6) | 21(5) | 40(6) | 5(4) | −2(4) | 3(4) |
| C(24) | 41(6) | 20(5) | 35(5) | 5(4) | 4(4) | −1(4) |
| C(25) | 34(6) | 24(5) | 28(5) | 9(4) | 8(4) | 4(4) |
| C(26) | 43(7) | 18(6) | 25(5) | 6(4) | 4(4) | 0(4) |
| C(27) | 22(6) | 33(7) | 34(6) | 3(5) | 0(4) | −2(4) |
| C(28) | 38(7) | 47(8) | 23(6) | −3(5) | −1(4) | 5(5) |
| C(29) | 38(7) | 32(6) | 20(6) | −5(4) | 0(4) | 5(5) |
| C(30) | 40(7) | 27(6) | 26(6) | 8(5) | 0(4) | 4(5) |
| C(31) | 48(7) | 25(6) | 21(5) | 1(4) | 0(4) | 2(5) |
| C(32) | 65(9) | 34(7) | 45(7) | 13(6) | 5(5) | −4(6) |
| C(33) | 19(5) | 31(6) | 36(6) | 12(5) | 4(4) | −2(4) |
| C(34) | 29(6) | 20(6) | 33(6) | 1(4) | −1(4) | −2(4) |
| C(35) | 28(6) | 19(6) | 45(7) | 0(5) | 7(4) | −2(4) |
| C(36) | 28(6) | 31(7) | 31(6) | 15(5) | 5(4) | 0(5) |
| C(37) | 20(5) | 34(7) | 22(5) | 12(5) | 0(4) | 2(4) |
| C(38) | 28(6) | 29(6) | 29(6) | 14(5) | 3(4) | 1(4) |
| C(39) | 19(6) | 43(7) | 33(6) | 9(5) | 0(4) | 5(4) |
| C(40) | 40(7) | 42(7) | 23(5) | 10(5) | 2(4) | 4(5) |
| C(41) | 28(6) | 42(7) | 28(6) | 10(5) | 8(4) | 1(5) |
| C(42) | 22(6) | 33(7) | 45(7) | 22(6) | 1(4) | −1(4) |

Alternate Synthesis of Example 97

1-[(1R,3S)-3-Fluorocyclopentyl]-2-[(5-methyl-1,2-oxazol-3-yl)methyl]-1H-imidazo[4,5-c]quinoline-8-carbonitrile (97)

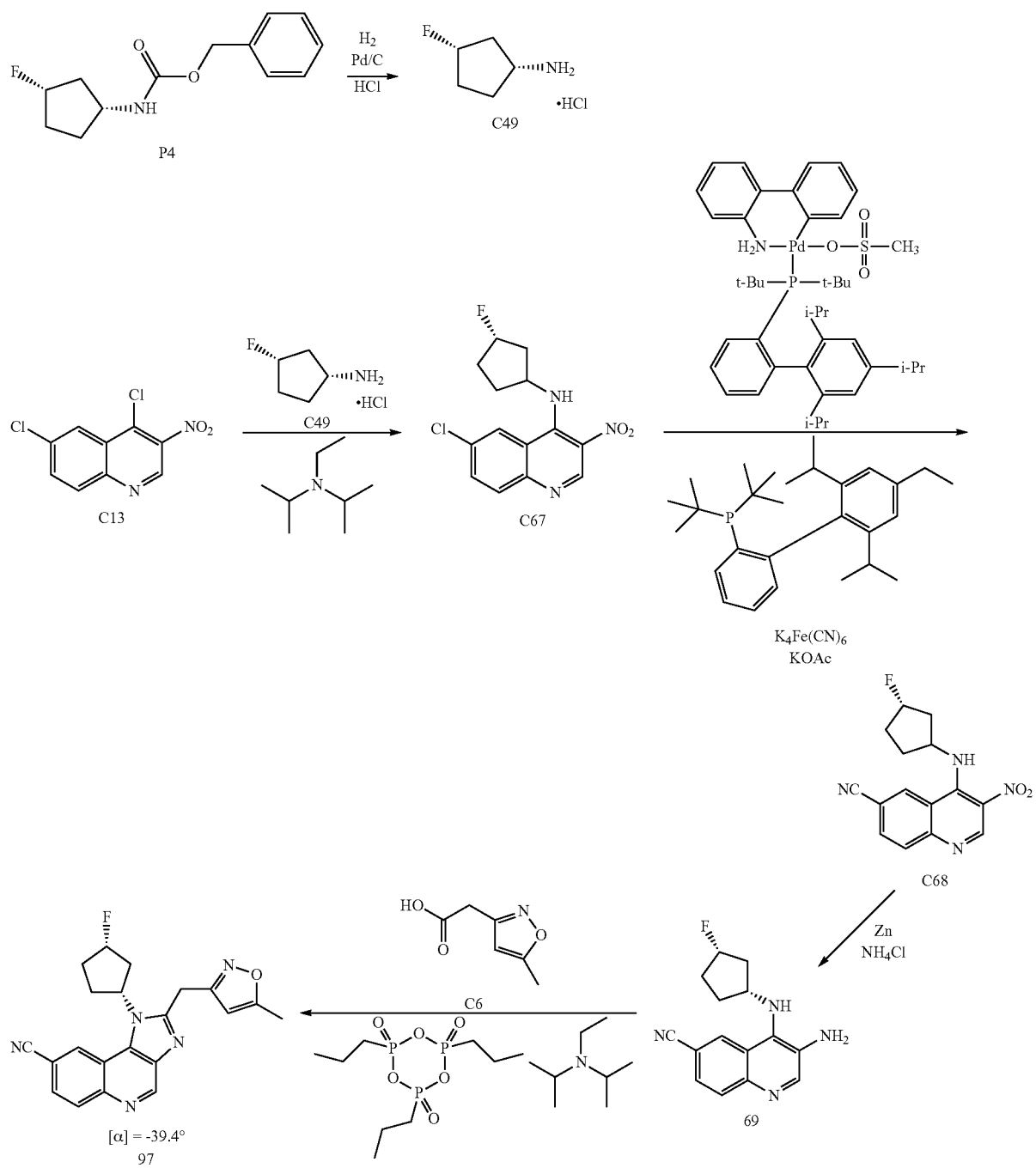

chloride in methanol (1.25 M, 12.6 mL, 15.8 mmol). Palladium on carbon (10%, 250 mg) was added, and the reaction vessel was pressurized to 100 psi with nitrogen three times, followed by pressurization to 40 psi with hydrogen three times. The reaction mixture was then hydrogenated at room temperature and 40 psi overnight, whereupon it was purged three times with nitrogen and combined with a similar reaction carried out on P4 (270 mg, 1.14 mmol). After the mixture had been filtered through a polyethylene filter, the filtrate was concentrated in vacuo, azeotroped once with toluene, and washed twice with heptane, affording the product as a white solid. Yield: 315 mg,

Step 1. Synthesis of (1R,3S)-3-fluorocyclopentanamine, hydrochloride salt (C49)

Compound P4 (from Alternate Preparation of P4 above, 250 mg, 1.05 mmol) was dissolved in a solution of hydrogen assumed quantitative. ¹H NMR (400 MHz, CD₃OD) δ [5.24-5.29 (m) and 5.11-5.16 (m), $J_{HF}$=53 Hz, total 1H], 3.67-3.77 (br m, 1H), 2.35 (dddd, J=35.9, 15.6, 8.6, 4.7 Hz, 1H), 1.79-2.27 (m, 5H).

Step 2. Synthesis of 6-chloro-N-[(1R,3S)-3-fluoro-cyclopentyl]-3-nitroquinolin-4-amine (C67)

Reaction of C13 with C49 was effected using the method described for synthesis of C53 from C13 in Example 93. In this case, the purified material from silica gel chromatography was crystallized from dichloromethane/heptane, affording the product as a solid. Yield: 685 mg, 2.21 mmol, 89%. ¹H NMR (400 MHz, CDCl₃) δ 9.80 (br d, J=7 Hz, 1H), 9.36 (s, 1H), 8.24 (d, J=2.3 Hz, 1H), 7.96 (d, J=9.0 Hz, 1H), 7.71 (dd, J=8.9, 2.2 Hz, 1H), [5.38-5.43 (m) and 5.25-5.30 (m), $J_{HF}$=53 Hz, total 1H], 4.71-4.81 (m, 1H), 2.43-2.54 (m, 1H), 2.28-2.43 (m, 3H), 2.16-2.27 (m, 1H), 1.88-2.08 (m, 1H).

Step 3. Synthesis of 4-{[(1R,3S)-3-fluorocyclopentyl]amino}-3-nitroquinoline-6-carbonitrile (C68)

Conversion of C67 to the product was carried out using the method described for synthesis of C56 from C53 in Example 94. In this case, purification was effected using silica gel chromatography (Gradient: 0% to 60% ethyl acetate in heptane, followed by 100% ethyl acetate), providing the product as a solid. Yield: 332 mg, 1.11 mmol, 50%. ¹H NMR (400 MHz, CDCl₃) δ 10.04 (br d, J=7 Hz, 1H), 9.46 (s, 1H), 8.61 (d, J=1.8 Hz, 1H), 8.09 (d, half of AB quartet, J=8.8 Hz, 1H), 7.92 (dd, half of ABX pattern, J=8.7, 1.7 Hz, 1H), [5.42-5.46 (m) and 5.29-5.33 (m), total 1H], 4.71-4.80 (m, 1H), 2.48-2.59 (m, 1H), 2.29-2.46 (m, 3H), 2.19-2.29 (m, 1H), 1.92-2.13 (m, 1H).

Step 4. Synthesis of 3-amino-4-{[(1R,3S)-3-fluoro-cyclopentyl]amino}quinoline-6-carbonitrile (C69)

Zinc (97.5%, 0.739 g, 11.0 mmol) was added in one portion to a mixture of C68 (331 mg, 1.10 mmol) in methanol (5.5 mL) and concentrated ammonium hydroxide (5.5 mL). After 1 hour at room temperature, the reaction mixture was filtered through diatomaceous earth, and the filter pad was washed with methanol. The combined filtrates were concentrated in vacuo, and the residue was purified via chromatography on silica gel (Gradient: 0% to 10% methanol in ethyl acetate). The resulting material was triturated with diethyl ether and washed with heptane to afford the product. Yield: 114 mg, 0.422 mmol, 38%. ¹H NMR (400 MHz, CDCl₃) δ 8.57 (s, 1H), 8.28 (d, J=1.6 Hz, 1H), 8.02 (d, J=8.6 Hz, 1H), 7.60 (dd, J=8.6, 1.8 Hz, 1H), [5.39-5.43 (m) and 5.26-5.30 (m), $J_{HF}$=53.5 Hz, total 1H], 4.23-4.33 (m, 1H), 3.99-4.07 (m, 1H), 3.91 (br s, 2H), 2.20-2.35 (m, 1H), 2.04-2.17 (m, 2H), 1.82-2.03 (m, 3H).

Step 5. Synthesis of 1-[(1R,3S)-3-fluorocyclopentyl]-2-[(5-methyl-1,2-oxazol-3-yl)methyl]-1H-imidazo[4,5-c]quinoline-8-carbonitrile (97)

N,N-Diisopropylethylamine (39.1 μL, 0.224 mmol) and 2,4,6-tripropyl-1,3,5,2,4,6-trioxatriphosphinane 2,4,6-trioxide (50% solution in ethyl acetate, 0.191 mL, 0.321 mmol) were added to a mixture of C69 (60 mg, 0.22 mmol) and C6 (31.3 mg, 0.222 mmol) in toluene (2.2 mL). The reaction mixture was heated at 70° C. for 1 hour, and then at 110° C. for 3 hours, whereupon it was cooled to room temperature and directly subjected to two chromatographic purifications on silica gel (Gradient: 0% to 20% methanol in ethyl acetate). The resulting material was triturated with ethyl acetate and diethyl ether to provide the product as an off-white to light yellow solid. Yield: 41.2 mg, 0.110 mmol, 50%. Specific rotation: [α]−39.4° (c 0.120, dichloromethane). ¹H NMR (400 MHz, CDCl₃) δ 9.41 (s, 1H), 8.92-8.97 (m, 1H), 8.36 (d, J=8.8 Hz, 1H), 7.85 (dd, J=8.7, 1.7 Hz, 1H), 6.00 (br s, 1H), 5.32-5.54 (m, 2H), 4.53 (s, 2H), 2.46-2.76 (m, 4H), 2.41 (br s, 3H), 1.92-2.15 (m, 2H).

Example 98

1-[(2R,4R)-2-Methyltetrahydro-2H-pyran-4-yl]-2-(pyrazin-2-ylmethyl)-1H-imidazo[4,5-c]quinoline-8-carbonitrile, formate salt (98)

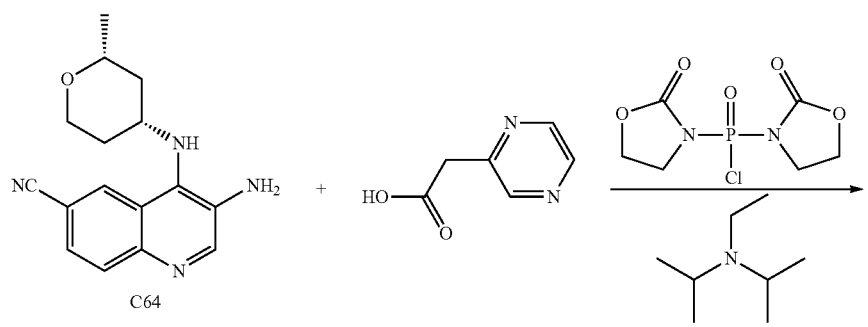

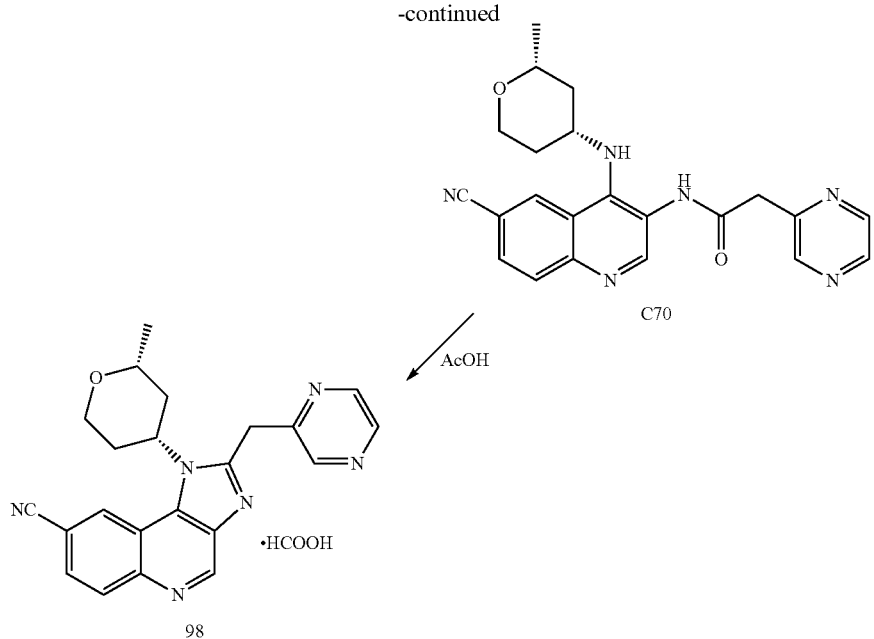

Step 1. Synthesis of N-(6-cyano-4-{[(2R,4R)-2-methyltetrahydro-2H-pyran-4-yl]amino}quinolin-3-yl)-2-(pyrazin-2-yl)acetamide (C70)

Compound C64 was reacted with pyrazin-2-ylacetic acid using the method described in Example 96 for synthesis of C65 from C64. The product was taken directly to the next step.

Step 2. Synthesis of 1-[(2R,4R)-2-methyltetrahydro-2H-pyran-4-yl]-2-(pyrazin-2-ylmethyl)-1H-imidazo[4,5-c]quinoline-8-carbonitrile, formate salt (98)

Conversion of C70 to the product was effected using the method described for synthesis of 96 from C65 in Example 96. Purification via reversed phase HPLC (Column: Agela Durashell C18, 5 μm; Mobile phase A: aqueous ammonia, pH 10; Mobile phase B: acetonitrile; Gradient: 18% to 48% B) provided the product. Yield: 3.0 mg, 7.0 μmol, 7%. LCMS m/z 385 [M+H]$^+$. Retention time: 2.30 minutes via analytical HPLC (Column: Waters XBridge C18, 2.1×50 mm, 5 μm; Mobile phase A: 0.05% ammonium hydroxide in water; Mobile phase B: acetonitrile; Gradient: 5% B for 0.5 minutes; 5% to 100% B over 2.9 minutes; 100% B for 0.8 minutes; Flow rate: 0.8 mL/minute).

Example 99

8-Chloro-1-[(2R,4R)-2-methyltetrahydro-2H-pyran-4-yl]-2-{[4-(trifluoromethyl)-1H-1,2,3-triazol-1-yl]methyl}-1H-imidazo[4,5-c]quinoline, formate salt (99)

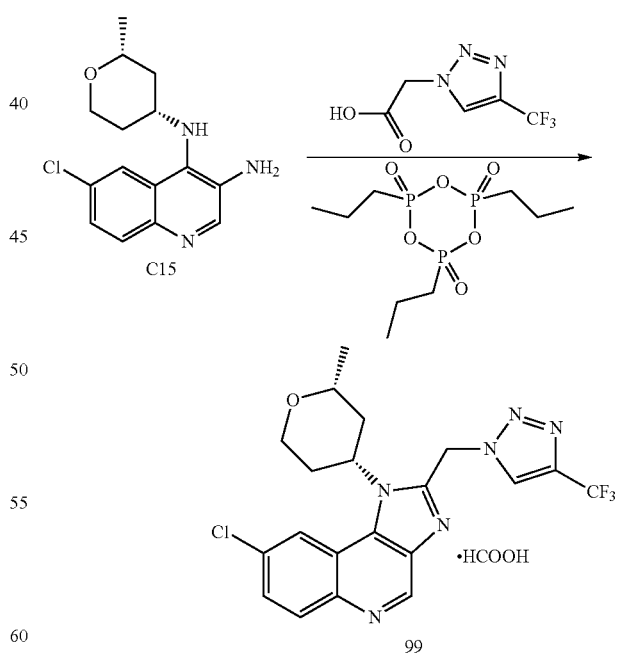

A mixture of C15 (29 mg, 100 μmol), [4-(trifluoromethyl)-1H-1,2,3-triazol-1-yl]acetic acid (see M. D. Andrews et al., US 20150218172 A1, Aug. 6, 2015) (23 mg, 120 μmol), and 2,4,6-tripropyl-1,3,5,2,4,6-trioxatriphosphinane 2,4,6-trioxide (50% solution in ethyl acetate, 1.0 mL, 1.7 mmol) was prepared in a vial, which was then capped and shaken at 120° C. for 16 hours. After solvent had been removed using a Speedvac® concentrator, the residue was purified via reversed phase HPLC (Column: Agela Durashell C18, 5 μm; Mobile phase A: 0.225% formic acid in water; Mobile phase B: acetonitrile; Gradient: 17% to 57% B) to provide the product. Yield: 10.2 mg, 20.5 μmol, 20%. LCMS m/z 451 [M+H]$^+$. Retention time: 2.90 minutes via analytical HPLC (Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL/minute).

Example 100

8-Chloro-2-[(5-methylpyridin-2-yl)methyl]-1-[(2R,4R)-2-methyltetrahydro-2H-pyran-4-yl]-1H-imidazo[4,5-c]quinoline (100)

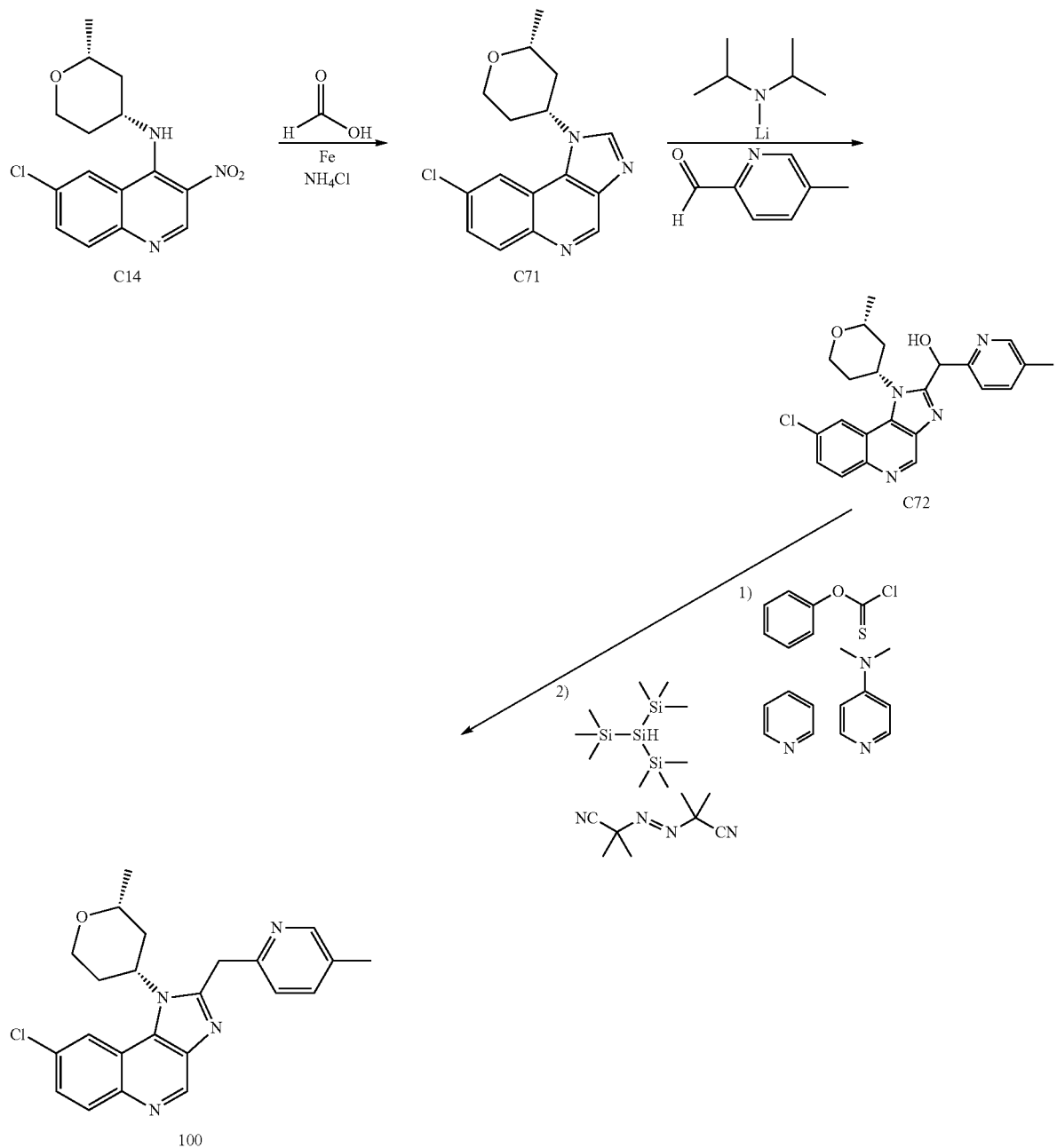

Step 1. Synthesis of 8-chloro-1-[(2R,4R)-2-methyl-tetrahydro-2H-pyran-4-yl]-1H-imidazo[4,5-c]quinoline (C71)

Formic acid (310 mL) was added to a mixture of iron powder (34.7 g, 621 mmol), ammonium chloride (33.2 g, 621 mmol), and C14 (20 g, 62.2 mmol) in 2-propanol (310 mL) at room temperature (14° C.). The reaction mixture was heated at 80° C. for 16 hours, whereupon it was diluted with ethanol (300 mL), and filtered. The collected solids were washed with 2-propanol (200 mL) and dichloromethane (100 mL), and the combined filtrates were concentrated in vacuo, then co-evaporated with ethanol (200 mL). The residue was diluted with dichloromethane (300 mL), basified via addition of saturated aqueous sodium bicarbonate solution (500 mL), and then filtered through diatomaceous earth; the filter pad was washed with dichloromethane (300 mL). The aqueous layer of the combined filtrates was extracted with dichloromethane (4×100 mL), and the combined organic layers were washed with saturated aqueous sodium chloride solution (100 mL), dried over sodium sulfate, filtered, and concentrated under reduced pressure. Silica gel chromatography (Gradient: 0% to 5% methanol in dichloromethane) afforded a solid, which was washed with a mixture of petroleum ether and ethyl acetate (3:1, 100 mL) and with petroleum ether (50 mL) to provide the product as a beige solid. Yield: 10.05 g, 33.3 mmol, 54%. LCMS m/z 301.8 (chlorine isotope pattern observed) [M+H]$^+$. $^1$H NMR (400 MHz, CDCl$_3$) δ 9.35 (s, 1H), 8.25 (d, J=9.0 Hz, 1H), 8.19 (s, 1H), 8.09 (d, J=2.3 Hz, 1H), 7.66 (dd, J=8.8, 2.3 Hz, 1H), 5.02 (tt, J=12.0, 3.8 Hz, 1H), 4.30 (ddd, J=11.9, 4.6, 1.6 Hz, 1H), 3.77-3.89 (m, 2H), 2.33-2.46 (m, 2H), 2.09-2.22 (m, 1H), 1.83-1.95 (m, 1H), 1.38 (d, J=6.3 Hz, 3H).

Step 2. Synthesis of {8-chloro-1-[(2R,4R)-2-methyltetrahydro-2H-pyran-4-yl]-1H-imidazo[4,5-c]quinolin-2-yl}(5-methylpyridin-2-yl) methanol (C72)

A solution of lithium diisopropylamide in heptane/tetrahydrofuran/ethylbenzene (2 M, 3.0 mL, 6.0 mmol) was added to a −78° C. solution of C71 (1.64 g, 5.43 mmol) in tetrahydrofuran (28 mL), and the reaction mixture was allowed to stir at −78° C. for 15 minutes. A solution of 5-methylpyridine-2-carbaldehyde (29 mg, 0.24 mmol) in tetrahydrofuran (0.4 mL) was cooled to −78° C. and treated with a portion of the C71-containing reaction mixture (0.9 mL, approximately 0.15 mmol); stirring was continued at −78° C. for 15 minutes, whereupon the cooling bath was removed, and the reaction mixture was allowed to warm to room temperature. It was then partitioned between water (1.5 mL) and ethyl acetate (2.4 mL) with vortexing. The organic layer was eluted through a solid phase extraction cartridge (6 mL) charged with sodium sulfate (~1 g); this extraction procedure was repeated twice, and the combined eluents were concentrated in vacuo and used directly in the following step.

Step 3. Synthesis of 8-chloro-2-[(5-methylpyridin-2-yl)methyl]-1-[(2R,4R)-2-methyltetrahydro-2H-pyran-4-yl]-1H-imidazo[4,5-c]quinoline (100)

Pyridine (45 μL, 0.56 mmol) was added to C72 (from the previous step, 50.15 mmol), followed by a solution of 4-(dimethylamino)pyridine (2.5 mg, 20 μmol) in 1,2-dichloroethane (0.3 mL). The reaction vessel was evacuated and charged with nitrogen; this evacuation cycle was repeated twice, and then a solution of O-phenyl carbonochloridothioate (52 mg, 0.30 mmol) in 1,2-dichloroethane (0.3 mL) was added. After the reaction mixture had been shaken at room temperature for 2 hours, it was partitioned between water (1.5 mL) and ethyl acetate (2.4 mL) with vortexing. The organic layer was eluted through a solid phase extraction cartridge (6 mL) charged with sodium sulfate (~1 g); this extraction procedure was repeated twice, and the combined eluents were concentrated in vacuo. The resulting material was treated with a solution of 2,2'-azobisisobutyronitrile (2 mg, 10 μmol) in toluene (0.6 mL) and 1,1,1,3,3,3-hexamethyl-2-(trimethylsilyl)trisilane (40 uL, 0.13 mmol) and the reaction mixture was shaken at 110° C. for 20 hours. It was then partitioned between water (1.5 mL) and ethyl acetate (2.4 mL) with vortexing, and the organic layer was eluted through a solid phase extraction cartridge (6 mL) charged with sodium sulfate (~1 g); this extraction procedure was repeated twice, and the combined eluents were concentrated in vacuo and purified using reversed phase HPLC (Column: Waters XBridge C18, 5 μm; Mobile phase A: 0.05% ammonium hydroxide in water; Mobile phase B: 0.05% ammonium hydroxide in acetonitrile; Gradient: 5% to 100% B). Yield: 4.7 mg, 12 μmol, 8% over 2 steps. LCMS m/z 407.4 (chlorine isotope pattern observed) [M+H]$^+$. Retention time: 1.89 minutes via analytical HPLC (Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 20% to 95% B, linear over 4.0 minutes; Flow rate: 2 mL/minute).

Example 101

1-(cis-3-Fluorocyclopentyl)-2-[(4-methyl-1H-1,2,3-triazol-1-yl)methyl]-1H-imidazo[4,5-c]quinoline-8-carbonitrile, ENT-2 (101)

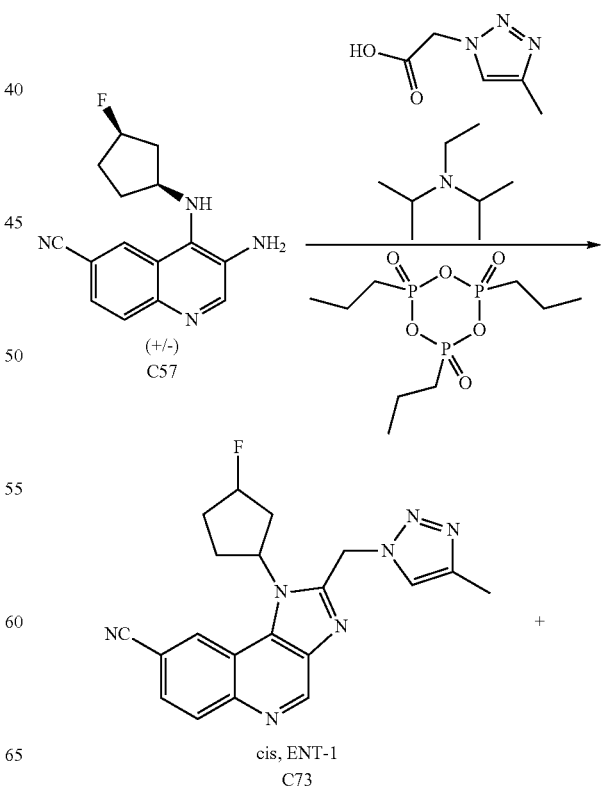

109

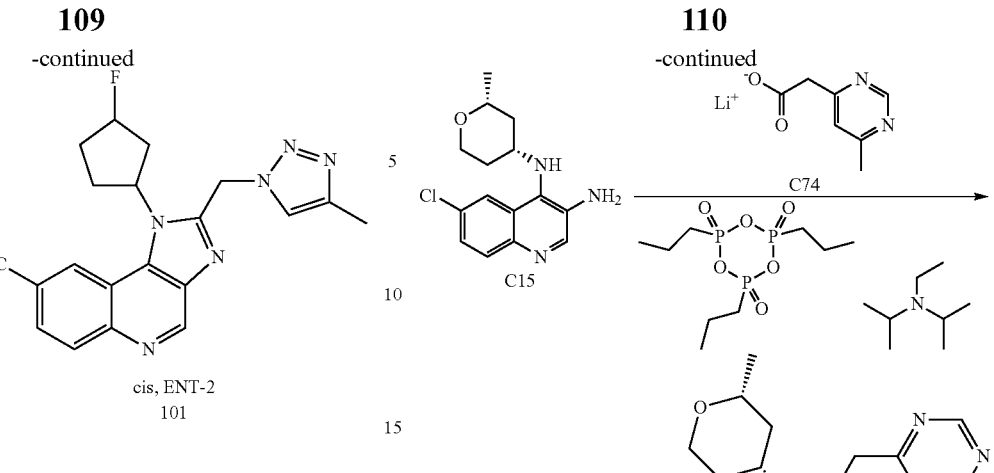

cis, ENT-2
101

Reaction of C57 with (4-methyl-1H-1,2,3-triazol-1-yl) acetic acid was effected using the method described for synthesis of 97 from C57 and C6 in Example 97, providing a racemic mixture of C73 and 101 as an off-white solid. Yield of racemic material: 54.0 mg, 0.144 mmol, 40%. LCMS m/z 376.4 [M+H]$^+$. $^1$H NMR (400 MHz, CDCl$_3$) δ 9.43 (s, 1H), 8.93-8.99 (m, 1H), 8.37 (d, J=8.6 Hz, 1H), 7.89 (dd, J=8.6, 1.6 Hz, 1H), 7.48 (br s, 1H), 6.01 (AB quartet, $J_{AB}$=15.4 Hz, $\Delta v_{AB}$=11.7 Hz, 2H), [5.49-5.63 (m) and 5.36-5.42 (m), total 2H], 2.46-2.75 (m, 4H), 2.33 (br s, 3H), 1.92-2.19 (m, 2H).

The component enantiomers were separated using supercritical fluid chromatography [Column: Phenomenex Lux Cellulose-2, 5 μm; Mobile phase: 1:1 carbon dioxide/(methanol containing 0.2% ammonium hydroxide)]. The first-eluting enantiomer, isolated as a white solid, was C73, 1-(cis-3-fluorocyclopentyl)-2-[(4-methyl-1H-1,2,3-triazol-1-yl)methyl]-1H-imidazo[4,5-c]quinoline-8-carbonitrile, ENT-1. Yield: 8.4 mg, 22 μmol, 16% for the separation. LCMS m/z 376.1 [M+H]$^+$. Retention time: 8.32 minutes via analytical HPLC [Column: Phenomenex Lux Cellulose-2, 4.6×100 mm, 5 μm; Mobile phase: 1:1 carbon dioxide/(methanol containing 0.2% ammonium hydroxide); Flow rate: 1.5 mL/minute]. The second-eluting enantiomer was 101, also obtained as a white solid. Yield: 6.6 mg, 18 μmol, 12% for the separation. LCMS m/z 376.0 [M+H]$^+$. Retention time: 9.93 minutes (analytical HPLC conditions identical to those described above for C73).

Example 102

8-Chloro-2-[(6-methylpyrimidin-4-yl)methyl]-1-[(2R,4R)-2-methyltetrahydro-2H-pyran-4-yl]-1H-imidazo[4,5-c]quinoline (102)

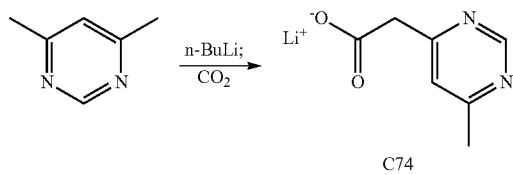

C74

110

Step 1. Synthesis of lithium (6-methylpyrimidin-4-yl)acetate (C74)

n-Butyllithium (2.5 M in hexanes; 5.00 mL, 12.5 mmol) was slowly added drop-wise to a −78° C. solution of 4,6-dimethylpyrimidine (1.08 g, 9.99 mmol) in tetrahydrofuran (20 mL). After the reaction mixture had been stirred for 20 minutes at −78° C., solid carbon dioxide (dry ice, 5.0 g) was added, and the reaction mixture was warmed to room temperature (15° C.) and stirred for 1 hour. Water (3.0 mL) was then added, and the resulting mixture was concentrated in vacuo to provide the product as a white solid. Yield: 1.53 g, 9.68 mmol, 97%. $^1$H NMR (400 MHz, D$_2$O) δ 8.78 (s, 1H), 7.28 (s, 1H), [3.60 (s) and 3.59 (br s), total 2H], 2.43 (s, 3H).

Step 2. Synthesis of 8-chloro-2-[(6-methylpyrimidin-4-yl)methyl]-1-[(2R,4R)-2-methyltetrahydro-2H-pyran-4-yl]-1H-imidazo[4,5-c]quinoline (102)

2,4,6-Tripropyl-1,3,5,2,4,6-trioxatriphosphinane 2,4,6-trioxide (50% solution in ethyl acetate, 795 mg, 1.25 mmol) and N,N-diisopropylethylamine (194 mg, 1.50 mmol) were added to a mixture of C15 (146 mg, 0.500 mmol) and C74 (87.5 mg, 0.553 mmol) in ethyl acetate (2 mL) at room temperature (15° C.). The reaction mixture was heated at 80° C. for 16 hours, whereupon it was combined with a reaction mixture from a similar reaction carried out using C15 (100 mg, 0.343 mmol). The mixture was partitioned between water (40 mL) and ethyl acetate (40 mL), and the aqueous layer was extracted with ethyl acetate (6×40 mL). The combined organic layers were concentrated in vacuo and purified via reversed phase HPLC (Column: Agela Durashell, 5 μm; Mobile phase A: 0.05% ammonium hydroxide in water; Mobile phase B: acetonitrile; Gradient: 26% to 56% B) to afford the product as a yellow solid. Yield: 195 mg, 0.478 mmol, 57%. Chromatography on silica gel (Gradient: 0% to 10% methanol in dichloromethane), followed by trituration with diethyl ether, provided a further purified sample as a light yellow solid. This sample was crystalline via powder X-ray diffraction. LCMS m/z 408.4

(chlorine isotope pattern observed) [M+H]⁺. $^1$H NMR (400 MHz, DMSO-d$_6$), characteristic peaks: δ 9.19 (s, 1H), 8.94 (s, 1H), 8.56-8.75 (br m, 1H), 8.20 (d, J=9.0 Hz, 1H), 7.75 (dd, J=9.0, 2.0 Hz, 1H), 7.46 (br s, 1H), 5.10-5.34 (br m, 1H), 4.72 (s, 2H), 4.06-4.22 (br m, 1H), 3.48-3.77 (br m, 2H), 2.46 (s, 3H), 2.10-2.28 (br m, 1H), 1.93-2.09 (br m, 1H), 1.76-1.93 (br m, 1H), 1.21 (d, J=5.9 Hz, 3H).

Example 103

8-Chloro-1-[(2R,4R)-2-methyltetrahydro-2H-pyran-4-yl]-2-[(4-methyl-2H-1,2,3-triazol-2-yl)methyl]-1H-imidazo[4,5-c]quinoline (103)

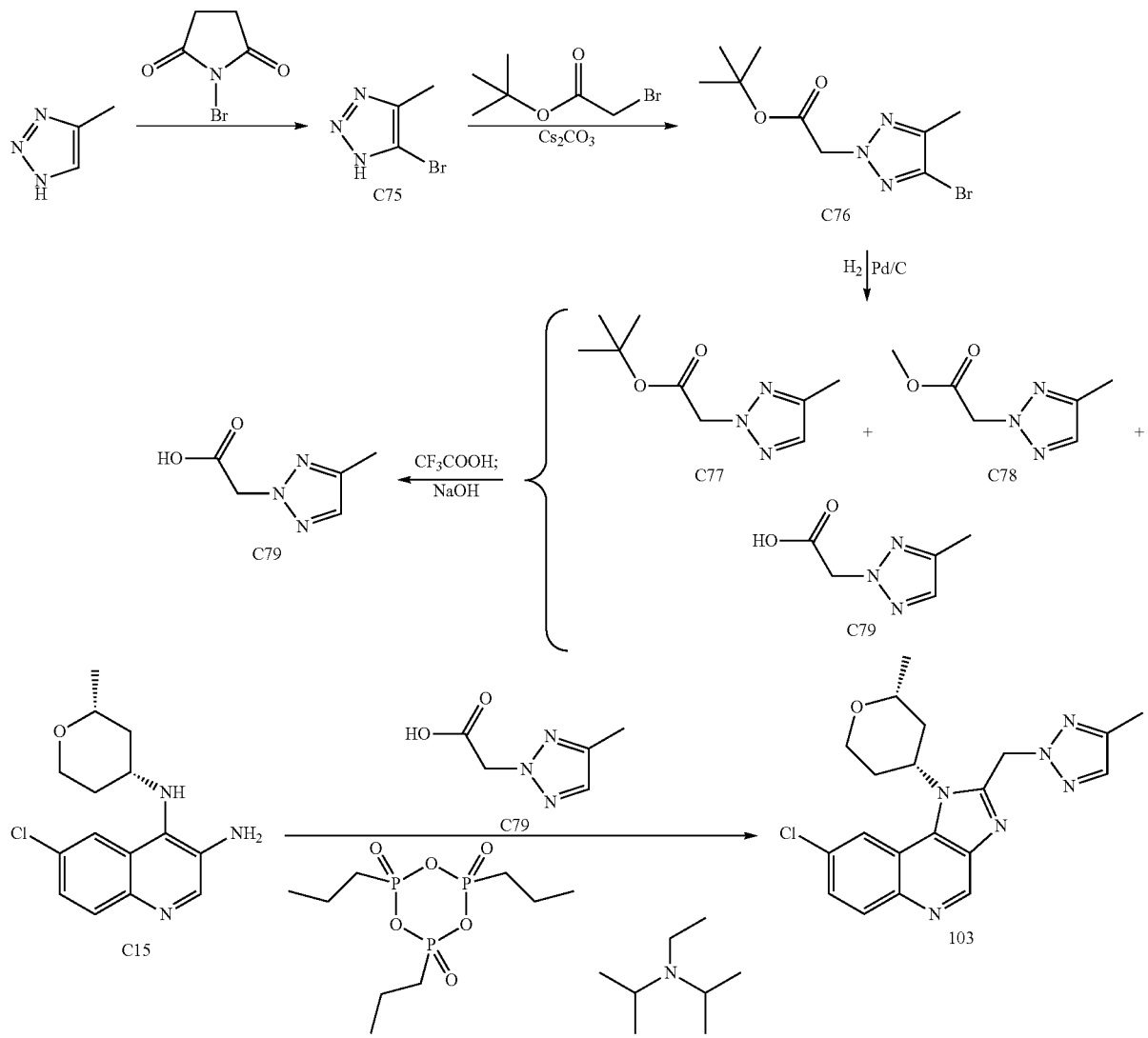

Step 1. Synthesis of 4-bromo-5-methyl-1H-1,2,3-triazole (C75)

N-Bromosuccinimide (5.89 g, 33.1 mmol) was added to a solution of 4-methyl-1H-1,2,3-triazole (2.50 g, 30.1 mmol) in chloroform (30 mL), and the reaction mixture was stirred for 16 hours at room temperature (15° C.). It was then diluted with dichloromethane (100 mL), washed with water (2×100 mL), dried over sodium sulfate, filtered, and concentrated in vacuo to provide the product as a white solid (4.9 g), which was used directly in the next step.

Step 2. Synthesis of tert-butyl (4-bromo-5-methyl-2H-1,2,3-triazol-2-yl)acetate (C76)

tert-Butyl bromoacetate (8.8 g, 45 mmol) was added in one portion to a mixture of C75 (from the previous step, 4.9 g, ≤30.1 mmol) and cesium carbonate (17.6 g, 54.0 mmol) in N,N-dimethylformamide (80 mL). The reaction mixture was stirred at room temperature (20° C.) for 16 hours, whereupon it was diluted with water (100 mL) and extracted with ethyl acetate (2×80 mL). The combined organic layers were washed with saturated aqueous sodium chloride solution (2×100 mL), dried over sodium sulfate, filtered, and concentrated in vacuo. Silica gel chromatography (Gradient: 0% to 15%, ethyl acetate in petroleum ether) provided the product as a colorless oil. Yield: 4.00 g, 14.5 mmol, 48% over 2 steps.

Step 3. Synthesis of tert-butyl (4-methyl-2H-1,2,3-triazol-2-yl)acetate (C77), methyl (4-methyl-2H-1,2,3-triazol-2-yl)acetate (C78), and (4-methyl-2H-1,2,3-triazol-2-yl)acetic acid (C79)

A mixture of C76 (3.50 g, 12.7 mmol) and palladium on carbon (10%, 500 mg) in methanol (35 mL) was stirred under hydrogen (40 psi) for 4 hours at room temperature (17° C.). The reaction mixture was filtered, and the filtrate was concentrated in vacuo, providing a yellow oil (3.00 g). On the basis of $^1$H NMR, the product was assigned as a mixture of C77 (tert-butyl ester), C78 (methyl ester), and C79 (carboxylic acid); this material was taken directly to the following step for ester hydrolysis. $^1$H NMR peaks (400 MHz, CD$_3$OD) δ [7.50 (s) and 7.49 (s), total 1H], [5.23 (s), 5.17 (s), and 5.10 (s), total 2H], 3.75 (s, from methyl ester), 2.30 (s, 3H), 1.46 (s, from tert-butyl ester).

Step 4. Synthesis of (4-methyl-2H-1,2,3-triazol-2-yl)acetic acid (C79)

A mixture of C77, C78, and C79 (from the previous step, 3.00 g, 512.7 mmol) in trifluoroacetic acid (3 mL) was stirred for 2 hours at room temperature (17° C.). After removal of solvent in vacuo, the residue was dissolved in tetrahydrofuran (10 mL) and treated with aqueous sodium hydroxide solution (2 M, 10 mL). The reaction mixture was stirred for 1 hour at room temperature (17° C.), concentrated in vacuo, and partitioned between water (50 mL) and dichloromethane (20 mL). The aqueous layer was extracted with dichloromethane (2×20 mL), and then acidified with 1 M aqueous hydrochloric acid to a pH of 1. This acidic aqueous layer was extracted with ethyl acetate (3×40 mL), and the combined ethyl acetate layers were dried over sodium sulfate, filtered, and concentrated under reduced pressure to provide the product as a yellow solid. Yield: 1.9 g, 13 mmol, 100% over 2 steps. $^1$H NMR (400 MHz, CDCl$_3$) δ 7.46 (s, 1H), 5.25 (s, 2H), 2.34 (s, 3H).

Step 5. Synthesis of 8-chloro-1-[(2R,4R)-2-methyltetrahydro-2H-pyran-4-yl]-2-[(4-methyl-2H-1,2,3-triazol-2-yl)methyl]-1H-imidazo[4,5-c]quinoline (103)

Reaction of C15 with C79 was carried out using the method described for synthesis of 95 from C64 and (3-methyl-1,2-oxazol-5-yl)acetic acid in Example 95. Purification was effected via reversed phase HPLC (Column: Agela Durashell C18, 5 μm; Mobile phase A: 0.05% ammonium hydroxide in water; Mobile phase B: acetonitrile; Gradient: 35% to 55% B), affording the product as a pale yellow gum. Yield: 95 mg, 0.24 mmol, 48%. LCMS m/z 397.0 (chlorine isotope pattern observed) [M+H]$^+$. $^1$H NMR (400 MHz, CDCl$_3$) δ 9.33 (s, 1H), 8.54-8.70 (br m, 1H), 8.23 (d, J=9.0 Hz, 1H), 7.65 (dd, J=8.9, 2.1 Hz, 1H), 7.44 (br s, 1H), 6.02 (s, 2H), 5.15-5.30 (m, 1H), 4.29 (dd, J=12, 5 Hz, 1H), 3.58-3.78 (m, 2H), 2.55-2.81 (br m, 1H), 2.31 (s, 3H), 2.3-2.52 (br m, 1H), 1.62-1.78 (br m, 1H), 1.44-1.62 (br m, 1H), 1.34 (d, J=6.0 Hz, 3H).

Example 104

8-Chloro-2-[(5-methylpyrazin-2-yl)methyl]-1-[(2R,4R)-2-methyltetrahydro-2H-pyran-4-yl]-1H-imidazo[4,5-c]quinoline (104)

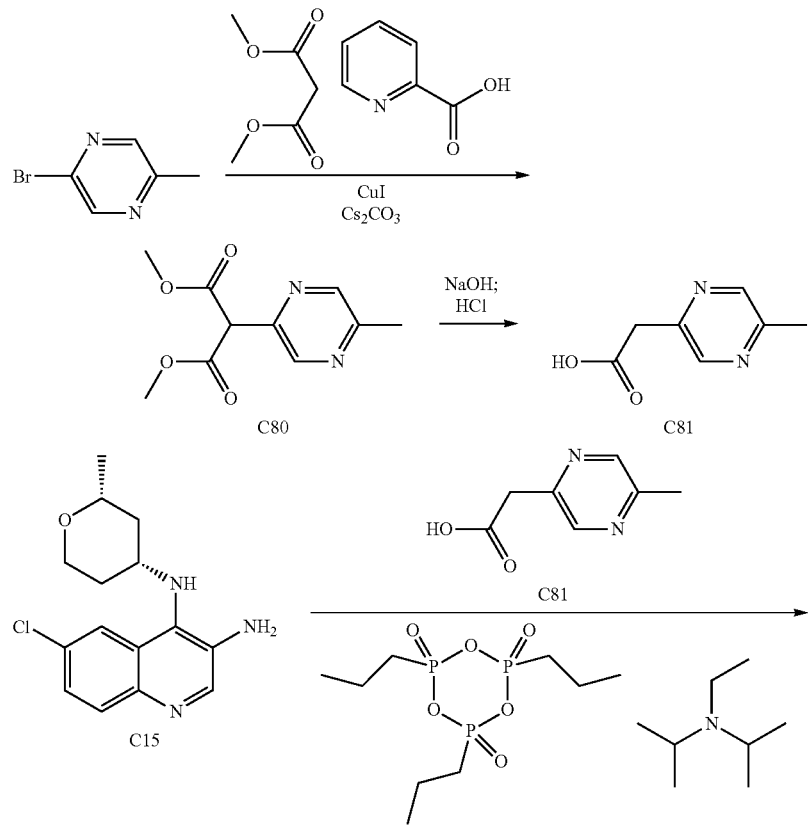

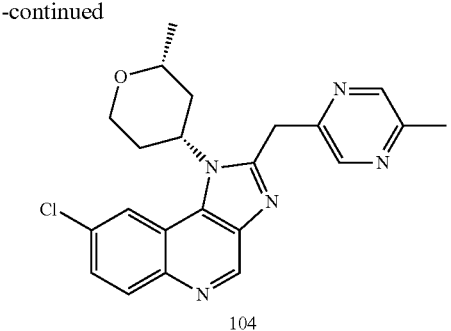

104

Step 1. Synthesis of dimethyl (5-methylpyrazin-2-yl)propanedioate (C80)

To a solution of 2-bromo-5-methylpyrazine (5.0 g, 28.9 mmol) in 1,4-dioxane (150 mL) were added dimethyl propanedioate (11.5 g, 87.0 mmol), pyridine-2-carboxylic acid (712 mg, 5.78 mmol), copper(I) iodide (2.20 g, 11.6 mmol), and cesium carbonate (28.2 g, 86.6 mmol). The reaction mixture was stirred at 95° C. for 16 hours, whereupon it was cooled to ambient temperature and combined with a similar reaction carried out using 2-bromo-5-methylpyrazine (100 mg, 0.578 mmol). The combined material was diluted with ethyl acetate (150 mL), washed with saturated aqueous sodium chloride solution (150 mL), dried over sodium sulfate, filtered and concentrated in vacuo. Silica gel chromatography (Gradient: 1% to 67% ethyl acetate in petroleum ether) provided the product as a yellow solid. Yield: 5.1 g, 23 mmol, 78%. LCMS m/z 224.9 [M+H]$^+$. $^1$H NMR (400 MHz, CDCl$_3$) δ 8.62 (d, J=1.5 Hz, 1H), 8.42-8.44 (m, 1H), 4.94 (s, 1H), 3.80 (s, 6H), 2.58 (s, 3H).

Step 2. Synthesis of (5-methylpyrazin-2-yl)acetic acid (C81)

Aqueous sodium hydroxide solution (2 M, 44.6 ml, 89.2 mmol) was added to a 10° C. solution of C80 (5.00 g, 22.3 mmol) in tetrahydrofuran (15 mL). After the reaction mixture had been stirred for 16 hours, it was combined with a similar reaction carried out using C80 (100 mg, 0.45 mmol) and washed with 4-methylpentan-2-one. The aqueous layer was then adjusted to pH 3 via addition of 6 M aqueous hydrochloric acid, while the temperature of the mixture was maintained between 20° C. and 25° C. After the mixture had been concentrated to dryness, the residue was extracted with 4-methylpentan-2-one (2×150 mL), and the two combined organic layers were dried over magnesium sulfate, filtered, and concentrated in vacuo. Recrystallization from dichloromethane/tert-butyl methyl ether (1:20, 50 mL) afforded the product as a yellow solid. Yield: 1.80 g, 11.8 mmol, 52%. LCMS m/z 153.0 [M+H]$^+$. $^1$H NMR (400 MHz, CDCl$_3$) δ 8.33 (s, 1H), 8.20 (s, 1H), 3.62 (s, 2H), 2.45 (s, 3H).

Step 3. Synthesis of 8-chloro-2-[(5-methylpyrazin-2-yl)methyl]-1-[(2R,4R)-2-methyltetrahydro-2H-pyran-4-yl]-1H-imidazo[4,5-c]quinoline (104)

2,4,6-Tripropyl-1,3,5,2,4,6-trioxatriphosphinane 2,4,6-trioxide (50% solution in ethyl acetate, 4.30 g, 6.76 mmol) and N,N-diisopropylethylamine (1.05 g, 8.12 mmol) were added to a mixture of C15 (788 mg, 2.70 mmol) and C81 (452 mg, 2.97 mmol) in ethyl acetate (11 mL) at room temperature (15° C.). The reaction mixture was heated at 80° C. for 44 hours, whereupon it was cooled to room temperature and combined with a similar reaction carried out using C15 (87.5 mg, 0.300 mmol). The mixture was partitioned between water (40 mL) and dichloromethane (100 mL), and the aqueous layer was extracted with dichloromethane (6×100 mL). The combined organic layers were concentrated in vacuo and purified using silica gel chromatography (Gradient: 0% to 10% methanol in dichloromethane), followed by reversed phase HPLC (Column: Agela Durashell C18, 5 μm; Mobile phase A: 0.05% ammonium hydroxide in water; Mobile phase B: acetonitrile; Gradient: 35% to 65% B). The product was obtained as a pale yellow gum. Yield: 490 mg, 1.20 mmol, 40%. LCMS m/z 408.0 (chlorine isotope pattern observed) [M+H]$^+$. $^1$H NMR (400 MHz, CDCl$_3$) δ 9.26 (s, 1H), 8.6-8.70 (br m, 1H), 8.58 (s, 1H), 8.38 (s, 1H), 8.21 (d, J=8.8 Hz, 1H), 7.62 (dd, J=8.9, 2.1 Hz, 1H), 5.18-5.35 (br m, 1H), 4.65 (s, 2H), 4.30 (br dd, J=11.8, 5.0 Hz, 1H), 3.58-3.80 (br m, 2H), 2.61-2.82 (br m, 1H), 2.55 (s, 3H), 2.34-2.54 (br m, 1H), 1.58-1.91 (br m, 2H), 1.34 (d, J=6.3 Hz, 3H).

Potential Improvement to Step 3 (Synthesis of 104), Demonstrated Using the Racemate of C15

2,4,6-Tripropyl-1,3,5,2,4,6-trioxatriphosphinane 2,4,6-trioxide (50% solution in ethyl acetate, 436 mg, 0.685 mmol) was added to a solution of the racemate of C15 (100 mg, 0.343 mmol), C81 (52.1 mg, 0.342 mmol), and N,N-diisopropylethylamine (66 μL, 0.38 mmol) in ethyl acetate (3 mL). The reaction mixture was allowed to stir at room temperature for 1.5 hours, at which time LCMS analysis indicated complete conversion to the uncyclized amide (LCMS m/z 426.4 [M+H]+). The reaction mixture was concentrated in vacuo to remove ethyl acetate, and the resulting oil was dissolved in toluene (5 mL) and heated to 105° C. for 1 hour and 40 minutes. The reaction mixture was partitioned between ethyl acetate and saturated aqueous sodium bicarbonate solution, and the organic layer was washed with saturated aqueous sodium chloride solution, dried over magnesium sulfate, filtered, and concentrated in vacuo. Silica gel chromatography (Gradient: 10% to 20% methanol in ethyl acetate) provided an oil, which was dissolved in minimal ethyl acetate and treated with heptane. Concentration in vacuo provided the racemate of 104 as a nearly colorless solid. Yield: 78 mg, 0.19 mmol, 55%. LCMS m/z 408.3 (chlorine isotope pattern observed) [M+H]$^+$. $^1$H NMR (600 MHz, DMSO-d$_6$), characteristic peaks: δ 9.16 (br s, 1H), 8.59-8.71 (m, 2H), 8.46 (s, 1H), 8.19 (d, J=8.8 Hz, 1H), 7.74 (br d, J=8.8 Hz, 1H), 5.20-5.35 (br m, 1H), 4.76 (s, 2H), 4.10-4.20 (br m, 1H), 3.54-3.76 (br m, 2H), 2.48 (s, 3H), 2.12-2.28 (br m, 1H), 1.92-2.07 (br m, 1H), 1.78-1.92 (br m, 1H), 1.22 (d, J=5.9 Hz, 3H).

Example 105

8-Chloro-1-[(2R,4R)-2-methyltetrahydro-2H-pyran-4-yl]-2-{[5-(trifluoromethyl)pyrazin-2-yl]methyl}-1H-imidazo[4,5-c]quinoline (105)

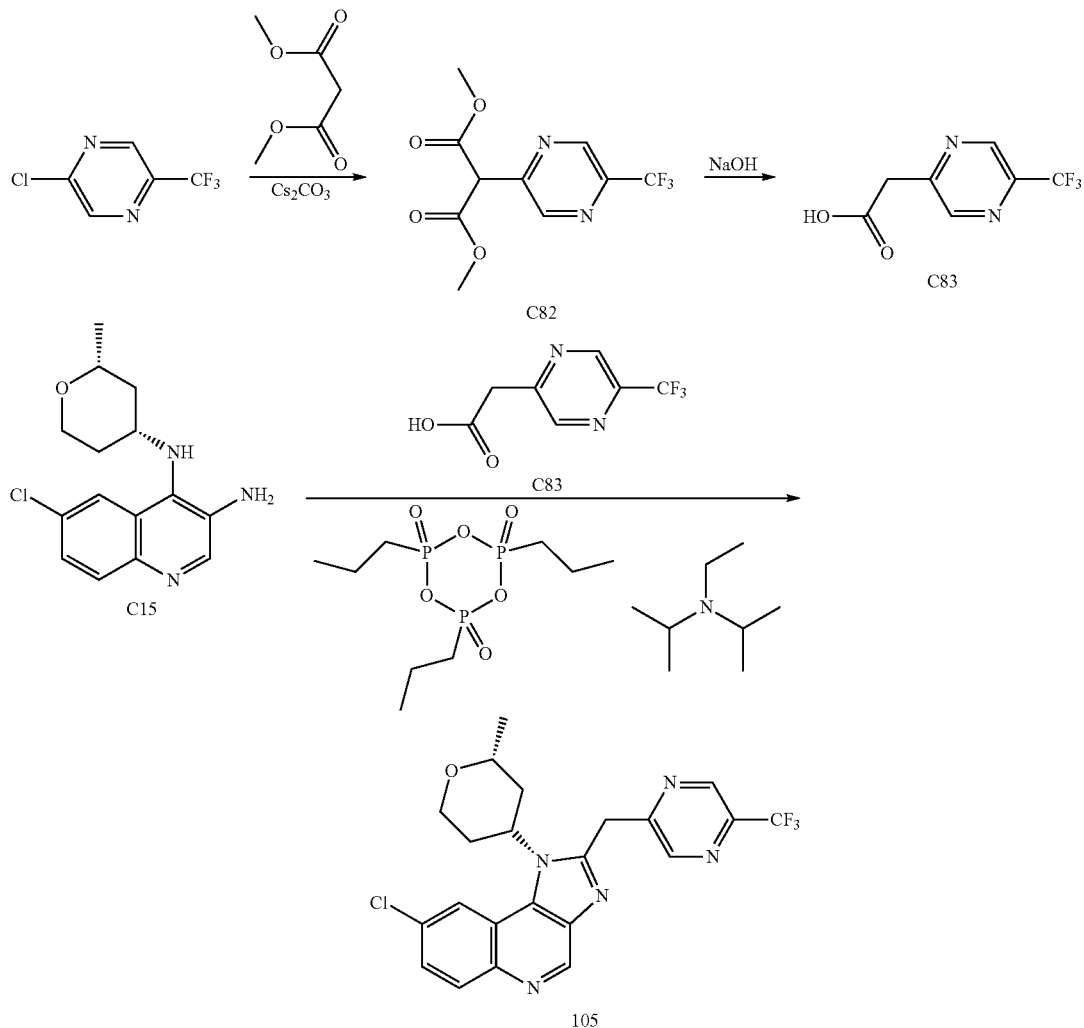

Step 1. Synthesis of dimethyl [5-(trifluoromethyl)pyrazin-2-yl]propanedioate (C82)

A mixture of 2-chloro-5-(trifluoromethyl)pyrazine (6.10 g, 33.4 mmol), dimethyl propanedioate (4.64 g, 35.1 mmol), and cesium carbonate (12.0 g, 36.8 mmol) in N,N-dimethylformamide (40 mL) was stirred at 15° C. for 16 hours. The reaction mixture was then partitioned between ethyl acetate (200 mL) and saturated aqueous sodium chloride solution (150 mL), and the organic layer was washed with saturated aqueous sodium chloride solution (100 mL), dried over sodium sulfate, filtered, and concentrated in vacuo. Purification via chromatography on silica gel (Gradient: 0% to 30% ethyl acetate in petroleum ether) afforded the product as a yellow oil (6.1 g). By $^1$H NMR, it was determined that the product contained dimethyl propanedioate. Yield, corrected for dimethyl propanedioate contaminant: 4.30 g, 15.5 mmol, 46%. $^1$H NMR (400 MHz, CDCl$_3$), product peaks only: δ 8.91 (s, 2H), 5.08 (s, 1H), 3.83 (s, 6H).

Step 2. Synthesis of [5-(trifluoromethyl)pyrazin-2-yl]acetic acid (C83)

To a solution of C82 (2.78 g from the previous step; corrected for dimethyl propanedioate contaminant: 1.96 g, 7.05 mmol) in tetrahydrofuran (15 mL) was added aqueous sodium hydroxide solution (2 M, 20 mL, 40 mmol) in one portion, and the reaction mixture was stirred at 45° C. for 16 hours. After it had been cooled to 20° C., the reaction mixture was washed with tert-butyl methyl ether (2×30 mL). The aqueous layer was then acidified to pH 3 via addition of 6 M aqueous hydrochloric acid, and extracted with ethyl acetate (2×40 mL). The combined organic layers were washed with saturated aqueous sodium chloride solution (2×20 mL), dried over sodium sulfate, filtered, and concentrated in vacuo to provide the product as a yellow oil. Yield: 1.0 g, 4.9 mmol, 70%. $^{1}$H NMR (400 MHz, CDCl$_3$) δ 8.93 (br s, 1H), 8.75 (br s, 1H), 4.07 (s, 2H).

Step 3. Synthesis of 8-chloro-1-[(2R,4R)-2-methyl-tetrahydro-2H-pyran-4-yl]-2-{[5-(trifluoromethyl)pyrazin-2-yl]methyl}-1H-imidazo[4,5-c]quinoline (105)

N,N-Diisopropylethylamine (111 mg, 0.859 mmol) and 2,4,6-tripropyl-1,3,5,2,4,6-trioxatriphosphinane 2,4,6-triox-ide (50% solution in ethyl acetate, 545 mg, 0.856 mmol) were added to a solution of C15 (100 mg, 0.343 mmol) and C83 (70.6 mg, 0.343 mmol) in ethyl acetate (2 mL) at room temperature (19° C.). The reaction mixture was stirred at 80° C. for 40 hours, whereupon it was washed sequentially with water (3×50 mL) and with saturated aqueous sodium chloride solution (100 mL). The organic layer was dried over sodium sulfate, filtered, and concentrated in vacuo. Reversed phase HPLC (Column: Agela Durashell, 5 µm; Mobile phase A: 0.05% ammonium hydroxide in water; Mobile phase B: acetonitrile; Gradient: 44% to 74% B) afforded the product as a brown solid. Yield: 125 mg, 0.271 mmol, 79%. LCMS m/z 462.0 (chlorine isotope pattern observed) [M+H]$^{+}$. $^{1}$H NMR (400 MHz, CD$_3$OD) δ 9.09 (br s, 1H), 8.98 (br s, 1H), 8.96 (br s, 1H), 8.75-8.90 (br m, 1H), 8.19 (d, J=9.0 Hz, 1H), 7.74 (dd, J=8.9, 2.1 Hz, 1H), 5.25-5.45 (br m, 1H), 4.93-4.98 (m, 2H), 4.28 (br dd, J=12.0, 5.3 Hz, 1H), 3.69-3.86 (m, 2H), 2.62-2.83 (br m, 1H), 2.32-2.52 (br m, 1H), 1.93-2.22 (br m, 2H), 1.34 (d, J=6.0 Hz, 3H).

Example 106

1-[(2R,4R)-2-Methyltetrahydro-2H-pyran-4-yl]-2-[(4-methyl-1H-1,2,3-triazol-1-yl)methyl]-1H-imidazo[4,5-c]quinoline-8-carbonitrile (106)

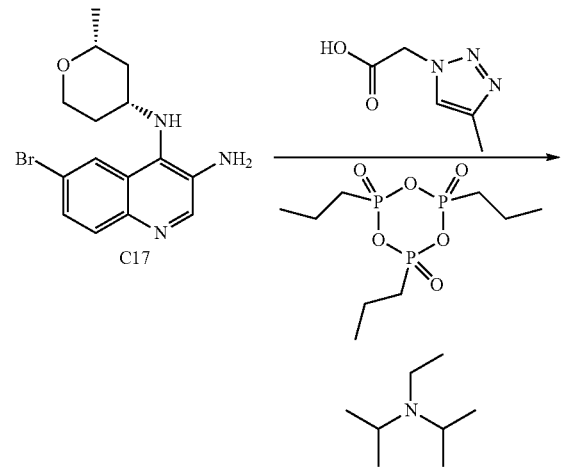

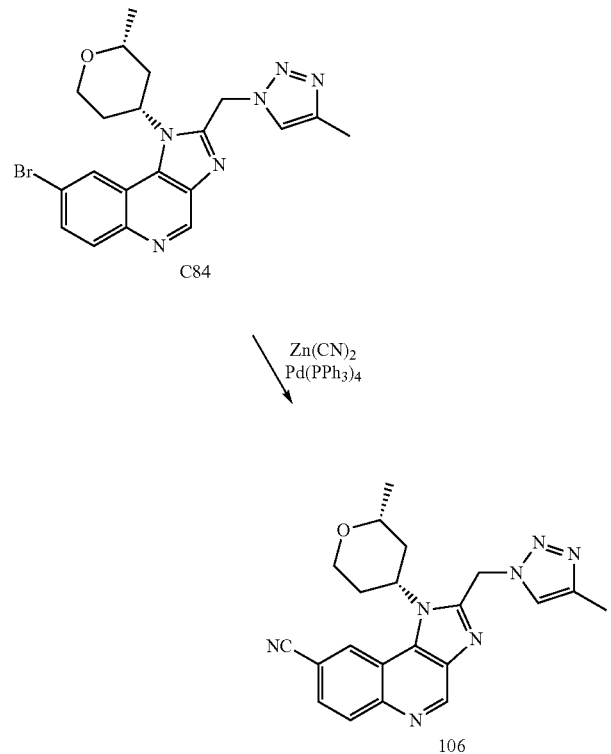

Step 1. Synthesis of 8-bromo-1-[(2R,4R)-2-methyl-tetrahydro-2H-pyran-4-yl]-2-[(4-methyl-1H-1,2,3-triazol-1-yl)methyl]-1H-imidazo[4,5-c]quinoline (C84)

N,N-Diisopropylethylamine (169 mg, 1.31 mmol) and 2,4,6-tripropyl-1,3,5,2,4,6-trioxatriphosphinane 2,4,6-triox-ide (50% solution in ethyl acetate, 1.2 g, 1.9 mmol) were added to a mixture of C17 (200 mg, 0.595 mmol) and (4-methyl-1H-1,2,3-triazol-1-yl)acetic acid (101 mg, 0.716 mmol) in N,N-dimethylformamide (10 mL), and the reaction mixture was heated at 100° C. overnight. It was then diluted with water (30 mL) and extracted with dichloromethane (3×20 mL). The combined organic layers were washed with saturated aqueous sodium chloride solution (50 mL), dried over sodium sulfate, filtered, and concentrated in vacuo. Reversed phase HPLC (Column: YMC-Actus Triart C18, 5 µm; Mobile phase A: water containing 0.225% formic acid; Mobile phase B: acetonitrile; Gradient: 31% to 51% B) provided the product as a yellow solid. Yield: 18.9 mg, 42.8 µmol, 7%. LCMS m/z 442.8 (bromine isotope pattern observed) [M+H]$^{+}$. $^{1}$H NMR (400 MHz, DMSO-d$_6$), characteristic peaks: δ 9.24 (s, 1H), 8.70-8.89 (m, 1H), 8.13 (d, J=8.5 Hz, 1H), 7.97 (s, 1H), 7.88 (br dd, J=9, 2 Hz, 1H), 6.22 (s, 2H), 5.21-5.40 (br m, 1H), 4.11-4.23 (m, 1H), 3.54-3.78 (m, 2H), 2.25 (s, 3H), 2.05-2.24 (br m, 1H), 1.69-2.04 (br m, 2H), 1.23 (d, J=6.0 Hz, 3H).

Step 2. Synthesis of 1-[(2R,4R)-2-methyltetrahydro-2H-pyran-4-yl]-2-[(4-methyl-1H-1,2,3-triazol-1-yl)methyl]-1H-imidazo[4,5-c]quinoline-8-carbonitrile (106)

Tetrakis(triphenylphosphine)palladium(0) (52.4 mg, 45.3 µmol) and zinc cyanide (426 mg, 3.63 mmol) were added to a solution of C84 (200 mg, 0.453 mmol) in N,N-dimethyl-

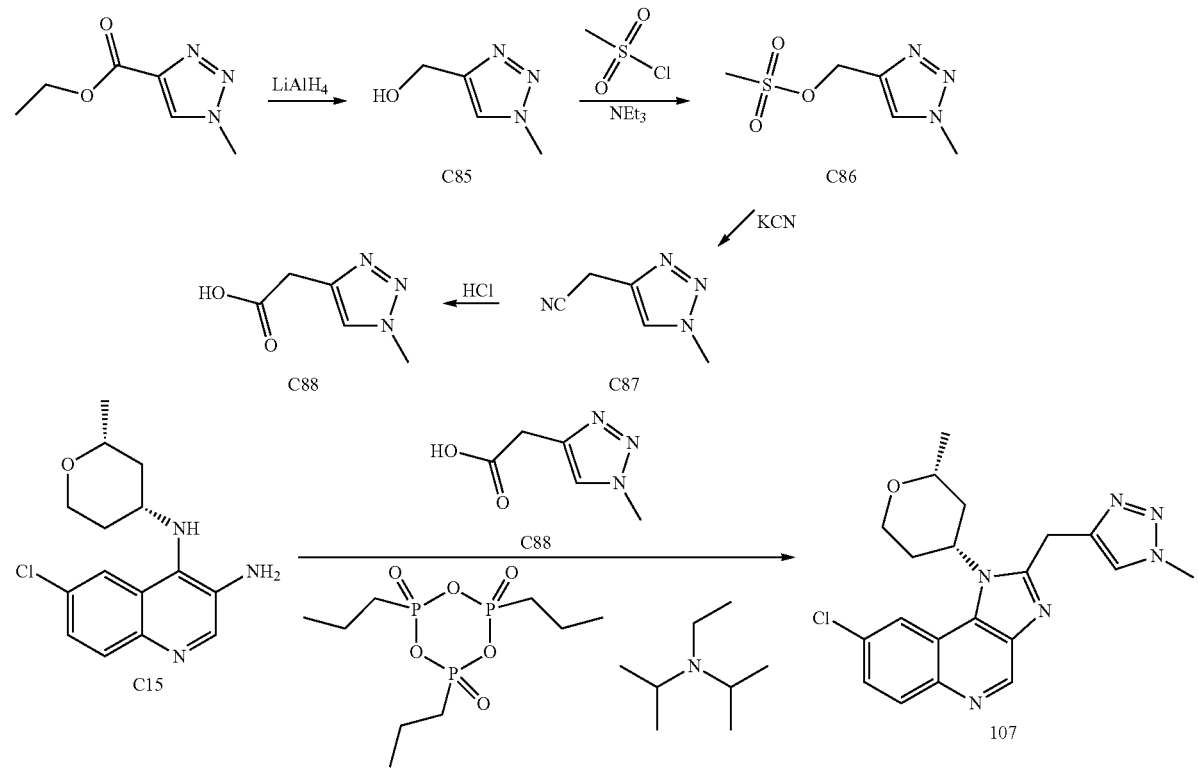

formamide (15 mL), and the reaction vessel was evacuated and charged with nitrogen. This evacuation cycle was repeated twice, and the reaction mixture was then heated at 140° C. overnight. After filtration of the reaction mixture, the filtrate was diluted with water (50 mL) and extracted with ethyl acetate (3×50 mL); the combined organic layers were washed with saturated aqueous sodium chloride solution (50 mL), dried over sodium sulfate, and concentrated in vacuo. Purification via reversed phase HPLC (Column: Phenomenex Gemini C18, 8 µm; Mobile phase A: aqueous ammonia, pH 10; Mobile phase B: acetonitrile; Gradient: 21% to 41% B) afforded the product as a white solid. Yield: 43.6 mg, 0.113 mmol, 25%. LCMS m/z 387.9 [M+H]+. 1H NMR (400 MHz, CDCl3) δ 9.43 (s, 1H), 8.91-9.10 (br m, 1H), 8.39 (d, J=8.8 Hz, 1H), 7.90 (dd, J=9, 1 Hz, 1H), 7.45-7.51 (br s, 1H), 6.01 (s, 2H), 5.34-5.48 (br m, 1H), 4.31 (br dd, J=12, 5 Hz, 1H), 3.68-3.83 (m, 2H), 2.50-2.67 (br m, 1H), 2.33 (s, 3H), 2.21-2.38 (br m, 1H), 1.48-1.82 (br m, 2H, assumed; partially obscured by water peak), 1.35 (d, J=6.0 Hz, 3H).

Example 107

8-Chloro-1-[(2R,4R)-2-methyltetrahydro-2H-pyran-4-yl]-2-[(1-methyl-1H-1,2,3-triazol-4-yl)methyl]-1H-imidazo[4,5-c]quinoline (107)

Step 1. Synthesis of (1-methyl-1H-1,2,3-triazol-4-yl)methanol (C85)

Lithium aluminum hydride (685 mg, 18.0 mmol) was added to a 0° C. suspension of ethyl 1-methyl-1H-1,2,3-triazole-4-carboxylate (1.40 g, 9.02 mmol) in tetrahydrofuran (20 mL) and the reaction mixture was stirred at 0° C. for 1 hour. Water was then added drop-wise at 0° C. until no further gas evolution was observed, whereupon sodium sulfate was added, and the mixture was stirred for 10 minutes. The mixture was then filtered, and the filtrate was concentrated in vacuo, affording the product as a yellow oil. Yield: 700 mg, 6.19 mmol, 69%. 1H NMR (400 MHz, DMSO-d6) δ 7.90 (s, 1H), 5.15 (t, J=5.5 Hz, 1H), 4.49 (d, J=5.5 Hz, 2H), 4.01 (s, 3H).

Step 2. Synthesis of (I-methyl-1H-1,2,3-triazol-4-yl)methyl methanesulfonate (C86)

Methanesulfonyl chloride (851 mg, 7.43 mmol) was added to a 0° C. solution of C85 (700 mg, 6.19 mmol) and triethylamine (1.00 g, 9.88 mmol) in dichloromethane (20 mL). The reaction mixture was stirred at 0° C. for 2 hours, whereupon water (100 mL) was added, and the mixture was extracted with dichloromethane (2×100 mL). The combined organic layers were dried over sodium sulfate, filtered, and concentrated in vacuo to provide the product as a yellow oil, which was used directly in the next step. Yield: 800 mg, 4.18 mmol, 68%.

Step 3. Synthesis of (1-methyl-1H-1,2,3-triazol-4-yl)acetonitrile (C87)

To a solution of C86 (800 mg, 4.18 mmol) in acetonitrile (20 mL) was added potassium cyanide (1.50 g, 23.0 mmol). The reaction mixture was stirred at 60° C. overnight, whereupon it was treated with water (150 mL) and extracted with dichloromethane (3×100 mL). The combined organic layers were washed with saturated aqueous sodium chloride solution (80 mL), dried over sodium sulfate, filtered, and concentrated in vacuo to afford the product as a brown solid. Yield: 200 mg, 1.64 mmol, 39%. $^1$H NMR (400 MHz, CDCl$_3$) δ 7.61 (s, 1H), 4.13 (s, 3H), 3.89 (br s, 2H).

Step 4. Synthesis of (1-methyl-1H-1,2,3-triazol-4-yl)acetic acid (C88)

A solution of C87 (200 mg, 1.64 mmol) in concentrated hydrochloric acid (4 mL) was stirred at 60° C. for 2 hours. After the reaction mixture had cooled to room temperature, it was diluted with water (10 mL) and washed with tert-butyl methyl ether (2×20 mL). The aqueous layer was then concentrated to dryness, providing the product as a brown solid. Yield: 200 mg, 1.42 mmol, 87%. LCMS m/z 142.0 [M+H]$^+$. $^1$H NMR (400 MHz, DMSO-d$_6$) δ 7.94 (s, 1H), 4.01 (s, 3H), 3.66 (s, 2H).

Step 5. Synthesis of 8-chloro-1-[(2R,4R)-2-methyl-tetrahydro-2H-pyran-4-yl]-2-[(1-methyl-1H-1,2,3-triazol-4-yl)methyl]-1H-imidazo[4,5-c]quinoline (107)

N,N-Diisopropylethylamine (133 mg, 1.03 mmol) and 2,4,6-tripropyl-1,3,5,2,4,6-trioxatriphosphinane 2,4,6-trioxide (327 mg, 1.03 mmol) were added to a mixture of C15 (100 g, 0.343 mmol) and C88 (100 mg, 0.709 mmol) in N,N-dimethylformamide (2 mL). The reaction mixture was heated at 100° C. overnight, whereupon it was cooled to room temperature, diluted with saturated aqueous sodium chloride solution (30 mL), and extracted with dichloromethane (2×30 mL). The combined organic layers were concentrated in vacuo and purified using reversed phase HPLC (Column: Phenomenex Gemini C18, 8 μm; Mobile phase A: aqueous ammonia, pH 10; Mobile phase B: acetonitrile; Gradient: 25% to 45% B) to afford the product as a white solid. Yield: 30.6 mg, 77.1 μmol, 22%. LCMS m/z 396.9 (chlorine isotope pattern observed) [M+H]$^+$. $^1$H NMR (400 MHz, DMSO-d$_6$) δ 9.18 (s, 1H), 8.57-8.71 (br m, 1H), 8.19 (d, J=8.8 Hz, 1H), 8.03 (br s, 1H), 7.74 (dd, J=9.0, 2.0 Hz, 1H), 5.22-5.39 (br m, 1H), 4.62 (s, 2H), 4.11-4.21 (br m, 1H), 4.02 (s, 3H), 3.55-3.76 (br m, 2H), 2.36-2.5 (br m, 1H, assumed; partially obscured by solvent peak), 2.09-2.25 (br m, 1H), 1.73-2.04 (br m, 2H), 1.22 (d, J=6.0 Hz, 3H).

Example 108

2-[(5-Methylpyrazin-2-yl)methyl]-1-[(2R,4R)-2-methyltetrahydro-2H-pyran-4-yl]-1H-imidazo[4,5-c]quinoline-8-carbonitrile (108)

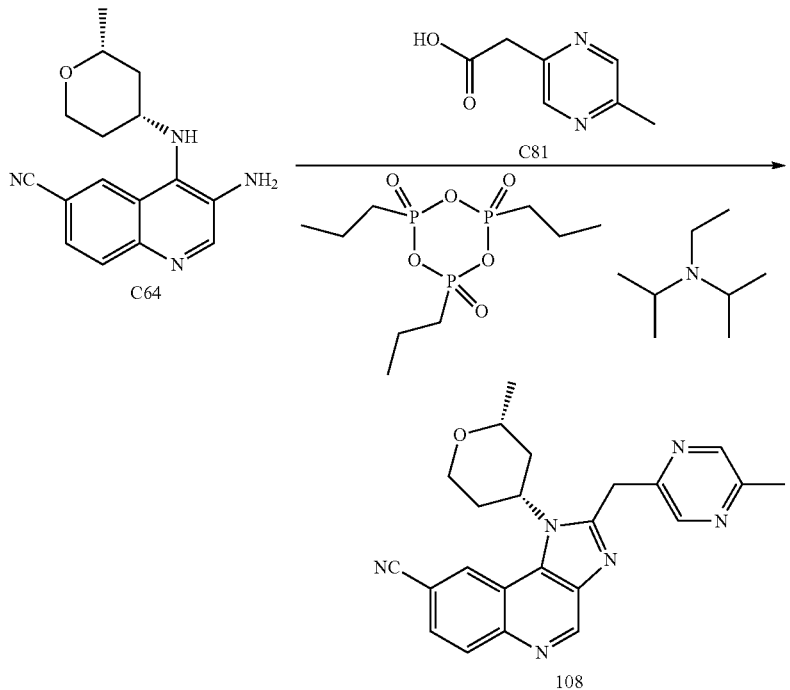

N,N-Diisopropylethylamine (150 mg, 1.16 mmol) and 2,4,6-tripropyl-1,3,5,2,4,6-trioxatriphosphinane 2,4,6-trioxide (50% solution in ethyl acetate, 0.493 mL, 0.828 mmol) were added to a mixture of C64 (148 mg, 0.524 mmol) and C81 (80 mg, 0.53 mmol) in N,N-dimethylformamide (2 mL), and the reaction mixture was stirred at 110° C. for 15 hours. It was then poured into water (10 mL) and extracted with dichloromethane (3×20 mL). The combined organic layers were washed with water (2×20 mL), dried over sodium sulfate, filtered, concentrated under reduced pressure, and purified using reversed phase HPLC (Column: Agela Durashell, 5 μm; Mobile phase A: 0.225% formic acid in water; Mobile phase B: acetonitrile; Gradient: 25% to 55% B) to afford the product as a light yellow solid. Yield: 41.1 mg, 0.103 mmol, 20%. LCMS m/z 399.1 [M+H]+. $^1$H NMR (400 MHz, CD$_3$OD) δ 9.23 (s, 1H), 9.07-9.20 (br m, 1H), 8.64 (s, 1H), 8.47 (s, 1H), 8.32 (d, J=9.0 Hz, 1H), 7.97 (br d, J=8.5 Hz, 1H), 5.35-5.54 (br m, 1H), 4.81 (s, 2H), 4.22-4.33 (m, 1H), 3.68-3.86 (br m, 2H), 2.57-2.75 (br m, 1H), 2.55 (s, 3H), 2.24-2.44 (br m, 1H), 1.84-2.21 (br m, 2H), 1.33 (d, J=6.0 Hz, 3H).

Example 109

1-(cis-3-Fluorocyclopentyl)-2-[(5-methylpyrazin-2-yl)methyl]-1H-imidazo[4,5-c]quinoline-8-carbonitrile, ENT-1 (109)

tioned between water and ethyl acetate. The aqueous layer was extracted three times with ethyl acetate, and the combined organic layers were washed with water (3×20 mL), dried over sodium sulfate, filtered, and concentrated in vacuo. Silica gel chromatography (Gradient: 0% to 10% methanol in ethyl acetate) afforded a mixture of 109 and C89 as a solid. Yield of racemic product: 444 mg, 1.15 mmol, 62%. This was combined with the product of a similar reaction (14 mg) and separated into its component enantiomers via supercritical fluid chromatography [Column: Chiral Technologies Chiralpak AS-H, 5 μm; Mobile phase: 4:1 carbon dioxide/(ethanol containing 0.2% ammonium hydroxide)]. The first-eluting enantiomer was 109, obtained as a solid. Yield: 164 mg, 36% for the separation. LCMS m/z 387.5 [M+H]+. $^1$H NMR (400 MHz, CDCl$_3$) δ 9.39 (s, 1H), 8.90-8.95 (m, 1H), 8.61 (s, 1H), 8.38 (s, 1H), 8.35 (d, J=8.6 Hz, 1H), 7.85 (br d, J=8.6 Hz, 1H), 5.35-5.58 (m, 2H), 4.69 (s, 2H), 2.61-2.81 (m, 3H), 2.57 (s, 3H), 2.46-2.61 (m, 1H), 1.90-2.18 (m, 2H).

The second-eluting enantiomer, also isolated as a solid, was C89, 1-(cis-3-fluorocyclopentyl)-2-[(5-methylpyrazin-

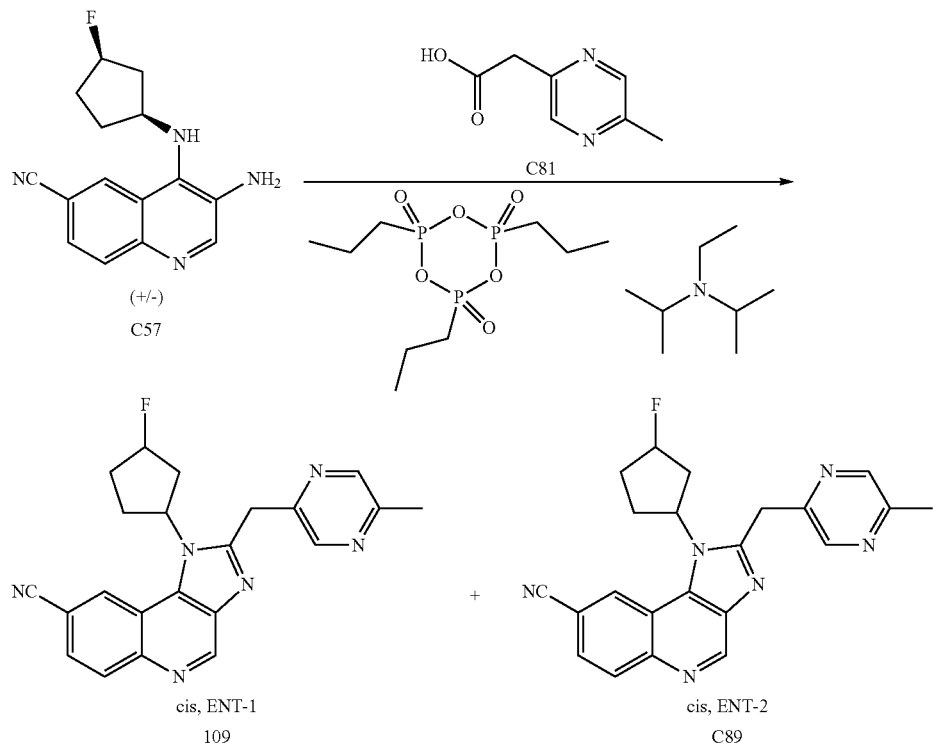

N,N-Diisopropylethylamine (1.29 mL, 7.41 mmol) and 2,4,6-tripropyl-1,3,5,2,4,6-trioxatriphosphinane 2,4,6-trioxide (50% solution in ethyl acetate, 3.53 g, 5.55 mmol) were added to a mixture of C57 (500 mg, 1.85 mmol) and C81 (296 mg, 1.94 mmol) in N,N-dimethylformamide (9.2 mL). The reaction mixture was heated to 110° C. overnight, whereupon it was cooled to room temperature and partitioned 2-yl)methyl]-1H-imidazo[4,5-c]quinoline-8-carbonitrile, ENT-2. Yield: 179 mg, 39% for the separation. LCMS m/z 387.5 [M+H]+. $^1$H NMR (400 MHz, CDCl$_3$) δ 9.39 (s, 1H), 8.90-8.95 (m, 1H), 8.60 (br s, 1H), 8.38 (br s, 1H), 8.35 (d, J=9.0 Hz, 1H), 7.85 (dd, J=8.6, 1.2 Hz, 1H), 5.35-5.58 (m, 2H), 4.68 (s, 2H), 2.61-2.80 (m, 3H), 2.57 (s, 3H), 2.46-2.61 (m, 1H), 1.90-2.17 (m, 2H).

Example 110

8-Chloro-2-[(4-methoxy-1H-pyrazol-1-yl)methyl]-1-[(2R,4R)-2-methyl/tetrahydro-2H-pyran-4-yl]-1H-imidazo[4,5-c]quinoline (110)

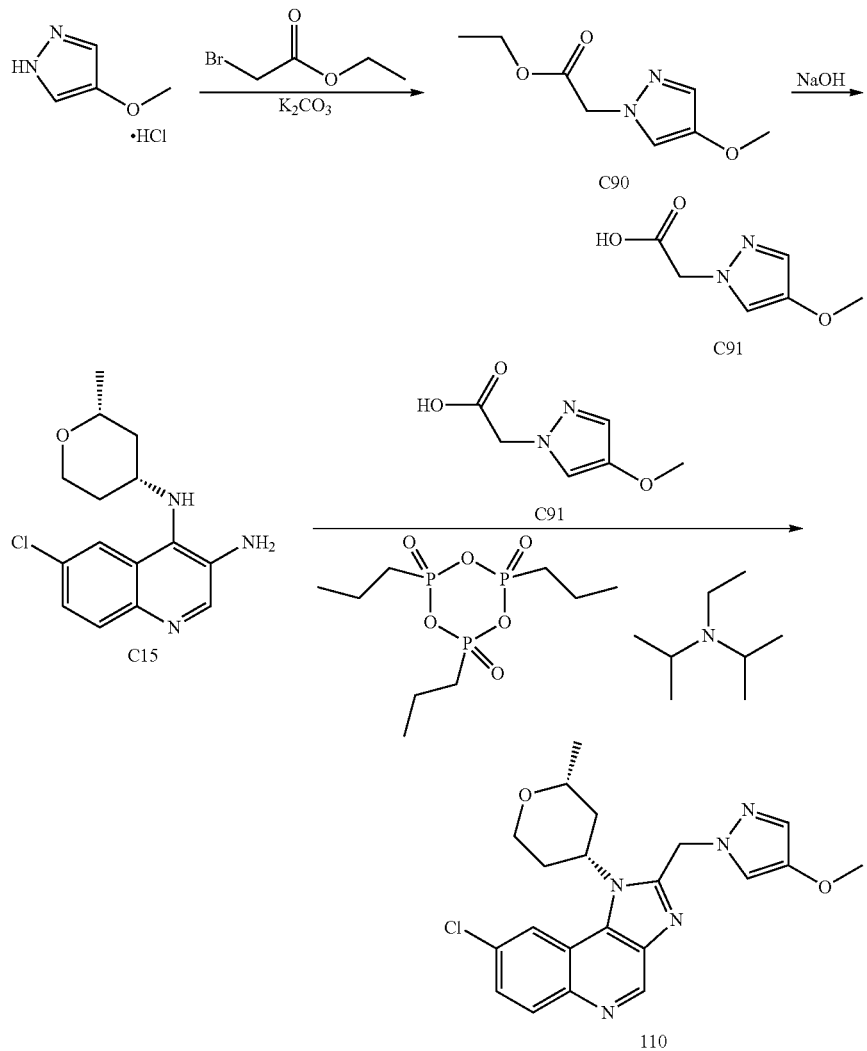

Step 1. Synthesis of ethyl (4-methoxy-1H-pyrazol-1-yl)acetate (C90)

Ethyl bromoacetate (2.59 g, 15.5 mmol) was added in one portion to a mixture of 4-methoxy-1H-pyrazole, hydrochloride salt (1.90 g, 14.1 mmol) and potassium carbonate (4.10 g, 29.7 mmol) in N,N-dimethylformamide (20 mL), and the reaction mixture was stirred at room temperature (20° C.) for 60 hours. It was then diluted with water (100 mL) and extracted with ethyl acetate (3×80 mL). The combined organic layers were washed with saturated aqueous sodium chloride solution (2×150 mL), dried over sodium sulfate, filtered, and concentrated in vacuo. Silica gel chromatography (Gradient: 0% to 30% ethyl acetate in petroleum ether) provided the product as a colorless oil. Yield: 1.90 g, 10.3 mmol, 73%. $^1$H NMR (400 MHz, CDCl$_3$) δ 7.30 (s, 1H), 7.15 (s, 1H), 4.80 (s, 2H), 4.24 (q, J=7.2 Hz, 2H), 3.76 (s, 3H), 1.29 (t, J=7.2 Hz, 3H).

Step 2. Synthesis of (4-methoxy-1H-pyrazol-1-yl)acetic acid (C91)

Aqueous sodium hydroxide solution (2 M, 10.3 mL, 20.6 mmol) was added in one portion to a room temperature (17° C.) solution of C90 (1.90 g, 10.3 mmol) in tetrahydrofuran (10 mL), and the reaction mixture was stirred at room temperature (17° C.) for 3 hours. After removal of tetrahydrofuran in vacuo, the residue was dissolved in water (20 mL) and washed with dichloromethane (2×20 mL). The aqueous phase was acidified to pH 1 with 1 M hydrochloric acid, and then extracted with ethyl acetate (3×30 mL). The combined ethyl acetate layers were dried over sodium sulfate, filtered, and concentrated under reduced pressure to afford the product as a white solid. Yield: 1.5 g, 9.6 mmol, 93%. $^1$H NMR (400 MHz, CDCl$_3$) δ 7.35 (s, 1H), 7.15 (s, 1H), 4.87 (s, 2H), 3.77 (s, 3H).

Step 3. Synthesis of 8-chloro-2-[(4-methoxy-1H-pyrazol-1-yl)methyl]-1-[(2R,4R)-2-methyltetrahydro-2H-pyran-4-yl]-1H-imidazo[4,5-c]quinoline (110)

2,4,6-Tripropyl-1,3,5,2,4,6-trioxatriphosphinane 2,4,6-trioxide (50% solution in ethyl acetate, 436 mg, 0.685 mmol) and N,N-diisopropylethylamine (106 mg, 0.820 mmol) were added to a mixture of C15 (80 mg, 0.27 mmol) and C91 (42.8 mg, 0.274 mmol) in ethyl acetate (2 mL). The reaction mixture was heated at 85° C. for 16 hours, whereupon it was partitioned between ethyl acetate (10 mL) and water (30 mL). The organic layer was washed sequentially with water (2×30 mL) and with saturated aqueous sodium chloride solution (50 mL), dried, filtered, and concentrated in vacuo. Reversed phase HPLC (Column: Waters XBridge C18 OBD, 5 μm; Mobile phase A: water containing 0.05% ammonium hydroxide; Mobile phase B: acetonitrile; Gradient: 5% to 95% B) provided the product as a white solid. Yield: 64.6 mg, 0.157 mmol, 58%. LCMS m/z 412.0 (chlorine isotope pattern observed) [M+H]$^+$. $^1$H NMR (400 MHz, CDCl$_3$) δ 9.32 (s, 1H), 8.57-8.70 (br m, 1H), 8.23 (d, J=8.5 Hz, 1H), 7.66 (dd, J=9.0, 2.0 Hz, 1H), 7.29 (s, 1H), 7.14 (s, 1H), 5.70 (s, 2H), 5.27-5.41 (m, 1H), 4.28 (br dd, J=12.0, 5.0 Hz, 1H), 3.67 (s, 3H), 3.63-3.77 (m, 2H), 2.53-2.74 (br m, 1H), 2.26-2.47 (br m, 1H), 1.56-1.7 (br m, 1H, assumed; partially obscured by water peak), 1.40-1.56 (br m, 1H), 1.33 (d, J=6.0 Hz, 3H).

Example 111

1-(2,2-Difluorocyclohexyl)-2-[(5-methyl-1,2-oxazol-3-yl)methyl]-1H-imidazo[4,5-c]quinoline-8-carbonitrile, ENT-1 (111)

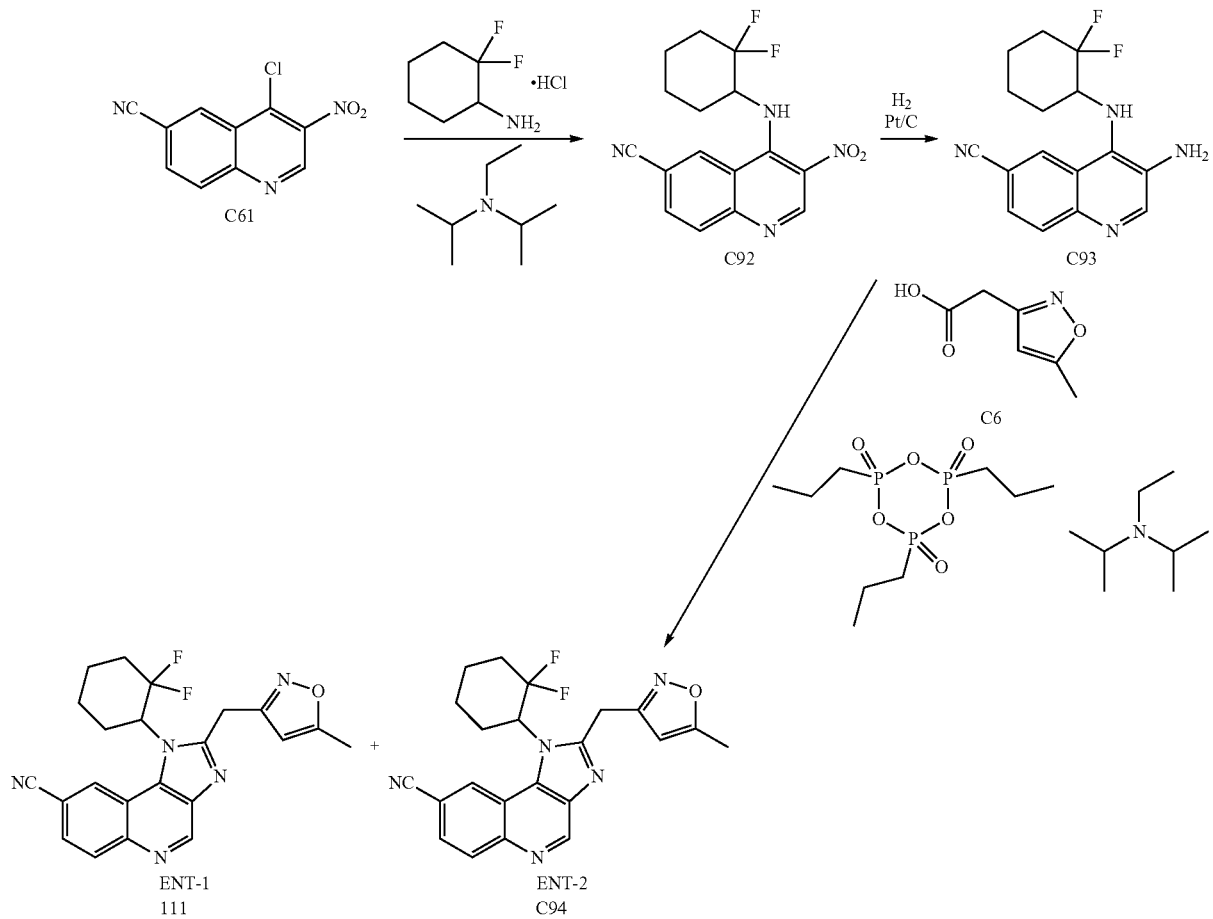

Step 1. Synthesis of 4-[(2,2-difluorocyclohexyl)amino]-3-nitroquinoline-6-carbonitrile (C92)

This reaction was run in two identical batches. 2,2-Difluorocyclohexanamine, hydrochloride salt (410 mg, 2.39 mmol) and N,N-diisopropylethylamine (900 mg, 6.96 mmol) were added to a mixture of C61 (620 mg, 2.6 mmol) in acetonitrile (10 mL), and the reaction mixture was stirred at room temperature for 15 hours. The two batches were combined, concentrated in vacuo, and purified using silica gel chromatography (Gradient: 0% to 30% ethyl acetate in petroleum ether) to provide the product as a yellow solid. Yield: 790 mg, 2.38 mmol, 50%. LCMS m/z 332.7 [M+H]$^+$. $^1$H NMR (400 MHz, CDCl$_3$) δ 9.49 (s, 1H), 9.05 (brd, J=9.8 Hz, 1H), 8.43 (brs, 1H), 8.15 (d, J=8.5 Hz, 1H), 7.96 (dd, J=8.8, 1.8 Hz, 1H), 4.10-4.24 (m, 1H), 2.22-2.42 (m, 2H), 1.43-2.01 (m, 6H, assumed; partially obscured by water peak).

Step 2. Synthesis of 3-amino-4-[(2,2-difluorocyclo-hexyl)amino]quinoline-6-carbonitrile (C93)

Platinum on carbon (5%, 81 mg) was added in one portion to a mixture of C92 (690 mg, 2.08 mmol) in tetrahydrofuran (50 mL). The reaction mixture was purged three times with nitrogen, and then purged three times with hydrogen, whereupon it was hydrogenated for 2 hours at room temperature (~20° C.) under 40 psi of hydrogen. After the reaction mixture had remained at room temperature for 16 hours, it was filtered through diatomaceous earth; the filter pad was washed sequentially with tetrahydrofuran (150 mL) and ethyl acetate (50 mL), and the combined filtrates were concentrated in vacuo to afford the product as an orange solid. Yield: 650 mg, quantitative. LCMS m/z 302.7 [M+H]$^+$.

Step 3. Synthesis of 1-(2,2-difluorocyclohexyl)-2-[(5-methyl-1,2-oxazol-3-yl)methyl]-1H-imidazo[4,5-c]quinoline-8-carbonitrile, ENT-1 (111) and 1-(2,2-difluorocyclohexyl)-2-[(5-methyl-1,2-oxazol-3-yl)methyl]-1H-imidazo[4,5-c]quinoline-8-carbonitrile, ENT-2 (C94)

N,N-Diisopropylethylamine (80 mg, 0.62 mmol) was added to a mixture of C93 (100 mg, 0.33 mmol) and C6 (68 mg, 0.48 mmol) in toluene (1 mL). 2,4,6-Tripropyl-1,3,5,2,4,6-trioxatriphosphinane 2,4,6-trioxide (50% solution in ethyl acetate, 411 mg, 0.646 mmol) was then added, and the reaction mixture was heated at 70° C. for 45 minutes, and then at 105° C. for 2.5 days. After cooling to room temperature, it was combined with a similar reaction carried out using C93 (20 mg, 66 μmol), and the resulting mixture was taken up in ethyl acetate (40 mL) and washed with saturated aqueous sodium bicarbonate solution (20 mL). The aqueous layer was extracted with ethyl acetate (2×30 mL), and the combined organic layers were washed with saturated aqueous sodium chloride solution (30 mL), dried over sodium sulfate, filtered, and concentrated under reduced pressure. Purification using reversed phase HPLC (Column: Agela Durashell, 5 μm; Mobile phase A: 0.225% formic acid in water; Mobile phase B: acetonitrile; Gradient: 35% to 65% B) afforded a racemic mixture of 111 and C94 as a yellow solid. From analysis of the $^1$H NMR spectrum, this material was assumed to exist as a mixture of rotamers. Yield of racemic material: 40 mg, 98 μmol, 25%. LCMS m/z 407.8 [M+H]$^+$. $^1$H NMR (400 MHz, CDCl$_3$) δ [9.40 (s) and 9.40 (s), total 1H], [8.94 (br s) and 8.51 (br s), total 1H], [8.39 (d, J=8.8 Hz) and 8.33 (d, J=8.5 Hz), total 1H], [7.87 (dd, J=8.7, 1.6 Hz) and 7.82 (dd, J=8.7, 1.6 Hz), total 1H], [6.11-6.13 (m) and 6.04-6.06 (m), total 1H], 5.18-5.42 (m, 1H), [4.62 (AB quartet, J$_{AB}$=16.7 Hz, Δv$_{AB}$=21.8 Hz) and 4.51 (AB quartet, J$_{AB}$=15.8 Hz, Δv$_{AB}$=10.7 Hz), total 2H], 2.47-2.88 (m, 2H), [2.43 (d, J=1.0 Hz) and 2.40 (d, J=0.8 Hz), total 3H], 2.03-2.25 (m, 4H), 1.78-1.98 (m, 2H). The racemic material (34.3 mg) was separated into its component enantiomers via supercritical fluid chromatography [Column: Chiral Technologies Chiralpak AD-H, 5 μm; Mobile phase: 95:5 carbon dioxide/(methanol containing 0.2% ammonium hydroxide)]. The first-eluting enantiomer was 111. Yield: 5.6 mg, 16% for the separation. LCMS m/z 408.4 [M+H]$^+$. Retention time: 3.66 minutes via analytical HPLC [Column: Chiral Technologies AD-H, 4.6×100 mm, 5 μm; Mobile phase: 90:10 carbon dioxide/(methanol containing 0.2% ammonium hydroxide); Flow rate: 1.5 mL/minute].

The second-eluting enantiomer was C94. Yield: 4.3 mg, 12% for the separation. LCMS m/z 408.1 [M+H]$^+$. Retention time 4.63 minutes (analytical HPLC conditions identical to those used above for 111).

Example 112

2-[(5-Methyl-1,2,4-oxadiazol-3-yl)methyl]-1-[(3R)-1-methylpyrrolidin-3-yl]-1H-imidazo[4,5-c]quinoline-8-carbonitrile (112)

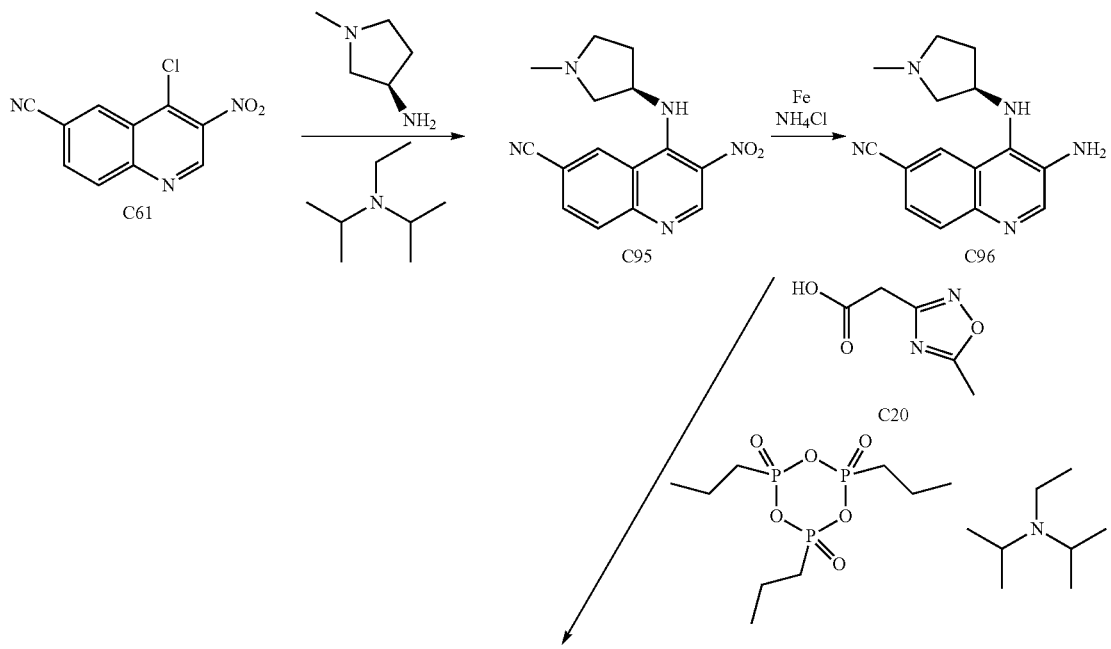

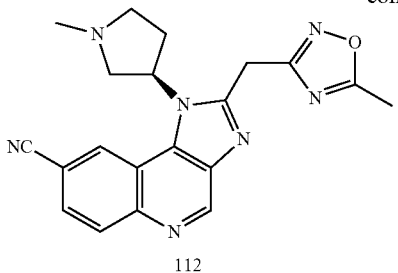

112

Step 1. Synthesis of 4-{[(3R)-1-methylpyrrolidin-3-yl]amino}-3-nitroquinoline-6-carbonitrile (C95)

N,N-Diisopropylethylamine (251 mg, 1.94 mmol) was added to a 20° C. solution of C61 (210 mg, 0.899 mmol) and (3R)-1-methylpyrrolidin-3-amine (77.9 mg, 0.778 mmol) in acetonitrile (3 mL). The reaction mixture was stirred at 20° C. for 2 hours, whereupon it was concentrated in vacuo. Purification of the residue via silica gel chromatography (Gradient: 0% to 1% methanol in dichloromethane) afforded the product as a yellow solid. Yield: 210 mg, 0.706 mmol, 91%. LCMS m/z 297.9 [M+H]$^+$. $^1$H NMR (400 MHz, CDCl$_3$) δ 10.04-10.15 (br m, 1H), 9.45 (s, 1H), 8.55 (d, J=1.5 Hz, 1H), 8.07 (d, half of AB quartet, J=8.5 Hz, 1H), 7.92 (dd, half of ABX pattern, J=8.5, 1.8 Hz, 1H), 4.65-4.74 (m, 1H), 3.02-3.10 (m, 1H), 2.84-2.90 (m, 1H), 2.80 (dd, half of ABX pattern, J=9.9, 5.6 Hz, 1H), 2.61-2.71 (m, 1H) 2.46 (s, 3H), 2.41-2.50 (m, 1H), 2.06-2.16 (m, 1H).

Step 2. Synthesis of 3-amino-4-{[(3R)-1-methylpyrrolidin-3-yl]amino}quinoline-6-carbonitrile (C96)

To a solution of C95 (100 mg, 0.336 mmol) in a mixture of ethanol (1 mL) and water (0.25 mL) were added ammonium chloride (36 mg, 0.673 mmol) and iron powder (75.1 mg, 1.34 mmol), and the reaction mixture was stirred at 80° C. for 1 hour. It was then filtered, and the filter cake was washed with methanol (30 mL). The organic layer from the combined filtrates was concentrated in vacuo and purified via silica gel chromatography (Gradient: 0% to 15% methanol in dichloromethane), affording the product as a yellow solid. Yield: 112 mg, assumed quantitative. $^1$H NMR (400 MHz, DMSO-d$_6$), characteristic peaks: δ 8.65-8.71 (br s, 1H), 8.58 (s, 1H), 7.89 (d, J=8.5 Hz, 1H), 7.62 (dd, J=8.5, 2.0 Hz, 1H), 5.56-5.70 (br s, 1H), 5.43 (d, J=10.5 Hz, 1H), 4.32-4.46 (br m, 1H), 2.81 (s, 3H), 1.84-1.95 (m, 1H).

Step 3. Synthesis of 2-[(5-methyl-1,2,4-oxadiazol-3-yl)methyl]-1-[(3R)-1-methylpyrrolidin-3-yl]-1H-imidazo[4,5-c]quinoline-8-carbonitrile (112)

N,N-Diisopropylethylamine (25.4 mg, 0.196 mmol) and 2,4,6-tripropyl-1,3,5,2,4,6-trioxatriphosphinane 2,4,6-trioxide (50% solution in ethyl acetate, 238 mg, 0.374 mmol) were added to a solution of C96 (50 mg, 0.19 mmol) and C20 (27.1 mg, 0.191 mmol) in toluene (1 mL), and the reaction mixture was stirred at 70° C. for 1 hour. LCMS at this point indicated conversion to the intermediate amide (LCMS m/z 392.2 [M+H]+), and the reaction mixture was then stirred at 105° C. for 16 hours, whereupon it was concentrated in vacuo and purified by reversed phase HPLC (Column: Agela Durashell, 5 µm; Mobile phase A: 0.05% ammonium hydroxide in water; Mobile phase B: acetonitrile; Gradient: 27% to 47% B), affording the product as a yellow solid. Yield: 13.0 mg, 34.8 µmol, 18%. LCMS m/z 374.1 [M+H]$^+$. $^1$H NMR (400 MHz, CDCl$_3$) δ 10.00-10.26 (br s, 1H), 9.39 (s, 1H), 8.32 (d, J=8.6 Hz, 1H), 7.84 (dd, J=8.7, 1.6 Hz, 1H), 5.50-5.62 (m, 1H), 4.72 (br AB quartet, J$_{AB}$=16.3 Hz, Δν$_{AB}$=20.5 Hz, 2H), 3.38-3.48 (m, 2H), 2.86 (dd, J=11.0, 10.8 Hz, 1H), 2.60 (s, 3H), 2.57 (s, 3H), 2.42-2.63 (m, 2H), 2.32-2.42 (br m, 1H).

Example 113

1-[(3R)-1-Methylpyrrolidin-3-yl]-2-(pyrazin-2-ylmethyl)-1H-imidazo[4,5-c]quinoline-8-carbonitrile (113)

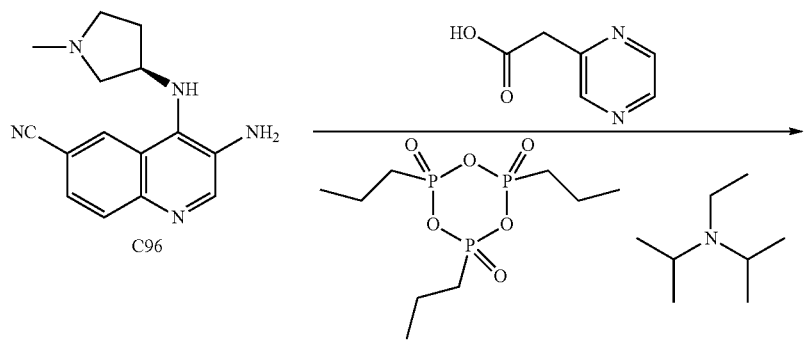

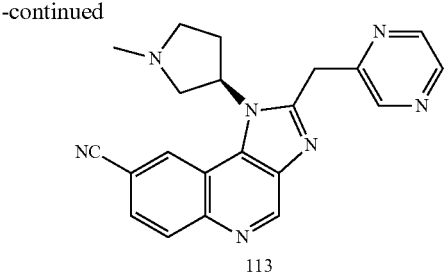

113

N,N-Diisopropylethylamine (25.4 mg, 0.196 mmol) and 2,4,6-tripropyl-1,3,5,2,4,6-trioxatriphosphinane 2,4,6-trioxide (50% solution in ethyl acetate, 238 mg, 0.374 mmol) were added to a solution of C96 (50 mg, 0.19 mmol) and pyrazin-2-ylacetic acid (26.4 mg, 0.191 mmol) in toluene (1 mL). The reaction mixture was stirred at 70° C. for 1 hour, and then at 105° C. for 16 hours. Removal of solvent in vacuo provided a residue, which was purified using reversed phase HPLC (Column: Agela Durashell, 5 μm; Mobile phase A: 0.05% ammonium hydroxide in water; Mobile phase B: acetonitrile; Gradient: 25% to 55% B) to afford the product as a yellow solid. Yield: 10.3 mg, 30.6 μmol, 16%. LCMS m/z 370.1 [M+H]$^+$. $^1$H NMR (400 MHz, CDCl$_3$) δ 10.18-10.32 (br s, 1H), 9.38 (s, 1H), 8.72 (d, J=1.3 Hz, 1H), 8.52-8.54 (m, 2H), 8.32 (d, J=8.5 Hz, 1H), 7.83 (dd, J=8.6, 1.6 Hz, 1H), 5.64-5.74 (m, 1H), 4.78 (br s, 2H), 3.40-3.46 (m, 1H), 3.38 (dd, J=11.0, 4.3 Hz, 1H), 2.79 (dd, J=11.0, 10.8 Hz, 1H), 2.56 (s, 3H), 2.53-2.61 (m, 1H), 2.41-2.52 (m, 1H), 2.15-2.27 (br m, 1H).

Example 114

2-[(5-Methyl-1,2,4-oxadiazol-3-yl)methyl]-1-[(2R,4R)-2-methyltetrahydro-2H-pyran-4-yl]-8-(trifluoromethyl)-1H-imidazo[4,5-c]quinoline (114)

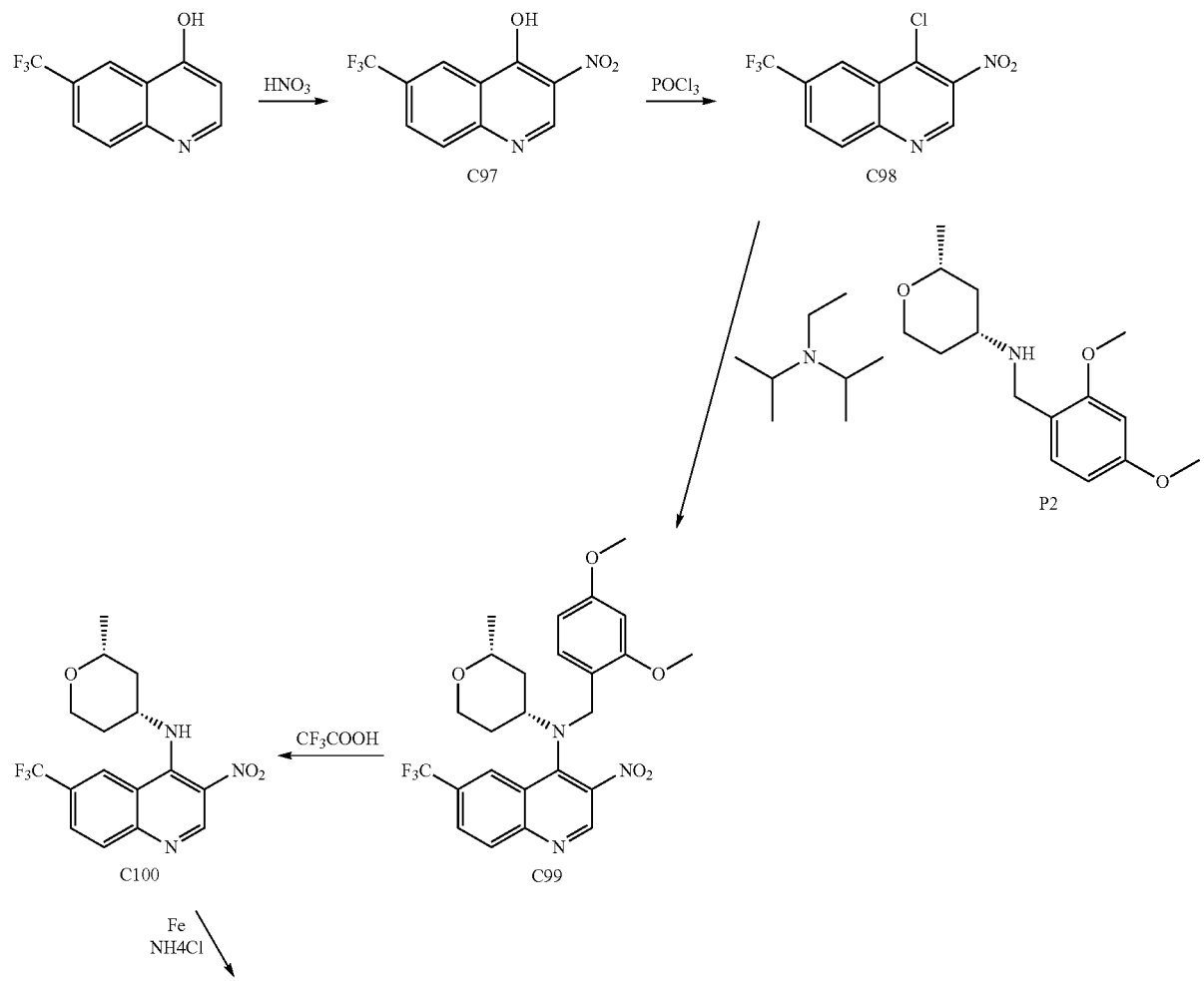

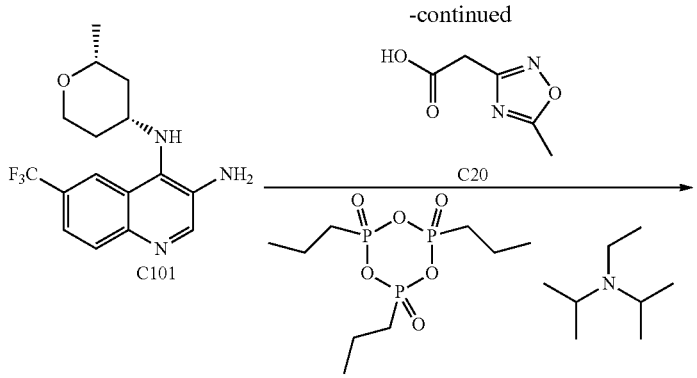

Step 1. Synthesis of 3-nitro-6-(trifluoromethyl)quinolin-4-ol (C97)

A solution of 6-(trifluoromethyl)quinolin-4-ol (2.00 g, 9.38 mmol) in concentrated nitric acid (10 mL) was stirred for 14 hours at 50° C., whereupon it was poured into water (50 mL). The resulting solid was isolated via filtration, providing the product as a pale yellow solid. Yield: 1.80 g, 6.97 mmol, 74%. $^1$H NMR (400 MHz, DMSO-$d_6$) δ 9.29 (s, 1H), 8.46 (s, 1H), 8.11 (d, J=9.0 Hz, 1H), 7.92 (d, J=8.5 Hz, 1H).

Step 2. Synthesis of 4-chloro-3-nitro-6-(trifluoromethyl)quinoline (C98)

Phosphorus oxychloride (3.25 mL, 34.9 mmol) was added to a 15° C. solution of compound C97 (3.00 g, 11.6 mmol) in N,N-dimethylformamide (10 mL), and the reaction mixture was stirred for 2 hours at 15° C. It was then poured into water (80 mL). Collection of the precipitate via filtration provided the product as a solid (2.40 g). This material was impure by $^1$H NMR analysis, and was taken directly into the following step. $^1$H NMR (400 MHz, DMSO-$d_6$), product peaks only: δ 9.22 (s, 1H), 8.40 (br s, 1H), 8.03 (br d, J=8.5 Hz, 1H), 7.92-7.97 (m, 1H).

Step 3. Synthesis of N-(2,4-dimethoxybenzyl)-N-[(2R,4R)-2-methyltetrahydro-2H-pyran-4-yl]-3-nitro-6-(trifluoromethyl)quinolin-4-amine (C99)

N,N-Diisopropylethylamine (3.36 g, 26.0 mmol) and P2 (2.43 g, 9.16 mmol) were slowly added to a 15° C. solution of C98 (from the previous step, 2.40 g, 58.68 mmol) in acetonitrile (30 mL), and the reaction mixture was stirred for 30 minutes at 80° C. Water (100 mL) was added, and the resulting mixture was extracted with ethyl acetate (3×100 mL). The combined organic layers were concentrated in vacuo, and the residue was purified via silica gel chromatography (Gradient: 9% to 25% ethyl acetate in petroleum ether) to provide the product as a yellow solid. Yield: 3.40 g, 6.73 mmol, 58% over 2 steps. $^1$H NMR (400 MHz, CDCl$_3$) δ 9.11 (s, 1H), 8.60 (br s, 1H), 8.15 (d, J=9.0 Hz, 1H), 7.92 (dd, J=8.8, 1.8 Hz, 1H), 6.84 (d, J=8.0 Hz, 1H), 6.22 (dd, J=8.3, 2.3 Hz, 1H), 6.16 (d, J=2.0 Hz, 1H), 4.33-4.44 (m, 2H), 4.02-4.10 (m, 1H), 3.77-3.87 (m, 1H), 3.68 (s, 3H), 3.50 (s, 3H), 3.36-3.46 (m, 2H), 1.95-2.10 (m, 3H), 1.67-1.78 (m, 1H), 1.23 (d, J=6.0 Hz, 3H).

Step 4. Synthesis of N-[(2R,4R)-2-methyltetrahydro-2H-pyran-4-yl]-3-nitro-6-(trifluoromethyl)quinolin-4-amine (C100)

Trifluoroacetic acid (7.67 g, 67.3 mmol) was added to a 15° C. solution of compound C99 (3.40 g, 6.73 mmol) in dichloromethane (30 mL), and the reaction mixture was stirred for 30 minutes at 15° C. Solvents were removed in vacuo, and the residue was diluted with water (100 mL) and extracted with ethyl acetate (3×100 mL). The combined organic layers were concentrated in vacuo to afford the product (2.50 g) as a pale yellow solid, a portion of which was used directly in the following step. LCMS m/z 355.8 [M+H]$^+$.

Step 5. Synthesis of $N^4$-[(2R,4R)-2-methyltetrahydro-2H-pyran-4-yl]-6-(trifluoromethyl)quinoline-3,4-diamine (C101)

Iron powder (314 mg, 5.62 mmol) and ammonium chloride (301 mg, 5.63 mmol) were added to a solution of C100 (from the previous step, 200 mg, 50.54 mmol) in ethanol (5 mL) and water (1 mL), and the reaction mixture was stirred for 1 hour at 80° C. It was then filtered through diatomaceous earth, and the filtrate was concentrated in vacuo. Silica gel chromatography (Gradient: 9% to 33% ethyl acetate in petroleum ether) afforded the product as a pale grey solid. Yield: 140 mg, 0.430 mmol, 80% over 2 steps. LCMS m/z 325.9 [M+H]$^+$.

Step 6. Synthesis of 2-[(5-methyl-1,2,4-oxadiazol-3-yl)methyl]-1-[(2R,4R)-2-methyltetrahydro-2H-pyran-4-yl]-8-(trifluoromethyl)-1H-imidazo[4,5-c]quinoline (114)

To a solution of C20 (60.0 mg, 0.422 mmol) in N,N-dimethylformamide (2 mL) were added C101 (137 mg, 0.421 mmol), N,N-diisopropylethylamine (161 mg, 1.25 mmol), and 2,4,6-tripropyl-1,3,5,2,4,6-trioxatriphosphinane 2,4,6-trioxide (50% solution in ethyl acetate, 0.39 mL, 0.655 mmol). The reaction mixture was stirred for 2 hours at 110° C., whereupon it was diluted with water (80 mL) and extracted with ethyl acetate (3×80 mL). The combined organic layers were concentrated in vacuo and purified by reversed phase HPLC (Column: Agela Durashell, 5 μm; Mobile phase A: 0.05% ammonium hydroxide in water; Mobile phase B: acetonitrile; Gradient: 40% to 70% B), providing the product as a pale grey solid. Yield: 16.8 mg, 38.9 μmol, 9%. LCMS m/z 432.0 [M+H]$^+$. $^1$H NMR (400 MHz, CDCl$_3$) δ 9.41 (s, 1H), 8.94-9.11 (br m, 1H), 8.41 (d, J=8.8 Hz, 1H), 7.90 (dd, J=8.8, 1.8 Hz, 1H), 4.99-5.19 (br m, 1H), 4.62 (s, 2H), 4.33 (br dd, J=12, 5 Hz, 1H), 3.64-3.79 (m, 2H), 2.67-2.87 (br m, 1H), 2.61 (s, 3H), 2.38-2.63 (br m, 1H), 1.80-2.09 (br m, 2H), 1.35 (d, J=6.0 Hz, 3H).

Example 115

8-Chloro-2-[(3-methyl-1,2-oxazol-5-yl)methyl]-1-[(2R,4R)-2-methyltetrahydro-2H-pyran-4-yl]-1H-imidazo[4,5-c]quinoline (115)

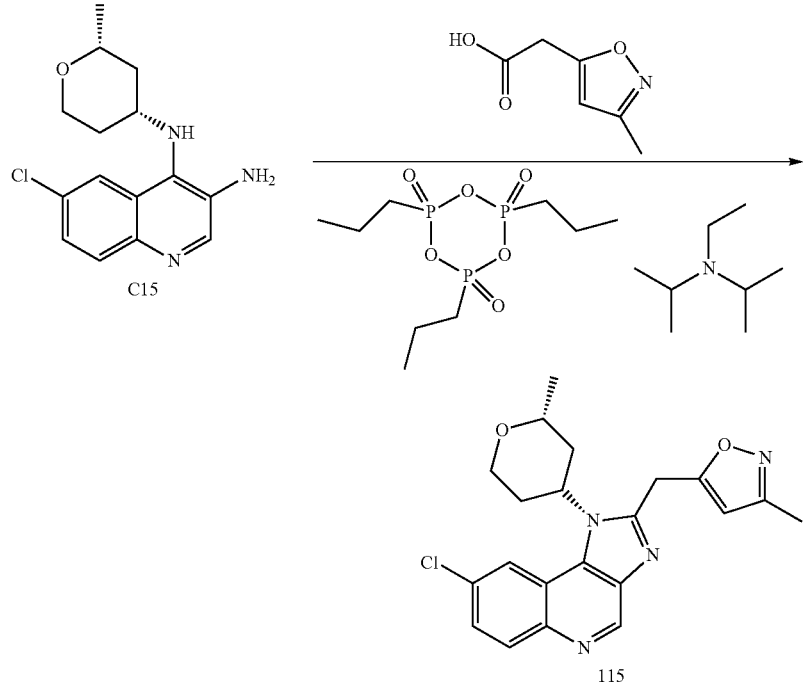

N,N-Diisopropylethylamine (71.6 μL, 0.411 mmol) and 2,4,6-tripropyl-1,3,5,2,4,6-trioxatriphosphinane 2,4,6-trioxide (50% solution in ethyl acetate, 0.245 mL, 0.412 mmol) were added to a mixture of C15 (40.0 mg, 0.137 mmol) and (3-methyl-1,2-oxazol-5-yl)acetic acid (19.3 mg, 0.137 mmol) in ethyl acetate (0.8 mL), and the reaction mixture was heated at 80° C. overnight. It was then partitioned between saturated aqueous sodium bicarbonate solution and ethyl acetate, and the aqueous layer was extracted twice with ethyl acetate. The combined organic layers were dried over sodium sulfate, filtered, and concentrated under reduced pressure. Chromatography on silica gel (Gradient: 0% to 10% methanol in dichloromethane), followed by trituration with diethyl ether, provided the product as a yellow solid. Yield: 33.2 mg, 83.6 μmol, 61%. LCMS m/z 397.3 [M+H]$^+$. $^1$H NMR (400 MHz, CDCl$_3$) δ 9.28 (s, 1H), 8.55-8.75 (br m, 1H), 8.24 (d, J=8.6 Hz, 1H), 7.66 (dd, J=9.0, 2.0 Hz, 1H), 6.07 (s, 1H), 4.90-5.13 (br m, 1H), 4.61 (s, 2H), 4.34 (br dd, J=11.7, 4.3 Hz, 1H), 3.64-3.82 (m, 2H), 2.62-2.88 (br m, 1H), 2.36-2.59 (br m, 1H), 2.28 (s, 3H), 1.71-2.02 (br m, 2H), 1.37 (d, J=5.9 Hz, 3H).

Example 116

8-Chloro-1-[(2R,4R)-2-methyltetrahydro-2H-pyran-4-yl]-2-[(5-methyl-1,3,4-thiadiazol-2-yl)methyl]-1H-imidazo[4,5-c]quinoline (116)

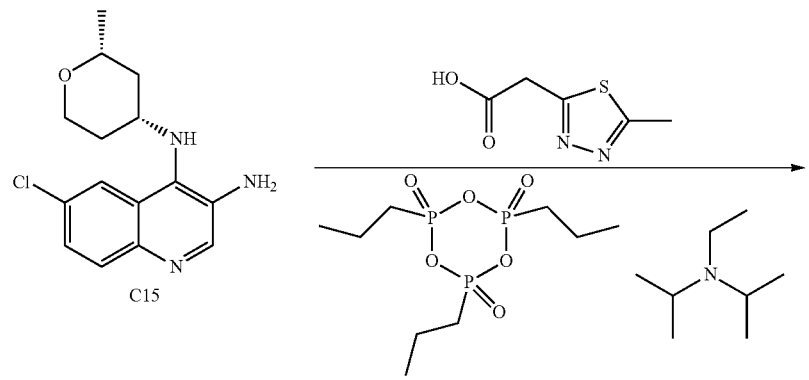

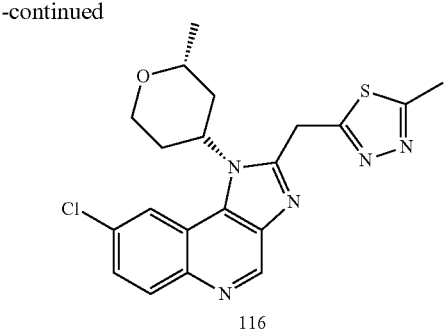

116

N,N-Diisopropylethylamine (52 mg, 0.40 mmol) and 2,4,6-tripropyl-1,3,5,2,4,6-trioxatriphosphinane 2,4,6-trioxide (50% solution in ethyl acetate, 480 mg, 0.75 mmol) were added to a solution of C15 (102 mg, 0.350 mmol) and (5-methyl-1,3,4-thiadiazol-2-yl)acetic acid (60 mg, 0.38 mmol) in toluene (3 mL). The reaction mixture was heated to 70° C. for 2 hours, and then at 105° C. for 18 hours. Saturated aqueous sodium bicarbonate solution (10 mL) was added, and the resulting mixture was extracted with ethyl acetate (6×10 mL). The combined organic layers were dried over sodium sulfate, filtered, and concentrated in vacuo. Purification via reversed phase HPLC (Column: Agela Durashell, 5 μm; Mobile phase A: 0.225% formic acid in water; Mobile phase B: acetonitrile; Gradient: 34% to 54% B) afforded the product as a red solid. Yield: 38 mg, 92 μmol, 26%. LCMS m/z 414.0 (chlorine isotope pattern observed) [M+H]⁺. ¹H NMR (400 MHz, CDCl₃) δ 9.28 (s, 1H), 8.56-8.76 (br m, 1H), 8.23 (d, J=9.0 Hz, 1H), 7.65 (dd, J=8.9, 2.1 Hz, 1H), 5.23-5.37 (m, 1H), 4.94 (s, 2H), 4.31 (br dd, J=12, 5 Hz, 1H), 3.68-3.82 (m, 2H), 2.76 (s, 3H), 2.57-2.80 (br m, 1H), 2.31-2.52 (br m, 1H), 1.58-1.9 (br m, 2H, assumed; partially obscured by water peak), 1.36 (d, J=6.0 Hz, 3H).

Method A

Conversion of vicinal chloro-nitro bicyclic heteroaromatics to 1,2-disubstituted-imidazo[4,5-c]-fused tricyclic compounds M1

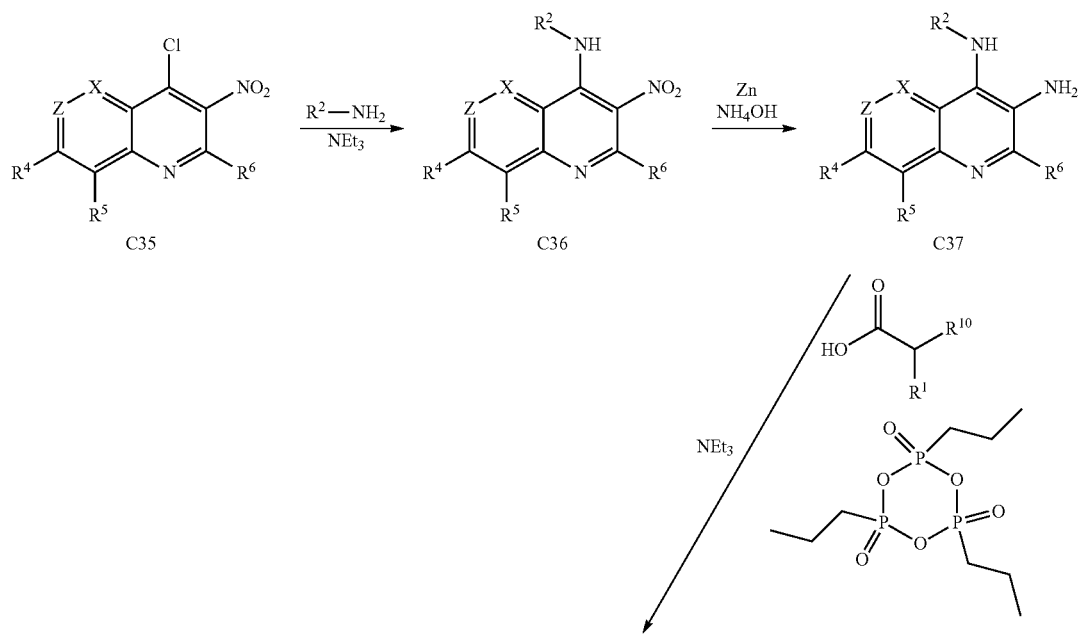

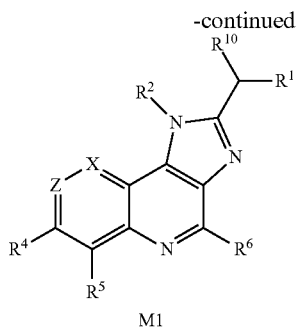

M1

Step 1. Synthesis of vicinal amino-nitro bicyclic heteroaromatic C36

The vicinal chloro-nitro bicyclic heteroaromatic starting material C35 (1 mmol) was combined in a vial with amine $R^2$—$NH_2$ (1.2 mmol) and N,N-dimethylformamide (4 mL). Triethylamine (300 μL, 2 mmol) was added, the vial was sealed, and the reaction mixture was shaken at 30° C. for 16 hours. Solvent was removed using a Speedvac® concentrator to provide the product.

Step 2. Synthesis of vicinal diamino bicyclic heteroaromatic C37

Compound C36 from the previous step was mixed with methanol (2 mL) and aqueous ammonium hydroxide solution (2 mL). Activated zinc dust (650 mg, 10 mmol) was added to the vial, which was then sealed and shaken at 30° C. for 1 hour. The reaction mixture was filtered, and the filtrate was concentrated using a Speedvac® concentrator. Water (10 mL) was added to the residue, and the mixture was extracted with ethyl acetate (3×10 mL); the combined organic layers were dried over sodium sulfate, filtered, and concentrated to afford the product.

Step 3. Synthesis of 1,2-disubstituted-imidazo[4,5-c]-fused tricyclic compound M1

A solution of C37 in 1,4-dioxane (0.125 M, 800 μL, 100 μmol) was added to the carboxylic acid $(R^1)(R^{10})$CHCOOH (100 μmol). Triethylamine (45 μL, 320 μmol) and 2,4,6-tripropyl-1,3,5,2,4,6-trioxatriphosphinane 2,4,6-trioxide (50% solution in ethyl acetate, 80 μL, 130 μmol) were added, the vial was sealed, and the reaction mixture was shaken at 130° C. for 16 hours. After concentration using a Speedvac®, the product was purified using one of the following reversed phase HPLC systems: 1) Column: Phenomenex Gemini C18, 8 μm; Gradient: acetonitrile in aqueous ammonium hydroxide (pH 10); 2) Column: DIKMA Diamonsil(2) C18, 5 μm; Gradient: acetonitrile in (water containing 0.225% formic acid); 3) Column: YMC-Actus Triart C18, 5 μm; Gradient: acetonitrile in aqueous ammonium hydroxide (pH 10).

Method B

Conversion of vicinal chloro-nitro bicyclic heteroaromatics to 1,2-disubstituted-imidazo[4,5-c]-fused tricyclic compounds M1

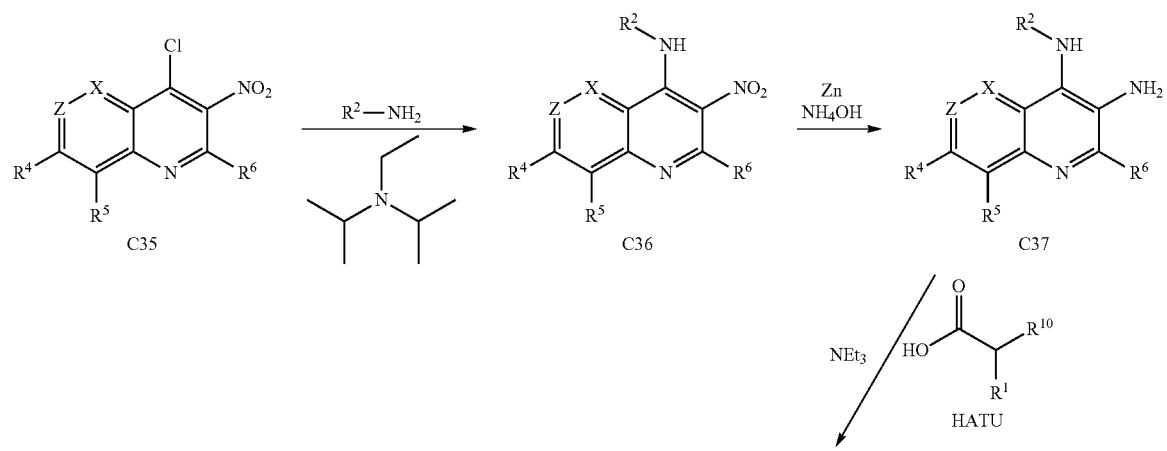

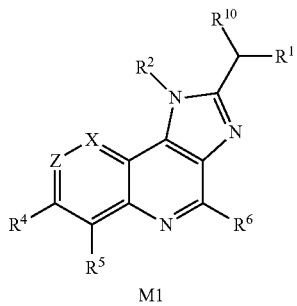

M1

Step 1. Synthesis of vicinal amino-nitro bicyclic heteroaromatic C36

Compound C35 (0.15 mmol) was combined with amine $R^2$—$NH_2$ (0.18 mmol) and N,N-diisopropylethylamine (0.10 mL, 0.6 mmol) in acetonitrile (0.5 mL), and the reaction vial was shaken at 45° C. for 2 hours. The reaction mixture was then partitioned between water (1.5 mL) and ethyl acetate (2.4 mL) with vortexing. The organic layer was eluted through a solid-phase extraction cartridge (6 mL) loaded with sodium sulfate (~1 g); this extraction process was repeated twice, and solvent was removed in vacuo to provide the product.

Step 2. Synthesis of vicinal diamino bicyclic heteroaromatic C37

Compound C36 (from the previous step, ~0.15 mmol) was treated with methanol (0.3 mL) and aqueous ammonium hydroxide solution (0.3 mL). Zinc dust (~100 mg, 1.5 mmol) was added, and the reaction mixture was shaken at room temperature for 1 hour, then filtered through diatomaceous earth. The filter pad was washed with ethyl acetate (2×2.5 mL), and the combined filtrates were concentrated in vacuo. The residue was partitioned between water (1.5 mL) and ethyl acetate (2.4 mL) with vortexing. The organic layer was eluted through a solid-phase extraction cartridge (6 mL) loaded with sodium sulfate (~1 g); this extraction process was repeated twice, and solvent was removed under reduced pressure to provide the product.

Step 3. Synthesis of 1,2-disubstituted-imidazo[4,5-c]-fused tricyclic compound M1

Compound C37 (from the previous step, ~0.15 mmol) was dissolved in 1-methylpyrrolidin-2-one (0.4 mL) and added to carboxylic acid $(R^1)(R^{10})$CHCOOH (0.19 mmol). Triethylamine (23 µL, 0.16 mmol) and a solution of O-(7-azabenzotriazol-1-yl)-N,N,N',N'-tetramethyluronium hexafluorophosphate (HATU, 71 mg, 0.19 mmol) in 1-methylpyrrolidin-2-one (0.3 mL) were added. (An extra equivalent of triethylamine was employed if the carboxylic acid was a hydrochloride salt.) The reaction mixture was shaken at 100° C. for 20 hours, then partitioned between water (1.5 mL) and ethyl acetate (2.4 mL) with vortexing. The organic layer was eluted through a solid-phase extraction cartridge (6 mL) loaded with sodium sulfate (~1 g); this extraction process was repeated twice, and solvent was removed under reduced pressure to provide the product. Purification was carried out via gradient elution, using one of the following reversed phase HPLC systems: 1) Column: Waters Sunfire C18, 5 µm; Mobile phase A: 0.05% trifluoroacetic acid in water (v/v); Mobile phase B: 0.05% trifluoroacetic acid in acetonitrile (v/v); or 2) Column: Waters XBridge C18, 5 µm; Mobile phase A: 0.03% ammonium hydroxide in water (v/v); Mobile phase B: 0.03% ammonium hydroxide in acetonitrile (v/v).

Table 1, below, provides the method of preparation, structure, and physicochemical data for the compounds of Examples 12-92 and 117-145.

TABLE 1

| Example Number | Method of Preparation; Non-commercial starting materials | Structure | ¹H NMR (400 MHz, DMSO-d₆) δ (ppm); Mass spectrum, observed ion m/z [M + H]⁺ or HPLC retention time; Mass spectrum m/z [M + H]⁺ (unless otherwise indicated) |
|---|---|---|---|
| 12 | Example 2[1,2]; P1 | 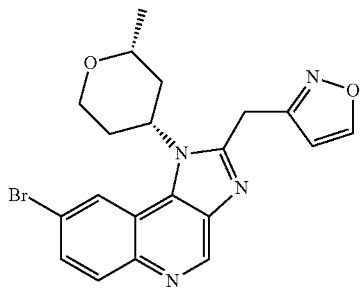 | ¹H NMR (400 MHz, CDCl₃) δ 9.33 (s, 1H), 8.71-8.99 (br m, 1H), 8.42 (s, 1H), 8.18 (d, J = 9.0 Hz, 1H), 7.80 (dd, J = 9.0, 2.0 Hz, 1H), 6.30-6.53 (br m, 1H), 5.01-5.34 (br m, 1H), 4.63 (s, 2H), 4.33 (dd, J = 11.7, 4.7 Hz, 4H), 3.62-3.87 (br m, 2H), 2.57-2.88 (br m, 2H), 2.26-2.56 (br m, 1H), 1.73-1.92 (br m, 1H), 1.38 (d, J = 6.2 Hz, 3H); 427.2, 429.1 |
| 13 | Example 9[3] | 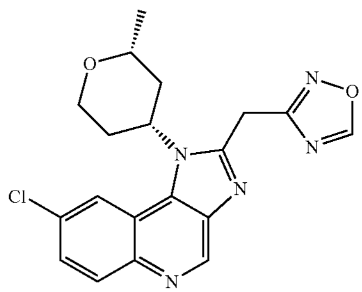 [SMILES: C[C@@H]1C[C@H](n2c(Cc3ncon3)nc3cnc4ccc(Cl)cc4c32)CCO1] | ¹H NMR (400 MHz, CDCl₃) δ 9.31 (s, 1H), 8.79 (s, 1H), 8.50-8.87 (br m, 1H), 8.26 (d, J = 9.0 Hz, 1H), 7.68 (dd, J = 8.8, 2.2 Hz, 1H), 4.91-5.34 (br m, 1H), 4.73 (s, 2H), 4.28-4.47 (br m, 1H), 3.64-3.88 (br m, 2H), 2.70-2.94 (br m, 1H), 2.39-2.69 (br m, 1H), 1.80-2.15 (br m, 1H), 1.40 (d, J = 6.2 Hz, 3H), 1.29 (br m, 1H); 384.3, 386.2 |
| 14 | Example 3[4] | 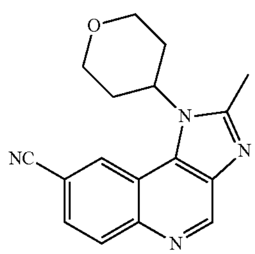 [SMILES: Cc1nc2cnc3ccc(C#N)cc3c2n1C1CCOCC1] | ¹H NMR (400 MHz, CDCl₃) δ 9.36 (s, 1H), 8.57-8.82 (br m, 1H), 8.38 (d, J = 8.7 Hz, 1H), 7.86 (br d, J = 8.7 Hz, 1H), 5.02-5.24 (br m, 1H), 4.35 (br dd, J = 12, 4 Hz, 2H), 3.73 (br dd, J = 12, 12 Hz, 2H), 2.89 (s, 3H), 2.59-2.76 (br m, 2H), 2.02-2.16 (br m, 2H); 292.9 |
| 15 | Example 6 | 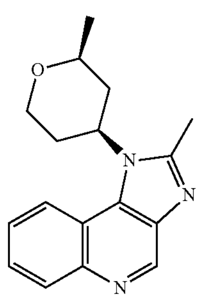 | characteristic peaks: δ 9.11 (s, 1H), 8.45-8.57 (br m, 1H), 8.17 (br d, J = 7.6 Hz, 1H), 7.65-7.76 (m, 2H), 4.87-5.59 (v br m, 1H), 4.02-4.23 (br m, 1H), 3.63-3.87 (m, 2H), 2.77 (s, 3H), 1.91-2.30 (br m, 3H), 1.22 (d, J = 6.0 Hz, 3H); 281.9 |
| 16 | Method A[5] | 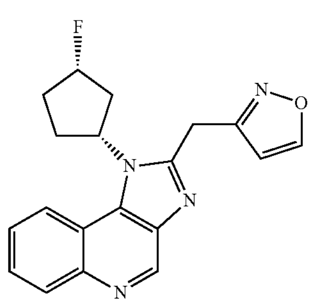 [SMILES: F[C@H]1CC[C@@H](n2c(Cc3ccon3)nc3cnc4ccccc4c32)C1] | 2.32 minutes[6]; 337 |

TABLE 1-continued

| Example Number | Method of Preparation; Non-commerical starting materials | Structure | ¹H NMR (400 MHz, DMSO-d₆) δ (ppm); Mass spectrum, observed ion m/z [M + H]⁺ or HPLC retention time; Mass spectrum m/z [M + H]⁺ (unless otherwise indicated) |
|---|---|---|---|
| 17 | Example 6; C13 | 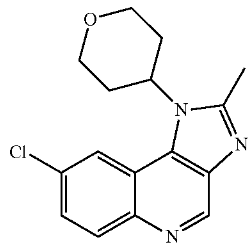 [SMILES: Cc1nc2cnc3ccc(Cl)cc3c2n1C1CCOCC1] | ¹H NMR (400 MHz, CDCl₃) δ 9.25 (s, 1H), 8.27 (d, J = 9.0 Hz, 1H), 8.17 (s, 1H), 7.65 (dd, J = 8.8, 2.3 Hz, 1H), 4.34 (br d, J = 8.5 Hz, 2H), 3.72 (br t, J = 12.0 Hz, 2H), 2.86 (s, 2H), 2.67 (br m 4H), 2.05 (br m, 2H); 301.9 |
| 18 | Method A | 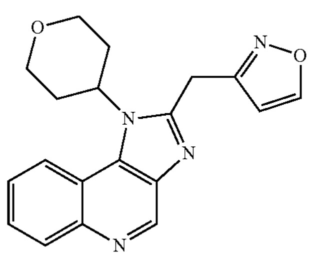 [SMILES: c1ccc2c(c1)ncc1nc(Cc3ccon3)n(C3CCOCC3)c12] | 2.10 minutes⁶; 335 |
| 19 | Example 3⁷ | 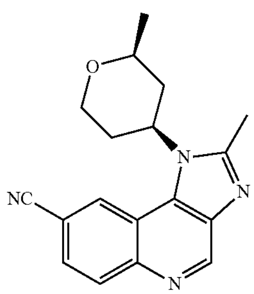 | 9.29 (s, 1H), 8.89-8.94 (m, 1H), 8.32 (d, J = 8.5 Hz, 1H), 8.04 (dd, J = 8.5, 1.5 Hz, 1H), 6.56-6.79 (br m, 1H), 5.40-5.65 (br m, 1H), 4.33-4.49 (br m, 1H), 3.97-4.10 (br m, 1H), 3.81-3.94 (br m, 1H), 2.84 (s, 3H), 2.53-2.63 (br m, 1H), 1.92-2.14 (br m, 2H), 1.55 (d, J = 7.0 Hz, 3H); 306.9 |
| 20 | Example 3; Example 6 | 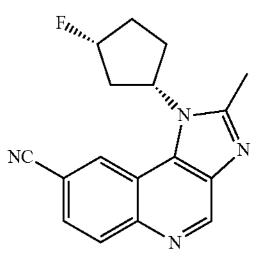 [SMILES: Cc1nc2cnc3ccc(C#N)cc3c2n1[C@H]1CC[C@@H](F)C1] | 9.28 (s, 1H), 9.08 (s, 1H), 8.29 (d, J = 8.5 Hz, 1H), 8.01 (dd, J = 8.5, 1.5 Hz, 1H), 5.54-5.68 (br m, 1H), 5.51 (br m, 1H), 5.37 (br m, 1H), 2.82-3.00 (br m, 1H), 2.80 (s, 3H), 2.35-2.49 (br m, 1H), 2.15-2.35 (br m, 2H), 1.99-2.14 (br m, 1H); 294.9 |
| 21 | Example 3⁸ | 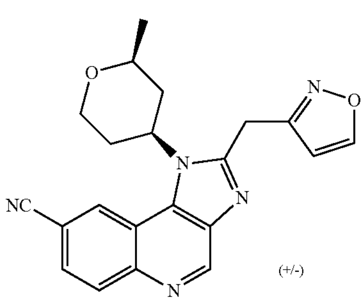 [SMILES: C[C@H]1C[C@@H](n2c(Cc3ccon3)nc3cnc4ccc(C#N)cc4c32)CCO1] | 9.38 (s, 1H), 8.96 (br s, 1H), 8.94 (br s, 1H), 8.36 (d, J = 8.5 Hz, 1H), 8.09 (d, J = 10.0 Hz, 1H), 6.62 (br s, 1H), 5.30-5.53 (m, 1H), 4.82 (br d, J = 17.1 Hz, 1H), 4.71 (d, J = 16.6 Hz, 1H), 4.35-4.46 (br m, 1H), 3.92-4.03 (br m, 1H), 3.89 (br m, 1H), 2.57 (br m, 2H), 1.89-2.09 (br m, 1H), 1.69-1.88 (br m, 1H), 1.40 (br s, 3H); 374.0 |

TABLE 1-continued

| Example Number | Method of Preparation; Non-commerical starting materials | Structure | $^1$H NMR (400 MHz, DMSO-d$_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 22 | Example 3[9,1,10]; P1 | 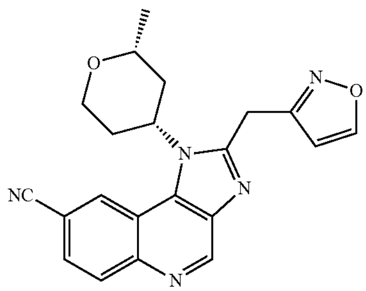 [SMILES: C[C@@H]1C[C@H](n2c(Cc3ccon3)nc3cnc4ccc(C#N)cc4c32)CCO1] | 9.32-9.38 (m, 1H), 8.97-9.05 (m, 1H), 8.89-8.94 (m, 1H), 8.35 (d, J = 8.5 Hz, 1H), 8.06 (d, J = 9.0 Hz, 1H), 6.61-6.66 (m, 1H), 5.14-5.44 (m, 1H), 4.67-4.82 (m, 2H), 4.07-4.28 (m, 1H), 3.55-3.91 (m, 2H), 2.01-2.36 (m, 3H), 1.80-2.00 (m, 1H), 1.23 (d, J = 6.0 Hz, 3H); 374.0 |
| 23 | Example 3[8] | (+/-) | 9.37 (s, 1H), 8.91-8.97 (m, 2H), 8.35 (d, J = 8.8 Hz, 1H), 8.08 (br d, J = 8.5 Hz, 1H), 6.61 (d, J = 1.5 Hz, 1H), 5.26-5.53 (br m, 1H), 4.75 (AB quartet, downfield d is broadened, J$_{AB}$ = 17.1 Hz, Δν$_{AB}$ = 40 Hz, 2H), 4.35-4.44 (m, 1H), 3.82-4.01 (br m, 2H), 2.5-2.63 (m, 2H, assumed; partially obscured by solvent peak), 1.90-2.05 (br m, 1H), 1.70-1.89 (br m, 1H), 1.31-1.47 (br m, 3H); 374.0 |
| 24 | Example 23[11] | 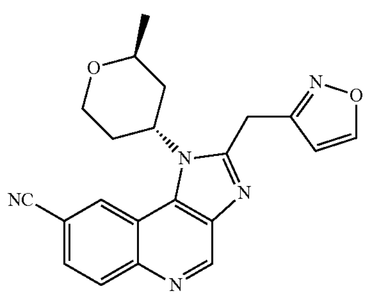 [SMILES: C[C@H]1C[C@H](n2c(Cc3ccon3)nc3cnc4ccc(C#N)cc4c32)CCO1] | 9.31-9.42 (m, 1H), 8.97-9.07 (m, 1H), 8.88-8.97 (m, 1H), 8.34 (d, J = 8.5 Hz, 1H), 8.07 (dd, J = 8.5, 2.5 Hz, 1H), 6.64 (br d, J = 1.0 Hz, 1H), 5.17-5.40 (m, 1H), 4.67-4.80 (m, 2H), 4.07-4.25 (m, 1H), 3.54-3.92 (m, 2H), 2.36-2.47 (m, 1H), 2.01-2.27 (m, 2H), 1.84-2.00 (m, 1H), 1.23 (d, J = 6.0 Hz, 3H); 374.0 |
| 25 | Example 7; C22 | •HCOOH | 9.21 (s, 1H), 8.92 (d, J = 1.5 Hz, 1H), 8.70 (br s, 1H), 8.11 (d, J = 9.0 Hz, 1H), 7.85 (dd, J = 8.8, 1.8 Hz, 1H), 6.63 (d, J = 1.5 Hz, 1H), 5.32-5.53 (m, 2H), 4.69 (s, 2H), 2.81 (br m, 1H), 2.40 (br m, 1H), 2.11-2.32 (br m, 3H), 2.03 (br m, 1H); 416.8 |
| 26 | Method A[5] | 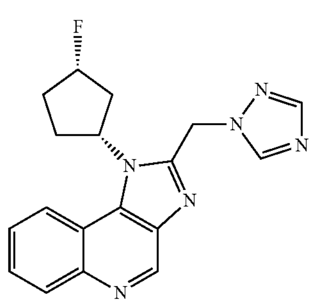 [SMILES: F[C@H]1CC[C@@H](n2c(Cn3cncn3)nc3cnc4ccccc4c32)C1] | 2.11 minutes[6]; 337 |

TABLE 1-continued

| Example Number | Method of Preparation; Non-commerical starting materials | Structure | ¹H NMR (400 MHz, DMSO-d₆) δ (ppm); Mass spectrum, observed ion m/z [M + H]⁺ or HPLC retention time; Mass spectrum m/z [M + H]⁺ (unless otherwise indicated) |
|---|---|---|---|
| 27 | Method A[5] | 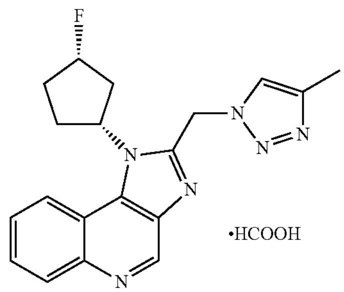 [SMILES: Cc1cn(Cc2nc3cnc4ccccc4c3n2[C@@H]2CC[C@H](F)C2)nn1 ; "·HCOOH"] | 2.20 minutes[6]; 351 |
| 28 | Method A[5] | 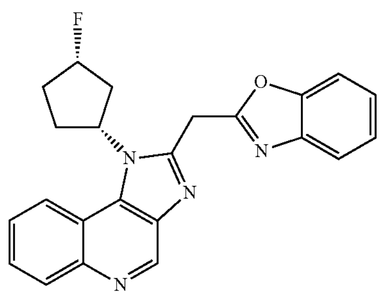 [SMILES: F[C@H]1CC[C@@H](n2c(Cc3nc4ccccc4o3)nc3cnc4ccccc4c32)C1] | 2.39 minutes[12]; 387 |
| 29 | Method A | 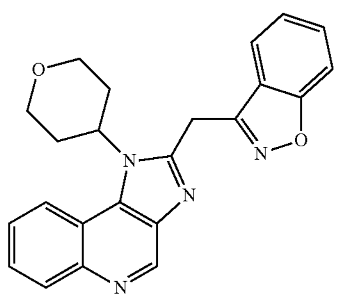 [SMILES: c1ccc2c(c1)ncc1nc(Cc3noc4ccccc34)n(C3CCOCC3)c12] | 2.48 minutes[6]; 385 |
| 30 | Method A | 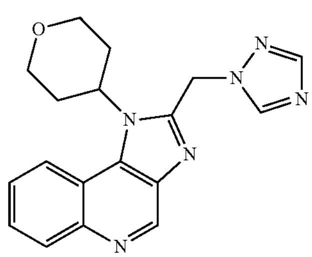 [SMILES: c1ccc2c(c1)ncc1nc(Cn3cncn3)n(C3CCOCC3)c12] | 2.10 minutes[13]; 335 |
| 31 | Method A | 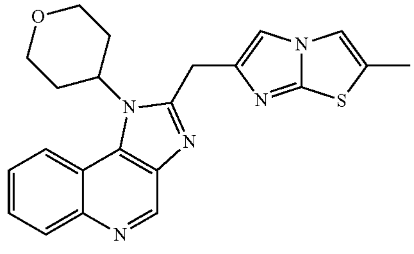 | 2.03 minutes[6]; 404 |

TABLE 1-continued

| Example Number | Method of Preparation; Non-commerical starting materials | Structure | ¹H NMR (400 MHz, DMSO-d₆) δ (ppm); Mass spectrum, observed ion m/z [M + H]⁺ or HPLC retention time; Mass spectrum m/z [M + H]⁺ (unless otherwise indicated) |
|---|---|---|---|
| 32 | Method A | 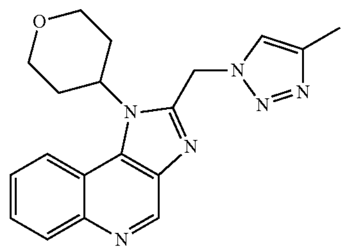 [SMILES: Cc1cn(Cc2nc3cnc4ccccc4c3n2C2CCOCC2)nn1] | 1.99 minutes[6]; 349 |
| 33 | Method A | 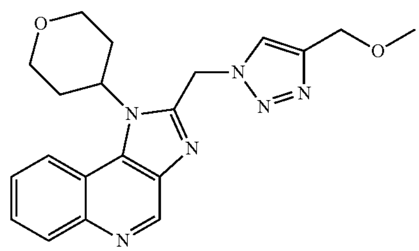 [SMILES: COCc1cn(Cc2nc3cnc4ccccc4c3n2C2CCOCC2)nn1] | 2.00 minutes[6]; 379 |
| 34 | Method A | 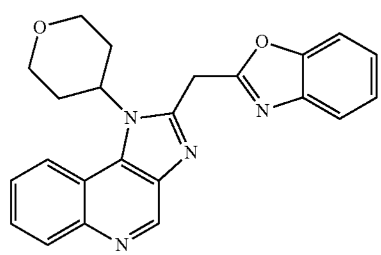 [SMILES: c1ccc2oc(Cc3nc4cnc5ccccc5c4n3C3CCOCC3)nc2c1] | 2.42 minutes[6]; 385 |
| 35 | Method A | 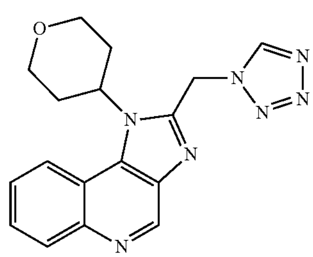 [SMILES: c1ccc2c(c1)ncc1nc(Cn3cnnn3)n(C3CCOCC3)c12] | 1.93 minutes[6]; 336 |
| 36 | Method A | 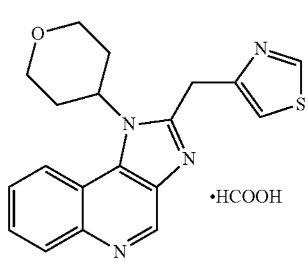 [SMILES: c1ccc2c(c1)ncc1nc(Cc3cscn3)n(C3CCOCC3)c12 ; "·HCOOH"] | 2.09 minutes[6]; 351 |

TABLE 1-continued

| Example Number | Method of Preparation; Non-commerical starting materials | Structure | $^1$H NMR (400 MHz, DMSO-d$_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 37 | Method A | 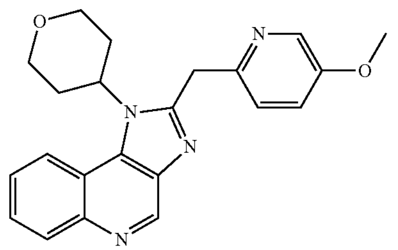 [SMILES: COc1ccc(Cc2nc3cnc4ccccc4c3n2C2CCOCC2)nc1] | 2.14 minutes[6]; 375 |
| 38 | Method A | 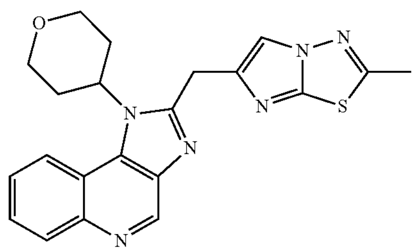 [SMILES: Cc1nn2cc(Cc3nc4cnc5ccccc5c4n3C3CCOCC3)nc2s1] | 2.18 minutes[6]; 405 |
| 39 | Method A; C6 | 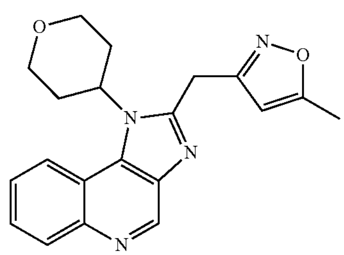 [SMILES: Cc1cc(Cc2nc3cnc4ccccc4c3n2C2CCOCC2)no1] | 2.21 minutes[6]; 349 |
| 40 | Method A | 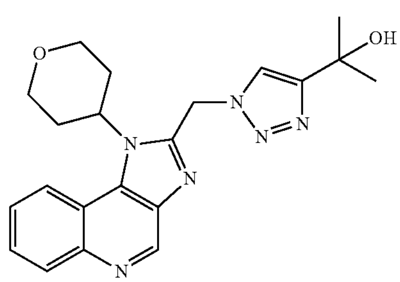 [SMILES: CC(C)(O)c1cn(Cc2nc3cnc4ccccc4c3n2C2CCOCC2)nn1] | 1.99 minutes[6]; 393 |
| 41 | Method A | 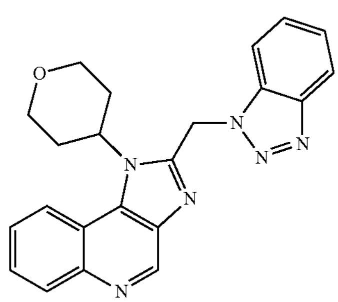 [SMILES: c1ccc2c(c1)ncc1nc(Cn3nnc4ccccc43)n(C3CCOCC3)c12] | 2.29 minutes[6]; 385 |

TABLE 1-continued
| Example Number | Method of Preparation; Non-commerical starting materials | Structure | $^1$H NMR (400 MHz, DMSO-d$_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 42 | Method A | 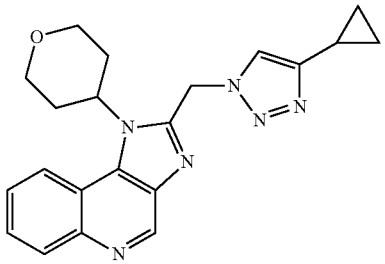 [SMILES: c1ccc2c(c1)ncc1nc(Cn3cc(C4CC4)nn3)n(C3CCOCC3)c12] | 2.19 minutes$^6$; 375 |
| 43 | Method A | 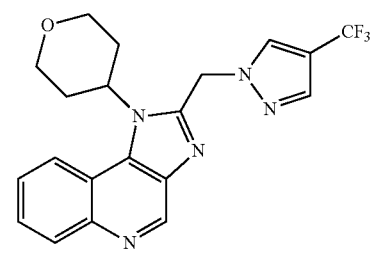 [SMILES: FC(F)(F)c1cnn(Cc2nc3cnc4ccccc4c3n2C2CCOCC2)c1] | 2.51 minutes$^6$; 402 |
| 44 | Method A | 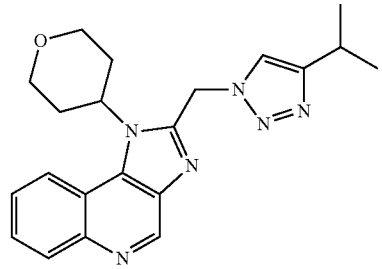 [SMILES: CC(C)c1cn(Cc2nc3cnc4ccccc4c3n2C2CCOCC2)nn1] | 2.27 minutes$^6$; 377 |
| 45 | Method A | 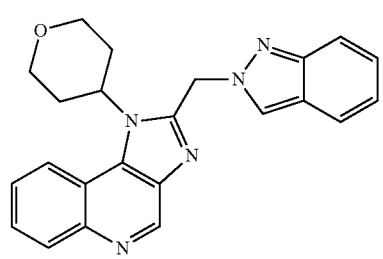 [SMILES: c1ccc2nn(Cc3nc4cnc5ccccc5c4n3C3CCOCC3)cc2c1] | 2.43 minutes$^6$; 384 |
| 46 | Method A | 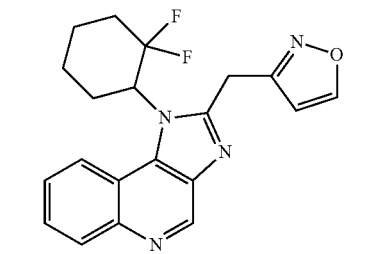 [SMILES: FC1(F)CCCCC1n1c(Cc2ccon2)nc2cnc3ccccc3c21] | 2.23 minutes$^{12}$; 369 |

TABLE 1-continued

| Example Number | Method of Preparation; Non-commerical starting materials | Structure | ¹H NMR (400 MHz, DMSO-d₆) δ (ppm); Mass spectrum, observed ion m/z [M + H]⁺ or HPLC retention time; Mass spectrum m/z [M + H]⁺ (unless otherwise indicated) |
|---|---|---|---|
| 47 | Method A | 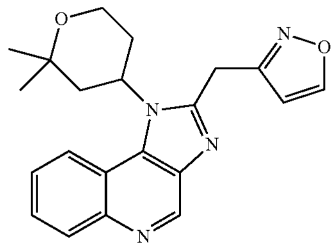 [SMILES: CC1(C)CC(n2c(Cc3ccon3)nc3cnc4ccccc4c32)CCO1] | 2.33 minutes[6]; 363 |
| 48 | Method A | 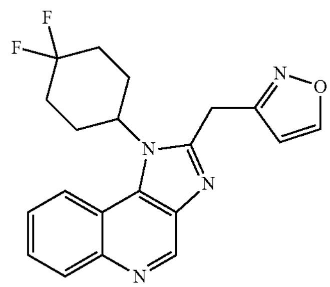 [SMILES: FC1(F)CCC(n2c(Cc3ccon3)nc3cnc4ccccc4c32)CC1] | 2.51 minutes[6]; 369 |
| 49 | Method A | (+/−) | 2.13 minutes[6]; 349 |
| 50 | Method A | 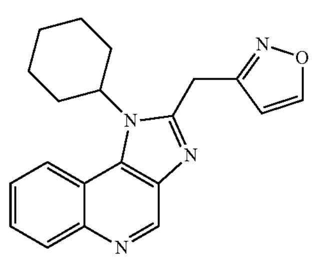 [SMILES: c1ccc2c(c1)ncc1nc(Cc3ccon3)n(C3CCCCC3)c12] | 2.28 minutes[12]; 333 |
| 51 | Example 5[14]; P1, C20 | 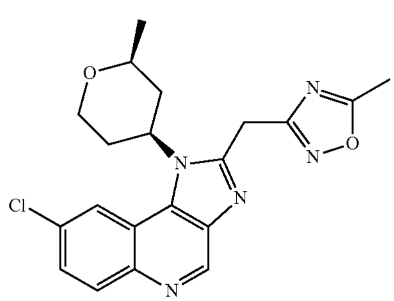 [SMILES: Cc1nc(Cc2nc3cnc4ccc(Cl)cc4c3n2[C@H]2CCO[C@@H](C)C2)no1] | 9.20 (s, 1H), 8.55-8.79 (m, 1H), 8.21 (d, J = 9.0 Hz, 1H), 7.77 (dd, J = 8.8, 1.8 Hz, 1H), 5.13-5.34 (m, 1H), 4.77 (br s, 2H), 4.11-4.26 (m, 1H), 3.57-3.80 (m, 2H), 3.39-3.50 (m, 1H), 2.60 (s, 3H), 1.91-2.40 (m, 3H), 1.24 (d, J = 6.0 Hz, 3H); 398.0 |

TABLE 1-continued

| Example Number | Method of Preparation; Non-commerical starting materials | Structure | $^1$H NMR (400 MHz, DMSO-$d_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 52 | Example 2; C15 | 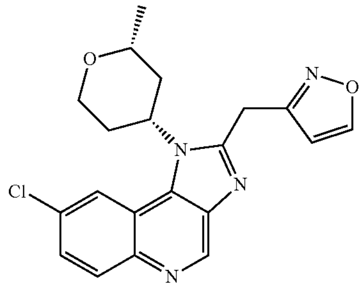 [SMILES: C[C@@H]1C[C@H](n2c(Cc3ccon3)nc3cnc4ccc(Cl)cc4c32)CCO1] | 9.20-9.22 (m, 1H), 8.93 (d, J = 1.5 Hz, 1H), 8.55-8.77 (m, 1H), 8.21 (d, J = 9.0 Hz, 1H), 7.77 (dd, J = 9.0, 2.0 Hz, 1H), 6.64 (d, J = 1.5 Hz, 1H), 5.07-5.29 (m, 1H), 4.69-4.76 (m, 1H), 4.10-4.25 (m, 1H), 3.54-3.78 (m, 1H), 2.40-2.65 (br m, 1H, assumed; partially obscured by solvent peak), 2.11-2.29 (m, 1H), 1.97-2.11 (m, 1H), 1.80-1.96 (m, 1H), 1.23 (d, J = 6.0 Hz, 1H); 383.0 |
| 53 | Example 2; C15 | 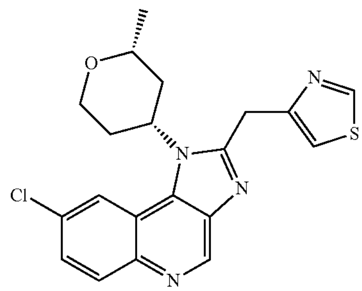 [SMILES: C[C@@H]1C[C@H](n2c(Cc3cscn3)nc3cnc4ccc(Cl)cc4c32)CCO1] | 9.16-9.28 (m, 1H), 9.08 (d, J = 1.0 Hz, 1H), 8.52-8.75 (m, 1H), 8.20 (d, J = 9.0 Hz, 1H), 7.75 (dd, J = 8.5, 1.5 Hz, 1H), 7.51-7.70 (m, 1H), 5.18-5.45 (m, 1H), 4.66-4.84 (m, 2H), 4.04-4.24 (m, 1H), 3.50-3.76 (m, 2H), 3.20-3.49 (br m, 1H, assumed; partially obscured by solvent peak), 2.01-2.29 (m, 1H), 1.80-1.95 (m, 1H), 1.53-1.79 (m, 1H), 1.21 (d, J = 6.0 Hz, 3H); 398.9 |
| 54 | Example 1$^{1,15}$; P1 | 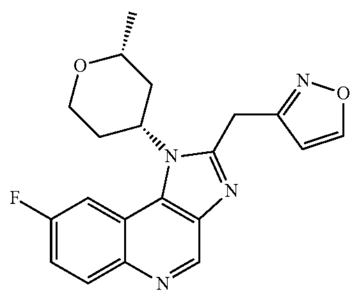 [SMILES: C[C@@H]1C[C@H](n2c(Cc3ccon3)nc3cnc4ccc(F)cc4c32)CCO1] | 9.14-9.21 (m, 1H), 8.92 (s, 1H), 8.27 (d, J = 6.0 Hz, 1H), 8.25 (d, J = 6.0 Hz, 1H), 7.66 (td, J = 8.0, 2.5 Hz, 1H), 6.63 (s, 1H), 5.03-5.30 (m, 1H), 4.72 (br s, 2H), 4.06-4.28 (m, 1H), 3.49-3.88 (m, 2H), 2.11-2.29 (m, 1H), 1.96-2.09 (m, 1H), 1.75-1.94 (m, 1H), 1.22 (d, J = 6.0 Hz, 4H); 367.0 |
| 55 | Example 1$^{16}$; P1 | 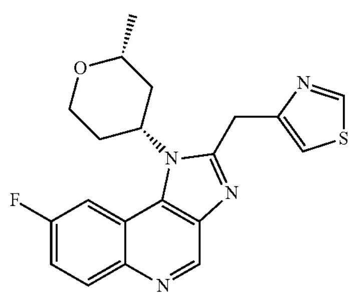 [SMILES: C[C@@H]1C[C@H](n2c(Cc3cscn3)nc3cnc4ccc(F)cc4c32)CCO1] | 9.14-9.19 (m, 1H), 9.07 (d, J = 2.0 Hz, 1H), 8.27 (d, J = 6.0 Hz, 1H), 8.24 (d, J = 6.5 Hz, 1H), 7.64 (td, J = 8.5, 2.0 Hz, 2H), 5.17-5.38 (m, 1H), 4.72-4.78 (m, 2H), 4.05-4.24 (m, 1H), 3.49-3.83 (m, 3H), 1.99-2.26 (m, 1H), 1.76-1.92 (m, 1H), 1.57-1.76 (m, 1H), 1.19 (d, J = 6.0 Hz, 3H); 383.0 |
| 56 | Example 1; P1 | 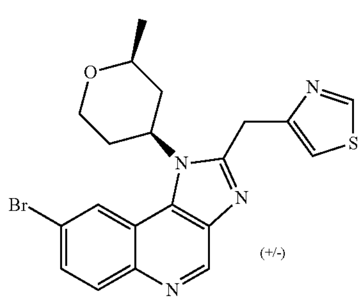 [SMILES: C[C@H]1C[C@@H](n2c(Cc3cscn3)nc3cnc4ccc(Br)cc4c32)CCO1] | 9.22 (s, 1H), 9.08 (d, J = 1.5 Hz, 1H), 8.73-8.87 (m, 1H), 8.13 (d, J = 9.0 Hz, 1H), 7.85 (dd, J = 8.5, 2.0 Hz, 1H), 7.61-7.72 (m, 1H), 5.20-5.38 (m, 1H), 4.76 (s, 2H), 4.09-4.21 (m, 1H), 3.62-3.75 (m, 1H), 3.51-3.62 (m, 1H), 2.27-2.46 (m, 1H), 2.07-2.25 (m, 1H), 1.78-1.97 (m, 1H), 1.60-1.78 (m, 1H), 1.21 (d, J = 6.0 Hz, 3H); 443.0 |

TABLE 1-continued

| Example Number | Method of Preparation; Non-commerical starting materials | Structure | $^1$H NMR (400 MHz, DMSO-d$_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 57 | Example 3$^{17}$; Example 56 | 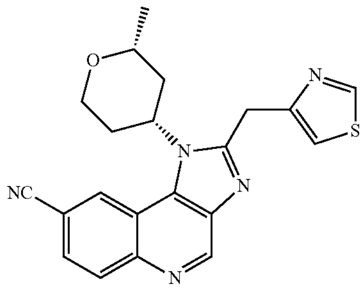 [SMILES: C[C@@H]1C[C@H](n2c(Cc3cscn3)nc3cnc4ccc(C#N)cc4c32)CCO1] | characteristic peaks: δ 9.28-9.40 (m, 1H), 9.07 (d, J = 2.0 Hz, 1H), 8.94-9.02 (m, 1H), 8.33 (d, J = 8.5 Hz, 1H), 8.04 (dd, J = 8.5, 1.5 Hz, 1H), 7.58-7.75 (m, 1H), 5.25-5.49 (m, 1H), 4.70-4.86 (m, 2H), 4.07-4.22 (m, 1H), 3.59-3.79 (m, 2H), 2.00-2.23 (m, 1H), 1.79-2.00 (m, 1H), 1.60-1.79 (m, 1H), 1.21 (d, J = 6.0 Hz, 3H); 390.0 |
| 58 | Example 1; P1, C6 | (+/-) | characteristic peaks: δ 9.19-9.25 (m, 1H), 8.75-8.91 (m, 1H), 8.13 (d, J = 9.0 Hz, 1H), 7.87 (dd, J = 8.5, 1.5 Hz, 1H), 6.22-6.29 (m, 1H), 5.09-5.29 (m, 1H), 4.57-4.68 (m, 2H), 4.12-4.23 (m, 1H), 3.47-3.78 (m, 4H), 2.37-2.44 (m, 3H), 2.12-2.28 (m, 1H), 1.98-2.10 (m, 1H), 1.78-1.97 (m, 1H), 1.24 (d, J = 6.0 Hz, 1H); 443.0 |
| 59 | Example 1$^{18}$ | 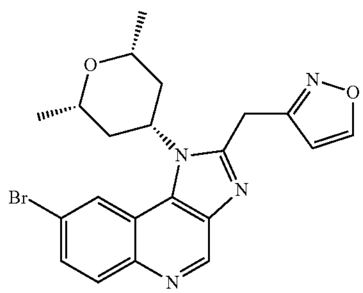 [SMILES: C[C@@H]1C[C@H](n2c(Cc3ccon3)nc3cnc4ccc(Br)cc4c32)C[C@H](C)O1] | 9.19-9.26 (m, 1H), 8.90-8.95 (m, 1H), 8.79-8.90 (m, 1H), 8.13 (d, J = 8.5 Hz, 1H), 7.87 (dd, J = 9.0, 2.0 Hz, 1H), 6.58-6.69 (m, 1H), 5.09-5.33 (m, 1H), 4.65-4.78 (m, 2H), 3.66-3.82 (m, 2H), 2.06-2.23 (m, 2H), 1.91-2.06 (m, 2H), 1.24 (d, J = 6.0 Hz, 6H); 441.0 |
| 60 | Example 1$^{18}$ | 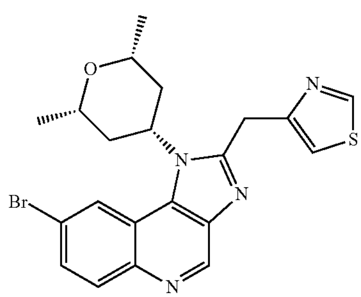 [SMILES: C[C@@H]1C[C@H](n2c(Cc3cscn3)nc3cnc4ccc(Br)cc4c32)C[C@H](C)O1] | 9.19-9.26 (m, 1H), 9.07 (d, J = 1.5 Hz, 1H), 8.77-8.88 (m, 1H), 8.13 (d, J = 8.5 Hz, 1H), 7.85 (dd, J = 9.0, 1.0 Hz, 1H), 7.61-7.71 (m, 1H), 5.23-5.43 (m, 1H), 4.67-4.80 (m, 2H), 3.62-3.80 (m, 2H), 1.97-2.21 (m, 2H), 1.73-1.91 (m, 2H), 1.21 (d, J = 5.5 Hz, 6H); 459.0 |
| 61 | Example 3; Example 60 | 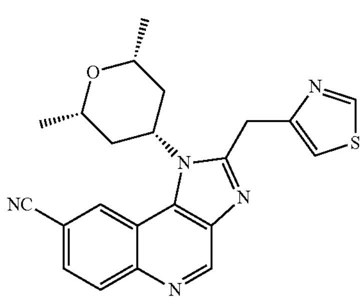 [SMILES: C[C@@H]1C[C@H](n2c(Cc3cscn3)nc3cnc4ccc(C#N)cc4c32)C[C@H](C)O1] | 9.31-9.39 (m, 1H), 9.08 (d, J = 1.5 Hz, 1H), 8.96-9.04 (m, 1H), 8.34 (d, J = 8.5 Hz, 1H), 8.05 (dd, J = 8.5, 1.5 Hz, 1H), 7.61-7.74 (m, 1H), 5.30-5.50 (m, 1H), 4.67-4.85 (m, 2H), 3.65-3.87 (m, 2H), 1.96-2.19 (m, 2H), 1.75-1.96 (m, 2H), 1.22 (d, J = 5.0 Hz, 6H); 404.1 |

TABLE 1-continued

| Example Number | Method of Preparation; Non-commerical starting materials | Structure | $^1$H NMR (400 MHz, DMSO-d$_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 62 | Example 1[19]; C11 | 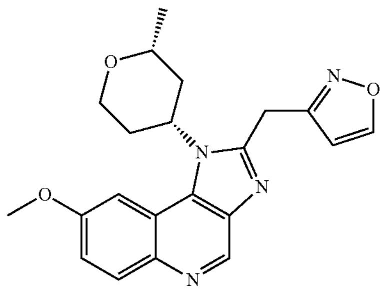 [SMILES: COc1ccc2ncc3nc(Cc4ccon4)n([C@@H]4CCO[C@H](C)C4)c3c2c1] | 9.02 (s, 1H), 8.92 (d, J = 1.5 Hz, 1H), 8.09 (d, J = 9.0 Hz, 1H), 7.84-7.97 (m, 1H), 7.36 (dd, J = 9.0, 2.5 Hz, 1H), 6.63 (d, J = 1.0 Hz, 1H), 5.02-5.24 (m, 1H), 4.71 (s, 2H), 4.11-4.26 (m, 1H), 3.98 (s, 3H), 3.53-3.74 (m, 2H), 3.38-3.49 (m, 1H), 2.21-2.41 (m, 1H), 1.92-2.09 (m, 1H), 1.74-1.92 (m, 1H), 1.22 (d, J = 6.5 Hz, 3H); 379.0 |
| 63 | Example 7 | ·HCOOH | $^1$H NMR (400 MHz, CDCl$_3$) δ 9.30 (s, 1H), 8.51-8.81 (m, 1H), 8.40 (d, J = 1.0 Hz, 1H), 8.25 (d, J = 9.0 Hz, 1H), 7.65 (dd, J = 8.8, 2.3 Hz, 1H), 6.39 (br s, 1H), 5.13 (br s, 1H), 4.62 (s, 2H), 4.30 (dd, J = 11.8, 5.3 Hz, 2H), 3.65 (t, J = 11.3 Hz, 2H), 2.75 (br s, 2H), 1.69 (br s, 2H); 369.0 |
| 64 | Example 7[20]; P1, C31 | 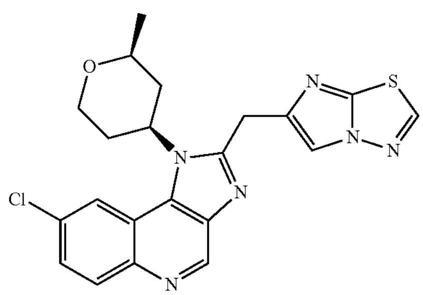 [SMILES: C[C@H]1C[C@@H](n2c(Cc3cn4ncsc4n3)nc3cnc4ccc(Cl)cc4c32)CCO1] | $^1$H NMR (400 MHz, CD$_3$OD) δ 9.14 (br s, 1H), 8.97 (s, 1H), 8.72-8.82 (br m, 1H), 8.19 (d, J = 8.9 Hz, 1H), 7.99-8.04 (m, 1H), 7.74 (dd, J = 9.0, 1.9 Hz, 1H), 5.31-5.45 (br m, 1H), 4.65 (s, 2H), 4.23 (br dd, J = 12, 5 Hz, 1H), 3.67-3.81 (br m, 2H), 2.59-2.73 (br m, 1H), 2.28-2.42 (br m, 1H), 1.87-2.00 (br m, 1H), 1.75-1.87 (br m, 1H), 1.26-1.32 (m, 3H); 438.9 |
| 65 | Example 7[21]; P1 | 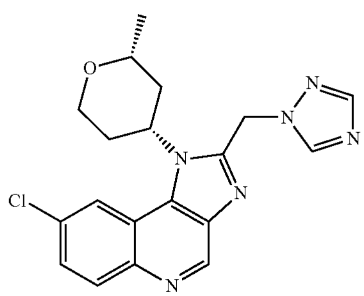 [SMILES: C[C@@H]1C[C@H](n2c(Cn3cncn3)nc3cnc4ccc(Cl)cc4c32)CCO1] | $^1$H NMR (400 MHz, CD$_3$OD) δ 9.16 (s, 1H), 8.76 (s, 2H), 8.19 (d, J = 9.0 Hz, 1H), 8.08 (s, 1H), 7.76 (dd, J = 8.8, 1.8 Hz, 1H), 6.10 (s, 2H), 5.34-5.61 (m, 1H), 4.30 (dd, J = 11.5, 4.5 Hz, 1H), 3.68-3.96 (m, 2H), 2.55-2.88 (m, 1H), 2.25-2.51 (m, 1H), 1.74-2.21 (m, 2H), 1.36 (d, J = 6.0 Hz, 3H); 382.9 |
| 66 | Example 1[22], 1 | (+/−) | $^1$H NMR (400 MHz, CDCl$_3$ with D$_2$O) δ 9.29 (s, 1H), 8.81 (br s, 1H), 8.39 (s, 1H), 8.15 (d, J = 9.0 Hz, 1H), 7.76 (dd, J = 9.0, 1.5 Hz, 1H), 6.38 (br s, 1H), 5.13 (br s, 1H), 4.74 (br s, 2H), 4.31 (dd, J = 12.0, 5.0 Hz, 1H), 3.59-3.88 (m, 1H), 3.52 (br s, 1H), 2.68 (br s, 1H), 2.43 (br s, 1H), 1.73 (dt, J = 14.0, 7.0 Hz, 2H), 1.62 (dd, J = 13.6, 6.5 Hz, 2H), 1.00 (t, J = 7.5 Hz, 3H); 443.0 |

TABLE 1-continued

| Example Number | Method of Preparation; Non-commerical starting materials | Structure | $^1$H NMR (400 MHz, DMSO-d$_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 67 | Example 3[23]; Example 66 | 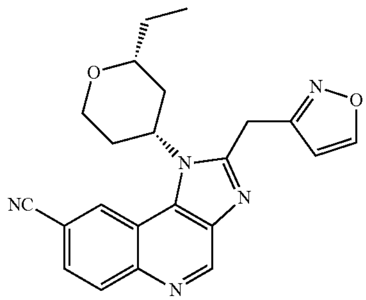 [SMILES: CC[C@@H]1C[C@H](n2c(Cc3ccon3)nc3cnc4ccc(C#N)cc4c32)CCO1] | 9.32-9.39 (m, 1H), 8.97-9.05 (m, 1H), 8.90-8.95 (m, 1H), 8.30-8.40 (m, 1H), 8.02-8.12 (m, 1H), 6.59-6.68 (m, 1H), 5.11-5.40 (m, 1H), 4.69-4.81 (m, 2H), 4.15-4.28 (m, 1H), 3.46-3.74 (m, 2H), 1.82-2.35 (m, 4H), 1.48-1.64 (m, 2H), 0.94 (d, J = 7.5 Hz, 3H); 388.0 |
| 68 | Example 7[24]; C27 | 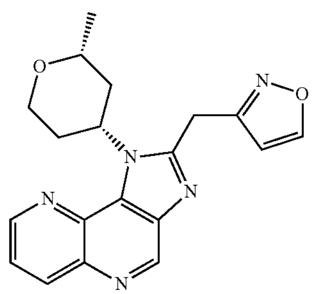 [SMILES: C[C@@H]1C[C@H](n2c(Cc3ccon3)nc3cnc4cccnc4c32)CCO1] | 9.27 (s, 1H), 9.05 (dd, J = 4.0, 1.5 Hz, 1H), 8.92 (d, J = 1.5 Hz, 1H), 8.55 (dd, J = 8.0, 1.5 Hz, 1H), 7.77 (dd, J = 8.5, 4.5 Hz, 1H), 6.63 (d, J = 1.5 Hz, 1H), 4.81-4.99 (m, 1H), 4.74 (s, 2H), 4.06 (dd, J = 11.0, 4.0 Hz, 1H), 3.50-3.69 (m, 2H), 3.41-3.48 (m, 1H), 2.91-3.13 (m, 1H), 1.44-1.87 (m, 2H), 1.17 (d, J = 6.0 Hz, 3H); 349.9 |
| 69 | Method B; C31 | 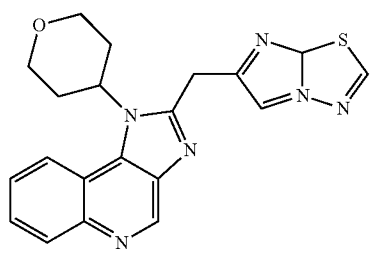 | 1.45 minutes[25]; 391.3 |
| 70 | Method B | 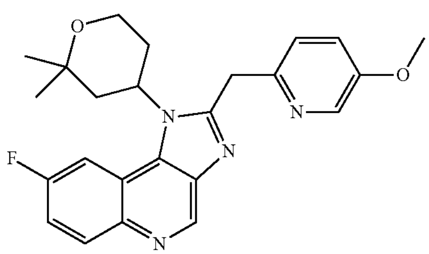 [SMILES: COc1ccc(Cc2nc3cnc4ccc(F)cc4c3n2C2CCOC(C)(C)C2)nc1] | 1.89 minutes[25]; 421.1 |
| 71 | Method B | 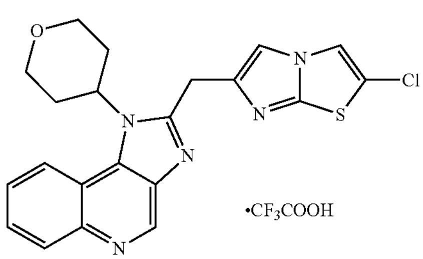 [SMILES: Clc1cn2cc(Cc3nc4cnc5ccccc5c4n3C3CCOCC3)nc2s1 ; "·CF3COOH"] | 1.73 minutes[25]; 424.2, 426.2 |

TABLE 1-continued

| Example Number | Method of Preparation; Non-commerical starting materials | Structure | $^1$H NMR (400 MHz, DMSO-d$_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 72 | Method B | 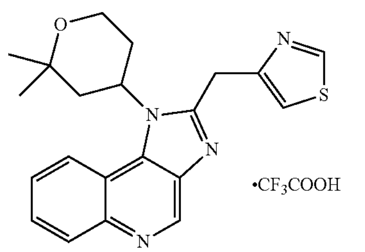 | 1.73 minutes[25]; 379.3 |
| 73 | Method B; C31 | 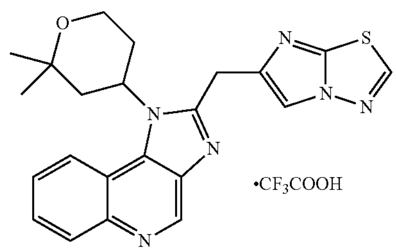 | 1.68 minutes[25]; 419.3 |
| 74 | Method B | 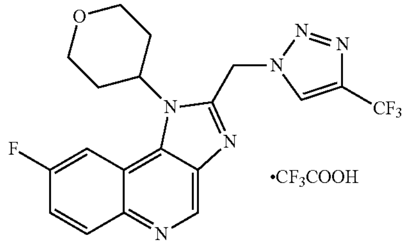 | 2.02 minutes[25]; 421.1 |
| 75 | Method B | 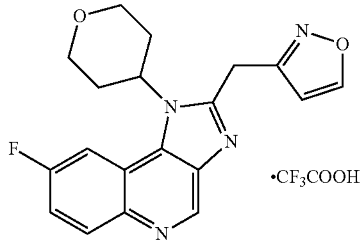 | 1.59 minutes[25]; 353.1 |
| 76 | Method B | 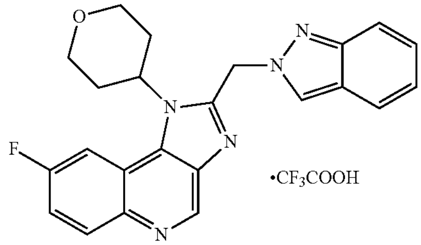 | 2.08 minutes[25]; 402.1 |

TABLE 1-continued

| Example Number | Method of Preparation; Non-commerical starting materials | Structure | ¹H NMR (400 MHz, DMSO-d₆) δ (ppm); Mass spectrum, observed ion m/z [M + H]⁺ or HPLC retention time; Mass spectrum m/z [M + H]⁺ (unless otherwise indicated) |
|---|---|---|---|
| 77 | Method B | 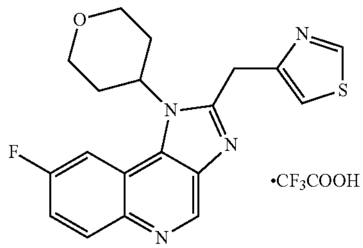 | 1.59 minutes[25]; 369.1 |
| 78 | Method B | 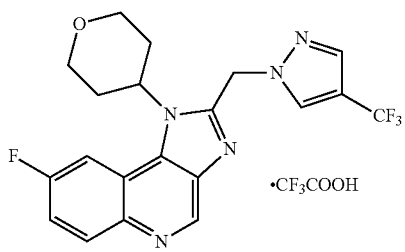 | 2.16 minutes[25]; 420.1 |
| 79 | Method B | 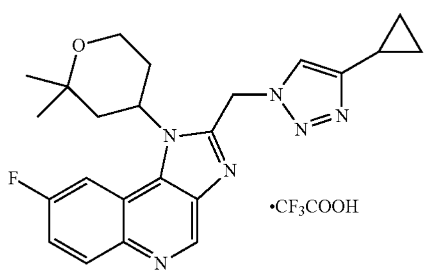 | 2.04 minutes[25]; 421.1 |
| 80 | Method B | 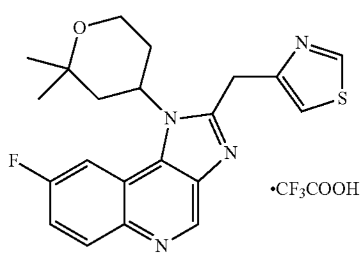 | 1.90 minutes[25]; 397.1 |
| 81 | Method B | 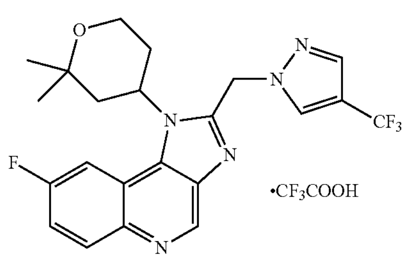 | 2.45 minutes[25]; 448.1 |

TABLE 1-continued

| Example Number | Method of Preparation; Non-commerical starting materials | Structure | ¹H NMR (400 MHz, DMSO-d₆) δ (ppm); Mass spectrum, observed ion m/z [M + H]⁺ or HPLC retention time; Mass spectrum m/z [M + H]⁺ (unless otherwise indicated) |
|---|---|---|---|
| 82 | Method B; C31 | 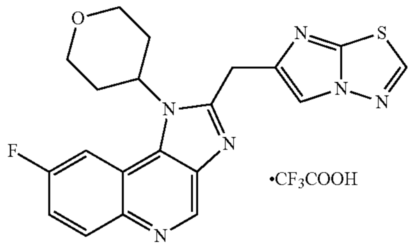 | 1.57 minutes[25]; 409.1 |
| 83 | Method B | 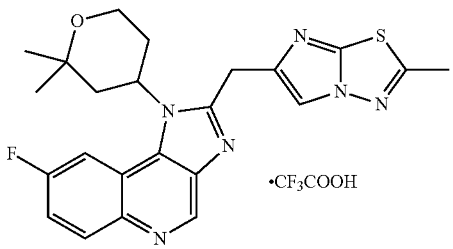 | 1.98 minutes[25]; 451.1 |
| 84 | Method B | 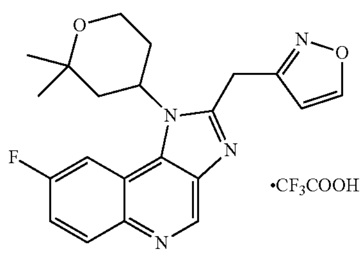 | 1.93 minutes[25]; 381.1 |
| 85 | C34[26] | 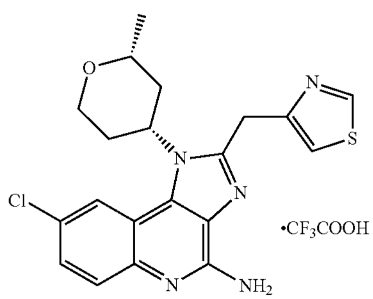 | 2.23 minutes[25]; 414.2, 416.2 |
| 86 | Example 7; P1, C31 | 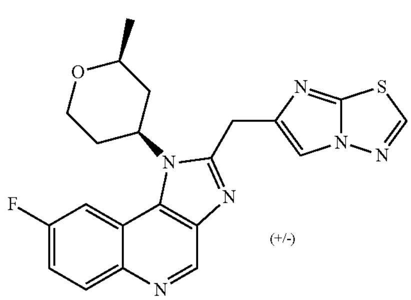 | 9.18 (s, 1H), 9.15 (br s, 1H), 8.24 (dd, J = 9.3, 6.2 Hz, 1H), 8.21-8.30 (br m, 1H), 8.15-8.21 (br m, 1H), 7.59-7.66 (m, 1H), 5.29-5.42 (m, 1H), 4.58 (s, 2H), 4.08-4.19 (br m, 1H), 3.54-3.77 (br m, 2H), 2.37-2.5 (br m, 1H, assumed; partially obscured by solvent peak), 2.05-2.23 (br m, 1H), 1.83-1.97 (br m, 1H), 1.69-1.83 (br m, 1H), 1.17 (d, J = 6.2 Hz, 3H); 423.0 |

TABLE 1-continued

| Example Number | Method of Preparation; Non-commerical starting materials | Structure | $^1$H NMR (400 MHz, DMSO-d$_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 87 | Example 1[27]; C11, C20 | 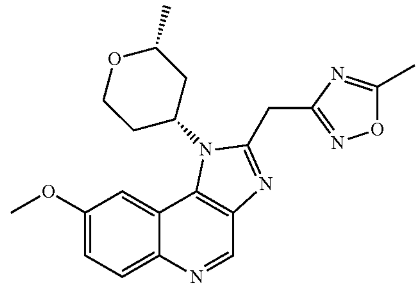 | 9.00 (s, 1H), 8.08 (d, J = 9.0 Hz, 1H), 7.89-7.96 (br m, 1H), 7.36 (dd, J = 9.2, 2.4 Hz, 1H), 5.10-5.24 (br m, 1H), 4.74 (br s, 2H), 4.14-4.24 (br m, 1H), 3.98 (s, 3H), 3.57-3.73 (br m, 2H), 2.61-2.76 (br m, 1H), 2.59 (s, 3H), 2.27-2.41 (br m, 1H), 2.04-2.16 (br m, 1H), 1.90-2.02 (br m, 1H), 1.23 (d, J = 6.2 Hz, 3H); 394.0 |
| 88 | Example 1[28]; C11 | 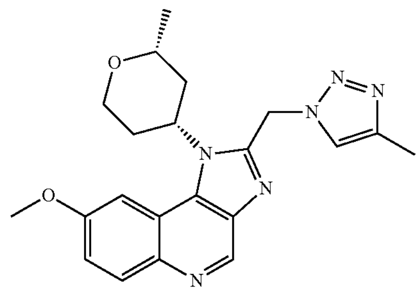 | characteristic peaks: δ 9.04 (s, 1H), 8.09 (d, J = 9.2 Hz, 1H), 7.97 (s, 1H), 7.86-7.91 (br m, 1H), 7.38 (dd, J = 9.2, 2.5 Hz, 1H), 6.20 (br s, 2H), 5.17-5.33 (br m, 1H), 4.12-4.23 (br m, 1H), 3.97 (s, 3H), 3.55-3.73 (br m, 2H), 2.5-2.70 (br m, 1H, assumed; partially obscured by solvent peak), 2.25 (s, 3H), 1.82-1.94 (br m, 1H), 1.67-1.80 (br m, 1H), 1.21 (d, J = 6.2 Hz, 3H); 393.1 |
| 89 | Example 1[29]; C11 | 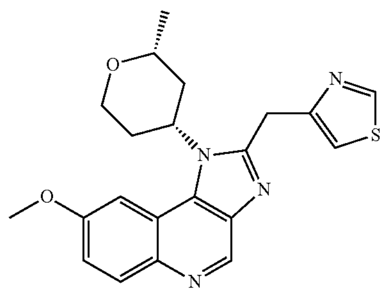 [SMILES: COc1ccc2ncc3nc(Cc4cscn4)n([C@@H]4CCO[C@H](C)C4)c3c2c1] | 9.06 (d, J = 1.6 Hz, 1H), 9.01 (s, 1H), 8.07 (d, J = 9.2 Hz, 1H), 7.83-7.90 (br m, 1H), 7.61-7.68 (br m, 1H), 7.33 (br d, J = 9.3 Hz, 1H), 5.16-5.32 (br m, 1H), 4.72 (br s, 2H), 4.08-4.20 (br m, 1H), 3.95 (s, 3H), 3.50-3.67 (br m, 2H), 2.5-2.69 (br m, 1H, assumed; partially obscured by solvent peak), 2.20-2.33 (br m, 1H), 1.74-1.85 (br m, 1H), 1.61-1.72 (br m, 1H), 1.18 (d, J = 6.0 Hz, 3H); 395.0 |
| 90 | Example 1[30]; C11, C31 | 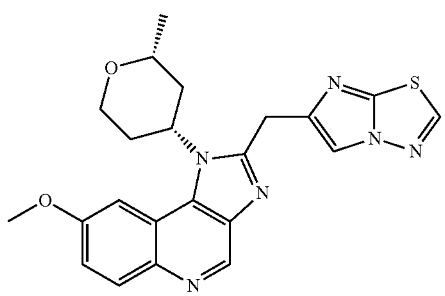 [SMILES: COc1ccc2ncc3nc(Cc4cn5ncsc5n4)n([C@@H]4CCO[C@H](C)C4)c3c2c1] | 9.18 (s, 1H), 9.00 (s, 1H), 8.17-8.21 (br m, 1H), 8.06 (d, J = 9.0 Hz, 1H), 7.85-7.91 (br m, 1H), 7.33 (dd, J = 9.2, 2.1 Hz, 1H), 5.26-5.41 (br m, 1H), 4.56 (br s, 2H), 4.09-4.20 (br m, 1H), 3.95 (s, 3H), 3.54-3.71 (br m, 2H), 2.57-2.70 (br m, 1H), 2.21-2.34 (br m, 1H), 1.82-1.95 (br m, 1H), 1.70-1.82 (br m, 1H), 1.17 (d, J = 6.3 Hz, 3H); 435.0 |
| 91 | Example 6[31,32] | 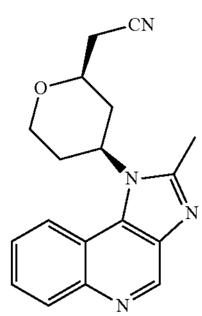 | characteristic peaks: δ 9.12 (s, 1H), 8.49-8.58 (br m, 1H), 8.14-8.21 (m, 1H), 7.65-7.74 (m, 2H), 4.96-5.64 (br m, 1H), 4.12-4.31 (br m, 1H), 3.92-4.10 (br m, 1H), 3.73-3.91 (br m, 1H), 2.95 (br dd, half of ABX pattern, J = 17, 3.5 Hz, 1H), 2.83 (dd, half of ABX pattern, J = 17.0, 6.3 Hz, 1H), 2.77 (s, 3H), 2.09-2.24 (br m, 1H), 1.92-2.09 (br m, 1H); 306.9 |

TABLE 1-continued

| Example Number | Method of Preparation; Non-commerical starting materials | Structure | $^1$H NMR (400 MHz, DMSO-d$_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 92 | Example 2[33]; C15 | 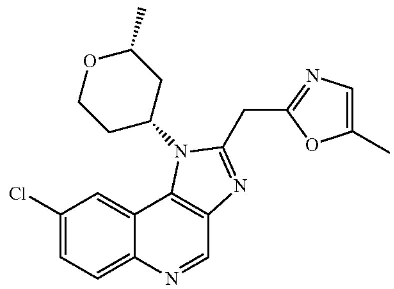 [SMILES: Cc1cnc(Cc2nc3cnc4ccc(Cl)cc4c3n2[C@@H]2CCO[C@H](C)C2)o1] | characteristic peaks: δ 9.30 (s, 1H), 8.63-8.73 (br m, 1H), 8.27 (br d, J = 9 Hz, 1H), 7.65 (br d, J = 9 Hz, 1H), 6.71 (br s, 1H), 5.08-5.24 (br m, 1H), 4.63 (s, 2H), 4.31 (br dd, J = 12, 5 Hz, 1H), 3.63-3.78 (m, 2H), 2.64-2.82 (br m, 1H), 2.36-2.54 (br m, 1H), 2.29 (s, 3H), 1.78-1.94 (br m, 1H), 1.36 (d, J = 6.2 Hz, 3H); 397.0 |
| 117 | Example 106[34]; Example 9 | 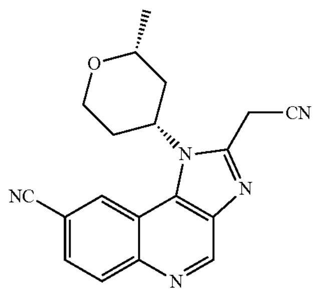 [SMILES: C[C@@H]1C[C@H](n2c(CC#N)nc3cnc4ccc(C#N)cc4c32)CCO1] | 1.93 minutes[25]; 332.3 |
| 118 | Example 93[35]; C57 | cis, ENT-1 | $^1$H NMR (400 MHz, CDCl$_3$) δ 9.40 (s, 1H), 8.88-8.92 (m, 1H), 8.37 (d, J = 8.6 Hz, 1H), 7.87 (dd, J = 8.7, 1.7 Hz, 1H), 6.06 (s, 1H), [5.51-5.56 (m) and 5.37-5.42 (m), J$_{HF}$ = 53.5 Hz, total 1H], 5.28-5.38 (m, 1H), 4.64 (AB quartet, J$_{AB}$ = 17.0 Hz, Δν$_{AB}$ = 7.0 Hz, 2H), 2.49-2.87 (m, 4H), 2.29 (s, 3H), 2.18-2.28 (m, 1H), 1.93-2.16 (m, 1H); 376.3 |
| 119 | Example 97[36]; C64 | 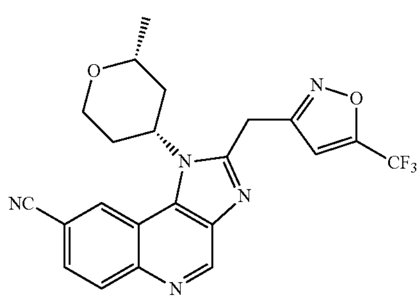 [SMILES: C[C@@H]1C[C@H](n2c(Cc3cc(C(F)(F)F)on3)nc3cnc4ccc(C#N)cc4c32)CCO1] | $^1$H NMR (400 MHz, CDCl$_3$) δ 9.40 (s, 1H), 8.5-9.1 (v br m, 1H), 8.39 (d, J = 8.6 Hz, 1H), 7.89 (dd, J = 8.6, 1.6 Hz, 1H), 6.81-6.95 (br m, 1H), 5.08-5.32 (br m, 1H), 4.65 (s, 2H), 4.36 (br dd, J = 12, 5 Hz, 1H), 3.67-3.84 (m, 2H), 2.50-2.77 (br m, 1H), 2.20-2.46 (br m, 1H), 1.69-2.20 (br m, 2H), 1.38 (d, J = 6.1 Hz, 3H); 442.3 |
| 120 | Example 96; C64 | ·HCOOH | 2.20 minutes[13]; 374 |

TABLE 1-continued

| Example Number | Method of Preparation; Non-commerical starting materials | Structure | ¹H NMR (400 MHz, DMSO-d₆) δ (ppm); Mass spectrum, observed ion m/z [M + H]⁺ or HPLC retention time; Mass spectrum m/z [M + H]⁺ (unless otherwise indicated) |
|---|---|---|---|
| 121 | Example 96; C64 | 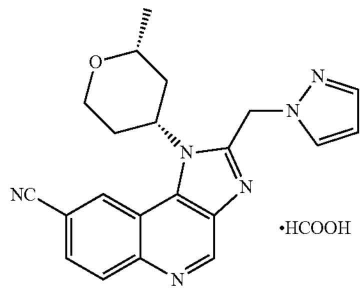 [SMILES: C[C@@H]1C[C@H](n2c(Cn3cccn3)nc3cnc4ccc(C#N)cc4c32)CCO1 ; "·HCOOH"] | 2.40 minutes[13]; 373 |
| 122 | Example 96[37]; C64 | 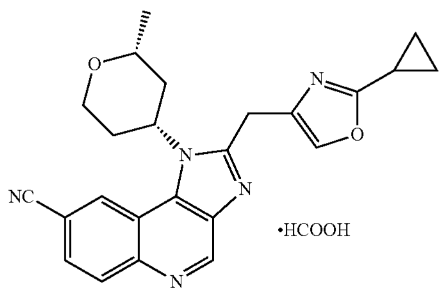 [SMILES: C[C@@H]1C[C@H](n2c(Cc3coc(C4CC4)n3)nc3cnc4ccc(C#N)cc4c32)CCO1 ; "·HCOOH"] | 2.66 minutes[6]; 414 |
| 123 | Example 97; C64, C20 | 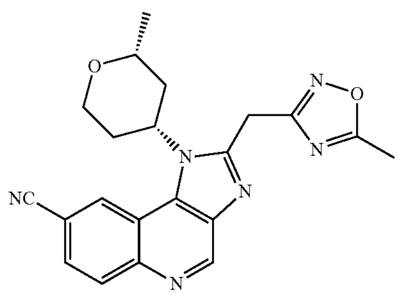 [SMILES: Cc1nc(Cc2nc3cnc4ccc(C#N)cc4c3n2[C@@H]2CCO[C@H](C)C2)no1] | ¹H NMR (400 MHz, CDCl₃) δ 9.41 (s, 1H), 8.5-9.2 (v br m, 1H), 8.38 (d, J = 8.8 Hz, 1H), 7.87 (dd, J = 8.6, 1.6 Hz, 1H), 4.97-5.35 (br m, 1H), 4.63 (s, 2H), 4.35 (br dd, J = 12, 5 Hz, 1H), 3.64-3.83 (m, 2H), 2.61 (s, 3H), 2.52-2.79 (br m, 1H), 1.80-2.50 (br m, 3H), 1.38 (d, J = 6.3 Hz, 3H); 389.3 |
| 124 | Example 96; C64 | 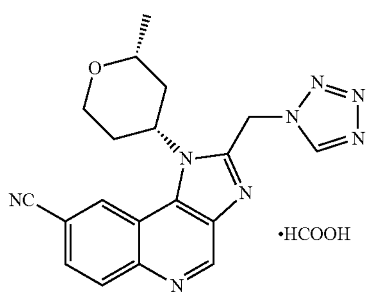 [SMILES: C[C@@H]1C[C@H](n2c(Cn3cnnn3)nc3cnc4ccc(C#N)cc4c32)CCO1 ; "·HCOOH"] | 2.26 minutes[13]; 375 |
| 125 | Example 99; C64 | 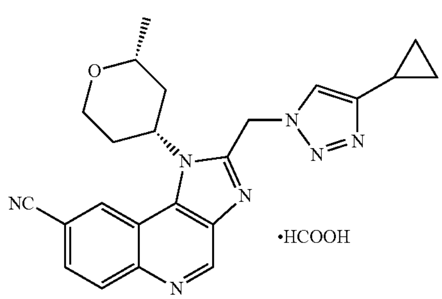 [SMILES: C[C@@H]1C[C@H](n2c(Cn3cc(C4CC4)nn3)nc3cnc4ccc(C#N)cc4c32)CCO1 ; "·HCOOH"] | 2.64 minutes[6]; 414 |

TABLE 1-continued
| Example Number | Method of Preparation; Non-commerical starting materials | Structure | $^1$H NMR (400 MHz, DMSO-d$_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 126 | Example 99; C64 | 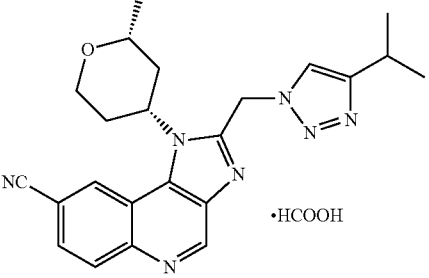 | 2.72 minutes[6]; 416 |
| 127 | Example 99[38]; C15 | 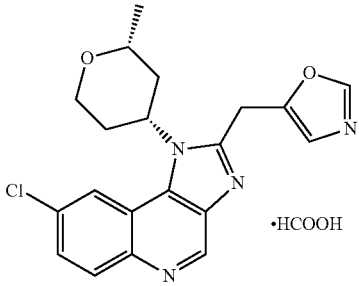 [SMILES: C[C@@H]1C[C@H](n2c(Cc3cnco3)nc3cnc4ccc(Cl)cc4c32)CCO1 ; "·HCOOH"] | 2.39 minutes[6]; 383 |
| 128 | Example 99; C15 | 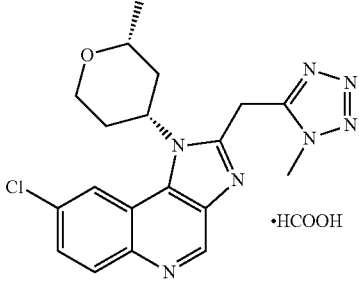 [SMILES: C[C@@H]1C[C@H](n2c(Cc3nnnn3C)nc3cnc4ccc(Cl)cc4c32)CCO1 ; "·HCOOH"] | 2.39 minutes[6]; 398 |
| 129 | Example 99; C15 | 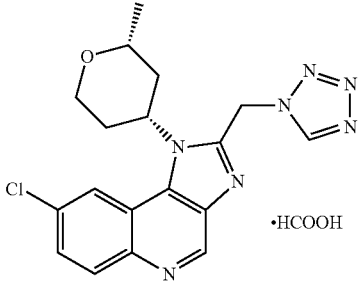 [SMILES: C[C@@H]1C[C@H](n2c(Cn3cnnn3)nc3cnc4ccc(Cl)cc4c32)CCO1 ; "·HCOOH"] | 2.44 minutes[6]; 384 |
| 130 | Example 99; C15 | 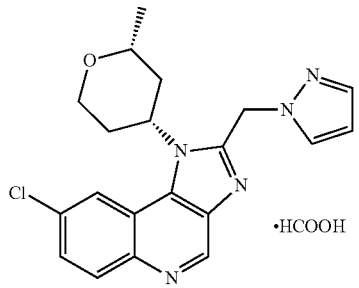 [SMILES: C[C@@H]1C[C@H](n2c(Cn3cccn3)nc3cnc4ccc(Cl)cc4c32)CCO1 ; "·HCOOH"] | 2.52 minutes[6]; 382 |

TABLE 1-continued

| Example Number | Method of Preparation; Non-commerical starting materials | Structure | $^1$H NMR (400 MHz, DMSO-d$_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 131 | Example 99; C15 | 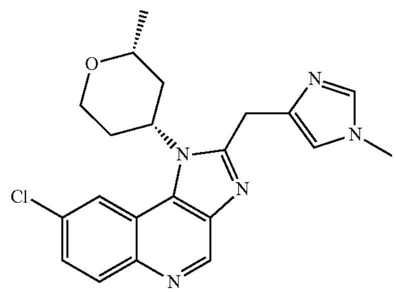 [SMILES: C[C@@H]1C[C@H](n2c(Cc3cn(C)cn3)nc3cnc4ccc(Cl)cc4c32)CCO1] | 2.15 minutes[6]; 396 |
| 132 | Example 97[39]; C57 | cis, ENT-1 | 2.54 minutes[40]; 406.0 |
| 133 | Example 105; C64 | 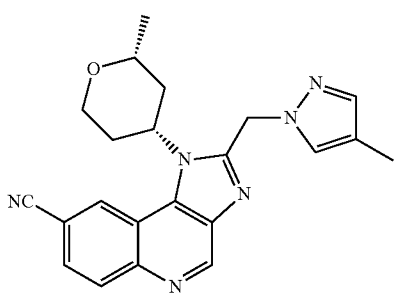 [SMILES: Cc1cnn(Cc2nc3cnc4ccc(C#N)cc4c3n2[C@@H]2CCO[C@H](C)C2)c1] | $^1$H NMR (400 MHz, CDCl$_3$) δ 9.43 (s, 1H), 8.89-9.08 (br m, 1H), 8.38 (d, J = 8.5 Hz, 1H), 7.88 (dd, J = 8.8, 1.5 Hz, 1H), 7.37 (s, 1H), 7.28 (s, 1H, assumed; largely obscured by solvent peak), 5.76 (s, 2H), 5.32-5.51 (br m, 1H), 4.28 (br dd, J = 12, 5 Hz, 1H), 3.63-3.78 (m, 2H), 2.46-2.64 (br m, 1H), 2.15-2.36 (br m, 1H), 2.03 (s, 3H), 1.41-1.73 (br m, 2H, assumed; partially obscured by water peak), 1.33 (d, J = 6.3 Hz, 3H); 387.0 |
| 134 | Example 109[41,42,43]; C13, C6 | cis, ENT-1 | $^1$H NMR (400 MHz, CDCl$_3$) δ 9.29 (s, 1H), 8.45-8.59 (br m, 1H), 8.23 (d, J = 9.0 Hz, 1H), 7.65 (dd, J = 8.9, 2.1 Hz, 1H), 6.00 (br s, 1H), 5.17-5.33 (br m, 1H), 4.52 (s, 2H), 4.39 (br dd, J = 12, 5 Hz, 1H), 3.86-3.95 (br m, 1H), 3.72-3.82 (m, 1H), 2.75 (dd, half of ABX pattern, J = 16.7, 6.1 Hz, 1H), 2.7-2.87 (br m, 1H), 2.66 (dd, half of ABX pattern, J = 16.8, 6.0 Hz, 1H), 2.46-2.60 (br m, 1H), 2.40 (s, 3H), 1.83-1.98 (br m, 1H), 1.69-1.83 (br m, 1H); 421.9 (chlorine isotope pattern observed) |

TABLE 1-continued

| Example Number | Method of Preparation; Non-commerical starting materials | Structure | $^1$H NMR (400 MHz, DMSO-$d_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 135 | Example 134[44]; C20 | 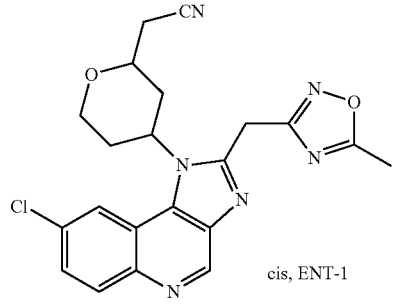 [SMILES: Cc1nc(Cc2nc3cnc4ccc(Cl)cc4c3n2C2CCOC(CC#N)C2)no1] cis, ENT-1 | $^1$H NMR (400 MHz, CDCl$_3$) δ 9.30 (s, 1H), 8.48-8.62 (br m, 1H), 8.24 (d, J = 9.0 Hz, 1H), 7.66 (dd, J = 9.0, 2.0 Hz, 1H), 5.02-5.26 (br m, 1H), 4.62 (AB quartet, upfield doublet is broadened, J$_{AB}$ = 16.7 Hz, Δν$_{AB}$ = 14 Hz, 2H), 4.38-4.49 (br m, 1H), 3.87-3.98 (br m, 1H), 3.70-3.85 (m, 1H), 2.60 (s, 3H), 2.50-2.97 (m, 4H), 2.12-2.29 (br m, 1H), 1.87-2.05 (br m, 1H); 422.9 (chlorine isotope pattern observed) |
| 136 | Example 109[45,46]; C13, C20 | 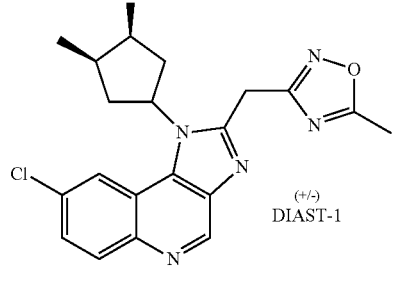 (+/−) DIAST-1 | $^1$H NMR (400 MHz, CD$_3$OD) δ 9.10 (s, 1H), [8.73-8.76 (m) and 8.68-8.72 (m), total 1H], 8.17 (d, J = 8.5 Hz, 1H), 7.73 (dd, J = 9.0, 2.0 Hz, 1H), 5.51-5.66 (m, 1H), [5.21-5.26 (m) and 5.07-5.12 (m), J$_{HF}$ = 55 Hz, total 1H], 4.68-4.75 (m, 2H), 2.59 (s, 3H), 2.24-3.08 (m, 5H), 1.30 (br d, J = 6 Hz, 3H); 400.0 (chlorine isotope pattern observed) |
| 137 | Example 4[47] | 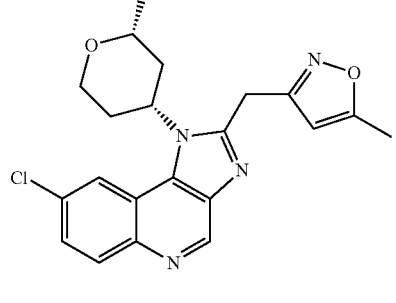 | $^1$H NMR (600 MHz, DMSO-$d_6$), characteristic peaks: δ 9.21 (s, 1H), 8.58-8.71 (br m, 1H), 8.20 (d, J = 8.9 Hz, 1H), 7.75 (dd, J = 8.9, 2.1 Hz, 1H), 6.26 (s, 1H), 5.08-5.30 (br m, 1H), 4.63 (s, 2H), 4.13-4.29 (br m, 1H), 2.40 (s, 3H), 2.18-2.35 (br m, 1H), 1.82-2.04 (br m, 2H); 412.8 (chlorine isotope pattern observed) |
| 138 | Example 4[48] | 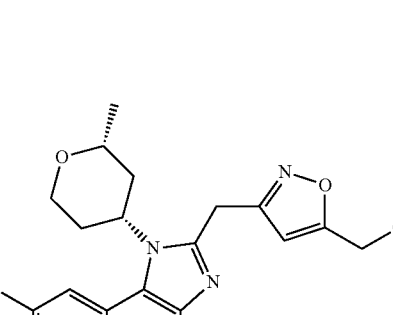 | $^1$H NMR (600 MHz, DMSO-$d_6$) δ 9.20 (s, 1H), 8.56-8.75 (br m, 1H), 8.20 (d, J = 8.9 Hz, 1H), 7.75 (dd, J = 8.9, 2.2 Hz, 1H), 6.39 (s, 1H), 5.54-5.76 (br m, 1H), 5.10-5.29 (br m, 1H), 4.66 (br s, 2H), 4.56 (s, 2H), 4.12-4.21 (br m, 1H), 3.57-3.76 (br m, 2H), 2.39-2.50 (br m, 1H, assumed; partially obscured by solvent peak), 2.11-2.28 (br m, 1H), 1.96-2.11 (br m, 1H), 1.80-1.96 (br m, 1H), 1.22 (d, J = 6.0 Hz, 3H); 412.8 (chlorine isotope pattern observed) |

TABLE 1-continued

| Example Number | Method of Preparation; Non-commerical starting materials | Structure | ¹H NMR (400 MHz, DMSO-d₆) δ (ppm); Mass spectrum, observed ion m/z [M + H]⁺ or HPLC retention time; Mass spectrum m/z [M + H]⁺ (unless otherwise indicated) |
|---|---|---|---|
| 139 | Example 138[49] | 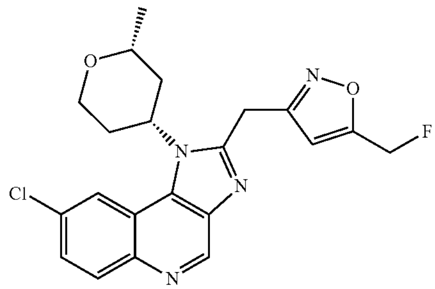 [SMILES: C[C@@H]1C[C@H](n2c(Cc3cc(CF)on3)nc3cnc4ccc(Cl)cc4c32)CCO1] | ¹H NMR (600 MHz, DMSO-d₆), characteristic peaks: δ 9.20 (s, 1H), 8.61-8.70 (br m, 1H), 8.20 (d, J = 9.0 Hz, 1H), 7.76 (dd, J = 8.8, 2.1 Hz, 1H), 6.78 (d, J = 3.5 Hz, 1H), 5.58 (d, $J_{HF}$ = 47.3 Hz, 2H), 5.13-5.25 (br m, 1H), 4.73 (br s, 2H), 4.13-4.22 (br m, 1H), 3.59-3.76 (br m, 2H), 2.14-2.26 (br m, 1H), 2.00-2.12 (br m, 1H), 1.89-2.00 (br, m, 1H), 1.23 (d, J = 5.9 Hz, 3H); 414.8 (chlorine isotope pattern observed) |
| 140 | P2[50,51,52] | 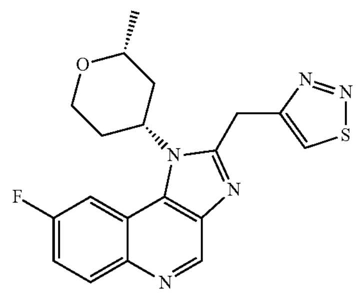 [SMILES: C[C@@H]1C[C@H](n2c(Cc3csnn3)nc3cnc4ccc(F)cc4c32)CCO1] | ¹H NMR (400 MHz, CDCl₃) δ 9.24 (s, 1H), 8.59 (br s, 1H), 8.28 (dd, J = 9.0, 6.0 Hz, 1H), 8.18-8.34 (br m, 1H), 7.42-7.50 (m, 1H), 5.28-5.40 (m, 1H), 5.06 (s, 2H), 4.30 (br dd, J = 12.0, 5.0 Hz, 1H), 3.66-3.81 (m, 2H), 2.60-2.83 (br m, 1H), 2.30-2.51 (br m, 1H), 1.54-1.88 (br m, 2H, assumed; partially obscured by water peak), 1.34 (d, J = 6.0 Hz, 3H); 384.0 |
| 141 | C101[53] | 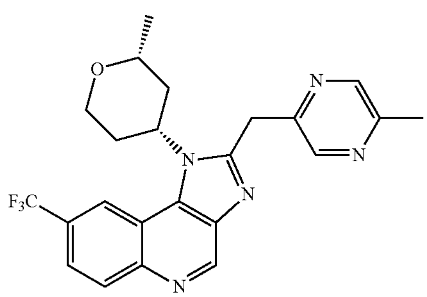 | ¹H NMR (400 MHz, CDCl₃) δ 9.39 (s, 1H), 8.91-9.09 (br m, 1H), 8.60 (s, 1H), 8.35-8.45 (m, 2H), 7.88 (br d, J = 8.8 Hz, 1H), 5.23-5.39 (br m, 1H), 4.68 (br s, 2H), 4.30 (br dd, J = 12, 5 Hz, 1H), 3.61-3.78 (m, 2H), 2.63-2.82 (br m, 1H), 2.57 (s, 3H), 2.36-2.54 (br m, 1H), 1.6-1.97 (br m, 2H, assumed; partially obscured by water peak), 1.33 (d, J = 6.2 Hz, 3H); 442.0 |
| 142 | Example 107[54]; C15 | 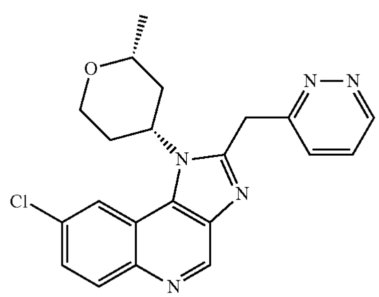 [SMILES: C[C@@H]1C[C@H](n2c(Cc3cccnn3)nc3cnc4ccc(Cl)cc4c32)CCO1] | ¹H NMR (400 MHz, CDCl₃) δ 9.28 (s, 1H), 9.14 (br d, J = 5 Hz, 1H), 8.56-8.72 (br m, 1H), 8.22 (d, J = 9.0 Hz, 1H), 7.60-7.69 (m, 2H), 7.48 (dd, J = 8.5, 5.0 Hz, 1H), 5.33-5.47 (br m, 1H), 4.89 (s, 2H), 4.28 (br dd, J = 11.5, 5.0 Hz, 1H), 3.65-3.80 (m, 2H), 2.57-2.76 (br m, 1H), 2.29-2.47 (br m, 1H), 1.46-1.8 (br m, 2H, assumed; partially obscured by water peak), 1.33 (d, J = 6.0 Hz, 3H); 394.0 (chlorine isotope pattern observed) |
| 143 | Example 112[55,56]; C61 | ENT-1 | ¹H NMR (400 MHz, CDCl₃) δ 9.41 (s, 1H), 8.56 (br s, 1H), 8.36 (d, J = 8.8 Hz, 1H), 7.85 (dd, J = 8.7, 1.6 Hz, 1H), 6.09 (br s, 1H), 5.60-5.75 (m, 1H), 4.50 (AB quartet, $J_{AB}$ = 16.2 Hz, $\Delta v_{AB}$ = 12.5 Hz, 2H), 2.54-2.76 (m, 3H), 2.42 (d, J = 0.8 Hz, 3H), 2.31-2.47 (m, 2H), 2.10-2.26 (m, 1H); 394.0 |

TABLE 1-continued

| Example Number | Method of Preparation; Non-commerical starting materials | Structure | $^1$H NMR (400 MHz, DMSO-$d_6$) δ (ppm); Mass spectrum, observed ion m/z [M + H]$^+$ or HPLC retention time; Mass spectrum m/z [M + H]$^+$ (unless otherwise indicated) |
|---|---|---|---|
| 144 | Example 112[55,56]; C61 | 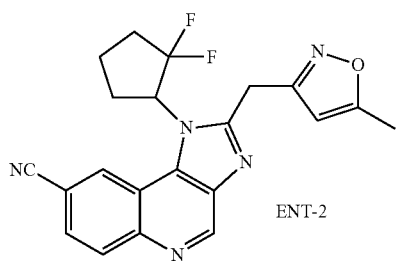 [SMILES: Cc1cc(Cc2nc3cnc4ccc(C#N)cc4c3n2C2CCCC2(F)F)no1] ENT-2 | $^1$H NMR (400 MHz, CDCl$_3$) δ 9.41 (s, 1H), 8.56 (br s, 1H), 8.36 (d, J = 8.5 Hz, 1H), 7.85 (dd, J = 8.7, 1.6 Hz, 1H), 6.09 (br s, 1H), 5.60-5.75 (m, 1H), 4.50 (AB quartet, J$_{AB}$ = 16.2 Hz, Δν$_{AB}$ = 12.5 Hz, 2H), 2.54-2.76 (m, 3H), 2.42 (d, J = 0.8 Hz, 3H), 2.32-2.47 (m, 2H), 2.10-2.26 (m, 1H); 394.0 |
| 145 | Example 106[57]; C17 | 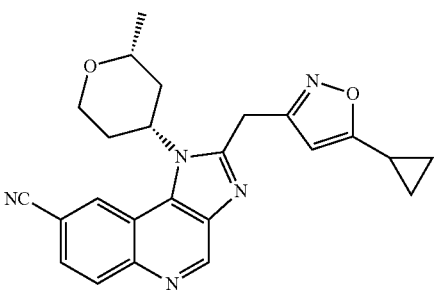 [SMILES: C[C@@H]1C[C@H](n2c(Cc3cc(C4CC4)on3)nc3cnc4ccc(C#N)cc4c32)CCO1] | 9.34 (s, 1H), 8.99 (br s, 1H), 8.33 (d, J = 8.5 Hz, 1H), 8.05 (br d, J = 8.5 Hz, 1H), 6.21 (s, 1H), 5.09-5.39 (br m, 1H), 4.61 (br s, 2H), 4.07-4.24 (br m, 1H), 3.55-3.85 (br m, 2H), 2.31-2.5 (br m, 1H, assumed; partially obscured by solvent peak), 1.80-2.25 (m, 4H), 1.22 (d, J = 6.0 Hz, 3H), 1.01-1.08 (m, 2H), 0.82-0.89 (m, 2H); 413.9 |

1. In this case, the 2,4-dimethoxybenzyl protecting group was removed using ammonium cerium(IV) nitrate.

2. The racemic product was separated into its enantiomers via supercritical fluid chromatography (Column: Lux Cellulose-1, 5 μm; Eluent: 4:1 carbon dioxide/methanol). The second-eluting compound was Example 12. The enantiomer of Example 12, 8-bromo-1-[(2S,4S)-2-methyltetrahydro-2H-pyran-4-yl]-2-(1,2-oxazol-3-ylmethyl)-1H-imidazo[4,5-c]quinoline, was the first-eluting enantiomer, and exhibited the following biological data: LRRK2, Format 1 WT IC$_{50}$, 510 nM; LRRK2, Format 1 G2019S mutant IC$_{50}$, 226 nM.

3. Example 9 was reacted with hydroxylamine and N,N-diisopropylethylamine in ethanol; the resulting 2-{8-chloro-1-[(2R,4R)-2-methyltetrahydro-2H-pyran-4-yl]-1H-imidazo[4,5-c]quinolin-2-yl}-N'-hydroxyethanimidamide was cyclized using trimethyl orthoformate and p-toluenesulfonic acid to afford Example 13.

4. The requisite 8-bromo-2-methyl-1-(tetrahydro-2H-pyran-4-yl)-1H-imidazo[4,5-c]quinoline was prepared using the general method of Example 6.

5. Reaction of tert-butyl [(1R,3R)-3-hydroxycyclopentyl] carbamate with (diethylamino)sulfur trifluoride, followed by treatment with hydrogen chloride in ethyl acetate, afforded (1R,3S)-3-fluorocyclopentanamine.

6. Conditions for analytical HPLC. Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL/minute.

7. The requisite 8-bromo-2-methyl-1-(2-methyltetrahydro-2H-pyran-4-yl)-1H-imidazo[4,5-c]quinoline was prepared using the general method of Example 6.

8. 8-Bromo-1-(2-methyltetrahydro-2H-pyran-4-yl)-2-(1,2-oxazol-3-ylmethyl)-1H-imidazo[4,5-c]quinoline was synthesized using the method of Example 7. The final product was generated as a mixture of Examples 21 and 23, which was separated via reversed phase HPLC (Column: YMC-Actus Triart C18, 5 μm; Mobile phase A: 0.225% formic acid in water; Mobile phase B: acetonitrile; Gradient: 29% to 49% B).

9. The requisite 8-bromo-1-(cis-2-methyltetrahydro-2H-pyran-4-yl)-2-(1,2-oxazol-3-ylmethyl)-1H-imidazo[4,5-c] quinoline was prepared using the general method of Example 1.

10. The racemic product was separated into its enantiomers via supercritical fluid chromatography (Column: Chiralpak AD-3, 3 μm; Mobile phase A: carbon dioxide; Mobile phase B: methanol containing 0.05% diethylamine; Gradient: 5% to 40% B). On analytical HPLC (Column: Chiralpak AD-3, 4.6×50 mm, 3 μm; same gradient system), Example 22 exhibited a retention time of 1.18 minutes. The enantiomer of Example 22, 1-[(2 S,4S)-2-methyltetrahydro-2H-pyran-4-yl]-2-(1,2-oxazol-3-ylmethyl)-1H-imidazo[4,5-c]quinoline-8-carbonitrile, had a retention time of 1.37 minutes under the same conditions. The enantiomer of Example 22, LCMS m/z 374.0 [M+H]$^+$, exhibited the following biological data: LRRK2, Format 1 WT IC$_{50}$, 534 nM; LRRK2, Format 1 G2019S mutant IC$_{50}$, 258 nM.

11. Example 23 was separated into its component enantiomers via supercritical fluid chromatography (Column: Chiralpak AD-3, 3 μm; Mobile phase A: carbon dioxide; Mobile phase B: methanol containing 0.05% diethylamine; Gradient: 5% to 40% B). On analytical HPLC (Column: Chiralpak AD-3, 4.6×50 mm, 3 μm; same gradient system), Example 24 exhibited a retention time of 1.37 minutes. The enantiomer of Example 24, 1-[(2R,4S)-2-methyltetrahydro-2H-pyran-4-yl]-2-(1,2-oxazol-3-ylm-ethyl)-1H-imidazo[4,5-c]quinoline-8-carbonitrile, had a retention time of 1.51 minutes under the same conditions. The enantiomer of Example 24, LCMS m/z 374.1 [M+H]$^+$, exhibited the following biological data: LRRK2, Format 1 WT IC$_{50}$, 267 nM; LRRK2, Format 1 G2019S mutant IC$_{50}$, 134 nM.

12. Conditions for analytical HPLC. Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 10% to 100% B over 4.0 minutes; Flow rate: 0.8 mL/minute.

13. Conditions for analytical HPLC. Column: Waters XBridge C18, 2.1×50 mm, 5 μm; Mobile phase A: 0.05% ammonium hydroxide in water; Mobile phase B: acetonitrile; Gradient: 5% B for 0.5 minutes; 5% to 100% B over 2.9 minutes; 100% B for 0.8 minutes; Flow rate: 0.8 mL/minute.

14. This Example was prepared as a racemate; the enantiomers were separated via supercritical fluid chromatography. Example 51 was the second-eluting enantiomer; retention time 6.21 minutes (Analytical column: Chiralpak AD-3, 4.6×150 mm, 3 μm; Mobile phase A: carbon dioxide; Mobile phase B: ethanol containing 0.05% diethylamine; Gradient: 5% to 40% B; Flow rate: 1.5 mL/minute). The enantiomer of Example 51 (Example 5) exhibited a retention time of 5.65 minutes in this analytical system.

15. The racemic product was separated into its enantiomers via supercritical fluid chromatography (Column: Chiralpak AD-H, 5 μm; Mobile phase A: carbon dioxide; Mobile phase B: methanol containing 0.05% diethylamine; Gradient: 5% to 40% B). On analytical HPLC (Column: Chiralpak AD-H, 4.6×250 mm, 5 μm; same gradient system), Example 54 exhibited a retention time of 6.28 minutes. The enantiomer of Example 54, 8-fluoro-1-[(2S,4S)-2-methyltetrahydro-2H-pyran-4-yl]-2-(1,2-oxazol-3-ylmethyl)-1H-imidazo[4,5-c]quinoline, had a retention time of 6.66 minutes under the same conditions. The enantiomer of Example 54, LCMS m/z 366.9 [M+H]$^+$, exhibited the following biological data: LRRK2, Format 1 WT IC$_{50}$, 332 nM; LRRK2, Format 1 G2019S mutant IC$_{50}$, 236 nM.

16. The racemic product was separated into its enantiomers via supercritical fluid chromatography (Column: Chiralcel OD-H, 5 μm; Mobile phase A: carbon dioxide; Mobile phase B: methanol containing 0.05% diethylamine; Gradient: 5% to 40% B). On analytical HPLC [Column: Chiralpak AS-H, 4.6×250 mm, 5 μm; Mobile phase: 10% ethanol (containing 0.05% diethylamine) in carbon dioxide], Example 55 exhibited a retention time of 5.85 minutes. The enantiomer of Example 55, 8-fluoro-1-[(2S,4S)-2-methyltetrahydro-2H-pyran-4-yl]-2-(1,3-thiazol-4-ylmethyl)-1H-imidazo[4,5-c]quinoline, LCMS m/z 383.0 [M+H]$^+$, had a retention time of 6.02 minutes under the same conditions. The enantiomer of Example 55, LCMS m/z 366.9 [M+H]$^+$, exhibited the following biological data: LRRK2, Format 1 WT IC$_{50}$, 725 nM; LRRK2, Format 1 G2019S mutant IC$_{50}$, 380 nM.

17. The racemic product was separated into its enantiomers via supercritical fluid chromatography (Column: Chiralcel OD-3, 3 μm; Mobile phase A: carbon dioxide; Mobile phase B: methanol containing 0.05% diethylamine; Gradient: 5% to 40% B). On analytical HPLC (Column: Chiralcel OD-3, 4.6×150 mm, 3 μm; same gradient system; Flow rate: 1.5 mL/minute), Example 57 exhibited a retention time of 8.22 minutes. The enantiomer of Example 57, 1-[(2S,4S)-2-methyltetrahydro-2H-pyran-4-yl]-2-(1,3-thiazol-4-ylmethyl)-1H-imidazo[4,5-c]quinoline-8-carbonitrile, had a retention time of 7.29 minutes under the same conditions. The enantiomer of Example 57, LCMS m/z 390.0 [M+H]$^+$, exhibited the following biological data: LRRK2, Format 1 WT IC$_{50}$, 382 nM; LRRK2, Format 1 G2019S mutant IC$_{50}$, 196 nM.

18. Hydrogenation of 2,6-dimethyl-4H-pyran-4-one over palladium on carbon afforded cis-2,6-dimethyltetrahydro-4H-pyran-4-one, which was converted to the requisite (2R,4r,6S)—N-(2,4-dimethoxybenzyl)-2,6-dimethyltetrahydro-2H-pyran-4-amine using the method described for synthesis of P1 in Preparation P1.

19. The racemic product was separated into its enantiomers via supercritical fluid chromatography (Column: Chiralpak AD-3, 3 μm; Mobile phase A: carbon dioxide; Mobile phase B: methanol containing 0.05% diethylamine; Gradient: 5% to 40% B). On analytical HPLC (Column: Chiralpak AD-3, 4.6×150 mm, 3 μm; same gradient system), Example 62 exhibited a retention time of 4.19 minutes. The enantiomer of Example 62, 8-methoxy-1-[(2S,4S)-2-methyltetrahydro-2H-pyran-4-yl]-2-(1,2-oxazol-3-ylmethyl)-1H-imidazo[4,5-c]quinoline, had a retention time of 5.07 minutes under the same conditions. The enantiomer of Example 62, LCMS m/z 379.0 [M+H]$^+$, exhibited the following biological data: LRRK2, Format 1 WT IC$_{50}$, 1713 nM; LRRK2, Format 1 G2019S mutant IC$_{50}$, 508 nM.

20. This Example was prepared as a racemate; the enantiomers were separated via supercritical fluid chromatography. Example 64 was the second-eluting enantiomer; retention time 8.87 minutes (Analytical column: Chiralpak AD-H, 4.6×250 mm, 5 μm; Mobile phase A: carbon dioxide; Mobile phase B: methanol containing 0.05% diethylamine; Gradient: 5% to 40% B). The enantiomer of Example 64 (Example 8) exhibited a retention time of 6.98 minutes in this analytical system.

21. This Example was prepared as a racemate; the enantiomers were separated via supercritical fluid chromatography. Example 65 was the second-eluting enantiomer; retention time 8.73 minutes (Analytical column: Chiralpak AD-H, 4.6×250 mm, 5 μm; Mobile phase A: carbon dioxide; Mobile phase B: methanol containing 0.05% diethylamine; Gradient: 5% to 40% B). The enantiomer of Example 65, 8-chloro-1-[(2S,4S)-2-methyltetrahydro-2H-pyran-4-yl]-2-(1H-1,2,4-triazol-1-ylmethyl)-1H-imidazo[4,5-c]quinoline, had a retention time of 7.97 minutes under the same conditions. The enantiomer of Example 65, LCMS m/z 382.9 [M+H]$^+$, exhibited the following biological data: LRRK2, Format 1 WT IC$_{50}$, 687 nM; LRRK2, Format 1 G2019S mutant IC$_{50}$, 241 nM.

22. The requisite cis-N-(2,4-dimethoxybenzyl)-2-ethyltetrahydro-2H-pyran-4-amine was prepared from propanal and but-3-en-1-ol in analogy with the syntheses of P1 and P2, except that pyridinium chlorochromate was used in place of Jones reagent.

23. The racemic product was separated into its enantiomers via supercritical fluid chromatography (Column: Chiralpak AD-3, 3 μm; Mobile phase A: carbon dioxide; Mobile phase B: methanol containing 0.05% diethylamine; Gradient: 5% to 40% B). On analytical HPLC (Column: Chiralpak AD-3, 4.6×150 mm, 3 μm; same gradient system), Example 67 exhibited a retention time of 1.17 minutes. The enantiomer of Example 67, 1-[(2S,4S)-2-ethyltetrahydro-2H-pyran-4-yl]-2-(1,2-oxazol-3-ylmethyl)-1H-imidazo[4,5-c]quinoline-8-carbonitrile, had a retention time of 1.38 minutes under the same conditions. The enantiomer of Example 67, LCMS m/z 388.0 [M+H]$^+$, exhibited the following biological data: LRRK2, Format 1 WT IC$_{50}$, 699 nM; LRRK2, Format 1 G2019S mutant IC$_{50}$, 403 nM.

24. The racemic product was separated into its enantiomers via supercritical fluid chromatography (Column: Chiralpak AD-3, 3 µm; Mobile phase A: carbon dioxide; Mobile phase B: methanol containing 0.05% diethylamine; Gradient: 5% to 40% B). On analytical HPLC (Column: Chiralpak AD-3, 4.6×150 mm, 3 µm; same gradient system), Example 68 exhibited a retention time of 5.76 minutes. The enantiomer of Example 68, 1-[(2 S,4S)-2-methyltetrahydro-2H-pyran-4-yl]-2-(1,2-oxazol-3-ylmethyl)-1H-imidazo[4,5-c][1,5]naphthyridine, had a retention time of 6.14 minutes under the same conditions. The enantiomer of Example 68, LCMS m/z 349.9 [M+H]$^+$, exhibited the following biological data: LRRK2, Format 1 WT IC$_{50}$, 853 nM; LRRK2, Format 1 G2019S mutant IC$_{50}$, 632 nM.

25. Conditions for analytical HPLC. Column: Waters Atlantis dC18, 4.6×50 mm, 5 µm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.

26. Compound C34 was combined with a solution of ammonia in methanol (7 M) and heated in a microwave reactor at 160° C. to afford Example 85.

27. The racemic product was separated into its enantiomers via supercritical fluid chromatography (Column: Chiralpak AD-H, 5 µm; Mobile phase A: carbon dioxide; Mobile phase B: ethanol containing 0.05% diethylamine; Gradient: 5% to 40% B). On analytical HPLC (Column: Chiralpak AD-H, 4.6×250 mm, 5 µm; same gradient system), Example 87 exhibited a retention time of 6.39 minutes. The enantiomer of Example 87, 8-methoxy-2-[(5-methyl-1,2,4-oxadiazol-3-yl)methyl]-1-[(2S,4S)-2-methyltetrahydro-2H-pyran-4-yl]-1H-imidazo[4,5-c]quinoline, had a retention time of 7.57 minutes under the same conditions. The enantiomer of Example 87, LCMS m/z 394.1 [M+H]$^+$, exhibited the following biological data: LRRK2, Format 1 WT IC$_{50}$, 2853 nM; LRRK2, Format 1 G2019S mutant IC$_{50}$, 929 nM.

28. The racemic product was separated into its enantiomers via supercritical fluid chromatography (Column: Chiralpak AD-H, 5 µm; Mobile phase A: carbon dioxide; Mobile phase B: methanol containing 0.05% diethylamine; Gradient: 5% to 40% B). On analytical HPLC (Column: Chiralpak AD-H, 4.6×250 mm, 5 µm; same gradient system), Example 88 exhibited a retention time of 6.96 minutes. The enantiomer of Example 88, 8-methoxy-1-[(2S,4S)-2-methyltetrahydro-2H-pyran-4-yl]-2-[(4-methyl-1H-1,2,3-triazol-1-yl)methyl]-1H-imidazo[4,5-c]quinoline, had a retention time of 7.78 minutes under the same conditions. The enantiomer of Example 88, LCMS m/z 393.1 [M+H]$^+$, exhibited the following biological data: LRRK2, Format 1 WT IC$_{50}$, 1055 nM; LRRK2, Format 1 G2019S mutant IC$_{50}$, 372 nM.

29. The racemic product was separated into its enantiomers via supercritical fluid chromatography (Column: Chiralpak AD-H, 5 µm; Mobile phase A: carbon dioxide; Mobile phase B: methanol containing 0.05% diethylamine; Gradient: 5% to 40% B). On analytical HPLC (Column: Chiralpak AD-H, 4.6×250 mm, 5 µm; same gradient system), Example 89 exhibited a retention time of 7.54 minutes. The enantiomer of Example 89, 8-methoxy-1-[(2S,4S)-2-methyltetrahydro-2H-pyran-4-yl]-2-(1,3-thiazol-4-ylmethyl)-1H-imidazo[4,5-c]quinoline, had a retention time of 8.17 minutes under the same conditions. The enantiomer of Example 89, LCMS m/z 395.0 [M+H]$^+$, exhibited the following biological data: LRRK2, Format 1 WT IC$_{50}$, 1218 nM; LRRK2, Format 1 G2019S mutant IC$_{50}$, 743 nM.

30. The racemic product was separated into its enantiomers via supercritical fluid chromatography (Column: Chiralpak AD-H, 5 µm; Mobile phase A: carbon dioxide; Mobile phase B: ethanol containing 0.05% diethylamine; Gradient: 5% to 40% B). On analytical HPLC (Column: Chiralpak AD-H, 4.6×250 mm, 5 µm; same gradient system), Example 90 exhibited a retention time of 8.60 minutes. The enantiomer of Example 90, 2-(imidazo[2,1-b][1,3,4]thiadiazol-6-ylmethyl)-8-methoxy-1-[(2S,4S)-2-methyltetrahydro-2H-pyran-4-yl]-1H-imidazo[4,5-c]quinoline, had a retention time of 9.48 minutes under the same conditions. The enantiomer of Example 90, LCMS m/z 435.1 [M+H]$^+$, exhibited the following biological data: LRRK2, Format 1 WT IC$_{50}$, 623 nM; LRRK2, Format 1 G2019S mutant IC$_{50}$, 245 nM.

31. Reagent cis-2-[(benzyloxy)methyl]-N-(2,4-dimethoxybenzyl)tetrahydro-2H-pyran-4-amine was prepared from (benzyloxy)acetaldehyde and but-3-en-1-ol in analogy with footnote 22.

32. Intermediate 1-{cis-2-[(benzyloxy)methyl]tetrahydro-2H-pyran-4-yl}-2-methyl-1H-imidazo[4,5-c]quinoline was deprotected with boron trichloride, and the resulting alcohol was converted to the 4-methylbenzenesulfonate derivative. Displacement with tetraethylammonium cyanide afforded Example 91.

33. The requisite (5-methyl-1,3-oxazol-2-yl)acetic acid was prepared using the method of A. S. K. Hashmi et al., *Org. Lett.* 2004, 6, 4391-4394.

34. In this case, the zinc cyanide reaction employed tris(dibenzylideneacetone)dipalladium(0) and dicyclohexyl(2',6'-dimethoxybiphenyl-2-yl)phosphane rather than tetrakis(triphenylphosphine)palladium(0), and was carried out using microwave irradiation.

35. The racemic product was separated into its enantiomers via supercritical fluid chromatography [Column: Phenomenex Lux Cellulose-1, 5 µm; Eluent: 4:1 carbon dioxide/(ethanol containing 0.2% ammonium hydroxide)]. The first-eluting compound was Example 118. The enantiomer of Example 118, 1-(cis-3-fluorocyclopentyl]-2-[(3-methyl-1,2-oxazol-5-yl)methyl]-1H-imidazo[4,5-c]quinoline-8-carbonitrile, ENT-2, was the second-eluting enantiomer, and exhibited the following biological data: LRRK2, Format 2 WT IC$_{50}$, 22.4 nM; LRRK2, Format 2 G2019S mutant IC$_{50}$, 26.1 nM.

36. Reaction of ethyl 5-(trifluoromethyl)-1,2-oxazole-3-carboxylate with sodium borohydride, followed by conversion of the primary alcohol to the corresponding mesylate and displacement with potassium cyanide, provided [5-(trifluoromethyl)-1,2-oxazol-3-yl]acetonitrile. Nitrile hydrolysis using concentrated hydrochloric acid then afforded the requisite [5-(trifluoromethyl)-1,2-oxazol-3-yl]acetic acid.

37. The requisite (2-cyclopropyl-1,3-oxazol-4-yl)acetic acid can be prepared using the method described by M. D. Andrews et al., PCT Int. Appl., 2012137089, Oct. 11, 2012.

38. Reaction of 5-(chloromethyl)-1,3-oxazole with sodium cyanide, followed by nitrile hydrolysis using aqueous sodium hydroxide, provided 1,3-oxazol-5-ylacetic acid.

39. The racemic product was separated into its enantiomers via supercritical fluid chromatography [Column: Chiral Technologies Chiralpak AD-H, 5 µm; Mobile phase: 1:1 carbon dioxide/(methanol containing 0.2% ammonium hydroxide)]. The first-eluting compound was Example 132. The enantiomer of Example 132, 1-(cis-3-fluorocyclopentyl)-2-{[4-(methoxymethyl)-1H-1,2,3-triazol-1-yl]methyl}-1H-imidazo[4,5-c]quinoline-8-carbonitrile, ENT-2, was the second-eluting enantiomer, and exhibited the following biological data: LRRK2, Format 2 WT IC$_{50}$, 26.8 nM; LRRK2, Format 2 G2019S mutant IC$_{50}$, 34.5 nM.

40. Conditions for analytical HPLC. Column: Chiral Technologies Chiralpak AD-H, 4.6×100 mm, 5 µm; Mobile phase: 1:1 carbon dioxide/(methanol containing 0.2% ammonium hydroxide); Flow rate: 3.0 mL/minute.

41. Reaction of but-3-en-1-ol and (benzyloxy)acetaldehyde in the presence of sulfuric acid provided 2-[(benzyloxy)methyl]tetrahydro-2H-pyran-4-ol, which was oxidized with pyridinium chlorochromate to afford 2-[(benzyloxy)methyl]tetrahydro-4H-pyran-4-one. Subsequent reductive amination with 1-(2,4-dimethoxyphenyl)methanamine and lithium borohydride gave cis-2-[(benzyloxy)methyl]-N-(2,4-dimethoxybenzyl)tetrahydro-2H-pyran-4-amine. This was reacted with C13 and triethylamine, and the product was deprotected using trifluoroacetic acid to yield N-{cis-2-[(benzyloxy)methyl]tetrahydro-2H-pyran-4-yl}-6-chloro-3-nitroquinolin-4-amine; hydrogenation of the nitro group over platinum(IV) oxide afforded $N^4$-{cis-2-[(benzyloxy)methyl]tetrahydro-2H-pyran-4-yl}-6-chloroquinoline-3,4-diamine.

42. 1-{(2R,4S)-2-[(Benzyloxy)methyl]tetrahydro-2H-pyran-4-yl}-8-chloro-2-[(5-methyl-1,2-oxazol-3-yl)methyl]-1H-imidazo[4,5-c]quinoline (the product from reaction of C6 and $N^4$-{cis-2-[(benzyloxy)methyl]tetrahydro-2H-pyran-4-yl}-6-chloroquinoline-3,4-diamine, described in footnote 41) was reacted with boron trichloride. The resulting primary alcohol was converted to the corresponding mesylate derivative and displaced using potassium cyanide with catalytic tetraethylammonium cyanide to afford the racemate of Example 134.

43. The racemate of Example 134 was separated into its component enantiomers via supercritical fluid chromatography (Column: Chiral Technologies Chiralpak AD-3, 4.6×150 mm, 3 μm; Mobile phase A: carbon dioxide; Mobile phase B: methanol containing 0.05% diethylamine; Gradient: 5% to 40% B). The first-eluting compound was Example 134. The enantiomer of Example 134, [cis-4-{8-chloro-2-[(5-methyl-1,2-oxazol-3-yl)methyl]-1H-imidazo[4,5-c]quinolin-1-yl}tetrahydro-2H-pyran-2-yl]acetonitrile, ENT-2, was the second-eluting enantiomer, and exhibited the following biological data: LRRK2, Format 1 WT $IC_{50}$, 353 nM; LRRK2, Format 1 G2019S mutant $IC_{50}$, 327 nM.

44. The racemate of Example 135 was separated into its component enantiomers via supercritical fluid chromatography (Column: Chiral Technologies Chiralpak AD-3, 4.6×150 mm, 3 μm; Mobile phase A: carbon dioxide; Mobile phase B: methanol containing 0.05% diethylamine; Gradient: 5% to 40% B). The first-eluting compound was Example 135. The enantiomer of Example 135, [cis-4-{8-chloro-2-[(5-methyl-1,2,4-oxadiazol-3-yl)methyl]-1H-imidazo[4,5-c]quinolin-1-yl}tetrahydro-2H-pyran-2-yl]acetonitrile, ENT-2, was the second-eluting enantiomer, and exhibited the following biological data: LRRK2, Format 1 WT $IC_{50}$, 1450 nM; LRRK2, Format 1 G2019S mutant $IC_{50}$, 1220 nM.

45. Reaction of tert-butyl cyclopent-3-en-1-ylcarbamate with 3-chloroperoxybenzoic acid, followed by epoxide opening with methylmagnesium bromide in the presence of copper(I) iodide, provided tert-butyl [rel-(3R,4R)-3-hydroxy-4-methylcyclopentyl]carbamate. Conversion of the secondary alcohol to the corresponding fluoride was carried out with (diethylamino)sulfur trifluoride; deprotection using hydrogen chloride afforded the requisite rel-(3S,4R)-3-fluoro-4-methylcyclopentanamine. This was reacted with C13 in the presence of triethylamine, and the nitro group of the product was hydrogenated over platinum(IV) oxide to provide 6-chloro-$N^4$-[rel-(3S,4R)-3-fluoro-4-methylcyclopentyl]quinoline-3,4-diamine.

46. The mixture of diastereomeric products was separated into its component racemic isomers via reversed phase HPLC (Column: Kromasil Eternity XT C18, 10 μm; Mobile phase A: 0.225% formic acid in water; Mobile phase B: acetonitrile; Gradient: 26% to 46% B). The first-eluting compound was Example 136. The diastereomer of Example 136, 8-chloro-1-[rel-(3S,4R)-3-fluoro-4-methylcyclopentyl]-2-[(5-methyl-1,2,4-oxadiazol-3-yl)methyl]-1H-imidazo[4,5-c]quinoline, DIAST-2, was the second-eluting compound, and exhibited the following biological data: LRRK2, Format 1 WT $IC_{50}$, 156 nM; LRRK2, Format 1 G2019S mutant $IC_{50}$, 105 nM, LRRK2, Format 2 WT $IC_{50}$, 63.2 nM; LRRK2, Format 2 G2019S mutant $IC_{50}$, 69.2 nM 47. MCYP-RXN buffer (545.0 mg, Codex®) was treated with deionized water (19.2 mL) and charged with a solution of MCYP0016 (41.38 mg, Codex® MicroCyp®) dissolved in potassium phosphate buffer (0.1 M, 4.0 mL) at pH 8.0. The mixture was treated with a solution of Example 4 (5.72 mg) dissolved in dimethyl sulfoxide (0.6 mL) and potassium phosphate buffer (0.1 M, 0.6 mL) at pH 8.0. The reaction mixture was shaken at 30° C. for 12 hours. Isolation via reversed phase HPLC (Column: Phenomenex Gemini NX C18, 5 μm; Mobile phase A: water containing 0.1% formic acid; Mobile phase B: acetonitrile containing 0.1% formic acid; Gradient: 5% to 90% B) afforded Example 137.

48. Example 4 was subjected to incubation with Codex® MicroCyp® MCYP0030 at 30° C., using the general procedure described in footnote 47. Isolation via reversed phase HPLC (Column: Phenomenex Gemini NX C18, 5 μm; Mobile phase A: water containing 0.1% formic acid; Mobile phase B: acetonitrile containing 0.1% formic acid; Gradient: 5% to 90% B) afforded Example 138.

49. Example 138 was reacted with (diethylamino)sulfur trifluoride to provide Example 139.

50. The requisite 6-fluoro-$N^4$-[(2R,4R)-2-methyltetrahydro-2H-pyran-4-yl]quinoline-3,4-diamine was synthesized from 6-fluoro-3-nitroquinolin-4-ol using the general method described in Example 1 for synthesis of C11 from C7, except that P2 was used in place of P1, and hydrogenation was carried out over platinum on carbon, rather than platinum(IV) oxide.

51. Reaction of 1,2,3-thiadiazol-4-ylmethanol with methanesulfonyl chloride, followed by displacement using potassium cyanide and hydrolysis in concentrated hydrochloric acid, provided the requisite 1,2,3-thiadiazol-4-ylacetic acid.

52. In this case, the final coupling and cyclization reaction was carried out in two steps: reaction of 6-fluoro-$N^4$-[(2R,4R)-2-methyltetrahydro-2H-pyran-4-yl]quinoline-3,4-diamine (footnote 50) with 1,2,3-thiadiazol-4-ylacetic acid (footnote 51) was effected with 2,4,6-tripropyl-1,3,5,2,4,6-trioxatriphosphinane 2,4,6-trioxide and triethylamine at 50° C., and intermediate N-(6-fluoro-4-{[(2R,4R)-2-methyltetrahydro-2H-pyran-4-yl]amino}quinolin-3-yl)-2-(1,2,3-thiadiazol-4-yl)acetamide was isolated. Further reaction with 2,4,6-tripropyl-1,3,5,2,4,6-trioxatriphosphinane 2,4,6-trioxide and N,N-diisopropylethylamine at 110° C. afforded Example 140.

53. The final coupling and cyclization reaction was carried out in two steps, as described for Example 140 in footnote 52.

54. Reaction of methyl pyridazin-3-ylacetate with lithium hydroxide provided lithium pyridazin-3-ylacetate.

55. 3-Amino-4-[(2,2-difluorocyclopentyl)amino]quinoline-6-carbonitrile was synthesized from C61 using the method described for preparation of C54 from C13 in Example 93.

56. The racemic product was separated into its enantiomers via supercritical fluid chromatography [Column: Chiral Technologies Chiralpak AS, 5 μm; Eluent: 4:1 carbon dioxide/2-propanol containing 0.1% ammonium hydroxide)]. The first-eluting compound was Example 143, and Example 144 was the second-eluting enantiomer.

57. Conversion of (5-cyclopropyl-1,2-oxazol-3-yl)methanol to the requisite (5-cyclopropyl-1,2-oxazol-3-yl)acetic acid was carried out using the method described in footnote 51.

Table 2, below, provides the structure and mass spectral data for the compounds of Examples 146-250.
TABLE 2
| Example Number | Structure | Mass spectrum m/z [M + H]+ |
|---|---|---|
| 146 | 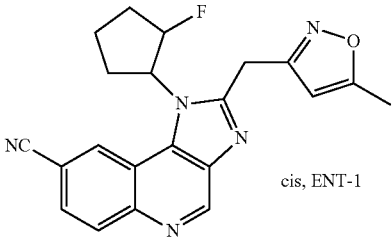 cis, ENT-1 | 376.2[1] |
| 147 | 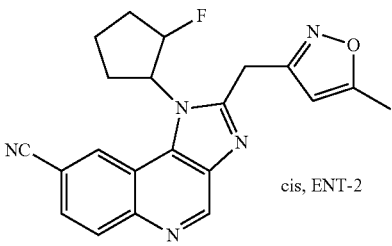 [SMILES: Cc1cc(Cc2nc3cnc4ccc(C#N)cc4c3n2C2CCCC2F)no1] cis, ENT-2 | 376.2[1] |
| 148 | 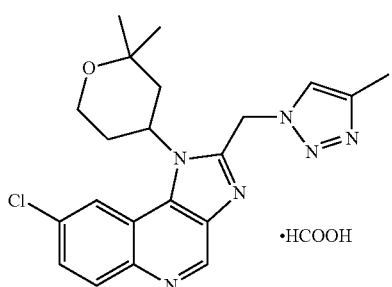 •HCOOH | 411 |
| 149 | 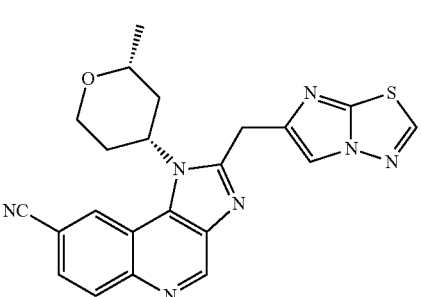 | 430.3 |
| 150 | 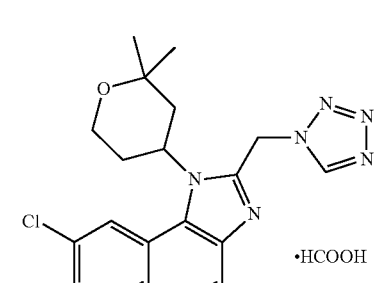 •HCOOH | 398 |

TABLE 2-continued

| Example Number | Structure | Mass spectrum m/z [M + H]+ |
|---|---|---|
| 151 | (structure) ·HCOOH | 408 |
| 152 | (structure) ·HCOOH | 358 |
| 153 | (structure) ·HCOOH | 424 |
| 154 | (structure) ·HCOOH | 424 |
| 155 | (structure) ·HCOOH | 428 |

TABLE 2-continued

| Example Number | Structure | Mass spectrum m/z [M + H]+ |
|---|---|---|
| 156 | (structure) ·HCOOH | 458 |
| 157 | (structure) ·HCOOH | 444 |
| 158 | (structure) ·HCOOH | 423 |
| 159 | (structure) | 447 |
| 160 | (structure) ·HCOOH | 422 |

TABLE 2-continued
| Example Number | Structure | Mass spectrum m/z [M + H]+ |
|---|---|---|
| 161 | 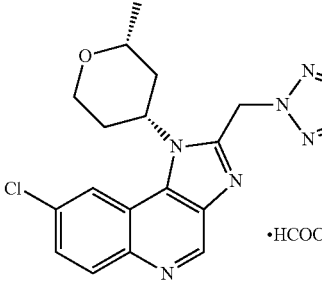 ·HCOOH | 383 |
| 162 | 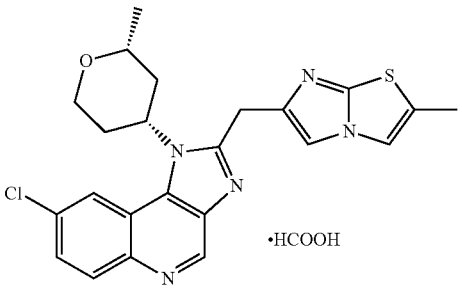 [SMILES: Cc1cn2cc(Cc3nc4cnc5ccc(Cl)cc5c4n3[C@@H]3CCO[C@H](C)C3)nc2s1 ; "·HCOOH"] ·HCOOH | 453 |
| 163 | 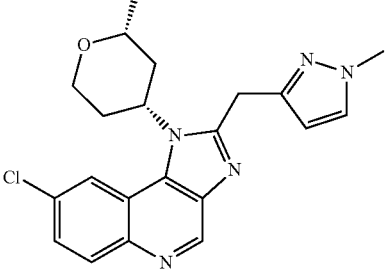 | 396.3 (chlorine isotope pattern observed) |
| 164 | 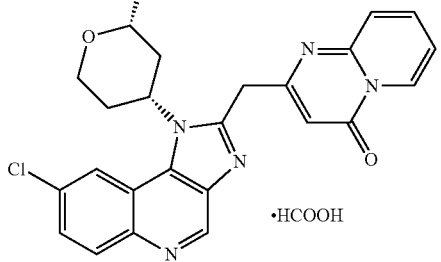 ·HCOOH | 460 |
| 165 | 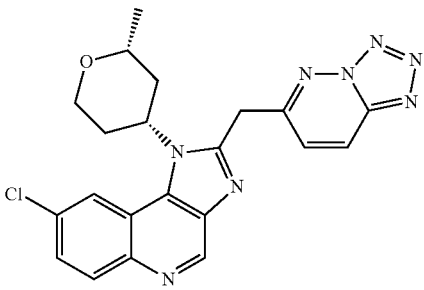 [SMILES: C[C@@H]1C[C@H](n2c(Cc3ccc4nnnn4n3)nc3cnc4ccc(Cl)cc4c32)CCO1] | 435 |

TABLE 2-continued

| Example Number | Structure | Mass spectrum m/z [M + H]+ |
|---|---|---|
| 166 | (structure) ·CF₃COOH | 422.4 (chlorine isotope pattern observed) |
| 167 | (structure) ·CF₃COOH | 432.3 (chlorine isotope pattern observed) |
| 168 | (structure) cis, ENT-1 | 432.0[2] |
| 169 | (structure) cis, ENT-2 | 432.0[2] |
| 170 | (structure) cis, ENT-1 | 313.3[3] |

TABLE 2-continued

| Example Number | Structure | Mass spectrum m/z [M + H]+ |
|---|---|---|
| 171 | 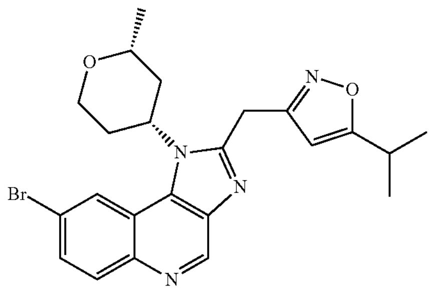 [SMILES: CC(C)c1cc(Cc2nc3cnc4ccc(Br)cc4c3n2[C@@H]2CCO[C@H](C)C2)no1] | 470.9 (bromine isotope pattern observed) |
| 172 | 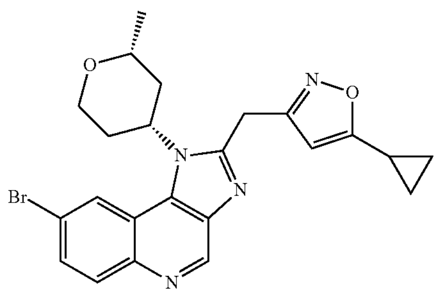 | 468.7 (bromine isotope pattern observed) |
| 173 | 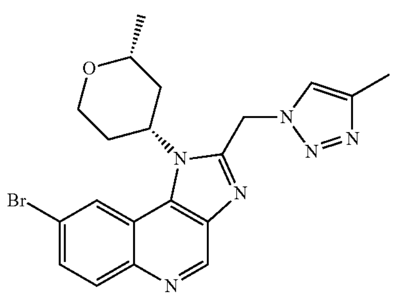 [SMILES: Cc1cn(Cc2nc3cnc4ccc(Br)cc4c3n2[C@@H]2CCO[C@H](C)C2)nn1] | 440.8 (bromine isotope pattern observed) |
| 174 | 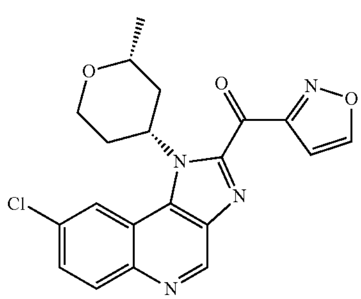 [SMILES: C[C@@H]1C[C@H](n2c(C(=O)c3ccon3)nc3cnc4ccc(Cl)cc4c32)CCO1] | 397.1 (chlorine isotope pattern observed) |
| 175 | 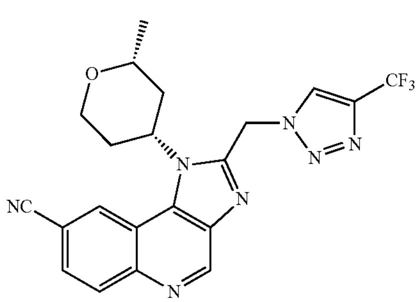 [SMILES: C[C@@H]1C[C@H](n2c(Cn3cc(C(F)(F)F)nn3)nc3cnc4ccc(C#N)cc4c32)CCO1] | 441.9 |

TABLE 2-continued
| Example Number | Structure | Mass spectrum m/z [M + H]+ |
|---|---|---|
| 176 | 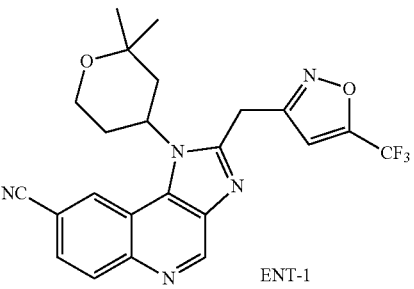 [SMILES: CC1(C)CC(n2c(Cc3cc(C(F)(F)F)on3)nc3cnc4ccc(C#N)cc4c32)CCO1] ENT-1 | 456.1[4] |
| 177 | 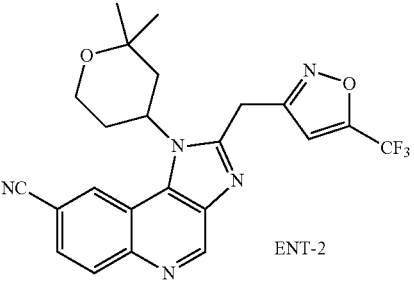 [SMILES: CC1(C)CC(n2c(Cc3cc(C(F)(F)F)on3)nc3cnc4ccc(C#N)cc4c32)CCO1] ENT-2 | 456.1[4] |
| 178 | 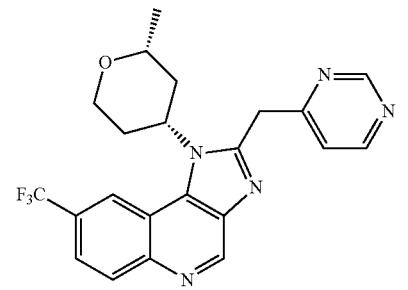 | 428.1 |
| 179 | 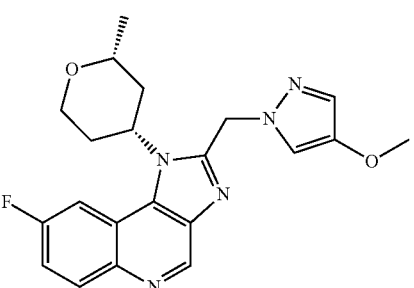 | 396.0 |
| 180 | 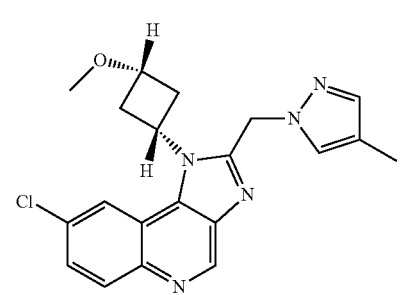 [SMILES: CO[C@H]1C[C@@H](n2c(Cn3cc(C)cn3)nc3cnc4ccc(Cl)cc4c32)C1] | 382.3 (chlorine isotope pattern observed) |

TABLE 2-continued

| Example Number | Structure | Mass spectrum m/z [M + H]+ |
|---|---|---|
| 181 | 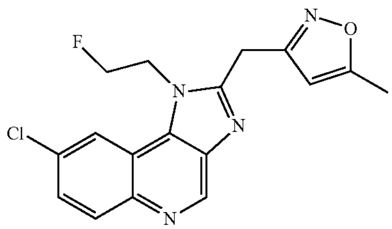 [SMILES: Cc1cc(Cc2nc3cnc4ccc(Cl)cc4c3n2CCF)no1] | 345.3 (chlorine isotope pattern observed) |
| 182 | 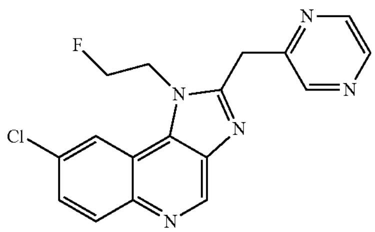 [SMILES: FCCn1c(Cc2cnccn2)nc2cnc3ccc(Cl)cc3c21] | 342.3 (chlorine isotope pattern observed) |
| 183 | 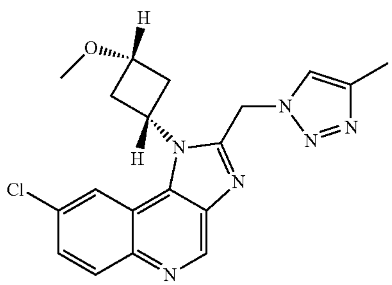 [SMILES: CO[C@H]1C[C@@H](n2c(Cn3cc(C)nn3)nc3cnc4ccc(Cl)cc4c32)C1] | 383.3 (chlorine isotope pattern observed) |
| 184 | 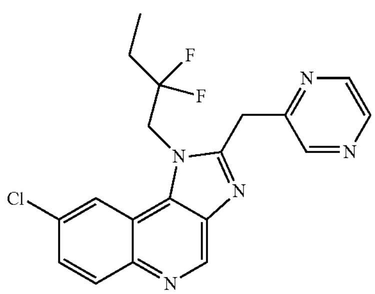 [SMILES: CCC(F)(F)Cn1c(Cc2cnccn2)nc2cnc3ccc(Cl)cc3c21] | 388.3 (chlorine isotope pattern observed) |
| 185 | 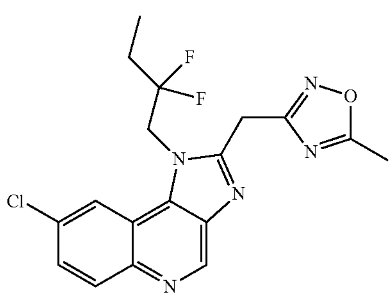 [SMILES: CCC(F)(F)Cn1c(Cc2noc(C)n2)nc2cnc3ccc(Cl)cc3c21] | 392.3 (chlorine isotope pattern observed) |

TABLE 2-continued

| Example Number | Structure | Mass spectrum m/z [M + H]+ |
|---|---|---|
| 186 | 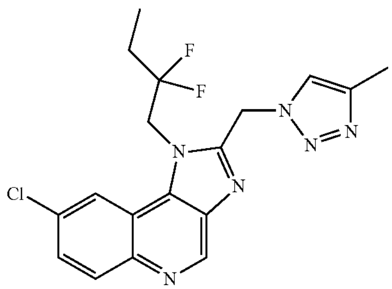 [SMILES: CCC(F)(F)Cn1c(Cn2cc(C)nn2)nc2cnc3ccc(Cl)cc3c21] | 391.3 (chlorine isotope pattern observed) |
| 187 | 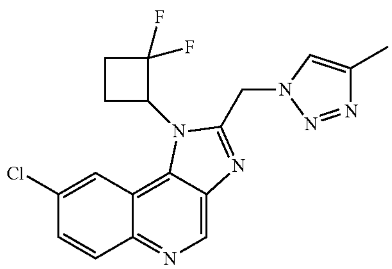 [SMILES: Cc1cn(Cc2nc3cnc4ccc(Cl)cc4c3n2C2CCC2(F)F)nn1] | 389.3 (chlorine isotope pattern observed) |
| 188 | 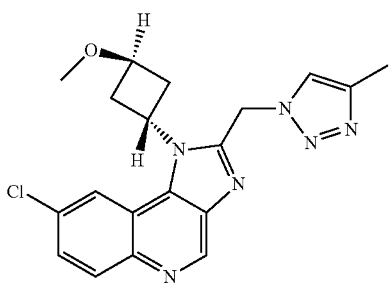 [SMILES: CO[C@H]1C[C@H](n2c(Cn3cc(C)nn3)nc3cnc4ccc(Cl)cc4c32)C1] | 383.3 (chlorine isotope pattern observed) |
| 189 | 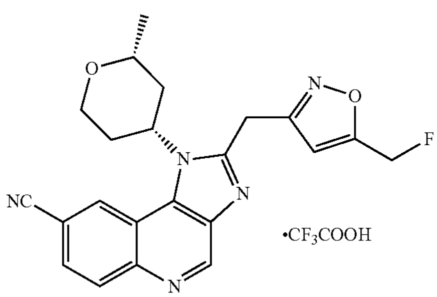 | 406.0 |
| 190 | 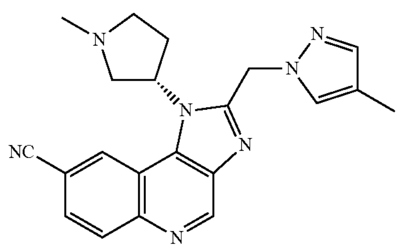 [SMILES: Cc1cnn(Cc2nc3cnc4ccc(C#N)cc4c3n2[C@H]2CCN(C)C2)c1] | 372.1 |

TABLE 2-continued

| Example Number | Structure | Mass spectrum m/z [M + H]+ |
|---|---|---|
| 191 | 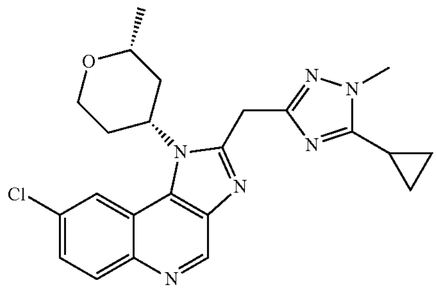 [SMILES: C[C@@H]1C[C@H](n2c(Cc3nc(C4CC4)n(C)n3)nc3cnc4ccc(Cl)cc4c32)CCO1] | 437.4 (chlorine isotope pattern observed) |
| 192 | 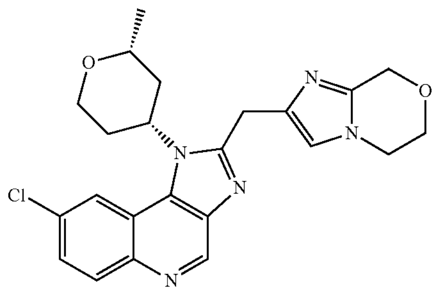 [SMILES: C[C@@H]1C[C@H](n2c(Cc3cn4c(n3)COCC4)nc3cnc4ccc(Cl)cc4c32)CCO1] | 438.4 (chlorine isotope pattern observed) |
| 193 | 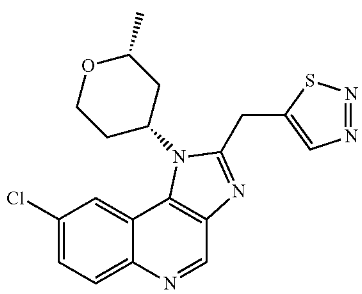 [SMILES: C[C@@H]1C[C@H](n2c(Cc3cnns3)nc3cnc4ccc(Cl)cc4c32)CCO1] | 400.3 (chlorine isotope pattern observed) |
| 194 | 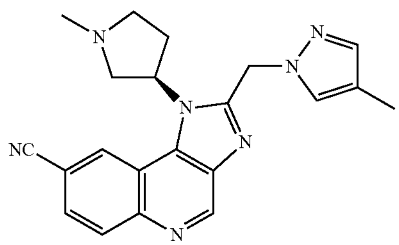 [SMILES: Cc1cnn(Cc2nc3cnc4ccc(C#N)cc4c3n2[C@@H]2CCN(C)C2)c1] | 372.1 |
| 195 | 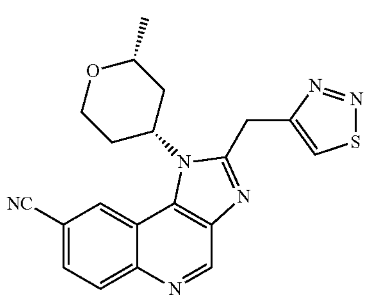 [SMILES: C[C@@H]1C[C@H](n2c(Cc3csnn3)nc3cnc4ccc(C#N)cc4c32)CCO1] | 391.0 |

TABLE 2-continued

| Example Number | Structure | Mass spectrum m/z [M + H]+ |
|---|---|---|
| 196 | ENT-1 | 394.0[5] |
| 197 | ENT-2 | 394.0[5] |
| 198 | 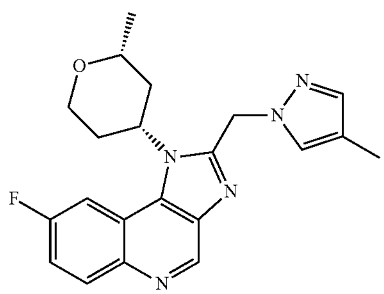 [SMILES: Cc1cnn(Cc2nc3cnc4ccc(F)cc4c3n2[C@@H]2CCO[C@H](C)C2)c1] | 380.4 |
| 199 | 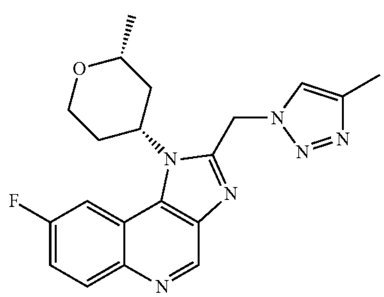 [SMILES: Cc1cn(Cc2nc3cnc4ccc(F)cc4c3n2[C@@H]2CCO[C@H](C)C2)nn1] | 381.5 |
| 200 | 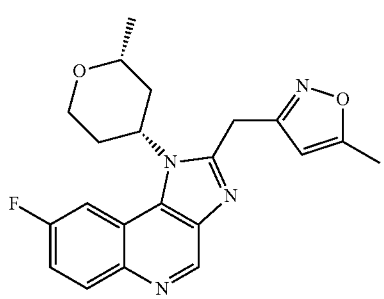 [SMILES: Cc1cc(Cc2nc3cnc4ccc(F)cc4c3n2[C@@H]2CCO[C@H](C)C2)no1] | 381.4 |

TABLE 2-continued
| Example Number | Structure | Mass spectrum m/z [M + H]+ |
|---|---|---|
| 201 | 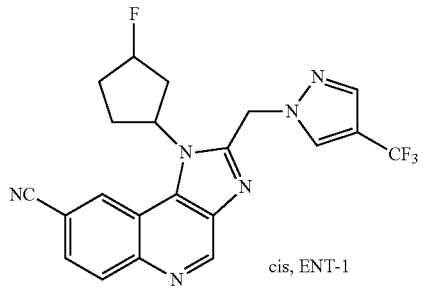 [SMILES: N#Cc1ccc2ncc3nc(Cn4cc(C(F)(F)F)cn4)n(C4CCC(F)C4)c3c2c1] cis, ENT-1 | 428.9 |
| 202 | 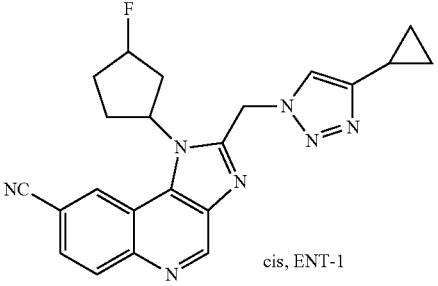 [SMILES: N#Cc1ccc2ncc3nc(Cn4cc(C5CC5)nn4)n(C4CCC(F)C4)c3c2c1] cis, ENT-1 | 401.9 |
| 203 | 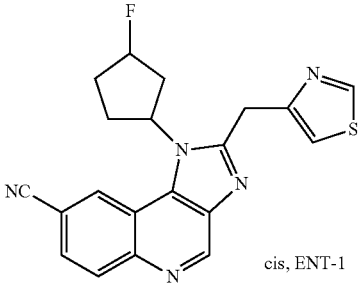 [SMILES: N#Cc1ccc2ncc3nc(Cc4cscn4)n(C4CCC(F)C4)c3c2c1] cis, ENT-1 | 377.9 |
| 204 | 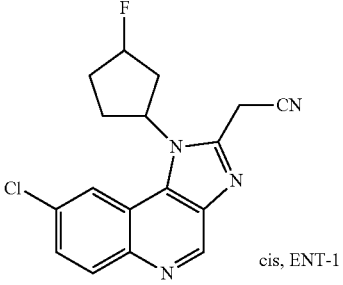 [SMILES: N#CCc1nc2cnc3ccc(Cl)cc3c2n1C1CCC(F)C1] cis, ENT-1 | 329.0 (chlorine isotope pattern observed) |
| 205 | 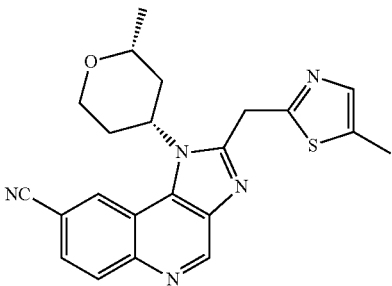 [SMILES: Cc1cnc(Cc2nc3cnc4ccc(C#N)cc4c3n2[C@@H]2CCO[C@H](C)C2)s1] | 404.0 |

TABLE 2-continued
| Example Number | Structure | Mass spectrum m/z [M + H]+ |
|---|---|---|
| 206 | 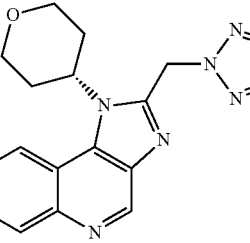 | 398.0 (chlorine isotope pattern observed) |
| 207 | 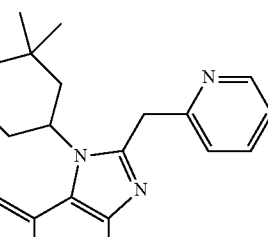 ENT-2 | 428.1[6] |
| 208 | 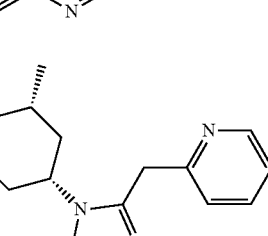 | 452.0 |
| 209 | 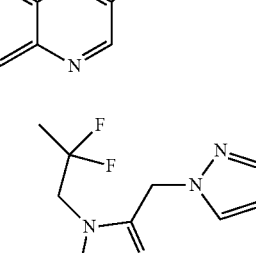 | 381.0[7] |
| 210 | 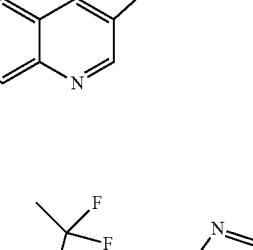 | 383.0[7] |

TABLE 2-continued
| Example Number | Structure | Mass spectrum m/z [M + H]+ |
|---|---|---|
| 211 | 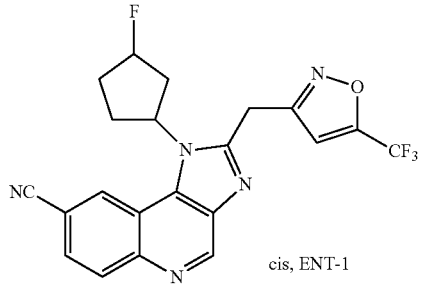 [SMILES: N#Cc1ccc2ncc3nc(Cc4cc(C(F)(F)F)on4)n(C4CCC(F)C4)c3c2c1] cis, ENT-1 | 430.5[8] |
| 212 | 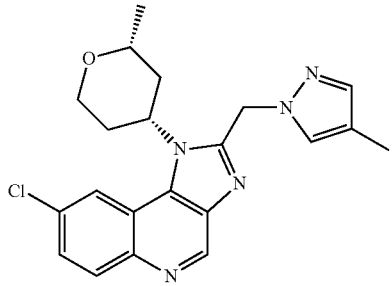 [SMILES: Cc1cnn(Cc2nc3cnc4ccc(Cl)cc4c3n2[C@@H]2CCO[C@H](C)C2)c1] | 396.1 (chlorine isotope pattern observed) |
| 213 | 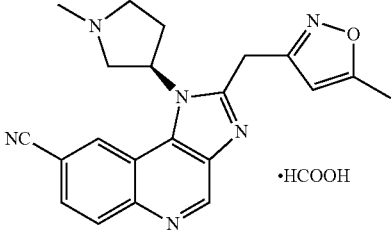 [SMILES: Cc1cc(Cc2nc3cnc4ccc(C#N)cc4c3n2[C@@H]2CCN(C)C2)no1 ; "·HCOOH"] ·HCOOH | 373 |
| 214 | 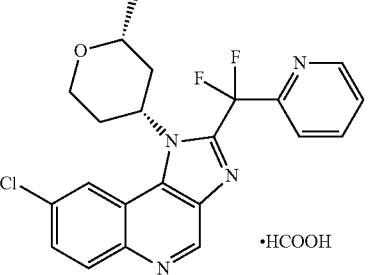 ·HCOOH | 429 |
| 215 | 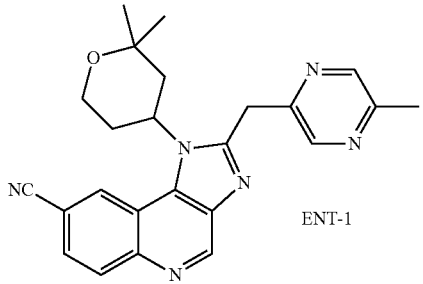 [SMILES: Cc1cnc(Cc2nc3cnc4ccc(C#N)cc4c3n2C2CCOC(C)(C)C2)cn1] ENT-1 | 413.1[9] |

TABLE 2-continued
| Example Number | Structure | Mass spectrum m/z [M + H]+ |
|---|---|---|
| 216 | 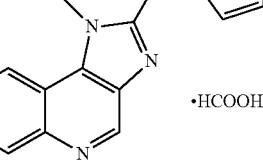 ·HCOOH | 344 |
| 217 | 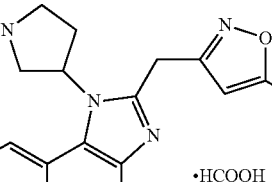 ·HCOOH | 373 |
| 218 | 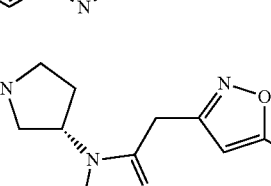 ·HCOOH | 373 |
| 219 | 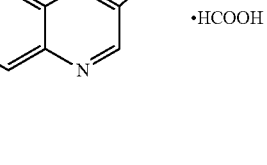 ·HCOOH | 402 |
| 220 | 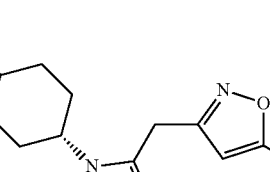 ·HCOOH | 418 |

TABLE 2-continued

| Example Number | Structure | Mass spectrum m/z [M + H]+ |
|---|---|---|
| 221 | 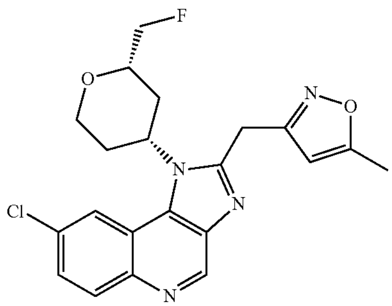 [SMILES: Cc1cc(Cc2nc3cnc4ccc(Cl)cc4c3n2[C@@H]2CCO[C@H](CF)C2)no1] | 414.8 (chlorine isotope pattern observed)[10] |
| 222 | 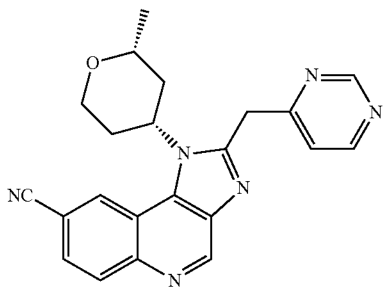 [SMILES: C[C@@H]1C[C@H](n2c(Cc3ccncn3)nc3cnc4ccc(C#N)cc4c32)CCO1] | 385 |
| 223 | 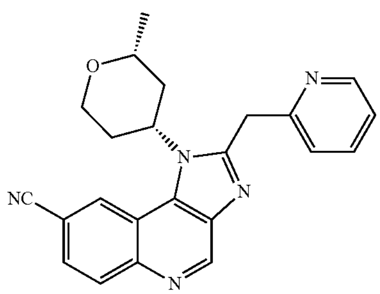 [SMILES: C[C@@H]1C[C@H](n2c(Cc3ccccn3)nc3cnc4ccc(C#N)cc4c32)CCO1] | 384 |
| 224 | 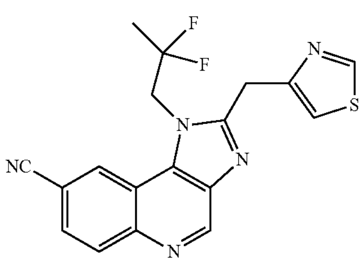 [SMILES: CC(F)(F)Cn1c(Cc2cscn2)nc2cnc3ccc(C#N)cc3c21] | 370.0 |
| 225 | 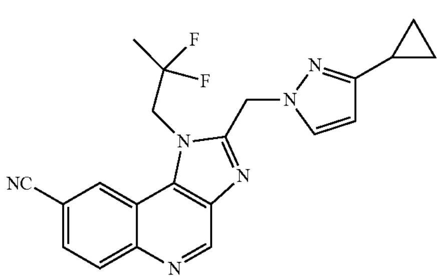 [SMILES: CC(F)(F)Cn1c(Cn2ccc(C3CC3)n2)nc2cnc3ccc(C#N)cc3c21] | 393.1 |

US 10,039,753 B2
TABLE 2-continued
| Example Number | Structure | Mass spectrum m/z [M + H]+ |
|---|---|---|
| 226 | 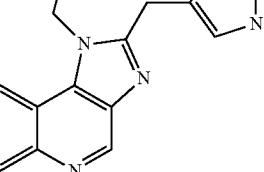 | 424.0 |
| 227 | 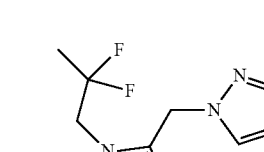 | 421.4 |
| 228 | 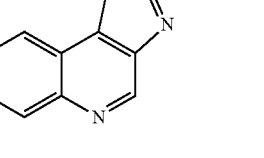 | 353.8 |
| 229 | 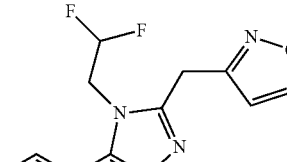 ·HCOOH | 374 |
| 230 | 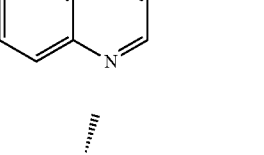 ·HCOOH | 402 |

TABLE 2-continued

| Example Number | Structure | Mass spectrum m/z [M + H]+ |
|---|---|---|
| 231 | (structure) ·HCOOH | 390 |
| 232 | (structure) | 398.1 |
| 233 | (structure) ·HCOOH | 387 |
| 234 | (structure) ·HCOOH | 404 |
| 235 | (structure) ·HCOOH | 387 |

TABLE 2-continued

| Example Number | Structure | Mass spectrum m/z [M + H]+ |
|---|---|---|
| 236 | (structure) ·HCOOH | 420 |
| 237 | (structure) DIAST-1 | 401.3 (chlorine isotope pattern observed)[11] |
| 238 | (structure) DIAST-2 | 401.3 (chlorine isotope pattern observed)[11] |
| 239 | (structure) ·HCOOH | 402 |
| 240 | (structure) ·HCOOH | 388 |

TABLE 2-continued

| Example Number | Structure | Mass spectrum m/z [M + H]+ |
|---|---|---|
| 241 | (structure) •HCOOH | 376 |
| 242 | (structure) •HCOOH (+/-) | 388 |
| 243 | (structure) •HCOOH | 350 |
| 244 | (structure) •HCOOH | 408 |
| 245 | (structure) •HCOOH (+/-) | 376 |

TABLE 2-continued

| Example Number | Structure | Mass spectrum m/z [M + H]+ |
|---|---|---|
| 246 | (structure) ·HCOOH | 394 |
| 247 | (structure) ·HCOOH | 402 |
| 248 | (structure) | 368.2 |
| 249 | (structure) ·CF₃COOH | 394.3 (chlorine isotope pattern observed) |
| 250 | (structure) ·HCOOH | 393 |

1. Examples 146 and 147 were synthesized as the racemic mixture, and then separated into individual enantiomers using supercritical fluid chromatography (Column: Phenomenex Lux Amylose-1, 5 μm; Mobile phase: 85:15 carbon dioxide/ethanol). Example 146 was the first-eluting enantiomer, followed by Example 147.

2. Examples 168 and 169 were synthesized as the racemic mixture, and then separated into individual enantiomers using supercritical fluid chromatography [Column: Phenomenex ChiralCel OD-H, 5 μm; Mobile phase: 85:15 carbon dioxide/(methanol containing 0.05% ammonium hydroxide)]. Example 168 was the first-eluting enantiomer, followed by Example 169.

3. Example 170 was isolated from the corresponding racemic mixture via supercritical fluid chromatography [Column: Chiral Technologies Chiralpak AD-H, 5 μm; Mobile phase: 85:15 carbon dioxide/(methanol containing 0.2% ammonium hydroxide)]. Example 170 was the first-eluting enantiomer.

4. Examples 176 and 177 were synthesized as the racemic mixture, and then separated into individual enantiomers using supercritical fluid chromatography [Column: Chiral Technologies Chiralpak AS, 5 μm; Mobile phase: 85:15 carbon dioxide/(2-propanol containing 0.1% ammonium hydroxide)]. Example 176 was the first-eluting enantiomer, followed by Example 177.

5. Examples 196 and 197 were synthesized as the racemic mixture. Separation and purification required two chromatographic steps: supercritical fluid chromatography [Column: Phenomenex Lux Cellulose-2, 10 μm; Mobile phase: 3:2 carbon dioxide/(methanol containing 0.1% ammonium hydroxide)] provided Example 196 as the first-eluting enantiomer and Example 197 as the second-eluting enantiomer. Further purification was effected using reversed phase HPLC (Column: Waters XBridge C18 OBD, 5 μm; Mobile phase A: water containing 0.05% ammonium hydroxide; Mobile phase B: acetonitrile; Gradient: 25% to 55% B).

6. Example 207 was isolated from the corresponding racemic mixture via supercritical fluid chromatography [Column: Chiral Technologies Chiralpak AD, 5 μm; Mobile phase: 3:1 carbon dioxide/(ethanol containing 0.1% ammonium hydroxide)]. Example 207 was the second-eluting enantiomer.

7. Reaction of C61 with 2,2-difluoropropan-1-amine and N,N-diisopropylethylamine provided 4-[(2,2-difluoropropyl)amino]-3-nitroquinoline-6-carbonitrile, which was reduced with iron in the presence of hydrochloric acid to afford the requisite intermediate 3-amino-4-[(2,2-difluoropropyl)amino]quinoline-6-carbonitrile.

8. Example 211 was isolated from the corresponding racemic mixture via supercritical fluid chromatography [Column: Phenomenex Lux Amylose-1, 5 μm; Mobile phase: 85:15 carbon dioxide/(methanol containing 0.2% ammonium hydroxide)]. Example 211 was the first-eluting enantiomer.

9. Example 215 was isolated from the corresponding racemic mixture via supercritical fluid chromatography. Under analytical HPLC [Column: Phenomenex Lux Cellulose-2, 3 μm; Mobile phase: 3:2 carbon dioxide/(2-propanol containing 0.05% diethylamine); Flow rate: 2.5 mL/minute], Example 215 was the first-eluting enantiomer.

10. Example 221 was synthesized from Example 137 via fluorination with (diethylamino)sulfur trifluoride.

11. Examples 237 and 238 were synthesized as the diastereomeric mixture, and then separated into individual diastereomers using supercritical fluid chromatography [Column: Phenomenex ChiralCel OJ-H, 5 μm; Mobile phase: 9:1 carbon dioxide/(methanol containing 0.2% ammonium hydroxide)]. Example 237 was the first-eluting diastereomer, followed by Example 238.

Biological Assays

LRRK2 Assay, Format 1

LRRK2 kinase activity was measured using Lantha Screen technology from Invitrogen. GST-tagged truncated LRRK2 from Invitrogen (Cat # PV4874) was incubated with a fluorescein-labeled peptide substrate based upon ezrin/radixin/moesin (ERM), also known as LRRKtide (Invitrogen cat # PR8976A), in the presence of a dose response of compound. Upon completion, the assay was stopped and detected with a terbium labeled anti-phospho-ERM antibody (Invitrogen, cat # PR8975A). The assay was carried out under the following protocol: 3 μL of a working solution of substrate (233 nM LRRKtide, 117 μM ATP) prepared in assay buffer (50 mM HEPES, pH 7.5, 3 mM $MgCl_2$, with 2 mM DTT and 0.01% Brij35 added fresh) was added to a low volume Greiner 384-well plate. The compound dose response was prepared by diluting compound to a top concentration of 3.16 mM in 100% DMSO and serial diluted by half-log in DMSO 11 times. Aliquots (3.5 μL) of the 100% DMSO dose response were mixed with 46.5 μL water then 1 μL of this mixture was added to the 3 μL substrate mix in the 384-well plate. The kinase reaction was started with 3 μL of a working solution of LRRK2 enzyme at a concentration of 4 μg/mL. The final reaction concentrations were 100 nM LRRKtide, 50 μM ATP, 1.7 μg/mL LRRK2 enzyme and a compound dose response with a top dose of 32 μM. The reaction was allowed to progress at room temperature for two hours and then stopped with the addition of 7 μL of detection buffer (20 mM Tris pH 7.6, 0.01% NP-40, 0.02% $NaN_3$, 6 mM EDTA with 2 nM terbium labeled anti-phospho-ERM). After an incubation of 1 hour at room temperature, the plate was read on an Envision with an excitation wavelength of 340 nm and a reading emission at both 520 nm and 495 nm. The ratio of the 520 nm and 495 nm emission was used to analyze the data.

Inhibition of mutant G2019S LRRK2 (Invitrogen cat # PV4881) was measured in the exact same method. All final concentrations of substrate ATP and enzyme were the same. However, since the mutant enzyme is more active the reaction time was reduced to 90 minutes to ensure that inhibition was measured at steady state before any substrate depletion could occur.

LRRK2 Assay, Format 2

LRRK2 kinase activity was measured using Lantha Screen technology from Invitrogen. GST-tagged truncated LRRK2 from Invitrogen (Cat # PV4874) was incubated with a fluorescein-labeled peptide substrate based upon ezrin/radixin/moesin (ERM), also known as LRRKtide (Invitrogen cat # PR8976A), in the presence of a dose response of compound. Upon completion, the assay was stopped and detected with a terbium labeled anti-phospho-ERM antibody (Invitrogen, cat # PR8975A). The assay was carried out under the following protocol: The compound dose response was prepared by diluting compound to a top concentration of 0.3 mM in 100% DMSO and serial diluted by half-log in DMSO to give an 11 point curve, 100× final assay concentration. Using Echo acoustic dispensing, 60 nL of compound was transferred to a low volume Corning 384-well assay plate. 3 μL of a working solution of substrate (200 nM LRRKtide, 2000 mM ATP) prepared in assay buffer (50 mM HEPES, pH 7.5, 3 mM $MgCl_2$, with 2 mM DTT and 0.01%

Brij35 added fresh) was added to the 60 nL compound assay plate. The kinase reaction was started with 3 mL of a working solution of LRRK2 enzyme at a concentration of 4 mg/mL. The final reaction concentrations were 100 nM LRRKtide, 1000 mM ATP, 2 mg/mL LRRK2 enzyme and a compound dose response with a top dose of 3 mM. The reaction was allowed to progress at room temperature for 30 minutes and then stopped with the addition of 6 mL of detection buffer (20 mM Tris pH 7.6, 0.01% NP-40, 6 mM EDTA with 2 nM terbium labeled anti-phospho-ERM). After an incubation of 1 hour at room temperature, the plate was read on an Envision with an excitation wavelength of 340 nm and a reading emission at both 520 nm and 495 nm. The ratio of the 520 nm and 495 nm emission was used to analyze the data. Inhibition of mutant G2019S LRRK2 (Invitrogen cat # PV4881) was measured in the exact same method. All final concentrations of substrate ATP and enzyme were the same.

Tables 3 and 4, below, provide the LRRK2 $IC_{50}$ data for the compounds of the invention.

TABLE 3

| IUPAC name and biological data for Examples 1-92 | | | |
|---|---|---|---|
| Example or Compound Number | IUPAC Name | LRRK2, Format 1 WT $IC_{50}$ (nM)* | LRRK2, Format 1 G2019S $IC_{50}$ (nM)* |
| 1 | 8-methoxy-2-[(5-methyl-1,2-oxazol-3-yl)methyl]-1-[(2R,4R)-2-methyltetrahydro-2H-pyran-4-yl]-1H-imidazo[4,5-c]quinoline | 39.3 | 14.4 |
| C12 | 8-methoxy-2-[(5-methyl-1,2-oxazol-3-yl)methyl]-1-[(2S,4S)-2-methyltetrahydro-2H-pyran-4-yl]-1H-imidazo[4,5-c]quinoline | $1258^b$ | $478^b$ |
| 2 | 8-chloro-2-[(5-methoxypyridin-2-yl)methyl]-1-[(2R,4R)-2-methyltetrahydro-2H-pyran-4-yl]-1H-imidazo[4,5-c]quinoline | $6.8^a$ | $5.6^a$ |
| 3 | 2-[(5-methyl-1,2-oxazol-3-yl)methyl]-1-[(2R,4R)-2-methyltetrahydro-2H-pyran-4-yl]-1H-imidazo[4,5-c]quinoline-8-carbonitrile | $4.9^a$ | $5.1^a$ |
| 4 | 8-chloro-2-[(5-methyl-1,2-oxazol-3-yl)methyl]-1-[(2R,4R)-2-methyltetrahydro-2H-pyran-4-yl]-1H-imidazo[4,5-c]quinoline | 8.3 | 4.9 |
| 5 | 8-chloro-2-[(5-methyl-1,2,4-oxadiazol-3-yl)methyl]-1-[(2R,4R)-2-methyltetrahydro-2H-pyran-4-yl]-1H-imidazo[4,5-c]quinoline | 4.6 | 2.7 |
| 6 | 8-bromo-1-[(1S,3R)-3-fluorocyclopentyl]-2-methyl-1H-imidazo[4,5-c]quinoline | $172^b$ | $168^b$ |
| 7 | 1-[(2R,4R)-2-methyltetrahydro-2H-pyran-4-yl]-2-(1,3-thiazol-4-ylmethyl)-1H-imidazo[4,5-c][1,5]naphthyridine | 22.4 | 22.0 |
| C29 | 1-[(2S,4S)-2-methyltetrahydro-2H-pyran-4-yl]-2-(1,3-thiazol-4-ylmethyl)-1H-imidazo[4,5-c][1,5]naphthyridine | $1510^b$ | $628^b$ |
| 8 | 8-chloro-2-(imidazo[2,1-b][1,3,4]thiadiazol-6-ylmethyl)-1-[(2R,4R)-2-methyltetrahydro-2H-pyran-4-yl]-1H-imidazo[4,5-c]quinoline | $4.4^a$ | $3.1^a$ |
| 9 | {8-chloro-1-[(2R,4R)-2-methyltetrahydro-2H-pyran-4-yl]-1H-imidazo[4,5-c]quinolin-2-yl}acetonitrile | 6.3 | 6.4 |
| 10 | 8-chloro-1-[(2R,4R)-2-methyltetrahydro-2H-pyran-4-yl]-2-(1,3-thiazol-4-ylmethyl)(4-$^2$H)-1H-imidazo[4,5-c]quinoline | $5.0^c$ | $3.0^c$ |
| 11 | 8-chloro-1-[(2R,4R)-2-methyltetrahydro-2H-pyran-4-yl]-2-[(4-methyl-1H-1,2,3-triazol-1-yl)methyl]-1H-imidazo[4,5-c]quinoline | $3.4^a$ | $2.6^a$ |
| 12 | 8-bromo-1-[(2R,4R)-2-methyltetrahydro-2H-pyran-4-yl]-2-(1,2-oxazol-3-ylmethyl)-1H-imidazo[4,5-c]quinoline | $4.5^a$ | $2.4^a$ |
| 13 | 8-chloro-1-[(2R,4R)-2-methyltetrahydro-2H-pyran-4-yl]-2-(1,2,4-oxadiazol-3-ylmethyl)-1H-imidazo[4,5-c]quinoline | 10.3 | 6.4 |
| 14 | 2-methyl-1-(tetrahydro-2H-pyran-4-yl)-1H-imidazo[4,5-c]quinoline-8-carbonitrile | 160 | 191 |
| 15 | 2-methyl-1-(cis-2-methyltetrahydro-2H-pyran-4-yl)-1H-imidazo[4,5-c]quinoline | 187 | 257 |

TABLE 3-continued

IUPAC name and biological data for Examples 1-92

| Example or Compound Number | IUPAC Name | LRRK2, Format 1 WT IC$_{50}$ (nM)* | LRRK2, Format 1 G2019S IC$_{50}$ (nM)* |
|---|---|---|---|
| 16 | 1-[(1R,3S)-3-fluorocyclopentyl]-2-(1,2-oxazol-3-ylmethyl)-1H-imidazo[4,5-c]quinoline | 158 | 184 |
| 17 | 8-chloro-2-methyl-1-(tetrahydro-2H-pyran-4-yl)-1H-imidazo[4,5-c]quinoline | 125[b] | 132[b] |
| 18 | 2-(1,2-oxazol-3-ylmethyl)-1-(tetrahydro-2H-pyran-4-yl)-1H-imidazo[4,5-c]quinoline | 153 | 250 |
| 19 | 2-methyl-1-(cis-2-methyltetrahydro-2H-pyran-4-yl)-1H-imidazo[4,5-c]quinoline-8-carbonitrile | 81.0 | 55.5 |
| 20 | 1-[(1S,3R)-3-fluorocyclopentyl]-2-methyl-1H-imidazo[4,5-c]quinoline-8-carbonitrile | 195[b] | 174[b] |
| 21 | 1-(cis-2-methyltetrahydro-2H-pyran-4-yl)-2-(1,2-oxazol-3-ylmethyl)-1H-imidazo[4,5-c]quinoline-8-carbonitrile | 7.5 | 4.5 |
| 22 | 1-[(2R,4R)-2-methyltetrahydro-2H-pyran-4-yl]-2-(1,2-oxazol-3-ylmethyl)-1H-imidazo[4,5-c]quinoline-8-carbonitrile | 5.2[a] | 3.9[a] |
| 23 | 1-(trans-2-methyltetrahydro-2H-pyran-4-yl)-2-(1,2-oxazol-3-ylmethyl)-1H-imidazo[4,5-c]quinoline-8-carbonitrile | 199[b] | 153[b] |
| 24 | 1-[(2S,4R)-2-methyltetrahydro-2H-pyran-4-yl]-2-(1,2-oxazol-3-ylmethyl)-1H-imidazo[4,5-c]quinoline-8-carbonitrile | 72.0 | 62.0 |
| 25 | 8-bromo-1-[(1S,3R)-3-fluorocyclopentyl]-2-(1,2-oxazol-3-ylmethyl)-1H-imidazo[4,5-c]quinoline, formate salt | 56.3 | 30.8 |
| 26 | 1-[(1R,3S)-3-fluorocyclopentyl]-2-(1H-1,2,4-triazol-1-ylmethyl)-1H-imidazo[4,5-c]quinoline | 162[b] | 155[b] |
| 27 | 1-[(1R,3S)-3-fluorocyclopentyl]-2-[(4-methyl-1H-1,2,3-triazol-1-yl)methyl]-1H-imidazo[4,5-c]quinoline, formate salt | 188[b] | 118[b] |
| 28 | 2-(1,3-benzoxazol-2-ylmethyl)-1-[(1R,3S)-3-fluorocyclopentyl]-1H-imidazo[4,5-c]quinoline | 153[b] | 157[b] |
| 29 | 2-(1,2-benzoxazol-3-ylmethyl)-1-(tetrahydro-2H-pyran-4-yl)-1H-imidazo[4,5-c]quinoline | 164[b] | 226[b] |
| 30 | 1-(tetrahydro-2H-pyran-4-yl)-2-(1H-1,2,4-triazol-1-ylmethyl)-1H-imidazo[4,5-c]quinoline | 120[b] | 146[b] |
| 31 | 2-[(2-methylimidazo[2,1-b][1,3]thiazol-6-yl)methyl]-1-(tetrahydro-2H-pyran-4-yl)-1H-imidazo[4,5-c]quinoline | 126[b] | 151[b] |
| 32 | 2-[(4-methyl-1H-1,2,3-triazol-1-yl)methyl]-1-(tetrahydro-2H-pyran-4-yl)-1H-imidazo[4,5-c]quinoline | 98.6 | 121 |
| 33 | 2-{[4-(methoxymethyl)-1H-1,2,3-triazol-1-yl]methyl}-1-(tetrahydro-2H-pyran-4-yl)-1H-imidazo[4,5-c]quinoline | 124[b] | 172[b] |
| 34 | 2-(1,3-benzoxazol-2-ylmethyl)-1-(tetrahydro-2H-pyran-4-yl)-1H-imidazo[4,5-c]quinoline | 111[b] | 139[b] |
| 35 | 1-(tetrahydro-2H-pyran-4-yl)-2-(1H-tetrazol-1-ylmethyl)-1H-imidazo[4,5-c]quinoline | 152[b] | 211[b] |
| 36 | 1-(tetrahydro-2H-pyran-4-yl)-2-(1,3-thiazol-4-ylmethyl)-1H-imidazo[4,5-c]quinoline, formate salt | 85.5 | 90.5 |
| 37 | 2-[(5-methoxypyridin-2-yl)methyl]-1-(tetrahydro-2H-pyran-4-yl)-1H-imidazo[4,5-c]quinoline | 133[b] | 143[b] |
| 38 | 2-[(2-methylimidazo[2,1-b][1,3,4]thiadiazol-6-yl)methyl]-1-(tetrahydro-2H-pyran-4-yl)-1H-imidazo[4,5-c]quinoline | 36.0 | 41.6 |

TABLE 3-continued

IUPAC name and biological data for Examples 1-92

| Example or Compound Number | IUPAC Name | LRRK2, Format 1 WT IC$_{50}$ (nM)* | LRRK2, Format 1 G2019S IC$_{50}$ (nM)* |
|---|---|---|---|
| 39 | 2-[(5-methyl-1,2-oxazol-3-yl)methyl]-1-(tetrahydro-2H-pyran-4-yl)-1H-imidazo[4,5-c]quinoline | 103[b] | 157[b] |
| 40 | 2-(1-{[1-(tetrahydro-2H-pyran-4-yl)-1H-imidazo[4,5-c]quinolin-2-yl]methyl}-1H-1,2,3-triazol-4-yl)propan-2-ol | 141[b] | 120[b] |
| 41 | 2-(1H-benzotriazol-1-ylmethyl)-1-(tetrahydro-2H-pyran-4-yl)-1H-imidazo[4,5-c]quinoline | 124 | 93.5 |
| 42 | 2-[(4-cyclopropyl-1H-1,2,3-triazol-1-yl)methyl]-1-(tetrahydro-2H-pyran-4-yl)-1H-imidazo[4,5-c]quinoline | 51.2 | 55.9 |
| 43 | 1-(tetrahydro-2H-pyran-4-yl)-2-{[4-(trifluoromethyl)-1H-pyrazol-1-yl]methyl}-1H-imidazo[4,5-c]quinoline | 119[b] | 110[b] |
| 44 | 2-{[4-(propan-2-yl)-1H-1,2,3-triazol-1-yl]methyl}-1-(tetrahydro-2H-pyran-4-yl)-1H-imidazo[4,5-c]quinoline | 62.5 | 72.2 |
| 45 | 2-(2H-indazol-2-ylmethyl)-1-(tetrahydro-2H-pyran-4-yl)-1H-imidazo[4,5-c]quinoline | 61.1 | 52.9 |
| 46 | 1-(2,2-difluorocyclohexyl)-2-(1,2-oxazol-3-ylmethyl)-1H-imidazo[4,5-c]quinoline | 186 | 90.8 |
| 47 | 1-(2,2-dimethyltetrahydro-2H-pyran-4-yl)-2-(1,2-oxazol-3-ylmethyl)-1H-imidazo[4,5-c]quinoline | 103 | 80.6 |
| 48 | 1-(4,4-difluorocyclohexyl)-2-(1,2-oxazol-3-ylmethyl)-1H-imidazo[4,5-c]quinoline | 194[b] | 118[b] |
| 49 | trans-3-[2-(1,2-oxazol-3-ylmethyl)-1H-imidazo[4,5-c]quinolin-1-yl]cyclohexanol | 152 | 81.2 |
| 50 | 1-cyclohexyl-2-(1,2-oxazol-3-ylmethyl)-1H-imidazo[4,5-c]quinoline | 127 | 57.7 |
| 51 | 8-chloro-2-[(5-methyl-1,2,4-oxadiazol-3-yl)methyl]-1-[(2S,4S)-2-methyltetrahydro-2H-pyran-4-yl]-1H-imidazo[4,5-c]quinoline | 109 | 49.3 |
| 52 | 8-chloro-1-[(2R,4R)-2-methyltetrahydro-2H-pyran-4-yl]-2-(1,2-oxazol-3-ylmethyl)-1H-imidazo[4,5-c]quinoline | 4.1 | 2.7 |
| 53 | 8-chloro-1-[(2R,4R)-2-methyltetrahydro-2H-pyran-4-yl]-2-(1,3-thiazol-4-ylmethyl)-1H-imidazo[4,5-c]quinoline | 3.1 | 1.9 |
| 54 | 8-fluoro-1-[(2R,4R)-2-methyltetrahydro-2H-pyran-4-yl]-2-(1,2-oxazol-3-ylmethyl)-1H-imidazo[4,5-c]quinoline | 8.8[a] | 8.0[a] |
| 55 | 8-fluoro-1-[(2R,4R)-2-methyltetrahydro-2H-pyran-4-yl]-2-(1,3-thiazol-4-ylmethyl)-1H-imidazo[4,5-c]quinoline | 5.7[a] | 5.0[a] |
| 56 | 8-bromo-1-(cis-2-methyltetrahydro-2H-pyran-4-yl)-2-(1,3-thiazol-4-ylmethyl)-1H-imidazo[4,5-c]quinoline | 10.0[a] | 5.2[a] |
| 57 | 1-[(2R,4R)-2-methyltetrahydro-2H-pyran-4-yl]-2-(1,3-thiazol-4-ylmethyl)-1H-imidazo[4,5-c]quinoline-8-carbonitrile | 6.1 | 4.0 |
| 58 | 8-bromo-2-[(5-methyl-1,2-oxazol-3-yl)methyl]-1-(cis-2-methyltetrahydro-2H-pyran-4-yl)-1H-imidazo[4,5-c]quinoline | 16.8 | 8.2 |
| 59 | 8-bromo-1-[(2R,4r,6S)-2,6-dimethyltetrahydro-2H-pyran-4-yl]-2-(1,2-oxazol-3-ylmethyl)-1H-imidazo[4,5-c]quinoline | 176 | 52.0 |
| 60 | 8-bromo-1-[(-[(2R,4r,6S)-2,6-dimethyltetrahydro-2H-pyran-4-yl]-2-(1,3-thiazol-4-ylmethyl)-1H-imidazo[4,5-c]quinoline | 35.1 | 11.5 |
| 61 | 1-[(2R,4r,6S)-2,6-dimethyltetrahydro-2H-pyran-4-yl]-2-(1,3-thiazol-4-ylmethyl)-1H-imidazo[4,5-c]quinoline-8-carbonitrile | 181 | 67.9 |

TABLE 3-continued

IUPAC name and biological data for Examples 1-92

| Example or Compound Number | IUPAC Name | LRRK2, Format 1 WT IC$_{50}$ (nM)* | LRRK2, Format 1 G2019S IC$_{50}$ (nM)* |
|---|---|---|---|
| 62 | 8-methoxy-1-[(2R,4R)-2-methyltetrahydro-2H-pyran-4-yl]-2-(1,2-oxazol-3-ylmethyl)-1H-imidazo[4,5-c]quinoline | 41.9[a] | 12.8[a] |
| 63 | 8-chloro-2-(1,2-oxazol-3-ylmethyl)-1-(tetrahydro-2H-pyran-4-yl)-1H-imidazo[4,5-c]quinoline, formate salt | 16.1 | 12.1 |
| 64 | 8-chloro-2-(imidazo[2,1-b][1,3,4]thiadiazol-6-ylmethyl)-1-[(2S,4S)-2-methyltetrahydro-2H-pyran-4-yl]-1H-imidazo[4,5-c]quinoline | 279 | 132 |
| 65 | 8-chloro-1-[(2R,4R)-2-methyltetrahydro-2H-pyran-4-yl]-2-(1H-1,2,4-triazol-1-ylmethyl)-1H-imidazo[4,5-c]quinoline | 2.8 | 1.8 |
| 66 | 8-bromo-1-(cis-2-ethyltetrahydro-2H-pyran-4-yl)-2-(1,2-oxazol-3-ylmethyl)-1H-imidazo[4,5-c]quinoline | 32.5 | 16.4 |
| 67 | 1-[(2R,4R)-2-ethyltetrahydro-2H-pyran-4-yl]-2-(1,2-oxazol-3-ylmethyl)-1H-imidazo[4,5-c]quinoline-8-carbonitrile | 5.8 | 4.0 |
| 68 | 1-[(2R,4R)-2-methyltetrahydro-2H-pyran-4-yl]-2-(1,2-oxazol-3-ylmethyl)-1H-imidazo[4,5-c][1,5]naphthyridine | 23.6 | 19.2 |
| 69 | 2-(imidazo[2,1-b][1,3,4]thiadiazol-6-ylmethyl)-1-(tetrahydro-2H-pyran-4-yl)-1H-imidazo[4,5-c]quinoline | 78.2 | 82.4 |
| 70 | 1-(2,2-dimethyltetrahydro-2H-pyran-4-yl)-8-fluoro-2-[(5-methoxypyridin-2-yl)methyl]-1H-imidazo[4,5-c]quinoline | 77.7 | 66.5 |
| 71 | 2-[(2-chloroimidazo[2,1-b][1,3]thiazol-6-yl)methyl]-1-(tetrahydro-2H-pyran-4-yl)-1H-imidazo[4,5-c]quinoline, trifluoroacetate salt | 106[b] | 120[b] |
| 72 | 1-(2,2-dimethyltetrahydro-2H-pyran-4-yl)-2-(1,3-thiazol-4-ylmethyl)-1H-imidazo[4,5-c]quinoline, trifluoroacetate salt | 156[b] | 170[b] |
| 73 | 1-(2,2-dimethyltetrahydro-2H-pyran-4-yl)-2-(imidazo[2,1-b][1,3,4]thiadiazol-6-ylmethyl)-1H-imidazo[4,5-c]quinoline, trifluoroacetate salt | 76.3 | 98.4 |
| 74 | 8-fluoro-1-(tetrahydro-2H-pyran-4-yl)-2-{[4-(trifluoromethyl)-1H-1,2,3-triazol-1-yl]methyl}-1H-imidazo[4,5-c]quinoline, trifluoroacetate salt | 112 | 102 |
| 75 | 8-fluoro-2-(1,2-oxazol-3-ylmethyl)-1-(tetrahydro-2H-pyran-4-yl)-1H-imidazo[4,5-c]quinoline, trifluoroacetate salt | 130[b] | 155[b] |
| 76 | 8-fluoro-2-(2H-indazol-2-ylmethyl)-1-(tetrahydro-2H-pyran-4-yl)-1H-imidazo[4,5-c]quinoline, trifluoroacetate salt | 67.5 | 54.5 |
| 77 | 8-fluoro-1-(tetrahydro-2H-pyran-4-yl)-2-(1,3-thiazol-4-ylmethyl)-1H-imidazo[4,5-c]quinoline, trifluoroacetate salt | 74.6 | 62.5 |
| 78 | 8-fluoro-1-(tetrahydro-2H-pyran-4-yl)-2-{[4-(trifluoromethyl)-1H-pyrazol-1-yl]methyl}-1H-imidazo[4,5-c]quinoline, trifluoroacetate salt | 145 | 115 |
| 79 | 2-[(4-cyclopropyl-1H-1,2,3-triazol-1-yl)methyl]-1-(2,2-dimethyltetrahydro-2H-pyran-4-yl)-8-fluoro-1H-imidazo[4,5-c]quinoline, trifluoroacetate salt | 53.8 | 47.3 |
| 80 | 1-(2,2-dimethyltetrahydro-2H-pyran-4-yl)-8-fluoro-2-(1,3-thiazol-4-ylmethyl)-1H-imidazo[4,5-c]quinoline, trifluoroacetate salt | 52.1 | 39.5 |
| 81 | 1-(2,2-dimethyltetrahydro-2H-pyran-4-yl)-8-fluoro-2-{[4-(trifluoromethyl)-1H-pyrazol-1-yl]methyl}-1H-imidazo[4,5-c]quinoline, trifluoroacetate salt | 159[b] | 121[b] |

TABLE 3-continued

IUPAC name and biological data for Examples 1-92

| Example or Compound Number | IUPAC Name | LRRK2, Format 1 WT IC$_{50}$ (nM)* | LRRK2, Format 1 G2019S IC$_{50}$ (nM)* |
|---|---|---|---|
| 82 | 8-fluoro-2-(imidazo[2,1-b][1,3,4]thiadiazol-6-ylmethyl)-1-(tetrahydro-2H-pyran-4-yl)-1H-imidazo[4,5-c]quinoline, trifluoroacetate salt | 17.6 | 16.2 |
| 83 | 1-(2,2-dimethyltetrahydro-2H-pyran-4-yl)-8-fluoro-2-[(2-methylimidazo[2,1-b][1,3,4]thiadiazol-6-yl)methyl]-1H-imidazo[4,5-c]quinoline, trifluoroacetate salt | 25.4 | 21.2 |
| 84 | 1-(2,2-dimethyltetrahydro-2H-pyran-4-yl)-8-fluoro-2-(1,2-oxazol-3-ylmethyl)-1H-imidazo[4,5-c]quinoline, trifluoroacetate salt | 31.4 | 24.9 |
| 85 | 8-chloro-1-[(2R,4R)-2-methyltetrahydro-2H-pyran-4-yl]-2-(1,3-thiazol-4-ylmethyl)-1H-imidazo[4,5-c]quinolin-4-amine, trifluoroacetate salt | 12.3 | 10.0 |
| 86 | 8-fluoro-2-(imidazo[2,1-b][1,3,4]thiadiazol-6-ylmethyl)-1-(cis-2-methyltetrahydro-2H-pyran-4-yl)-1H-imidazo[4,5-c]quinoline | 7.6 | 5.6 |
| 87 | 8-methoxy-2-[(5-methyl-1,2,4-oxadiazol-3-yl)methyl]-1-[(2R,4R)-2-methyltetrahydro-2H-pyran-4-yl]-1H-imidazo[4,5-c]quinoline | 111 | 38.8 |
| 88 | 8-methoxy-1-[(2R,4R)-2-methyltetrahydro-2H-pyran-4-yl]-2-[(4-methyl-1H-1,2,3-triazol-1-yl)methyl]-1H-imidazo[4,5-c]quinoline | 18.0 | 7.5 |
| 89 | 8-methoxy-1-[(2R,4R)-2-methyltetrahydro-2H-pyran-4-yl]-2-(1,3-thiazol-4-ylmethyl)-1H-imidazo[4,5-c]quinoline | 34.0 | 14.3 |
| 90 | 2-(imidazo[2,1-b][1,3,4]thiadiazol-6-ylmethyl)-8-methoxy-1-[(2R,4R)-2-methyltetrahydro-2H-pyran-4-yl]-1H-imidazo[4,5-c]quinoline | 14.8 | 6.4 |
| 91 | [cis-4-(2-methyl-1H-imidazo[4,5-c]quinolin-1-yl)tetrahydro-2H-pyran-2-yl]acetonitrile | 18.7 | 12.2 |
| 92 | 8-chloro-2-[(5-methyl-1,3-oxazol-2-yl)methyl]-1-[(2R,4R)-2-methyltetrahydro-2H-pyran-4-yl]-1H-imidazo[4,5-c]quinoline | 16.2 | 11.0 |

*Geometric mean of 2-4 determinations unless otherwise indicated
$^a$IC$_{50}$ value represents the geometric mean of ≥5 determinations.
$^b$IC$_{50}$ value derived from a single determination.
$^c$This value was determined on the trifluoroacetate salt of the Example.

The Examples presented in Table 4 may be prepared using the methods illustrated in the syntheses of Examples 1-92, either alone or in combination with techniques generally known in the art.

TABLE 4

IUPAC name and biological data for Examples 93-250

| Example or Compound Number | IUPAC Name | LRRK2, Format 1 WT IC$_{50}$ (nM)* | LRRK2, Format 1 G2019S IC$_{50}$ (nM)* | LRRK2, Format 2 WT IC$_{50}$ (nM)* | LRRK2, Format 2 G2019S IC$_{50}$ (nM)* |
|---|---|---|---|---|---|
| 93 | 8-chloro-1-(cis-3-fluorocyclopentyl)-2-[(4-methyl-1H-1,2,3-triazol-1-yl)methyl]-1H-imidazo[4,5-c]quinoline, ENT-1 | | | 5.62 | 8.18 |

TABLE 4-continued

IUPAC name and biological data for Examples 93-250

| Example or Compound Number | IUPAC Name | LRRK2, Format 1 WT IC$_{50}$ (nM)* | LRRK2, Format 1 G2019S IC$_{50}$ (nM)* | LRRK2, Format 2 WT IC$_{50}$ (nM)* | LRRK2, Format 2 G2019S IC$_{50}$ (nM)* |
|---|---|---|---|---|---|
| C55 | 8-chloro-1-(cis-3-fluorocyclopentyl)-2-[(4-methyl-1H-1,2,3-triazol-1-yl)methyl]-1H-imidazo[4,5-c]quinoline, ENT-2 | | | 18.2 | 22.7 |
| 94 | 1-(cis-3-fluorocyclopentyl)-2-[(4-methyl-1H-pyrazol-1-yl)methyl]-1H-imidazo[4,5-c]quinoline-8-carbonitrile, ENT-1 | | | 6.33[a] | 6.01[a] |
| C58 | 1-(cis-3-fluorocyclopentyl)-2-[(4-methyl-1H-pyrazol-1-yl)methyl]-1H-imidazo[4,5-c]quinoline-8-carbonitrile, ENT-2 | | | 21.9 | 25.6 |
| 95 | 2-[(3-methyl-1,2-oxazol-5-yl)methyl]-1-[(2R,4R)-2-methyltetrahydro-2H-pyran-4-yl]-1H-imidazo[4,5-c]quinoline-8-carbonitrile | | | 5.36 | 6.00 |
| 96 | 2-[(5-methoxypyridin-2-yl)methyl]-1-[(2R,4R)-2-methyltetrahydro-2H-pyran-4-yl]-1H-imidazo[4,5-c]quinoline-8-carbonitrile, formate salt | | | 6.31 | 4.65 |
| 97 | 1-[(1R,3S)-3-fluorocyclopentyl]-2-[(5-methyl-1,2-oxazol-3-yl)methyl]-1H-imidazo[4,5-c]quinoline-8-carbonitrile | | | 5.14[a] | 7.79[a] |
| C66 | 1-[(1S,3R)-3-fluorocyclopentyl]-2-[(5-methyl-1,2-oxazol-3-yl)methyl]-1H-imidazo[4,5-c]quinoline-8-carbonitrile | | | 29.8[a] | 42.2[a] |
| 98 | 1-[(2R,4R)-2-methyltetrahydro-2H-pyran-4-yl]-2-(pyrazin-2-ylmethyl)-1H-imidazo[4,5-c]quinoline-8-carbonitrile, formate salt | | | 7.56 | 6.16 |
| 99 | 8-chloro-1-[(2R,4R)-2-methyltetrahydro-2H-pyran-4-yl]-2-{[4-(trifluoromethyl)-1H-1,2,3-triazol-1-yl]methyl}-1H-imidazo[4,5-c]quinoline, formate salt | | | 5.84 | 5.42 |
| 100 | 8-chloro-2-[(5-methylpyridin-2-yl)methyl]-1-[(2R,4R)-2-methyltetrahydro-2H-pyran-4-yl]-1H-imidazo[4,5-c]quinoline | | | 4.74 | 5.01 |
| C73 | 1-(cis-3-fluorocyclopentyl)-2-[(4-methyl-1H-1,2,3-triazol-1-yl)methyl]-1H-imidazo[4,5-c]quinoline-8-carbonitrile, ENT-1 | | | 20.4 | 26.1 |
| 101 | 1-(cis-3-fluorocyclopentyl)-2-[(4-methyl-1H-1,2,3-triazol-1-yl)methyl]-1H-imidazo[4,5-c]quinoline-8-carbonitrile, ENT-2 | | | 4.94 | 8.61 |
| 102 | 8-chloro-2-[(6-methylpyrimidin-4-yl)methyl]-1-[(2R,4R)-2-methyltetrahydro-2H-pyran-4-yl]-1H-imidazo[4,5-c]quinoline | | | 6.00 | 7.05 |

TABLE 4-continued

IUPAC name and biological data for Examples 93-250

| Example or Compound Number | IUPAC Name | LRRK2, Format 1 WT IC$_{50}$ (nM)* | LRRK2, Format 1 G2019S IC$_{50}$ (nM)* | LRRK2, Format 2 WT IC$_{50}$ (nM)* | LRRK2, Format 2 G2019S IC$_{50}$ (nM)* |
|---|---|---|---|---|---|
| 103 | 8-chloro-1-[(2R,4R)-2-methyltetrahydro-2H-pyran-4-yl]-2-[(4-methyl-2H-1,2,3-triazol-2-yl)methyl]-1H-imidazo[4,5-c]quinoline | | | 11.2 | 10.6 |
| 104 | 8-chloro-2-[(5-methylpyrazin-2-yl)methyl]-1-[(2R,4R)-2-methyltetrahydro-2H-pyran-4-yl]-1H-imidazo[4,5-c]quinoline | | | 7.00 | 6.14 |
| 105 | 8-chloro-1-[(2R,4R)-2-methyltetrahydro-2H-pyran-4-yl]-2-{[5-(trifluoromethyl)pyrazin-2-yl]methyl}-1H-imidazo[4,5-c]quinoline | | | 10.2 | 10.8 |
| 106 | 1-[(2R,4R)-2-methyltetrahydro-2H-pyran-4-yl]-2-[(4-methyl-1H-1,2,3-triazol-1-yl)methyl]-1H-imidazo[4,5-c]quinoline-8-carbonitrile | 3.24 | 2.14 | 11.6 | 11.8 |
| 107 | 8-chloro-1-[(2R,4R)-2-methyltetrahydro-2H-pyran-4-yl]-2-[(1-methyl-1H-1,2,3-triazol-4-yl)methyl]-1H-imidazo[4,5-c]quinoline | 2.03 | 1.89 | 6.08 | 5.76 |
| 108 | 2-[(5-methylpyrazin-2-yl)methyl]-1-[(2R,4R)-2-methyltetrahydro-2H-pyran-4-yl]-1H-imidazo[4,5-c]quinoline-8-carbonitrile | | | 9.54 | 8.41 |
| 109 | 1-(cis-3-fluorocyclopentyl)-2-[(5-methylpyrazin-2-yl)methyl]-1H-imidazo[4,5-c]quinoline-8-carbonitrile, ENT-1 | | | 5.21 | 7.11 |
| C89 | 1-(cis-3-fluorocyclopentyl)-2-[(5-methylpyrazin-2-yl)methyl]-1H-imidazo[4,5-c]quinoline-8-carbonitrile, ENT-2 | | | 18.8 | 20.5 |
| 110 | 8-chloro-2-[(4-methoxy-1H-pyrazol-1-yl)methyl]-1-[(2R,4R)-2-methyltetrahydro-2H-pyran-4-yl]-1H-imidazo[4,5-c]quinoline | | | 7.12 | 6.48[b] |
| 111 | 1-(2,2-difluorocyclohexyl)-2-[(5-methyl-1,2-oxazol-3-yl)methyl]-1H-imidazo[4,5-c]quinoline-8-carbonitrile, ENT-1 | | | 9.41 | 12.2[b] |
| C94 | 1-(2,2-difluorocyclohexyl)-2-[(5-methyl-1,2-oxazol-3-yl)methyl]-1H-imidazo[4,5-c]quinoline-8-carbonitrile, ENT-2 | | | 21.4 | 30.5[b] |
| 112 | 2-[(5-methyl-1,2,4-oxadiazol-3-yl)methyl]-1-[(3R)-1-methylpyrrolidin-3-yl]-1H-imidazo[4,5-c]quinoline-8-carbonitrile | | | 9.19 | 14.8[b] |
| 113 | 1-[(3R)-1-methylpyrrolidin-3-yl]-2-(pyrazin-2-ylmethyl)-1H-imidazo[4,5-c]quinoline-8-carbonitrile | | | 6.51 | 9.73[b] |

TABLE 4-continued

IUPAC name and biological data for Examples 93-250

| Example or Compound Number | IUPAC Name | LRRK2, Format 1 WT IC$_{50}$ (nM)* | LRRK2, Format 1 G2019S IC$_{50}$ (nM)* | LRRK2, Format 2 WT IC$_{50}$ (nM)* | LRRK2, Format 2 G2019S IC$_{50}$ (nM)* |
|---|---|---|---|---|---|
| 114 | 2-[(5-methyl-1,2,4-oxadiazol-3-yl)methyl]-1-[(2R,4R)-2-methyltetrahydro-2H-pyran-4-yl]-8-(trifluoromethyl)-1H-imidazo[4,5-c]quinoline | | | 3.29 | 2.15[b] |
| 115 | 8-chloro-2-[(3-methyl-1,2-oxazol-5-yl)methyl]-1-[(2R,4R)-2-methyltetrahydro-2H-pyran-4-yl]-1H-imidazo[4,5-c]quinoline | | | 4.62 | 6.00[b] |
| 116 | 8-chloro-1-[(2R,4R)-2-methyltetrahydro-2H-pyran-4-yl]-2-[(5-methyl-1,3,4-thiadiazol-2-yl)methyl]-1H-imidazo[4,5-c]quinoline | | | 6.20 | 5.57[b] |
| 117 | 2-(cyanomethyl)-1-[(2R,4R)-2-methyltetrahydro-2H-pyran-4-yl]-1H-imidazo[4,5-c]quinoline-8-carbonitrile | | | 16.8 | 19.6 |
| 118 | 1-(cis-3-fluorocyclopentyl)-2-[(3-methyl-1,2-oxazol-5-yl)methyl]-1H-imidazo[4,5-c]quinoline-8-carbonitrile, ENT-1 | | | 4.15 | 6.19 |
| 119 | 1-[(2R,4R)-2-methyltetrahydro-2H-pyran-4-yl]-2-{[5-(trifluoromethyl)-1,2-oxazol-3-yl]methyl}-1H-imidazo[4,5-c]quinoline-8-carbonitrile | | | 7.53 | 8.21 |
| 120 | 1-[(2R,4R)-2-methyltetrahydro-2H-pyran-4-yl]-2-(1H-1,2,4-triazol-1-ylmethyl)-1H-imidazo[4,5-c]quinoline-8-carbonitrile, formate salt | | | 5.74 | 5.07 |
| 121 | 1-[(2R,4R)-2-methyltetrahydro-2H-pyran-4-yl]-2-(1H-pyrazol-1-ylmethyl)-1H-imidazo[4,5-c]quinoline-8-carbonitrile, formate salt | | | 6.19 | 5.61 |
| 122 | 2-[(2-cyclopropyl-1,3-oxazol-4-yl)methyl]-1-[(2R,4R)-2-methyltetrahydro-2H-pyran-4-yl]-1H-imidazo[4,5-c]quinoline-8-carbonitrile, formate salt | | | 4.30 | 3.70 |
| 123 | 2-[(5-methyl-1,2,4-oxadiazol-3-yl)methyl]-1-[(2R,4R)-2-methyltetrahydro-2H-pyran-4-yl]-1H-imidazo[4,5-c]quinoline-8-carbonitrile | | | 9.25 | 8.91 |
| 124 | 1-[(2R,4R)-2-methyltetrahydro-2H-pyran-4-yl]-2-(1H-tetrazol-1-ylmethyl)-1H-imidazo[4,5-c]quinoline-8-carbonitrile, formate salt | | | 6.22 | 5.33 |

TABLE 4-continued

IUPAC name and biological data for Examples 93-250

| Example or Compound Number | IUPAC Name | LRRK2, Format 1 WT IC$_{50}$ (nM)* | LRRK2, Format 1 G2019S IC$_{50}$ (nM)* | LRRK2, Format 2 WT IC$_{50}$ (nM)* | LRRK2, Format 2 G2019S IC$_{50}$ (nM)* |
|---|---|---|---|---|---|
| 125 | 2-[(4-cyclopropyl-1H-1,2,3-triazol-1-yl)methyl]-1-[(2R,4R)-2-methyltetrahydro-2H-pyran-4-yl]-1H-imidazo[4,5-c]quinoline-8-carbonitrile, formate salt | | | 7.00 | 6.19 |
| 126 | 1-[(2R,4R)-2-methyltetrahydro-2H-pyran-4-yl]-2-{[4-(propan-2-yl)-1H-1,2,3-triazol-1-yl]methyl}-1H-imidazo[4,5-c]quinoline-8-carbonitrile, formate salt | | | 8.39 | 8.04 |
| 127 | 8-chloro-1-[(2R,4R)-2-methyltetrahydro-2H-pyran-4-yl]-2-(1,3-oxazol-5-ylmethyl)-1H-imidazo[4,5-c]quinoline, formate salt | | | 7.02 | 8.01 |
| 128 | 8-chloro-1-[(2R,4R)-2-methyltetrahydro-2H-pyran-4-yl]-2-[(1-methyl-1H-tetrazol-5-yl)methyl]-1H-imidazo[4,5-c]quinoline, formate salt | | | 7.18 | 6.95 |
| 129 | 8-chloro-1-[(2R,4R)-2-methyltetrahydro-2H-pyran-4-yl]-2-(1H-tetrazol-1-ylmethyl)-1H-imidazo[4,5-c]quinoline, formate salt | | | 3.64 | 4.17 |
| 130 | 8-chloro-1-[(2R,4R)-2-methyltetrahydro-2H-pyran-4-yl]-2-(1H-pyrazol-1-ylmethyl)-1H-imidazo[4,5-c]quinoline, formate salt | | | 3.43 | 3.84 |
| 131 | 8-chloro-2-[(1-methyl-1H-imidazol-4-yl)methyl]-1-[(2R,4R)-2-methyltetrahydro-2H-pyran-4-yl]-1H-imidazo[4,5-c]quinoline | | | 7.23 | 7.86 |
| 132 | 1-(cis-3-fluorocyclopentyl)-2-{[4-(methoxymethyl)-1H-1,2,3-triazol-1-yl]methyl}-1H-imidazo[4,5-c]quinoline-8-carbonitrile, ENT-1 | | | 7.49 | 10.8 |
| 133 | 2-[(4-methyl-1H-pyrazol-1-yl)methyl]-1-[(2R,4R)-2-methyltetrahydro-2H-pyran-4-yl]-1H-imidazo[4,5-c]quinoline-8-carbonitrile | | | 7.68 | 7.16 |
| 134 | [cis-4-{8-chloro-2-[(5-methyl-1,2-oxazol-3-yl)methyl]-1H-imidazo[4,5-c]quinolin-1-yl}tetrahydro-2H-pyran-2-yl]acetonitrile, ENT-1 | 3.48 | 3.78 | 7.68 | 7.78 |
| 135 | [cis-4-{8-chloro-2-[(5-methyl-1,2,4-oxadiazol-3-yl)methyl]-1H-imidazo[4,5-c]quinolin-1-yl}tetrahydro-2H-pyran-2-yl]acetonitrile, ENT-1 | 3.78 | 3.65 | 16.0 | 15.5 |
| 136 | 8-chloro-1-[rel-(3S,4R)-3-fluoro-4-methylcyclopentyl]-2-[(5-methyl-1,2,4-oxadiazol-3-yl)methyl]-1H-imidazo[4,5-c]quinoline, DIAST-1 | 30.1 | 24.7 | 12.0 | 13.0 |

TABLE 4-continued

IUPAC name and biological data for Examples 93-250

| Example or Compound Number | IUPAC Name | LRRK2, Format 1 WT IC$_{50}$ (nM)* | LRRK2, Format 1 G2019S IC$_{50}$ (nM)* | LRRK2, Format 2 WT IC$_{50}$ (nM)* | LRRK2, Format 2 G2019S IC$_{50}$ (nM)* |
|---|---|---|---|---|---|
| 137 | [(2S,4R)-4-{8-chloro-2-[(5-methyl-1,2-oxazol-3-yl)methyl]-1H-imidazo[4,5-c]quinolin-1-yl}tetrahydro-2H-pyran-2-yl]methanol | | | 14.1[b] | 12.0 |
| 138 | [3-({8-chloro-1-[(2R,4R)-2-methyltetrahydro-2H-pyran-4-yl]-1H-imidazo[4,5-c]quinolin-2-yl}methyl)-1,2-oxazol-5-yl]methanol | | | 2.89[b] | 3.72 |
| 139 | 8-chloro-2-{[5-(fluoromethyl)-1,2-oxazol-3-yl]methyl}-1-[(2R,4R)-2-methyltetrahydro-2H-pyran-4-yl]-1H-imidazo[4,5-c]quinoline | | | 2.76[b] | 2.79[b] |
| 140 | 8-fluoro-1-[(2R,4R)-2-methyltetrahydro-2H-pyran-4-yl]-2-(1,2,3-thiadiazol-4-ylmethyl)-1H-imidazo[4,5-c]quinoline | | | N.D.[c] | N.D. |
| 141 | 2-[(5-methylpyrazin-2-yl)methyl]-1-[(2R,4R)-2-methyltetrahydro-2H-pyran-4-yl]-8-(trifluoromethyl)-1H-imidazo[4,5-c]quinoline | | | 2.07 | 1.38[b] |
| 142 | 8-chloro-1-[(2R,4R)-2-methyltetrahydro-2H-pyran-4-yl]-2-(pyridazin-3-ylmethyl)-1H-imidazo[4,5-c]quinoline | | | 7.11 | 5.63[b] |
| 143 | 1-(2,2-difluorocyclopentyl)-2-[(5-methyl-1,2-oxazol-3-yl)methyl]-1H-imidazo[4,5-c]quinoline-8-carbonitrile, ENT-1 | | | 53.9 | |
| 144 | 1-(2,2-difluorocyclopentyl)-2-[(5-methyl-1,2-oxazol-3-yl)methyl]-1H-imidazo[4,5-c]quinoline-8-carbonitrile, ENT-2 | | | 19.3 | 29.3[b] |
| 145 | 2-[(5-cyclopropyl-1,2-oxazol-3-yl)methyl]-1-[(2R,4R)-2-methyltetrahydro-2H-pyran-4-yl]-1H-imidazo[4,5-c]quinoline-8-carbonitrile | 4.78 | 4.80 | 6.98 | 7.33 |
| 146 | 1-(cis-2-fluorocyclopentyl)-2-[(5-methyl-1,2-oxazol-3-yl)methyl]-1H-imidazo[4,5-c]quinoline-8-carbonitrile, ENT-1 | | | 17.8 | 29.9 |
| 147 | 1-(cis-2-fluorocyclopentyl)-2-[(5-methyl-1,2-oxazol-3-yl)methyl]-1H-imidazo[4,5-c]quinoline-8-carbonitrile, ENT-2 | | | 14.5 | 22.6 |
| 148 | 8-chloro-1-(2,2-dimethyltetrahydro-2H-pyran-4-yl)-2-[(4-methyl-1H-1,2,3-triazol-1-yl)methyl]-1H-imidazo[4,5-c]quinoline, formate salt | | | 12.6 | 13.6 |
| 149 | 2-(imidazo[2,1-b][1,3,4]thiadiazol-6-ylmethyl)-1-[(2R,4R)-2-methyltetrahydro-2H-pyran-4-yl]-1H-imidazo[4,5-c]quinoline-8-carbonitrile | | | 2.04 | 2.12 |

TABLE 4-continued

IUPAC name and biological data for Examples 93-250

| Example or Compound Number | IUPAC Name | LRRK2, Format 1 WT IC$_{50}$ (nM)* | LRRK2, Format 1 G2019S IC$_{50}$ (nM)* | LRRK2, Format 2 WT IC$_{50}$ (nM)* | LRRK2, Format 2 G2019S IC$_{50}$ (nM)* |
|---|---|---|---|---|---|
| 150 | 8-chloro-1-(2,2-dimethyltetrahydro-2H-pyran-4-yl)-2-(1H-tetrazol-1-ylmethyl)-1H-imidazo[4,5-c]quinoline, formate salt | | | 11.6 | 12.1 |
| 151 | 1-(2,2-difluorocyclohexyl)-2-[(5-methyl-1,2-oxazol-3-yl)methyl]-1H-imidazo[4,5-c]quinoline-8-carbonitrile, formate salt | | | 16.7 | 25.5 |
| 152 | 1-cyclopentyl-2-[(5-methyl-1,2-oxazol-3-yl)methyl]-1H-imidazo[4,5-c]quinoline-8-carbonitrile, formate salt | | | 25.1 | 40.8 |
| 153 | 2-(1,3-benzoxazol-2-ylmethyl)-1-[(2R,4R)-2-methyltetrahydro-2H-pyran-4-yl]-1H-imidazo[4,5-c]quinoline-8-carbonitrile, formate salt | | | 6.04 | 5.34 |
| 154 | 2-(1,2-benzoxazol-3-ylmethyl)-1-[(2R,4R)-2-methyltetrahydro-2H-pyran-4-yl]-1H-imidazo[4,5-c]quinoline-8-carbonitrile, formate salt | | | 4.01 | 3.71 |
| 155 | 2-[(5-cyclopropyl-2-methyl-1,3-oxazol-4-yl)methyl]-1-[(2R,4R)-2-methyltetrahydro-2H-pyran-4-yl]-1H-imidazo[4,5-c]quinoline-8-carbonitrile, formate salt | | | 11.8 | 8.99 |
| 156 | 2-[(2-ethylimidazo[2,1-b][1,3,4]thiadiazol-6-yl)methyl]-1-[(2R,4R)-2-methyltetrahydro-2H-pyran-4-yl]-1H-imidazo[4,5-c]quinoline-8-carbonitrile, formate salt | | | 4.78 | 4.31 |
| 157 | 2-[(2-methylimidazo[2,1-b][1,3,4]thiadiazol-6-yl)methyl]-1-[(2R,4R)-2-methyltetrahydro-2H-pyran-4-yl]-1H-imidazo[4,5-c]quinoline-8-carbonitrile, formate salt | | | 3.96 | 3.79 |
| 158 | 2-(imidazo[1,2-a]pyridin-2-ylmethyl)-1-[(2R,4R)-2-methyltetrahydro-2H-pyran-4-yl]-1H-imidazo[4,5-c]quinoline-8-carbonitrile, formate salt | | | 6.01 | 5.22 |
| 159 | 8-chloro-2-[(7-methylimidazo[1,2-a]pyrimidin-2-yl)methyl]-1-[(2R,4R)-2-methyltetrahydro-2H-pyran-4-yl]-1H-imidazo[4,5-c]quinoline | | | 6.06 | 6.15 |
| 160 | 8-chloro-2-[(3-cyclopropyl-1H-pyrazol-1-yl)methyl]-1-[(2R,4R)-2-methyltetrahydro-2H-pyran-4-yl]-1H-imidazo[4,5-c]quinoline, formate salt | | | 6.23 | 6.36 |
| 161 | 8-chloro-1-[(2R,4R)-2-methyltetrahydro-2H-pyran-4-yl]-2-(2H-1,2,3-triazol-2-ylmethyl)-1H-imidazo[4,5-c]quinoline, formate salt | | | 6.39 | 6.94 |

TABLE 4-continued

| IUPAC name and biological data for Examples 93-250 | | | | | |
|---|---|---|---|---|---|
| Example or Compound Number | IUPAC Name | LRRK2, Format 1 WT IC$_{50}$ (nM)* | LRRK2, Format 1 G2019S IC$_{50}$ (nM)* | LRRK2, Format 2 WT IC$_{50}$ (nM)* | LRRK2, Format 2 G2019S IC$_{50}$ (nM)* |
| 162 | 8-chloro-2-[(2-methylimidazo[2,1-b][1,3,4]thiadiazol-6-yl)methyl]-1-[(2R,4R)-2-methyltetrahydro-2H-pyran-4-yl]-1H-imidazo[4,5-c]quinoline, formate salt | | | 3.86 | 3.83 |
| 163 | 8-chloro-2-[(1-methyl-1H-pyrazol-3-yl)methyl]-1-[(2R,4R)-2-methyltetrahydro-2H-pyran-4-yl]-1H-imidazo[4,5-c]quinoline | | | 7.01 | 7.25 |
| 164 | 2-({8-chloro-1-[(2R,4R)-2-methyltetrahydro-2H-pyran-4-yl]-1H-imidazo[4,5-c]quinolin-2-yl}methyl)-4H-pyrido[1,2-a]pyrimidin-4-one, formate salt | | | 5.88 | 6.18 |
| 165 | 8-chloro-1-[(2R,4R)-2-methyltetrahydro-2H-pyran-4-yl]-2-(tetrazolo[1,5-b]pyridazin-6-ylmethyl)-1H-imidazo[4,5-c]quinoline | | | 6.75 | 7.44 |
| 166 | 8-chloro-2-(5,6-dihydro-4H-pyrrolo[1,2-b]pyrazol-2-ylmethyl)-1-[(2R,4R)-2-methyltetrahydro-2H-pyran-4-yl]-1H-imidazo[4,5-c]quinoline, trifluoroacetate salt | | | 7.35 | 7.38 |
| 167 | 8-chloro-2-(imidazo[1,2-a]pyridin-2-ylmethyl)-1-[(2R,4R)-2-methyltetrahydro-2H-pyran-4-yl]-1H-imidazo[4,5-c]quinoline, trifluoroacetate salt | | | 8.26 | 8.43 |
| 168 | 1-(cis-3-fluorocyclopentyl)-2-[(2-methylimidazo[2,1-b][1,3,4]thiadiazol-6-yl)methyl]-1H-imidazo[4,5-c]quinoline-8-carbonitrile, ENT-1 | | | 7.33 | 11.5 |
| 169 | 1-(cis-3-fluorocyclopentyl)-2-[(2-methylimidazo[2,1-b][1,3,4]thiadiazol-6-yl)methyl]-1H-imidazo[4,5-c]quinoline-8-carbonitrile, ENT-2 | | | 3.59 | 5.55 |
| 170 | {8-fluoro-1-(cis-3-fluorocyclopentyl)-1H-imidazo[4,5-c]quinolin-2-yl}acetonitrile, ENT-1 | | | 64.4 | 106 |
| 171 | 8-bromo-1-[(2R,4R)-2-methyltetrahydro-2H-pyran-4-yl]-2-{[5-(propan-2-yl)-1,2-oxazol-3-yl]methyl}-1H-imidazo[4,5-c]quinoline | 17.1 | 15.9 | 5.20 | 5.35 |
| 172 | 8-bromo-2-[(5-cyclopropyl-1,2-oxazol-3-yl)methyl]-1-[(2R,4R)-2-methyltetrahydro-2H-pyran-4-yl]-1H-imidazo[4,5-c]quinoline | 14.4 | 9.17 | 6.00 | 6.34 |
| 173 | 8-bromo-1-[(2R,4R)-2-methyltetrahydro-2H-pyran-4-yl]-2-[(4-methyl-1H-1,2,3-triazol-1-yl)methyl]-1H-imidazo[4,5-c]quinoline | 5.14 | 3.62 | 6.70 | 6.72 |

TABLE 4-continued

IUPAC name and biological data for Examples 93-250

| Example or Compound Number | IUPAC Name | LRRK2, Format 1 WT IC$_{50}$ (nM)* | LRRK2, Format 1 G2019S IC$_{50}$ (nM)* | LRRK2, Format 2 WT IC$_{50}$ (nM)* | LRRK2, Format 2 G2019S IC$_{50}$ (nM)* |
|---|---|---|---|---|---|
| 174 | {8-chloro-1-[(2R,4R)-2-methyltetrahydro-2H-pyran-4-yl]-1H-imidazo[4,5-c]quinolin-2-yl}(1,2-oxazol-3-yl)methanone | | | 16.8 | 19.6 |
| 175 | 1-[(2R,4R)-2-methyltetrahydro-2H-pyran-4-yl]-2-{[4-(trifluoromethyl)-1H-1,2,3-triazol-1-yl]methyl}-1H-imidazo[4,5-c]quinoline-8-carbonitrile | | | 13.4 | 12.2 |
| 176 | 1-(2,2-dimethyltetrahydro-2H-pyran-4-yl)-2-{[5-(trifluoromethyl)-1,2-oxazol-3-yl]methyl}-1H-imidazo[4,5-c]quinoline-8-carbonitrile, ENT-1 | | | 13.0 | 12.7 |
| 177 | 1-(2,2-dimethyltetrahydro-2H-pyran-4-yl)-2-{[5-(trifluoromethyl)-1,2-oxazol-3-yl]methyl}-1H-imidazo[4,5-c]quinoline-8-carbonitrile, ENT-2 | | | 1220 | 914 |
| 178 | 1-[(2R,4R)-2-methyltetrahydro-2H-pyran-4-yl]-2-(pyrimidin-4-ylmethyl)-8-(trifluoromethyl)-1H-imidazo[4,5-c]quinoline | | | 5.64 | 3.32[b] |
| 179 | 8-fluoro-2-[(4-methoxy-1H-pyrazol-1-yl)methyl]-1-[(2R,4R)-2-methyltetrahydro-2H-pyran-4-yl]-1H-imidazo[4,5-c]quinoline | | | 14.0 | 12.6[b] |
| 180 | 8-chloro-1-[(1s,3s)-3-methoxycyclobutyl]-2-[(4-methyl-1H-pyrazol-1-yl)methyl]-1H-imidazo[4,5-c]quinoline | | | 30.4 | 29.9[b] |
| 181 | 8-chloro-1-(2-fluoroethyl)-2-[(5-methyl-1,2-oxazol-3-yl)methyl]-1H-imidazo[4,5-c]quinoline | | | 99.5 | |
| 182 | 8-chloro-1-(2-fluoroethyl)-2-(pyrazin-2-ylmethyl)-1H-imidazo[4,5-c]quinoline | | | 67.4 | |
| 183 | 8-chloro-1-[(1s,3s)-3-methoxycyclobutyl]-2-[(4-methyl-1H-1,2,3-triazol-1-yl)methyl]-1H-imidazo[4,5-c]quinoline | | | 33.8 | 30.8[b] |
| 184 | 8-chloro-1-(2,2-difluorobutyl)-2-(pyrazin-2-ylmethyl)-1H-imidazo[4,5-c]quinoline | | | 34.3 | 22.8[b] |
| 185 | 8-chloro-1-(2,2-difluorobutyl)-2-[(5-methyl-1,2,4-oxadiazol-3-yl)methyl]-1H-imidazo[4,5-c]quinoline | | | 73.2 | |
| 186 | 8-chloro-1-(2,2-difluorobutyl)-2-[(4-methyl-1H-1,2,3-triazol-1-yl)methyl]-1H-imidazo[4,5-c]quinoline | | | 22.5 | 16.4[b] |
| 187 | 8-chloro-1-(2,2-difluorocyclobutyl)-2-[(4-methyl-1H-1,2,3-triazol-1-yl)methyl]-1H-imidazo[4,5-c]quinoline | | | 28.1 | 33.3[b] |

TABLE 4-continued

IUPAC name and biological data for Examples 93-250

| Example or Compound Number | IUPAC Name | LRRK2, Format 1 WT IC$_{50}$ (nM)* | LRRK2, Format 1 G2019S IC$_{50}$ (nM)* | LRRK2, Format 2 WT IC$_{50}$ (nM)* | LRRK2, Format 2 G2019S IC$_{50}$ (nM)* |
|---|---|---|---|---|---|
| 188 | 8-chloro-1-[(1r,3r)-3-methoxycyclobutyl]-2-[(4-methyl-1H-1,2,3-triazol-1-yl)methyl]-1H-imidazo[4,5-c]quinoline | | | 110 | |
| 189 | 2-{[5-(fluoromethyl)-1,2-oxazol-3-yl]methyl}-1-[(2R,4R)-2-methyltetrahydro-2H-pyran-4-yl]-1H-imidazo[4,5-c]quinoline-8-carbonitrile, trifluoroacetate salt | | | 5.04 | 3.54[b] |
| 190 | 2-[(4-methyl-1H-pyrazol-1-yl)methyl]-1-[(3S)-1-methylpyrrolidin-3-yl]-1H-imidazo[4,5-c]quinoline-8-carbonitrile | | | 26.6 | 26.2[b] |
| 191 | 8-chloro-2-[(5-cyclopropyl-1-methyl-1H-1,2,4-triazol-3-yl)methyl]-1-[(2R,4R)-2-methyltetrahydro-2H-pyran-4-yl]-1H-imidazo[4,5-c]quinoline | | | 73.5 | |
| 192 | 8-chloro-2-(5,6-dihydro-8H-imidazo[2,1-c][1,4]oxazin-2-ylmethyl)-1-[(2R,4R)-2-methyltetrahydro-2H-pyran-4-yl]-1H-imidazo[4,5-c]quinoline | | | 12.6[b] | |
| 193 | 8-chloro-1-[(2R,4R)-2-methyltetrahydro-2H-pyran-4-yl]-2-(1,2,3-thiadiazol-5-ylmethyl)-1H-imidazo[4,5-c]quinoline | | | 37.3 | 32.6[b] |
| 194 | 2-[(4-methyl-1H-pyrazol-1-yl)methyl]-1-[(3R)-1-methylpyrrolidin-3-yl]-1H-imidazo[4,5-c]quinoline-8-carbonitrile | | | 19.9 | 25.1[b] |
| 195 | 1-[(2R,4R)-2-methyltetrahydro-2H-pyran-4-yl]-2-(1,2,3-thiadiazol-4-ylmethyl)-1H-imidazo[4,5-c]quinoline-8-carbonitrile | | | 3.46 | 2.28[b] |
| 196 | 1-(2,2-difluorocyclopentyl)-2-[(4-methyl-1H-1,2,3-triazol-1-yl)methyl]-1H-imidazo[4,5-c]quinoline-8-carbonitrile, ENT-1 | | | 18.8 | 15.8[b] |
| 197 | 1-(2,2-difluorocyclopentyl)-2-[(4-methyl-1H-1,2,3-triazol-1-yl)methyl]-1H-imidazo[4,5-c]quinoline-8-carbonitrile, ENT-2 | | | 12.7 | 18.7[b] |
| 198 | 8-fluoro-2-[(4-methyl-1H-pyrazol-1-yl)methyl]-1-[(2R,4R)-2-methyltetrahydro-2H-pyran-4-yl]-1H-imidazo[4,5-c]quinoline | | | 15.2 | 16.8 |
| 199 | 8-fluoro-1-[(2R,4R)-2-methyltetrahydro-2H-pyran-4-yl]-2-[(4-methyl-1H-1,2,3-triazol-1-yl)methyl]-1H-imidazo[4,5-c]quinoline | | | 10.3 | 11.8 |
| 200 | 8-fluoro-2-[(5-methyl-1,2-oxazol-3-yl)methyl]-1-[(2R,4R)-2-methyltetrahydro-2H-pyran-4-yl]-1H-imidazo[4,5-c]quinoline | | | 12.4 | 14.3 |

TABLE 4-continued

IUPAC name and biological data for Examples 93-250

| Example or Compound Number | IUPAC Name | LRRK2, Format 1 WT IC$_{50}$ (nM)* | LRRK2, Format 1 G2019S IC$_{50}$ (nM)* | LRRK2, Format 2 WT IC$_{50}$ (nM)* | LRRK2, Format 2 G2019S IC$_{50}$ (nM)* |
|---|---|---|---|---|---|
| 201 | 1-(cis-3-fluorocyclopentyl)-2-{[4-(trifluoromethyl)-1H-pyrazol-1-yl]methyl}-1H-imidazo[4,5-c]quinoline-8-carbonitrile, ENT-1 | | | 7.47 | 11.3 |
| 202 | 2-[(4-cyclopropyl-1H-1,2,3-triazol-1-yl)methyl]-1-(cis-3-fluorocyclopentyl)-1H-imidazo[4,5-c]quinoline-8-carbonitrile, ENT-1 | | | 15.5[b] | 20.4[b] |
| 203 | 1-(cis-3-fluorocyclopentyl)-2-(1,3-thiazol-4-ylmethyl)-1H-imidazo[4,5-c]quinoline-8-carbonitrile, ENT-1 | | | 12.2 | 16.3 |
| 204 | {8-chloro-1-(cis-3-fluorocyclopentyl)-1H imidazo[4,5-c]quinolin-2-yl}acetonitrile, ENT-1 | | | 22.8 | 35.1 |
| 205 | 1-[(2R,4R)-2-methyltetrahydro-2H-pyran-4-yl]-2-[(5-methyl-1,3-thiazol-2-yl)methyl]-1H-imidazo[4,5-c]quinoline-8-carbonitrile | | | 6.52 | 6.09 |
| 206 | 8-chloro-1-[(2R,4R)-2-methyltetrahydro-2H-pyran-4-yl]-2-[(5-methyl-2H-tetrazol-2-yl)methyl]-1H-imidazo[4,5-c]quinoline | | | 10.4 | 9.57 |
| 207 | 1-(2,2-dimethyltetrahydro-2H-pyran-4-yl)-2-[(5-methoxypyridin-2-yl)methyl]-1H-imidazo[4,5-c]quinoline-8-carbonitrile, ENT-2 | | | 7.53 | 6.84 |
| 208 | 1-[(2R,4R)-2-methyltetrahydro-2H-pyran-4-yl]-2-{[5-(trifluoromethyl)pyridin-2-yl]methyl}-1H-imidazo[4,5-c]quinoline-8-carbonitrile | | | 15.0 | 14.3 |
| 209 | 1-(2,2-difluoropropyl)-2-[(4-ethyl-1H-pyrazol-1-yl)methyl]-1H-imidazo[4,5-c]quinoline-8-carbonitrile | | | 8.02 | 9.93 |
| 210 | 1-(2,2-difluoropropyl)-2-[(4-methoxy-1H-pyrazol-1-yl)methyl]-1H-imidazo[4,5-c]quinoline-8-carbonitrile | | | 7.04 | 7.63 |
| 211 | 1-(cis-3-fluorocyclopentyl)-2-{[5-(trifluoromethyl)-1,2-oxazol-3-yl]methyl}-1H-imidazo[4,5-c]quinoline-8-carbonitrile, ENT-1 | | | 12.8 | 18.7 |
| 212 | 8-chloro-2-[(4-methyl-1H-pyrazol-1-yl)methyl]-1-[(2R,4R)-2-methyltetrahydro-2H-pyran-4-yl]-1H-imidazo[4,5-c]quinoline | | | 8.47 | 8.15 |
| 213 | 2-[(5-methyl-1,2-oxazol-3-yl)methyl]-1-[(3R)-1-methylpyrrolidin-3-yl]-1H-imidazo[4,5-c]quinoline-8-carbonitrile, formate salt | | | 3.38 | 7.03 |
| 214 | 8-chloro-2-[difluoro(pyridin-2-yl)methyl]-1-[(2R,4R)-2-methyltetrahydro-2H-pyran-4-yl]-1H-imidazo[4,5-c]quinoline, formate salt | | | 7.67 | 9.67 |

TABLE 4-continued

IUPAC name and biological data for Examples 93-250

| Example or Compound Number | IUPAC Name | LRRK2, Format 1 WT IC$_{50}$ (nM)* | LRRK2, Format 1 G2019S IC$_{50}$ (nM)* | LRRK2, Format 2 WT IC$_{50}$ (nM)* | LRRK2, Format 2 G2019S IC$_{50}$ (nM)* |
|---|---|---|---|---|---|
| 215 | 1-(2,2-dimethyltetrahydro-2H-pyran-4-yl)-2-[(5-methylpyrazin-2-yl)methyl]-1H-imidazo[4,5-c]quinoline-8-carbonitrile, ENT-1 | | | 13.4 | 13.9 |
| 216 | 1-cyclobutyl-2-[(5-methyl-1,2-oxazol-3-yl)methyl]-1H-imidazo[4,5-c]quinoline-8-carbonitrile, formate salt | | | 26.6 | 38.6 |
| 217 | 2-[(5-methyl-1,2-oxazol-3-yl)methyl]-1-(1-methylpyrrolidin-3-yl)-1H-imidazo[4,5-c]quinoline-8-carbonitrile, formate salt | | | 5.43 | 11.1 |
| 218 | 2-[(5-methyl-1,2-oxazol-3-yl)methyl]-1-[(3S)-1-methylpyrrolidin-3-yl]-1H-imidazo[4,5-c]quinoline-8-carbonitrile, formate salt | | | 21.4 | 32.2 |
| 219 | 1-(trans-4-methoxycyclohexyl)-2-[(5-methyl-1,2-oxazol-3-yl)methyl]-1H-imidazo[4,5-c]quinoline-8-carbonitrile, formate salt | | | 246 | 126 |
| 220 | 8-chloro-2-[fluoro(1,2,3-thiadiazol-4-yl)methyl]-1-[(2R,4R)-2-methyltetrahydro-2H-pyran-4-yl]-1H-imidazo[4,5-c]quinoline, formate salt | | | 4.81 | 5.03 |
| 221 | 8-chloro-1-[(2S,4R)-2-(fluoromethyl)tetrahydro-2H-pyran-4-yl]-2-[(5-methyl-1,2-oxazol-3-yl)methyl]-1H-imidazo[4,5-c]quinoline | | | 3.19$^b$ | 2.89$^b$ |
| 222 | 1-[(2R,4R)-2-methyltetrahydro-2H-pyran-4-yl]-2-(pyrimidin-4-ylmethyl)-1H-imidazo[4,5-c]quinoline-8-carbonitrile | | | 9.08 | 8.59 |
| 223 | 1-[(2R,4R)-2-methyltetrahydro-2H-pyran-4-yl]-2-(pyridin-2-ylmethyl)-1H-imidazo[4,5-c]quinoline-8-carbonitrile | | | 9.69 | 9.45 |
| 224 | 1-(2,2-difluoropropyl)-2-(1,3-thiazol-4-ylmethyl)-1H-imidazo[4,5-c]quinoline-8-carbonitrile | | | 9.15 | 11.1 |
| 225 | 2-[(3-cyclopropyl-1H-pyrazol-1-yl)methyl]-1-(2,2-difluoropropyl)-1H-imidazo[4,5-c]quinoline-8-carbonitrile | | | 7.23 | 8.70 |
| 226 | 1-(2,2-difluoropropyl)-2-[(2-methylimidazo[2,1-b][1,3,4]thiadiazol-6-yl)methyl]-1H-imidazo[4,5-c]quinoline-8-carbonitrile | | | 4.54 | 5.82 |
| 227 | 1-(2,2-difluoropropyl)-2-{[4-(trifluoromethyl)-1H-pyrazol-1-yl]methyl}-1H-imidazo[4,5-c]quinoline-8-carbonitrile | | | 9.06 | 10.8 |
| 228 | 1-(2,2-difluoroethyl)-2-[(5-methyl-1,2-oxazol-3-yl)methyl]-1H-imidazo[4,5-c]quinoline-8-carbonitrile | | | 46.7 | 69.4 |

TABLE 4-continued

IUPAC name and biological data for Examples 93-250

| Example or Compound Number | IUPAC Name | LRRK2, Format 1 WT IC$_{50}$ (nM)* | LRRK2, Format 1 G2019S IC$_{50}$ (nM)* | LRRK2, Format 2 WT IC$_{50}$ (nM)* | LRRK2, Format 2 G2019S IC$_{50}$ (nM)* |
|---|---|---|---|---|---|
| 229 | 1-[(2R,4R)-2-methyltetrahydro-2H-pyran-4-yl]-2-(1,3-oxazol-5-ylmethyl)-1H-imidazo[4,5-c]quinoline-8-carbonitrile, formate salt | | | 9.71 | 9.37 |
| 230 | 2-[(2,5-dimethyl-1,3-oxazol-4-yl)methyl]-1-[(2R,4R)-2-methyltetrahydro-2H-pyran-4-yl]-1H-imidazo[4,5-c]quinoline-8-carbonitrile, formate salt | | | 11.6 | 8.48 |
| 231 | 1-[(2R,4R)-2-methyltetrahydro-2H-pyran-4-yl]-2-(1,3-thiazol-5-ylmethyl)-1H-imidazo[4,5-c]quinoline-8-carbonitrile, formate salt | | | 24.9 | 26.6 |
| 232 | 2-[(5-methylpyridin-2-yl)methyl]-1-[(2R,4R)-2-methyltetrahydro-2H-pyran-4-yl]-1H-imidazo[4,5-c]quinoline-8-carbonitrile | | | 8.48 | 7.26[a] |
| 233 | 2-[(3-methyl-1H-pyrazol-1-yl)methyl]-1-[(2R,4R)-2-methyltetrahydro-2H-pyran-4-yl]-1H-imidazo[4,5-c]quinoline-8-carbonitrile, formate salt | | | 14.3 | 11.9 |
| 234 | 1-[(2R,4R)-2-methyltetrahydro-2H-pyran-4-yl]-2-[(2-methyl-1,3-thiazol-4-yl)methyl]-1H-imidazo[4,5-c]quinoline-8-carbonitrile, formate salt | | | 10.7 | 9.50 |
| 235 | 2-[(1-methyl-1H-imidazol-4-yl)methyl]-1-[(2R,4R)-2-methyltetrahydro-2H-pyran-4-yl]-1H-imidazo[4,5-c]quinoline-8-carbonitrile, formate salt | | | 10.6 | 9.43 |
| 236 | 2-[difluoro(pyridin-2-yl)methyl]-1-[(2R,4R)-2-methyltetrahydro-2H-pyran-4-yl]-1H-imidazo[4,5-c]quinoline-8-carbonitrile, formate salt | | | 13.0 | 11.9[a] |
| 237 | 8-chloro-2-[fluoro(1,2-oxazol-3-yl)methyl]-1-[(2R,4R)-2-methyltetrahydro-2H-pyran-4-yl]-1H-imidazo[4,5-c]quinoline, DIAST-1 | | | 4.00 | 3.92 |
| 238 | 8-chloro-2-[fluoro(1,2-oxazol-3-yl)methyl]-1-[(2R,4R)-2-methyltetrahydro-2H-pyran-4-yl]-1H-imidazo[4,5-c]quinoline, DIAST-2 | | | 3.88 | 3.82 |
| 239 | 1-(2,2-dimethyltetrahydro-2H-pyran-4-yl)-2-[(5-methyl-1,2-oxazol-3-yl)methyl]-1H-imidazo[4,5-c]quinoline-8-carbonitrile, formate salt | | | 9.74 | 10.8 |
| 240 | 1-(trans-4-hydroxycyclohexyl)-2-[(5-methyl-1,2-oxazol-3-yl)methyl]-1H-imidazo[4,5-c]quinoline-8-carbonitrile, formate salt | | | 51.8 | 35.7 |

TABLE 4-continued

IUPAC name and biological data for Examples 93-250

| Example or Compound Number | IUPAC Name | LRRK2, Format 1 WT IC$_{50}$ (nM)* | LRRK2, Format 1 G2019S IC$_{50}$ (nM)* | LRRK2, Format 2 WT IC$_{50}$ (nM)* | LRRK2, Format 2 G2019S IC$_{50}$ (nM)* |
|---|---|---|---|---|---|
| 241 | 1-[(1S,3R)-3-fluorocyclopentyl]-2-[(5-methyl-1,2-oxazol-3-yl)methyl]-1H-imidazo[4,5-c]quinoline-8-carbonitrile, formate salt | | | 29.3 | 33.5 |
| 242 | 1-(cis-2-hydroxycyclohexyl)-2-[(5-methyl-1,2-oxazol-3-yl)methyl]-1H-imidazo[4,5-c]quinoline-8-carbonitrile, formate salt | | | 122 | 119 |
| 243 | 1-[(2S)-1-fluoropropan-2-yl]-2-[(5-methyl-1,2-oxazol-3-yl)methyl]-1H-imidazo[4,5-c]quinoline-8-carbonitrile, formate salt | | | 48.7 | 85.9 |
| 244 | 1-(3,3-difluorocyclohexyl)-2-[(5-methyl-1,2-oxazol-3-yl)methyl]-1H-imidazo[4,5-c]quinoline-8-carbonitrile, formate salt | | | 79.4 | 89.7 |
| 245 | 1-(cis-2-fluorocyclopentyl)-2-[(5-methyl-1,2-oxazol-3-yl)methyl]-1H-imidazo[4,5-c]quinoline-8-carbonitrile, formate salt | | | 14.3 | 18.6 |
| 246 | 1-(3,3-difluorocyclopentyl)-2-[(5-methyl-1,2-oxazol-3-yl)methyl]-1H-imidazo[4,5-c]quinoline-8-carbonitrile, formate salt | | | 65.0 | 86.5 |
| 247 | 1-(trans-4-hydroxy-4-methylcyclohexyl)-2-[(5-methyl-1,2-oxazol-3-yl)methyl]-1H-imidazo[4,5-c]quinoline-8-carbonitrile, formate salt | | | 85.1 | 59.5 |
| 248 | 1-(2,2-difluoropropyl)-2-[(5-methyl-1,2-oxazol-3-yl)methyl]-1H-imidazo[4,5-c]quinoline-8-carbonitrile | | | 15.0 | 17.7 |
| 249 | 8-chloro-1-[(2R,4R)-2-methyltetrahydro-2H-pyran-4-yl]-2-(pyrazin-2-ylmethyl)-1H-imidazo[4,5-c]quinoline, trifluoroacetate salt | | | 16.9[b] | 18.6[b] |
| 250 | 8-chloro-1-[(2R,4R)-2-methyltetrahydro-2H-pyran-4-yl]-2-(pyridin-2-ylmethyl)-1H-imidazo[4,5-c]quinoline, formate salt | | | 10.4 | 11.0 |

*Geometric mean of 2-4 determinations unless otherwise indicated
[a]IC$_{50}$ value represents the geometric mean of ≥5 determinations.
[b]IC$_{50}$ value derived from a single determination.
[c]Not determined Table 5 below provides kinase selectivity data for the compounds of Examples 3, 4, 5 and 22. The compounds were run using a commercially available kinase selectivity assay which is available from CarnaBio USA, Inc. 209 West Central St., Suite 307, Natick, Mass. 01760 USA. The compounds of Examples 3, 4, 5 and 22 were run in the assay at a concentration of 1 μM using an ATP concentration of 1 mM. Table 5A below provides kinase selectivity from a further assay run for the compounds of Examples 4, 11, 5, 104, 102 and 116.

TABLE 5

| Kinase | Ex 3 | Ex 4 | Ex 5 | Ex 22 |
|---|---|---|---|---|
| ABL1 | −2.8 | −3.75 | −1.15 | −5.35 |
| AKT1 | −1.5 | 0.95 | −0.55 | −4.85 |
| AURKA | −11.95 | −2.1 | −12.2 | −0.1 |
| BTK | −2.6 | 6.5 | 3.15 | 11.6 |
| CDK2_CyclinA | 15.45 | 11.8 | 8.3 | 17.6 |
| CHEK1 | 5.85 | −3.4 | 6.3 | −5.25 |
| CHEK2 | −6.3 | 0 | 2.7 | −3.35 |
| CSNK1A1 | −8.4 | 0.7 | −0.55 | −4.45 |

TABLE 5-continued

| Kinase | Ex 3 | Ex 4 | Ex 5 | Ex 22 |
|---|---|---|---|---|
| EGFR | 1.9 | 9.7 | 6.6 | 13.3 |
| EPHA2 | -4.1 | -4.2 | 2.35 | -3.2 |
| FGFR1 | 0.1 | 29.85 | 23.85 | 3.2 |
| GSK3B | -9.65 | 0.8 | -10 | -7.35 |
| INSR | -1.15 | -0.55 | 2.1 | -4.45 |
| IRAK4 | -2.3 | 0.7 | 1.25 | 0.6 |
| JAK3 | 11.5 | 19.05 | 25.2 | 1.4 |
| KDR | 2.05 | 21.3 | 16.95 | 11 |
| LCK | -1.45 | 0.55 | 0.15 | -0.85 |
| MAP4K4 | 0.3 | 0.2 | -1.05 | -3.4 |
| MAPK1 | -16.4 | -31.05 | 0.1 | -5.7 |
| MAPK14 | -5.3 | -4.2 | -15.7 | -5.1 |
| MAPKAPK2 | -11.9 | -6.7 | -8.35 | -4.85 |
| MET | 3 | 7.05 | 7.55 | -2.75 |
| MYLK2 | -6.6 | -10 | -5.7 | -0.05 |
| NEK2 | 0 | -3.35 | 1 | -2.2 |
| NTRK1 | -0.5 | 16.85 | 8.65 | 1.5 |
| PDPK1 | -2.55 | -3.05 | -1.05 | -2.65 |
| PIM2 | 1.8 | 2.3 | 11.2 | 4.35 |
| PRKACA | -6.55 | 1.1 | -1.1 | -11.35 |
| ROCK1 | -3.75 | -9.4 | -2.6 | -1.15 |
| SGK1 | -2.05 | -1.85 | -1.45 | 0.85 |
| SRC | -2 | 6.5 | -5.75 | -0.85 |
| TEK | -10.1 | -15.9 | -7.3 | -22.35 |

TABLE 5A

Kinase selectivity (mini-panel) determined at 1 mM ATP and 1 μM drug concentration. Data expressed as percent inhibition.

| Kinase | Ex. 4 | Ex. 11 | Ex. 5 | Ex. 104 | Ex. 102 | Ex. 116 |
|---|---|---|---|---|---|---|
| ABL | -2.51 | 5.06 | 1.3 | -6.38 | 1.95 | -8.45 |
| AKT | 1.03 | 2.25 | -3.11 | -2.7 | 4.16 | 3 |
| AURA | 7.17 | 9.46 | -0.59 | 1.41 | 11.07 | 8.57 |
| BTK | 0.22 | 1.63 | -1.9 | -8.43 | -2.03 | -0.86 |
| CaMKIIa | 7.62 | 3.76 | 1.1 | -0.6 | 7.95 | 8.8 |
| CDK2_CyclinA | 8.08 | 10.91 | 3.76 | -1.29 | 7.12 | 7.76 |
| CHK1 | 8.15 | 9.08 | 4.68 | 1.3 | 7.04 | 9.11 |
| CHK2 | 2.72 | 4.45 | 2.05 | -4.6 | 0.5 | 0.39 |
| CKIa | 18.22 | 10.68 | 8.85 | -2.89 | 4.89 | 4.68 |
| CKIIa' | 4.36 | 3.12 | 5.19 | -0.31 | 2.15 | 1.67 |
| EGFR | 3.07 | 2.76 | -0.51 | -3.75 | 0.11 | 4.03 |
| EphA2 | 0.85 | 0.7 | 0.13 | -10.43 | 2.2 | 5.08 |
| ERK2 | 4.54 | 4.69 | 2.62 | -2.07 | 3.64 | 10.33 |
| FGFR1 | 20.35 | 21.95 | 12.6 | 17.09 | 34.71 | 23.36 |
| GSK3b | 4.45 | 3.91 | 3.4 | -4.34 | 2.8 | 2.43 |
| HGFR | -5.99 | -3.76 | -7.71 | -5.38 | 3.61 | -2.04 |
| IRAK4 | 3.88 | 4.95 | 1.85 | -7.15 | 8.34 | 11.9 |
| IRK | 2.83 | 0.67 | 1.53 | -2.45 | 2.41 | 3.5 |
| JAK3 | -1.51 | -0.46 | -0.03 | 17.09 | 50.75 | 5.86 |
| KDR (VEGF) | 14.24 | 29 | 15.08 | 12.2 | 51.75 | 24.23 |
| LCK | 15.63 | 9.31 | 17.19 | 1.74 | 18.64 | 0.41 |
| MK2 | 3.04 | -1.14 | -3.62 | -3.44 | 1.54 | 7.5 |
| MARK1 | 1.48 | 1.52 | 3.46 | -2.65 | 6.6 | 1.61 |
| MLCK_sk | 3.07 | 4.74 | 3.8 | -3.75 | 0.92 | 5.97 |
| MST2 | 16.25 | 23.23 | 14.89 | 10.18 | 51.42 | 24.53 |
| MST4 | 1.29 | 10.29 | 8.04 | -3.83 | 4.8 | 8.69 |
| p38 | 9.62 | 7.19 | 5.64 | -1.52 | 3.32 | 13.76 |
| PAK4 | 3.85 | 4.23 | -0.05 | -3.01 | 4.83 | 4.02 |
| PDK1 | 4.87 | 8.16 | 0.39 | -5.16 | 8.36 | 5.49 |
| PIM2 | -0.54 | 4.47 | -3.78 | -6.6 | 5.55 | 5.63 |
| PKACa | -0.89 | 5.23 | -8.79 | -1.49 | 0.21 | -0.26 |
| PRKCB2 | 4.71 | -0.76 | 9.78 | 1.13 | 10.52 | 22.9 |
| ROCKI | 1.89 | 6.94 | 0.07 | -0.53 | -0.87 | 3.61 |
| SGK | 1.58 | 4.89 | -0.06 | -2.75 | 7.15 | 3.22 |
| SRC | 4.66 | 1.86 | 2.47 | -1.31 | 5.87 | 5.44 |
| TAO2 | 0.82 | 5.98 | 0.55 | -4.56 | 2.75 | 6.14 |
| TIE2 | 4.72 | 5.85 | 2.53 | -3.92 | 2.01 | 7.08 |
| TRKA | 11.84 | 13.01 | 12.31 | 17.66 | 58.72 | 14.91 |
| ZC1 (HGK) | -3.58 | 2.87 | -0.79 | -5.31 | 3.72 | -1.13 |

We claim:

1. A compound of Formula (I)

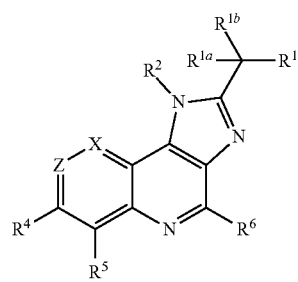

or a pharmaceutically acceptable salt thereof; wherein

X is $CR^7$ or N;

Z is $CR^3$ or N;

$R^1$ is selected from the group consisting of cyano and a 5- to 10-membered heteroaryl which contains 1 to 5 heteroatoms independently selected from N, O and S; wherein the 5- to 10-membered heteroaryl is optionally substituted with 1 to 3 $R^8$;

$R^{1a}$ and $R^{1b}$ are each independently hydrogen, halo, hydroxy or $C_1$-$C_3$alkyl;

$R^2$ is a $C_3$-$C_7$cycloalkyl or a 4- to 7-membered heterocycloalkyl which contains 1 to 3 heteroatoms independently selected from NR, O and S; wherein the $C_3$-$C_7$cycloalkyl and 4- to 7-membered heterocycloalkyl are each optionally substituted with 1 to 3 $R^9$; and wherein the $C_1$-$C_6$alkyl is optionally substituted with 1 to 3 $R^{10}$;

R is hydrogen, $C_1$-$C_6$alkyl or absent;

$R^3$, $R^4$, $R^5$, $R^6$ and $R^7$ are each independently selected from the group consisting of hydrogen, deutero, amino, halo, hydroxy, cyano, $C_1$-$C_6$alkyl, $C_3$-$C_6$cycloalkyl and $C_1$-$C_6$alkoxy; wherein the $C_1$-$C_6$alkyl, $C_3$-$C_6$cycloalkyl and $C_1$-$C_6$alkoxy are each optionally substituted with 1 to 3 halo or $C_1$-$C_3$alkoxy;

$R^8$ at each occurrence is independently selected from the group consisting of halo, —C(O)NH$_2$, —C(O)NH($C_1$-$C_3$alkyl), —C(O)N($C_1$-$C_3$alkyl)$_2$, $C_1$-$C_6$alkyl, $C_1$-$C_6$alkoxy and $C_3$-$C_6$cycloalkyl; wherein the $C_1$-$C_6$alkyl, $C_1$-$C_6$alkoxy and $C_3$-$C_6$cycloalkyl are each optionally substituted with 1 to 3 halo, cyano, hydroxy or $C_1$-$C_3$alkoxy;

$R^9$ at each occurrence is independently selected from the group consisting of halo, hydroxy, $C_1$-$C_6$alkyl, $C_1$-$C_6$alkoxy, and $C_1$-$C_6$alkoxy$C_1$-$C_6$alkyl, wherein the $C_1$-$C_6$alkyl, $C_1$-$C_6$alkoxy, and $C_1$-$C_6$alkoxy$C_1$-$C_6$alkyl are optionally substituted with one to three halo or a cyano; and $R^{10}$ at each occurrence is independently selected from the group consisting of halo, $C_1$-$C_6$alkoxy, $C_1$-$C_6$thioalkoxy, amino, $C_1$-$C_6$alkylamino and di($C_1$-$C_6$alkyl)amino.

2. A compound of Formula (I)

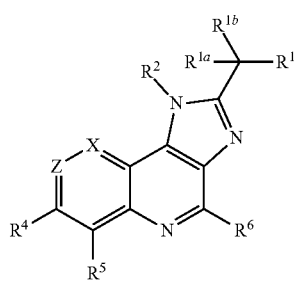

or a pharmaceutically acceptable salt thereof; wherein
X is CR$^7$ or N;
Z is CR$^3$ or N;
R$^1$ is selected from the group consisting of cyano and a 5- to 10-membered heteroaryl which contains 1 to 5 heteroatoms independently selected from N, O and S; wherein the 5- to 10-membered heteroaryl is optionally substituted with 1 to 3 R$^8$;
R$^{1a}$ and R$^{1b}$ are each independently hydrogen, halo, hydroxy or C$_1$-C$_3$alkyl;
R$^2$ is a C$_3$-C$_7$cycloalkyl or a 4- to 7-membered heterocycloalkyl which contains 1 to 3 heteroatoms independently selected from NR, O and S; wherein the C$_3$-C$_7$cycloalkyl and 4- to 7-membered heterocycloalkyl are each optionally substituted with 1 to 3 R$^9$; and wherein the C$_1$-C$_6$alkyl is optionally substituted with 1 to 3 R$^{10}$;
R is hydrogen, C$_1$-C$_6$alkyl or absent;
R$^3$, R$^4$, R$^5$, R$^6$ and R$^7$ are each independently selected from the group consisting of hydrogen, deutero, amino, halo, hydroxy, cyano, C$_1$-C$_6$alkyl, C$_3$-C$_6$cycloalkyl and C$_1$-C$_6$alkoxy; wherein the C$_1$-C$_6$alkyl, C$_3$-C$_6$cycloalkyl and C$_1$-C$_6$alkoxy are each optionally substituted with 1 to 3 halo or C$_1$-C$_3$alkoxy;
R$^8$ at each occurrence is independently selected from the group consisting of halo, —C(O)NH$_2$, —C(O)NH(C$_1$-C$_3$alkyl), —C(O)N(C$_1$-C$_3$alkyl)$_2$, C$_1$-C$_6$alkyl, C$_1$-C$_6$alkoxy and C$_3$-C$_6$cycloalkyl; wherein the C$_1$-C$_6$alkyl, C$_1$-C$_6$alkoxy and C$_3$-C$_6$cycloalkyl are each optionally substituted with 1 to 3 halo, cyano, hydroxy or C$_1$-C$_3$alkoxy;
R$^9$ at each occurrence is independently selected from the group consisting of halo, hydroxy, C$_1$-C$_6$alkyl, C$_1$-C$_6$alkoxy, and C$_1$-C$_6$alkoxyC$_1$-C$_6$alkyl, wherein the C$_1$-C$_6$alkyl, C$_1$-C$_6$alkoxy, and C$_1$-C$_6$alkoxyC$_1$-C$_6$alkyl are optionally substituted with one to three halo or a cyano; and
R$^{10}$ at each occurrence is independently selected from the group consisting of halo, C$_1$-C$_6$alkoxy, C$_1$-C$_6$thioalkoxy, amino, C$_1$-C$_6$alkylamino and di(C$_1$-C$_6$alkyl)amino.

3. The compound of claim 2 or a pharmaceutically acceptable salt thereof wherein
X is CR$^7$;
Z is CR$^3$;
R$^3$ is hydrogen, bromo, chloro, fluoro, methoxy or cyano; and
R$^4$, R$^5$, R$^6$ and R$^7$ are each hydrogen or deutero.

4. The compound of claim 3 or a pharmaceutically acceptable salt thereof wherein R$^1$ is a 5- to 10-membered heteroaryl which contains 1 to 4 heteroatoms independently selected from N, O and S; wherein the 5- to 10-membered heteroaryl is optionally substituted with 1 to 2 R$^8$;
R$^{1a}$ and R$^{1b}$ are each hydrogen; and
R$^8$ at each occurrence is independently selected from the group consisting of halo, C$_1$-C$_3$alkyl, C$_1$-C$_3$alkoxy and C$_3$-C$_6$cycloalkyl; wherein the C$_1$-C$_3$alkyl is optionally substituted with 1 to 3 fluoro, hydroxy or C$_1$-C$_3$alkoxy.

5. The compound of claim 4 or a pharmaceutically acceptable salt thereof wherein
R$^1$ is a 5- to 10-membered heteroaryl selected from the group consisting of oxazolyl, isoxazolyl, oxadiazolyl, thiazolyl, pyrazolyl, triazolyl, tetrazolyl, pyridinyl, benzoxazolyl, benzoisoxazolyl, benzopyrazolyl, benzotriazolyl, imidazothiazolyl and imidazothiadiazolyl; each of which is optionally substituted with an R$^8$; and
R$^8$ is selected from the group consisting of methyl, trifluoromethyl, isopropyl, 2-hydroxyisopropyl, methoxy, methoxymethyl, cyclopropyl and chloro.

6. The compound of claim 5 or a pharmaceutically acceptable salt thereof wherein R$^1$ is selected from the group consisting of

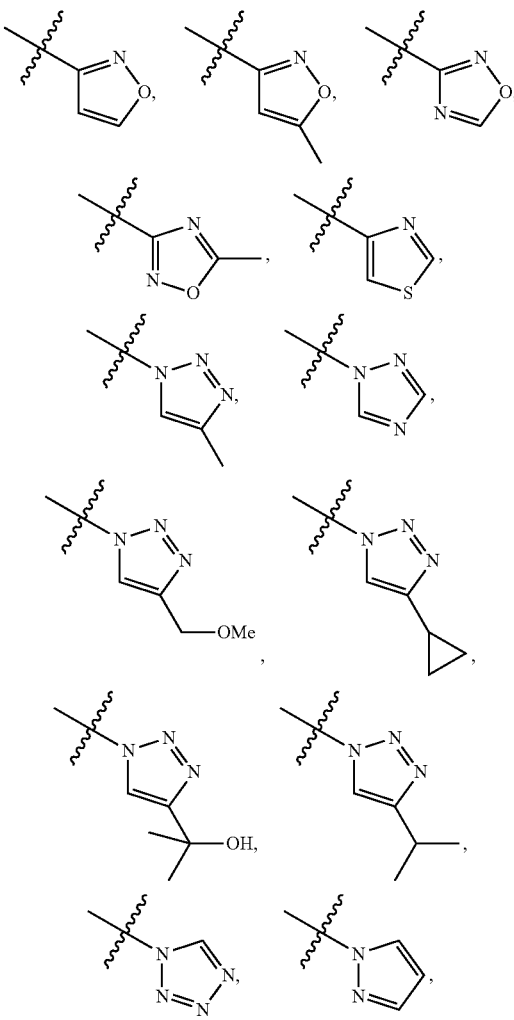

283

-continued

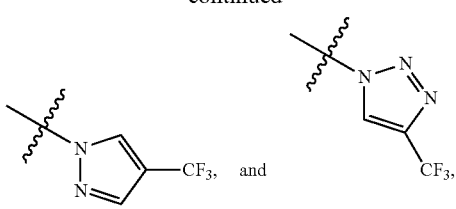

7. The compound of claim 5 or a pharmaceutically acceptable salt thereof wherein R¹ is selected from the group consisting of

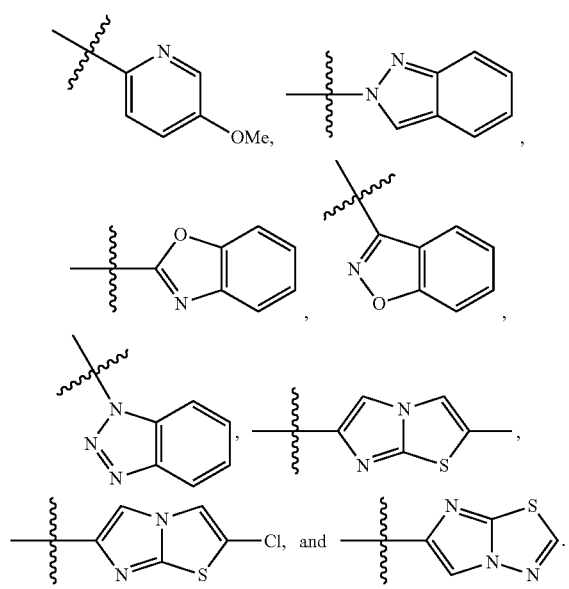

8. The compound of claim 5 or a pharmaceutically acceptable salt thereof wherein R² is tetrahydropyranyl, cyclopentyl or cyclohexyl; each of which is optionally substituted with 1 to 2 R⁹; and R⁹ at each occurrence is independently methyl, ethyl, cyanomethyl, hydroxy or fluoro.

9. The compound of claim 8 or a pharmaceutically acceptable salt thereof wherein R² is selected from the group consisting of

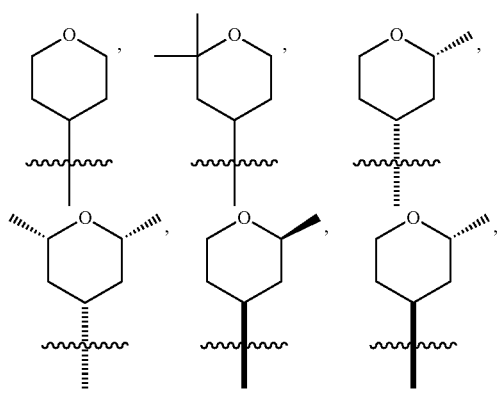

284

-continued

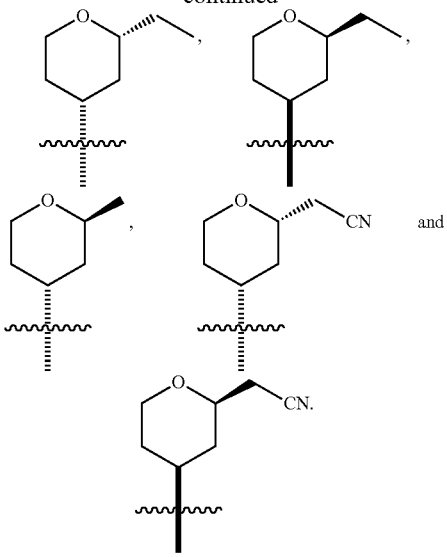

10. The compound of claim 9 or a pharmaceutically acceptable salt thereof wherein R² is

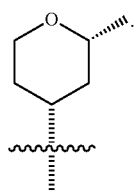

11. The compound of claim 8 or a pharmaceutically acceptable salt thereof wherein R² is selected from the group consisting of

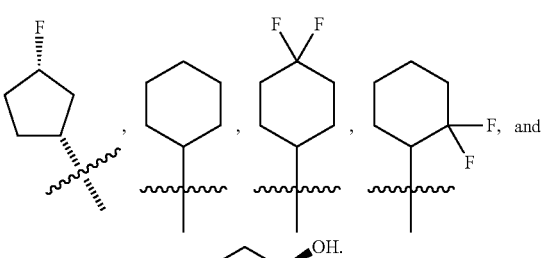

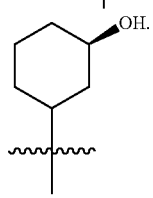

12. The compound of claim 2 or a pharmaceutically acceptable salt thereof wherein
X is N;
Z is CR³;
R¹ is a 5- to 10-membered heteroaryl selected from the group consisting of oxazolyl, isoxazolyl, oxadiazolyl, thiazolyl, pyrazolyl, triazolyl, tetrazolyl, pyridinyl, benzoxazolyl, benzoisoxazolyl, benzopyrazolyl, benzotriazolyl, imidazothiazolyl and imidazothiadiazolyl; each of which is optionally substituted with an R⁸;

$R^{1a}$ and $R^{1b}$ are each hydrogen; and
$R^8$ is methyl, trifluoromethyl, isopropyl, 2-hydroxyisopropyl, methoxy, methoxymethyl, cyclopropyl or chloro.

13. The compound of claim 12 or a pharmaceutically acceptable salt thereof wherein
$R^2$ is

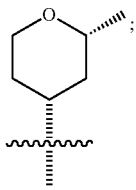

and
$R^3$, $R^4$, $R^5$ and $R^6$ are each hydrogen or deutero.

14. The compound of claim 2 or a pharmaceutically acceptable salt thereof wherein
X is $CR^7$;
Z is $CR^3$;
$R^1$ is cyano;
$R^{1a}$ and $R^{1b}$ are each hydrogen;
$R^2$ is tetrahydropyranyl or cyclopentyl; each of which is optionally substituted with 1 to 2 $R^9$; and
$R^9$ at each occurrence is independently methyl, cyanomethyl or fluoro.

15. The compound of claim 14 or a pharmaceutically acceptable salt thereof wherein
$R^2$ is

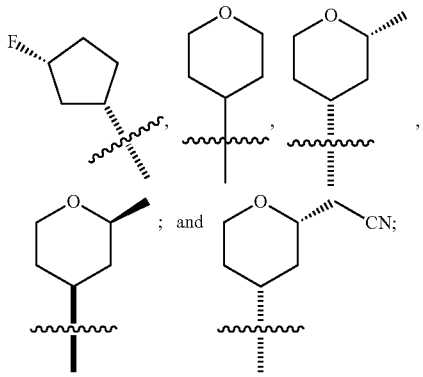

$R^3$ is hydrogen, bromo, chloro, methoxy or cyano; and
$R^4$, $R^5$, $R^6$ and $R^7$ are each hydrogen or deutero.

16. A compound selected from the group consisting of
8-methoxy-2-[(5-methyl-1,2-oxazol-3-yl)methyl]-1-[(2R,4R)-2-methyltetrahydro-2H-pyran-4-yl]-1H-imidazo[4,5-c]quinoline;
8-methoxy-2-[(5-methyl-1,2-oxazol-3-yl)methyl]-1-[(2S,4S)-2-methyltetrahydro-2H-pyran-4-yl]-1H-imidazo[4,5-c]quinoline;
8-chloro-2-[(5-methoxypyridin-2-yl)methyl]-1-[(2R,4R)-2-methyltetrahydro-2H-pyran-4-yl]-1H-imidazo[4,5-c]quinoline;
2-[(5-methyl-1,2-oxazol-3-yl)methyl]-1-[(2R,4R)-2-methyltetrahydro-2H-pyran-4-yl]-1H-imidazo[4,5-c]quinoline-8-carbonitrile;
8-chloro-2-[(5-methyl-1,2-oxazol-3-yl)methyl]-1-[(2R,4R)-2-methyltetrahydro-2H-pyran-4-yl]-1H-imidazo[4,5-c]quinoline;

8-chloro-2-[(5-methyl-1,2,4-oxadiazol-3-yl)methyl]-1-[(2R,4R)-2-methyltetrahydro-2H-pyran-4-yl]-1H-imidazo[4,5-c]quinoline;
8-bromo-1-[(1 S,3R)-3-fluorocyclopentyl]-2-methyl-1H-imidazo[4,5-c]quinoline;
1-[(2R,4R)-2-methyltetrahydro-2H-pyran-4-yl]-2-(1,3-thiazol-4-ylmethyl)-1H-imidazo[4,5-c][1,5]naphthyridine;
1-[(2S,4S)-2-methyltetrahydro-2H-pyran-4-yl]-2-(1,3-thiazol-4-ylmethyl)-1H-imidazo[4,5-c][1,5]naphthyridine;
8-chloro-2-(imidazo[2,1-b][1,3,4]thiadiazol-6-ylmethyl)-1-[(2R,4R)-2-methyltetrahydro-2H-pyran-4-yl]-1H-imidazo[4,5-c]quinoline;
{8-chloro-1-[(2R,4R)-2-methyltetrahydro-2H-pyran-4-yl]-1H-imidazo[4,5-c]quinolin-2-yl}acetonitrile;
8-chloro-1-[(2R,4R)-2-methyltetrahydro-2H-pyran-4-yl]-2-(1,3-thiazol-4-ylmethyl)(4-$^2$H)-1H-imidazo[4,5-c]quinoline;
8-chloro-1-[(2R,4R)-2-methyltetrahydro-2H-pyran-4-yl]-2-[(4-methyl-1H-1,2,3-triazol-1-yl)methyl]-1H-imidazo[4,5-c]quinoline;
8-bromo-1-[(2R,4R)-2-methyltetrahydro-2H-pyran-4-yl]-2-(1,2-oxazol-3-ylmethyl)-1H-imidazo[4,5-c]quinoline;
8-chloro-1-[(2R,4R)-2-methyltetrahydro-2H-pyran-4-yl]-2-(1,2,4-oxadiazol-3-ylmethyl)-1H-imidazo[4,5-c]quinoline;
2-methyl-1-(tetrahydro-2H-pyran-4-yl)-1H-imidazo[4,5-c]quinoline-8-carbonitrile;
2-methyl-1-(cis-2-methyltetrahydro-2H-pyran-4-yl)-1H-imidazo[4,5-c]quinoline;
1-[(1R,3S)-3-fluorocyclopentyl]-2-(1,2-oxazol-3-ylmethyl)-1H-imidazo[4,5-c]quinoline;
8-chloro-2-methyl-1-(tetrahydro-2H-pyran-4-yl)-1H-imidazo[4,5-c]quinoline;
2-(1,2-oxazol-3-ylmethyl)-1-(tetrahydro-2H-pyran-4-yl)-1H-imidazo[4,5-c]quinoline;
2-methyl-1-(cis-2-methyltetrahydro-2H-pyran-4-yl)-1H-imidazo[4,5-c]quinoline-8-carbonitrile;
1-[(1 S,3R)-3-fluorocyclopentyl]-2-methyl-1H-imidazo[4,5-c]quinoline-8-carbonitrile;
1-(cis-2-methyltetrahydro-2H-pyran-4-yl)-2-(1,2-oxazol-3-ylmethyl)-1H-imidazo[4,5-c]quinoline-8-carbonitrile;
1-[(2R,4R)-2-methyltetrahydro-2H-pyran-4-yl]-2-(1,2-oxazol-3-ylmethyl)-1H-imidazo[4,5-c]quinoline-8-carbonitrile;
1-(trans-2-methyltetrahydro-2H-pyran-4-yl)-2-(1,2-oxazol-3-ylmethyl)-1H-imidazo[4,5-c]quinoline-8-carbonitrile;
1-[(2S,4R)-2-methyltetrahydro-2H-pyran-4-yl]-2-(1,2-oxazol-3-ylmethyl)-1H-imidazo[4,5-c]quinoline-8-carbonitrile;
8-bromo-1-[(1 S,3R)-3-fluorocyclopentyl]-2-(1,2-oxazol-3-ylmethyl)-1H-imidazo[4,5-c]quinoline;
1-[(1R,3S)-3-fluorocyclopentyl]-2-(1H-1,2,4-triazol-1-ylmethyl)-1H-imidazo[4,5-c]quinoline;
1-[(1R,3S)-3-fluorocyclopentyl]-2-[(4-methyl-1H-1,2,3-triazol-1-yl)methyl]-1H-imidazo[4,5-c]quinoline;
2-(1,3-benzoxazol-2-ylmethyl)-1-[(1R,3S)-3-fluorocyclopentyl]-1H-imidazo[4,5-c]quinoline;
2-(1,2-benzoxazol-3-ylmethyl)-1-(tetrahydro-2H-pyran-4-yl)-1H-imidazo[4,5-c]quinoline;
1-(tetrahydro-2H-pyran-4-yl)-2-(1H-1,2,4-triazol-1-ylmethyl)-1H-imidazo[4,5-c]quinoline;

2-[(2-methylimidazo[2,1-b][1,3]thiazol-6-yl)methyl]-1-(tetrahydro-2H-pyran-4-yl)-1H-imidazo[4,5-c]quinoline;
2-[(4-methyl-1H-1,2,3-triazol-1-yl)methyl]-1-(tetrahydro-2H-pyran-4-yl)-1H-imidazo[4,5-c]quinoline;
2-{[4-(methoxymethyl)-1H-1,2,3-triazol-1-yl]methyl}-1-(tetrahydro-2H-pyran-4-yl)-1H-imidazo[4,5-c]quinoline;
2-(1,3-benzoxazol-2-ylmethyl)-1-(tetrahydro-2H-pyran-4-yl)-1H-imidazo[4,5-c]quinoline;
1-(tetrahydro-2H-pyran-4-yl)-2-(1H-tetrazol-1-ylmethyl)-1H-imidazo[4,5-c]quinoline;
1-(tetrahydro-2H-pyran-4-yl)-2-(1,3-thiazol-4-ylmethyl)-1H-imidazo[4,5-c]quinoline;
2-[(5-methoxypyridin-2-yl)methyl]-1-(tetrahydro-2H-pyran-4-yl)-1H-imidazo[4,5-c]quinoline;
2-[(2-methylimidazo[2,1-b][1,3,4]thiadiazol-6-yl)methyl]-1-(tetrahydro-2H-pyran-4-yl)-1H-imidazo[4,5-c]quinoline;
2-[(5-methyl-1,2-oxazol-3-yl)methyl]-1-(tetrahydro-2H-pyran-4-yl)-1H-imidazo[4,5-c]quinoline;
2-(1-{[1-(tetrahydro-2H-pyran-4-yl)-1H-imidazo[4,5-c]quinolin-2-yl]methyl}-1H-1,2,3-triazol-4-yl)propan-2-ol;
2-(1H-benzotriazol-1-ylmethyl)-1-(tetrahydro-2H-pyran-4-yl)-1H-imidazo[4,5-c]quinoline;
2-[(4-cyclopropyl-1H-1,2,3-triazol-1-yl)methyl]-1-(tetrahydro-2H-pyran-4-yl)-1H-imidazo[4,5-c]quinoline;
1-(tetrahydro-2H-pyran-4-yl)-2-{[4-(trifluoromethyl)-1H-pyrazol-1-yl]methyl}-1H-imidazo[4,5-c]quinoline;
2-{[4-(propan-2-yl)-1H-1,2,3-triazol-1-yl]methyl}-1-(tetrahydro-2H-pyran-4-yl)-1H-imidazo[4,5-c]quinoline;
2-(2H-indazol-2-ylmethyl)-1-(tetrahydro-2H-pyran-4-yl)-1H-imidazo[4,5-c]quinoline;
1-(2,2-difluorocyclohexyl)-2-(1,2-oxazol-3-ylmethyl)-1H-imidazo[4,5-c]quinoline;
1-(2,2-dimethyltetrahydro-2H-pyran-4-yl)-2-(1,2-oxazol-3-ylmethyl)-1H-imidazo[4,5-c]quinoline;
1-(4,4-difluorocyclohexyl)-2-(1,2-oxazol-3-ylmethyl)-1H-imidazo[4,5-c]quinoline;
trans-3-[2-(1,2-oxazol-3-ylmethyl)-1H-imidazo[4,5-c]quinolin-1-yl]cyclohexanol;
1-cyclohexyl-2-(1,2-oxazol-3-ylmethyl)-1H-imidazo[4,5-c]quinoline;
8-chloro-2-[(5-methyl-1,2,4-oxadiazol-3-yl)methyl]-1-[(2S,4S)-2-methyltetrahydro-2H-pyran-4-yl]-1H-imidazo[4,5-c]quinoline;
8-chloro-1-[(2R,4R)-2-methyltetrahydro-2H-pyran-4-yl]-2-(1,2-oxazol-3-ylmethyl)-1H-imidazo[4,5-c]quinoline;
8-chloro-1-[(2R,4R)-2-methyltetrahydro-2H-pyran-4-yl]-2-(1,3-thiazol-4-ylmethyl)-1H-imidazo[4,5-c]quinoline;
8-fluoro-1-[(2R,4R)-2-methyltetrahydro-2H-pyran-4-yl]-2-(1,2-oxazol-3-ylmethyl)-1H-imidazo[4,5-c]quinoline;
8-fluoro-1-[(2R,4R)-2-methyltetrahydro-2H-pyran-4-yl]-2-(1,3-thiazol-4-ylmethyl)-1H-imidazo[4,5-c]quinoline;
8-bromo-1-(cis-2-methyltetrahydro-2H-pyran-4-yl)-2-(1,3-thiazol-4-ylmethyl)-1H-imidazo[4,5-c]quinoline;
1-[(2R,4R)-2-methyltetrahydro-2H-pyran-4-yl]-2-(1,3-thiazol-4-ylmethyl)-1H-imidazo[4,5-c]quinoline-8-carbonitrile;
8-bromo-2-[(5-methyl-1,2-oxazol-3-yl)methyl]-1-(cis-2-methyltetrahydro-2H-pyran-4-yl)-1H-imidazo[4,5-c]quinoline;
8-bromo-1-[(2R,4r,6S)-2,6-dimethyltetrahydro-2H-pyran-4-yl]-2-(1,2-oxazol-3-ylmethyl)-1H-imidazo[4,5-c]quinoline;
8-bromo-1-[(2R,4r,6S)-2,6-dimethyltetrahydro-2H-pyran-4-yl]-2-(1,2-oxazol-3-ylmethyl)-1H-imidazo[4,5-c]quinoline;
8-bromo-1-[(-[(2R,4r,6S)-2,6-dimethyltetrahydro-2H-pyran-4-yl]-2-(1,3-thiazol-4-ylmethyl)-1H-imidazo[4,5-c]quinoline;
1-[(2R,4r,6S)-2,6-dimethyltetrahydro-2H-pyran-4-yl]-2-(1,3-thiazol-4-ylmethyl)-1H-imidazo[4,5-c]quinoline-8-carbonitrile;
8-methoxy-1-[(2R,4R)-2-methyltetrahydro-2H-pyran-4-yl]-2-(1,2-oxazol-3-ylmethyl)-1H-imidazo[4,5-c]quinoline;
8-chloro-2-(1,2-oxazol-3-ylmethyl)-1-(tetrahydro-2H-pyran-4-yl)-1H-imidazo[4,5-c]quinoline;
8-chloro-2-(imidazo[2,1-b][1,3,4]thiadiazol-6-ylmethyl)-1-[(2S,4S)-2-methyltetrahydro-2H-pyran-4-yl]-1H-imidazo[4,5-c]quinoline;
8-chloro-1-[(2R,4R)-2-methyltetrahydro-2H-pyran-4-yl]-2-(1H-1,2,4-triazol-1-ylmethyl)-1H-imidazo[4,5-c]quinoline;
8-bromo-1-(cis-2-ethyltetrahydro-2H-pyran-4-yl)-2-(1,2-oxazol-3-ylmethyl)-1H-imidazo[4,5-c]quinoline;
1-[(2R,4R)-2-ethyltetrahydro-2H-pyran-4-yl]-2-(1,2-oxazol-3-ylmethyl)-1H-imidazo[4,5-c]quinoline-8-carbonitrile;
1-[(2R,4R)-2-methyltetrahydro-2H-pyran-4-yl]-2-(1,2-oxazol-3-ylmethyl)-1H-imidazo[4,5-c][1,5]naphthyridine;
2-(imidazo[2,1-b][1,3,4]thiadiazol-6-ylmethyl)-1-(tetrahydro-2H-pyran-4-yl)-1H-imidazo[4,5-c]quinoline;
1-(2,2-dimethyltetrahydro-2H-pyran-4-yl)-8-fluoro-2-[(5-methoxypyridin-2-yl)methyl]-1H-imidazo[4,5-c]quinoline;
2-[(2-chloroimidazo[2,1-b][1,3]thiazol-6-yl)methyl]-1-(tetrahydro-2H-pyran-4-yl)-1H-imidazo[4,5-c]quinoline;
1-(2,2-dimethyltetrahydro-2H-pyran-4-yl)-2-(1,3-thiazol-4-ylmethyl)-1H-imidazo[4,5-c]quinoline;
1-(2,2-dimethyltetrahydro-2H-pyran-4-yl)-2-(imidazo[2,1-b][1,3,4]thiadiazol-6-ylmethyl)-1H-imidazo[4,5-c]quinoline;
8-fluoro-1-(tetrahydro-2H-pyran-4-yl)-2-{[4-(trifluoromethyl)-1H-1,2,3-triazol-1-yl]methyl}-1H-imidazo[4,5-c]quinoline;
8-fluoro-2-(1,2-oxazol-3-ylmethyl)-1-(tetrahydro-2H-pyran-4-yl)-1H-imidazo[4,5-c]quinoline;
8-fluoro-2-(2H-indazol-2-ylmethyl)-1-(tetrahydro-2H-pyran-4-yl)-1H-imidazo[4,5-c]quinoline;
8-fluoro-1-(tetrahydro-2H-pyran-4-yl)-2-(1,3-thiazol-4-ylmethyl)-1H-imidazo[4,5-c]quinoline;
8-fluoro-1-(tetrahydro-2H-pyran-4-yl)-2-{[4-(trifluoromethyl)-1H-pyrazol-1-yl]methyl}-1H-imidazo[4,5-c]quinoline;
2-[(4-cyclopropyl-1H-1,2,3-triazol-1-yl)methyl]-1-(2,2-dimethyltetrahydro-2H-pyran-4-yl)-8-fluoro-1H-imidazo[4,5-c]quinoline;
1-(2,2-dimethyltetrahydro-2H-pyran-4-yl)-8-fluoro-2-(1,3-thiazol-4-ylmethyl)-1H-imidazo[4,5-c]quinoline;
1-(2,2-dimethyltetrahydro-2H-pyran-4-yl)-8-fluoro-2-{[4-(trifluoromethyl)-1H-pyrazol-1-yl]methyl}-1H-imidazo[4,5-c]quinoline;
8-fluoro-2-(imidazo[2,1-b][1,3,4]thiadiazol-6-ylmethyl)-1-(tetrahydro-2H-pyran-4-yl)-1H-imidazo[4,5-c]quinoline;

1-(2,2-dimethyltetrahydro-2H-pyran-4-yl)-8-fluoro-2-[(2-methyl imidazo[2,1-b][1,3,4]thiadiazol-6-yl) methyl]-1H-imidazo[4,5-c]quinoline;
1-(2,2-dimethyltetrahydro-2H-pyran-4-yl)-8-fluoro-2-(1, 2-oxazol-3-ylmethyl)-1H-imidazo[4,5-c]quinoline;
8-chloro-1-[(2R,4R)-2-methyltetrahydro-2H-pyran-4-yl]-2-(1,3-thiazol-4-ylmethyl)-1H-imidazo[4,5-c]quinolin-4-amine;
8-fluoro-2-(imidazo[2,1-b][1,3,4]thiadiazol-6-ylmethyl)-1-(cis-2-methyltetrahydro-2H-pyran-4-yl)-1H-imidazo[4,5-c]quinoline;
8-methoxy-2-[(5-methyl-1,2,4-oxadiazol-3-yl)methyl]-1-[(2R,4R)-2-methyltetrahydro-2H-pyran-4-yl]-1H-imidazo[4,5-c]quinoline;
8-methoxy-1-[(2R,4R)-2-methyltetrahydro-2H-pyran-4-yl]-2-[(4-methyl-1H-1,2,3-triazol-1-yl)methyl]-1H-imidazo[4,5-c]quinoline;
8-methoxy-1-[(2R,4R)-2-methyltetrahydro-2H-pyran-4-yl]-2-(1,3-thiazol-4-ylmethyl)-1H-imidazo[4,5-c]quinoline;
2-(imidazo[2,1-b][1,3,4]thiadiazol-6-ylmethyl)-8-methoxy-1-[(2R,4R)-2-methyltetrahydro-2H-pyran-4-yl]-1H-imidazo[4,5-c]quinoline;
[cis-4-(2-methyl-1H-imidazo[4,5-c]quinolin-1-yl)tetrahydro-2H-pyran-2-yl]acetonitrile; and
8-chloro-2-[(5-methyl-1,3-oxazol-2-yl)methyl]-1-[(2R, 4R)-2-methyltetrahydro-2H-pyran-4-yl]-1H-imidazo[4,5-c]quinoline;
or a pharmaceutically acceptable salt thereof.

17. A compound of claim 2 selected from the group consisting of
8-chloro-2-[(5-methoxypyridin-2-yl)methyl]-1-[(2R,4R)-2-methyltetrahydro-2H-pyran-4-yl]-1H-imidazo[4,5-c]quinoline;
2-[(5-methyl-1,2-oxazol-3-yl)methyl]-1-[(2R,4R)-2-methyltetrahydro-2H-pyran-4-yl]-1H-imidazo[4,5-c]quinoline-8-carbonitrile;
8-chloro-2-[(5-methyl-1,2-oxazol-3-yl)methyl]-1-[(2R, 4R)-2-methyltetrahydro-2H-pyran-4-yl]-1H-imidazo[4,5-c]quinoline;
8-chloro-2-[(5-methyl-1,2,4-oxadiazol-3-yl)methyl]-1-[(2R,4R)-2-methyltetrahydro-2H-pyran-4-yl]-1H-imidazo[4,5-c]quinoline;
8-chloro-2-(imidazo[2,1-b][1,3,4]thiadiazol-6-ylmethyl)-1-[(2R,4R)-2-methyltetrahydro-2H-pyran-4-yl]-1H-imidazo[4,5-c]quinoline;
{8-chloro-1-[(2R,4R)-2-methyltetrahydro-2H-pyran-4-yl]-1H-imidazo[4,5-c]quinolin-2-yl}acetonitrile;
8-chloro-1-[(2R,4R)-2-methyltetrahydro-2H-pyran-4-yl]-2-(1,3-thiazol-4-ylmethyl)(4-$^{2}$H)-1H-imidazo[4,5-c]quinoline; and
8-chloro-1-[(2R,4R)-2-methyltetrahydro-2H-pyran-4-yl]-2-[(4-methyl-1H-1,2,3-triazol-1-yl)methyl]-1H-imidazo[4,5-c]quinoline;
or a pharmaceutically acceptable salt thereof.

18. The compound of claim 2 or a pharmaceutically acceptable salt thereof wherein
X is $CR^7$;
Z is $CR^3$;
$R^{1a}$, $R^{1b}$, $R^4$, $R^5$, $R^6$ and $R^7$ are each hydrogen; and
$R^3$ is chloro or cyano.

19. The compound of claim 18 or a pharmaceutically acceptable salt thereof wherein
$R^2$ is 1-methylpyrrolidinyl or 2-methyltetrahydropyranyl.

20. The compound of claim 19 or a pharmaceutically acceptable salt thereof wherein
$R^1$ is selected from the group consisting of isoxazolyl, pyrazolyl, triazolyl, oxadiazolyl, thiadiazolyl, pyrimidinyl and pyrazinyl; each of which is optionally substituted with an $R^8$; and $R^8$ is methyl or methoxy.

21. The compound of claim 20 or a pharmaceutically acceptable salt thereof wherein
$R^1$ is selected from the group consisting of methylisoxazolyl, methoxypyrazolyl, methyltriazolyl, methyloxadiazolyl, methylthiadiazolyl, methylpyrimidinyl and methylpyrazinyl;
$R^2$ is (2R, 4R)-2-methyltetrahydro-2H-pyran-4-yl; and
$R^3$ is chloro.

22. The compound of claim 20 or a pharmaceutically acceptable salt thereof wherein
$R^1$ is selected from the group consisting of methylisoxazolyl, methoxypyrazolyl, methyltriazolyl, methyloxadiazolyl, methylthiadiazolyl, methylpyrimidinyl and methylpyrazinyl;
$R^2$ is 1-methylpyrrolidinyl; and
$R^3$ is cyano.

23. The compound of claim 20 selected from the group consisting of
8-Chloro-2-[(5-methyl-1,2-oxazol-3-yl)methyl]-1-[(2R, 4R)-2-methyltetrahydro-2H-pyran-4-yl]-1H-imidazo[4,5-c]quinoline;
8-Chloro-2-[(5-methyl-1,2,4-oxadiazol-3-yl)methyl]-1-[(2R,4R)-2-methyltetrahydro-2H-pyran-4-yl]-1H-imidazo[4,5-c]quinoline;
8-Chloro-1-[(2R,4R)-2-methyltetrahydro-2H-pyran-4-yl]-2-[(4-methyl-1H-1,2,3-triazol-1-yl)methyl]-1H-imidazo[4,5-c]quinoline;
8-Chloro-2-[(6-methylpyrimidin-4-yl)methyl]-1-[(2R, 4R)-2-methyltetrahydro-2H-pyran-4-yl]-1H-imidazo[4,5-c]quinoline;
8-Chloro-2-[(5-methylpyrazin-2-yl)methyl]-1-[(2R,4R)-2-methyltetrahydro-2H-pyran-4-yl]-1H-imidazo[4,5-c]quinoline;
8-Chloro-2-[(4-methoxy-1H-pyrazol-1-yl)methyl]-1-[(2R,4R)-2-methyltetrahydro-2H-pyran-4-yl]-1H-imidazo[4,5-c]quinoline; and
8-Chloro-1-[(2R,4R)-2-methyltetrahydro-2H-pyran-4-yl]-2-[(5-methyl-1,3,4-thiadiazol-2-yl)methyl]-1H-imidazo[4,5-c]quinoline;
or a pharmaceutically acceptable salt thereof.

24. A pharmaceutical composition comprising a therapeutically effective amount of a compound according to claim 1, or a pharmaceutically acceptable salt thereof together with a pharmaceutically acceptable carrier.

25. The corn pound 8-Chloro-2-[(6-methylpyrimidin-4-yl)methyl]-1-[(2R,4R)-2-methyltetrahydro-2H-pyran-4-yl]-1H-imidazo[4,5-c]quinoline; or a pharmaceutically acceptable salt thereof.

26. The corn pound 8-Chloro-2-[(5-methylpyrazin-2-yl)methyl]-1-[(2R,4R)-2-methyltetrahydro-2H-pyran-4-yl]-1H-imidazo[4,5-c]quinoline; or a pharmaceutically acceptable salt thereof.

27. The corn pound 8-Chloro-2-[(4-methoxy-1H-pyrazol-1-yl)methyl]-1-[(2R,4R)-2-methyltetrahydro-2H-pyran-4-yl]-1H-imidazo[4,5-c]quinoline; or a pharmaceutically acceptable salt thereof.

28. The corn pound 8-Chloro-1-[(2R,4R)-2-methyltetrahydro-2H-pyran-4-yl]-2-[(5-methyl-1,3,4-thiadiazol-2yl) methyl]-1H-imidazo[4,5-c]quinoline; or a pharmaceutically acceptable salt thereof.

29. The compound 8-Chloro-2-[(5-methyl-1,2,4-oxadiazol-3-yl)methyl]-1-[(2R,4R)-2-methyltetrahydro-2H-pyran-4-yl]-1H-imidazo[4,5-c]quinoline; or a pharmaceutically acceptable salt thereof.

* * * * *